(12) United States Patent
McLean et al.

(10) Patent No.: US 12,324,837 B2
(45) Date of Patent: Jun. 10, 2025

(54) ROR1-SPECIFIC ANTIGEN BINDING MOLECULES

(71) Applicants: Estelle Grace McLean, Craigavon (GB); Paul Richard Trumper, Craigavon (GB); Jennifer Thom, Craigavon (GB); Timothy Harrison, Craigavon (GB); Graham John Cotton, Craigavon (GB); Caroline Barelle, Craigavon (GB); Andrew Porter, Craigavon (GB); Marina Kovaleva, Craigavon (GB)

(72) Inventors: Estelle Grace McLean, Craigavon (GB); Paul Richard Trumper, Craigavon (GB); Jennifer Thom, Craigavon (GB); Timothy Harrison, Craigavon (GB); Graham John Cotton, Craigavon (GB); Caroline Barelle, Craigavon (GB); Andrew Porter, Craigavon (GB); Marina Kovaleva, Craigavon (GB)

(73) Assignee: ALMAC DISCOVERY LIMITED, Craigavon (GB)

( * ) Notice: Subject to any disclaimer, the term of this patent is extended or adjusted under 35 U.S.C. 154(b) by 860 days.

(21) Appl. No.: 16/957,075

(22) PCT Filed: Dec. 21, 2018

(86) PCT No.: PCT/EP2018/086823
§ 371 (c)(1),
(2) Date: Jun. 22, 2020

(87) PCT Pub. No.: WO2019/122447
PCT Pub. Date: Jun. 27, 2019

(65) Prior Publication Data
US 2023/0203155 A1  Jun. 29, 2023

(30) Foreign Application Priority Data
Dec. 22, 2017 (GB) .................... 1721802

(51) Int. Cl.
*A61K 39/395* (2006.01)
*A61K 39/00* (2006.01)
(Continued)

(52) U.S. Cl.
CPC ........ *A61K 39/39558* (2013.01); *A61K 40/11* (2025.01); *A61K 40/31* (2025.01); *A61K 40/4202* (2025.01); *A61K 47/68031* (2023.08); *A61K 47/68035* (2023.08); *A61K 47/6817* (2017.08); *A61K 47/6849* (2017.08); *A61K 47/6851* (2017.08); *A61P 35/00* (2018.01); *C07K 16/2803* (2013.01); *C07K 16/2863* (2013.01); *C07K 16/46* (2013.01); *G01N 33/57492* (2013.01); *A61K 2039/5156* (2013.01); *C07K 2317/24* (2013.01);
(Continued)

(58) Field of Classification Search
CPC ...................... C07K 16/2803; C07K 16/2863; C07K 16/46; C07K 2317/24; C07K 2317/31; C07K 2317/33; C07K 2317/56; C07K 2317/565; C07K 2317/567; C07K 2317/73; C07K 2317/76; C07K 2317/77; C07K 2317/92; C07K 2317/94; C07K 2319/03; C07K 2319/30; C07K 2319/33; C07K 16/3007; C07K 2317/52; C07K 2317/64; C07K 2319/55; C07K 2319/60; C07K 16/3061; A61K 35/17; A61K 47/6803; A61K 47/6817; A61K 47/6849; A61K 47/6851; A61K 2039/5156; A61K 47/6809; A61K 47/6831; A61K 47/6853; A61K 47/6867; A61K 38/00; A61K 2039/572; A61K 39/39558; A61K 39/0011; A61K 2039/505; A61P 35/00; A61P 35/02; G01N 33/57492; G01N 2333/70503; G01N 2333/71
See application file for complete search history.

(56) References Cited

U.S. PATENT DOCUMENTS

| | | |
|---|---|---|
| 2013/0302250 A1 | 11/2013 | Barelle |
| 2016/0068600 A1* | 3/2016 | Barelle .................. C07K 16/40 |
| | | 435/69.6 |

(Continued)

FOREIGN PATENT DOCUMENTS

| | | |
|---|---|---|
| AU | 2017209099 A1 | 2/2018 |
| EP | 3342858 A1 | 4/2018 |

(Continued)

OTHER PUBLICATIONS

Barelle C et al. VNARs: An Ancient and Unique Repertoire of Molecules That Deliver Small, Soluble, Stable and High Affinity Binders of Proteins. (Antibodies 2015, 4, 240-258) (Year: 2015).*

(Continued)

*Primary Examiner* — Karen A. Canella
*Assistant Examiner* — John J Skoko, III
(74) *Attorney, Agent, or Firm* — Arrigo, Lee, Guttman & Mouta-Bellum LLP

(57) ABSTRACT

The present invention relates to receptor tyrosine kinase-like orphan receptor 1 (ROR1) specific antigen binding molecules and associated fusion proteins and conjugates. In a further aspect, the present invention relates to conjugated immunoglobulin-like shark variable novel antigen receptors (VNARs).

57 Claims, 40 Drawing Sheets
Specification includes a Sequence Listing.

(51) Int. Cl.

| | | |
|---|---|---|
| A61K 40/11 | (2025.01) | |
| A61K 40/31 | (2025.01) | |
| A61K 40/42 | (2025.01) | |
| A61K 47/68 | (2017.01) | |
| A61P 35/00 | (2006.01) | |
| C07K 16/28 | (2006.01) | |
| C07K 16/46 | (2006.01) | |
| G01N 33/574 | (2006.01) | |

(52) U.S. Cl.
CPC ...... C07K 2317/31 (2013.01); C07K 2317/33 (2013.01); C07K 2317/56 (2013.01); C07K 2317/565 (2013.01); C07K 2317/567 (2013.01); C07K 2317/73 (2013.01); C07K 2317/76 (2013.01); C07K 2317/77 (2013.01); C07K 2317/92 (2013.01); C07K 2317/94 (2013.01); C07K 2319/03 (2013.01); C07K 2319/30 (2013.01); C07K 2319/33 (2013.01); G01N 2333/70503 (2013.01); G01N 2333/71 (2013.01)

(56) References Cited

U.S. PATENT DOCUMENTS

| | | |
|---|---|---|
| 2018/0142016 A1 | 5/2018 | Wong et al. |
| 2021/0317204 A1 | 10/2021 | McLean et al. |

FOREIGN PATENT DOCUMENTS

| | | | |
|---|---|---|---|
| WO | 03014161 A2 | 2/2003 | |
| WO | 2010124188 A1 | 10/2010 | |
| WO | 2011054007 A1 | 5/2011 | |
| WO | 201107992 A2 | 7/2011 | |
| WO | 2011079902 A2 | 7/2011 | |
| WO | 2011130613 A1 | 10/2011 | |
| WO | 2012075158 A1 | 6/2012 | |
| WO | 2012097313 A2 | 7/2012 | |
| WO | 201431174 A1 | 3/2013 | |
| WO | 2013167883 A1 | 11/2013 | |
| WO | 2014011518 A1 | 1/2014 | |
| WO | 2014028776 A1 | 2/2014 | |
| WO | 2014031174 A1 | 2/2014 | |
| WO | 2014173959 A2 | 4/2014 | |
| WO | 2015107075 A1 | 1/2015 | |
| WO | 201520083 A1 | 2/2015 | |
| WO | 2015200883 A2 | 6/2015 | |
| WO | 2016016343 A1 | 2/2016 | |
| WO | 2016187216 A1 | 5/2016 | |
| WO | 2016094847 A1 | 6/2016 | |
| WO | WO-2016187220 A2 * | 11/2016 | ............ A61K 38/05 |
| WO | 2017127664 A1 | 1/2017 | |
| WO | 2017127499 A1 | 7/2017 | |
| WO | 2017127644 A1 | 7/2017 | |
| WO | 2017136607 A1 | 8/2017 | |
| WO | 2017142928 A1 | 8/2017 | |
| WO | 2017156479 A1 | 9/2017 | |
| WO | WO-2017196847 A1 * | 11/2017 | ............ C07K 16/10 |
| WO | WO-2018217799 A1 * | 11/2018 | ............ A61P 35/00 |
| WO | 2019122445 A1 | 12/2018 | |

OTHER PUBLICATIONS

Kovalenko OV et al. Atypical Antigen Recognition Mode of a Shark Immunoglobulin New Antigen Receptor (IgNAR) Variable Domain Characterized by Humanization and Structural Analysis. J Biol Chem. 2013 288(24): 17408-17419 (Year: 2013).*

Almagro & Fransson, Humanization of antibodies. Frontiers in Bioscience 2008; 13:1619-33 (Year: 2008).*

Gershoni et al., Epitope Mapping, Biodrugs 2007; 21 (3): 145-156 (Year: 2007).*

Blythe et al., Benchmarking B cell epitope prediction: Underperformance of existing methods, Protein Science (2005), 14:246-248 (Year: 2005).*

Schreiber et al., 3D-Epitope-Explorer (3DEX): Localization of Conformational Epitopes within Three-Dimensional Structures of Proteins, Wiley Interscience, 2005 42-44, 60596, p. 879 (Year: 2005).*

Rentero et al., Screening of Large Molecule Diversities by Phage Display Chimia, 65: 843-845 (2011) (Year: 2011).*

Geng M et al. Loss of Wnt5a and Ror2 protein in hepatocellular carcinoma associated with poor prognosis. (World J Gastroenterol. Mar. 28, 2012; 18(12): 1328-1338 (Year: 2012).*

Hassannia H et al. Inhibition of tumor growth by mouse ROR1 specific antibody in a syngeneic mouse tumor model. (Immunology Letters 2018 193 35-41, Epub Nov. 22, 2017.). (Year: 2017).*

De Groot AS et al. Beyond humanization and de-immunization: tolerization as a method for reducing the immunogenicity of biologics. (Expert Rev Clin Pharmacol. 2013 6(6): 651-662) (Year: 2013).*

ThermoFisher (Invitrogen PA5-14725 ROR1 Antibody https://www.thermofisher.com/antibody/product/ROR1-Antibody-Polyclonal/PA5-14725, available before Dec. 11, 2015 based on safety data sheet (Year: 2015).*

NCBI blast alignment human ROR1 vs mouse ROR1 (https://blast.ncbi.nlm.nih.gov/Blast.cgi?PAGE_TYPE=BlastSearch&PROG_DEF=blastn&BLAST_PROG_DEF=blastn&BLAST_SPEC=GlobalAln&LINK_LOC=BlastHomeLink) (Year: 2023).*

Kline T et al. Methods to Make Homogenous Antibody Drug Conjugates. (Pharm Res. 2015; 32(11): 3480-3493). (Year: 2015).*

NCBI blast alignment (https://blast.ncbi.nlm.nih.gov/Blast.cgi?PAGE_TYPE=BlastSearch&PROG_DEF=blastn&BLAST_PROG_DEF=blastn&BLAST_SPEC=GlobalAln&LINK_LOC=BlastHomeLink) (Year: 2023).*

Russian Search Report for Corresponding Application Serial No. PCT/EP2018/086823.

Zhang, Suping et al. "The onco-embryonic antigen ROR1 is expressed by a variety of human cancers." The American journal of pathology vol. 181,6 (2012): 1903-10.

Zhang, Suping et al. "ROR1 is expressed in human breast cancer and associated with enhanced tumor-cell growth." PloS one vol. 7,3 (2012): e31127.

Zhang, Suping et al. "Ovarian cancer stem cells express ROR1, which can be targeted for anti-cancer-stem-cell therapy." Proceedings of the National Academy of Sciences of the United States of America vol. 111,48 (2014): 17266-71.

Zhang, Huilin et al. "ROR1 expression correlated with poor clinical outcome in human ovarian cancer." Scientific reports vol. 4 5811. Jul. 24, 2014,.

Zheng, Yu-Zhu et al. "ROR1 is a novel prognostic biomarker in patients with lung adenocarcinoma." Scientific reports vol. 6 36447. Nov. 10, 2016.

Altschul, Stephen; "Basic Local Alignment Search Tool", Journal Molecular Biology, 1990, vol. 215, pp. 403-410.

Anderson, George; "Importance of Hyupervariable Region 2 for Stability and Affinity of a Shark Single-Domain Antibody Specific for Ebola Virus Nucleoprotein", PLOS One, Aug. 2016, 12 pages.

Arnett, Kelly L et al. "Crystal structure of a human CD3-epsilon/delta dimer in complex with a UCHT1 single-chain antibody fragment." Proceedings of the National Academy of Sciences of the United States of America vol. 101,46 (2004): 16268-73.

Balakrishnan, Ashwini et al. "Analysis of ROR1 Protein Expression in Human Cancer and Normal Tissues." Clinical cancer research : an official journal of the American Association for Cancer Research vol. 23, 12 (2017): 3061-3071.

Baskar, Sivasubramanian et al. "Unique cell surface expression of receptor tyrosine kinase ROR1 in human B-cell chronic lymphocytic leukemia." Clinical cancer research : an official journal of the American Association for Cancer Research vol. 14,2 (2008): 396-404.

Berger, Carolina et al. "Safety of targeting ROR1 in primates with chimeric antigen receptor-modified T cells." Cancer Immunology research vol. 3,2 (2015): 206-16.

(56) References Cited

OTHER PUBLICATIONS

Borcherding, Nicholas et al. "ROR1, an embryonic protein with an emerging role in cancer biology." Protein & cell vol. 6,7 (2014): 496-502.
Broome, H Elizabeth et al. "ROR1 is expressed on hematogones (non-neoplastic human B-lymphocyte precursors) and a minority of precursor-B acute lymphoblastic leukemia." Leukemia research vol. 35,10 (2011): 1390-4.
Chien, Hui-Ping et al. "Expression of ROR1 has prognostic significance in triple negative breast cancer." Virchows Archiv : an international journal of pathology vol. 468,5 (2016): 589-95.
Choi, Michael Y et al. "Pre-clinical Specificity and Safety of UC-961, a First-In-Class Monoclonal Antibody Targeting ROR1." Clinical lymphoma, myeloma & leukemia vol. 15 Suppl, 0 (2015): S167-9.
Cui, Bing et al. "Targeting ROR1 inhibits epithelial-mesenchymal transition and metastasis." Cancer research vol. 73,12 (2013): 3649-60.
Cui, Bing et al. "High-level ROR1 associates with accelerated disease progression in chronic lymphocytic leukemia." Blood vol. 128,25 (2016): 2931-2940.
Daneshmanesh, Amir H et al. "Ror1, a cell surface receptor tyrosine kinase is expressed in chronic lymphocytic leukemia and may serve as a putative target for therapy." International journal of cancer vol. 123,5 (2008): 1190-5.
Dave, Hema et al. "Restricted cell surface expression of receptor tyrosine kinase ROR1 in pediatric B-lineage acute ymphoblastic leukemia suggests targetability with therapeutic monoclonal antibodies." PloS one vol. 7,12 (2012): e52655.
Devereux, J et al. "A comprehensive set of sequence analysis programs for the VAX." Nucleic acids research vol. 12,1 Pt 1 (1984): 387-95.
Dooley, Helen et al. "Selection and characterization of naturally occurring single-domain (IgNAR) antibody fragments from immunized sharks by phage display." Molecular immunology vol. 40, 1 (2003): 25-33.
Dooley, Helen, and Martin F Flajnik. "Shark immunity bites back: affinity maturation and memory response in the nurse shark, Ginglymostoma cirratum." European journal of immunology vol. 35,3 (2005): 936-45.
Dooley, Helen et al. "First molecular and biochemical analysis of in vivo affinity maturation in an ectothermic vertebrate." Proceedings of the National Academy of Sciences of the United States of America vol. 103,6 (2006): 1846-51.
Fennell, B J et al. "Dissection of the IgNAR V domain: molecular scanning and orthologue database mining define novel IgNAR hallmarks and affinity maturation mechanisms." Journal of molecular biology vol. 400,2 (2010): 155-70.
Flajnik, Martin F et al. "A case of convergence: why did a simple alternative to canonical antibodies arise in sharks and camels ?. " PLoS biology vol. 9,8 (2011): e1001120.
Fukuda, Tetsuya et al. "Antisera induced by infusions of autologous Ad-CD154-leukemia B cells identify ROR1 as an oncofetal antigen and receptor for Wnt5a." Proceedings of the National Academy of Sciences of the United States of America vol. 105,8 (2008): 3047-52.
Garrard, L J, and D J Henner. "Selection of an anti-IGF-1 Fab from a Fab phage library created by mutagenesis of multiple CDR loops." Gene vol. 128, 1 (1993): 103-9.
Gentile, Alessandra et al. "Ror1 is a pseudokinase that is crucial for Met-driven tumorigenesis." Cancer research vol. 71,8 (2011): 3132-41.
Greenberg, A S et al. "A new antigen receptor gene family that undergoes rearrangement and extensive somatic diversification in sharks." Nature vol. 374,6518 (1995): 168-73.
Hamers-Casterman, C et al. "Naturally occurring antibodies devoid of light chains." Nature vol. 363,6428 (1993): 446-8.
Hudecek, Michael et al. "Receptor affinity and extracellular domain modifications affect tumor recognition by ROR1-specific chimeric antigen receptor T cells." Clinical cancer research : an official journal of the American Association for Cancer Research vol. 19, 12 (2013): 3153-64.
Ida, Lisa et al. "Receptor tyrosine kinase-like orphan receptor 1, a target of NKX2-1/TTF-1 lineage-survival oncogene, Inhibits apoptosis signal-regulating kinase 1-mediated pro-apoptotic signaling in lung adenocarcinoma." Cancer science vol. 107,2 (2016): 155-61.
Jeffrey, Scott C et al. "A potent anti-CD70 antibody-drug conjugate combining a dimeric pyrrolobenzodiazepine drug with site-specific conjugation technology." Bioconjugate chemistry vol. 24,7 (2013): 1256-63.
Knappik, A et al. "Fully synthetic human combinatorial antibody libraries (HuCAL) based on modular consensus frameworks and CDRs randomized with trinucleotides." Journal of molecular biology vol. 296, 1 (2000): 57-86.
Kovalenko, Oleg V et al. "Atypical antigen recognition mode of a shark immunoglobulin new antigen receptor (IgNAR) variable domain characterized by humanization and structural analysis." The Journal of biological chemistry vol. 288,24 (2013): 17408-19.
Kovaleva, Marina et al. "Shark variable new antigen receptor biologics—a novel technology platform for therapeutic drug development." Expert opinion on biological therapy vol. 14, 10 (2014): 1527-39.
Li, Chunlai et al. "A ROR1-HER3-lncRNA signalling axis modulates the Hippo-YAP pathway to regulate bone metastasis." Nature cell biology vol. 19,2 (2017): 106-119.
Liu, Jinny L et al. "Selection of cholera toxin specific IgNAR single-domain antibodies from a naïve shark library." Molecular immunology vol. 44,7 (2007): 1775-83.
Liu, Jinny L et al. "Thermal stability and refolding capability of shark derived single domain antibodies." Molecular Immunology vol. 59,2 (2014): 194-9.
Stefano, James E et al. "Micro- and mid-scale maleimide-based conjugation of cytotoxic drugs to antibody hinge region thiols for tumor targeting." Methods in molecular biology (Clifton, N.J.) vol. 1045 (2013): 145-71.
Muir, Tom W. "Chemical biology: cutting out the middle man." Nature vol. 442,7102 (2006): 517-8.
Müller, Mischa R et al. "Improving the pharmacokinetic properties of biologics by fusion to an anti-HSA shark VNAR domain." mAbs vol. 4,6 (2012): 673-85.
Rebagay, Guilly et al. "ROR1 and ROR2 in Human Malignancies: Potentials for Targeted Therapy." Frontiers in oncology vol. 2 34. Apr. 18, 2012.
Shao, Cui-Ying et al. "Rapid isolation of IgNAR variable single-domain antibody fragments from a shark synthetic library." Molecular immunology vol. 44,4 (2007): 656-65.
Stanfield, Robyn L et al. "Crystal structure of a shark single-domain antibody V region in complex with lysozyme." Science (New York, N.Y.) vol. 305,5691 (2004): 1770-3.
Stanfield, Robyn L et al. "Maturation of shark single-domain (IgNAR) antibodies: evidence for induced-fit binding." Journal of molecular biology vol. 367,2 (2007): 358-72.
Streltsov, V A et al. "Structural evidence for evolution of shark Ig new antigen receptor variable domain antibodies from a cell-surface receptor." Proceedings of the National Academy of Sciences of the United States of America vol. 101,34 (2004): 12444-9.
Streltsov, Victor A et al. "Structure of a shark IgNAR antibody variable domain and modeling of an early-developmental isotype." Protein science : a publication of the Protein Society vol. 14, 11 (2005): 2901-9.
Kung Sutherland, May S et al. "SGN-CD33A: a novel CD33-targeting antibody-drug conjugate using a pyrrolobenzodiazepine dimer is active in models of drug-resistant AML." Blood vol. 122,8 (2013): 1455-63.
Wesolowski, Janusz et al. "Single domain antibodies: promising experimental and therapeutic tools in infection and immunity." Medical microbiology and immunology vol. 198,3 (2009): 157-74.
Yamaguchi, Tomoya et al. "NKX2-1/TITF1/TTF-1-Induced ROR1 is required to sustain EGFR survival signaling in lung adenocarcinoma." Cancer cell vol. 21,3 (2012): 348-61.

(56) References Cited

OTHER PUBLICATIONS

Yamaguchi, Tomoya et al. "ROR1 sustains caveolae and survival signalling as a scaffold of cavin-1 and caveolin-1." Nature communications vol. 7 10060. Jan. 4, 2016.

Yu, Jian et al. "Wnt5a induces ROR1/ROR2 heterooligomerization to enhance leukemia chemotaxis and proliferation." The Journal of clinical investigation vol. 126,2 (2016): 585-98.

Zhou, Jian-Kang et al. "ROR1 expression as a biomarker for predicting prognosis in patients with colorectal cancer." Oncotarget vol. 8,20 (2017): 32864-32872.

Zielonka, Stefan et al. "The Shark Strikes Twice: Hypervariable Loop 2 of Shark IgNAR Antibody Variable Domains and Its Potential to Function as an Autonomous Paratope." Marine biotechnology (New York, N.Y.) vol. 17,4 (2015): 386-92.

European Search Report for Corresponding Application Serial No. 18839600.6, Dated Oct. 31, 2022, pp. 1-7.

Patterson, James T., et al. "Improving the serum stability of site-specific antibody conjugates with sulfone linkers." Bioconjugate chemistry 25.8 (2014): 1402-1407.

Hu, Eileen, et al. "Evaluation of ROR1 targeted antibody drug conjugates in acute and chronic lymphocytic leukemia and mantle cell lymphoma." Blood 130 (2017): 3017.

Cui, Bing, et al. "Cirmtuzumab vedotin (UC-961ADC3), an anti-ROR1-monomethyl auristatin E antibody-drug conjugate, is a potential treatment for ROR1-positive leukemia and solid tumors." Blood 122.21 (2013): 1637.

Derksen et al. Illegitimate WNT signaling promotes proliferation of multiple myeloma cells, Proceedings of the National Academy of Sciences, 2004, 101(16), 6122-6127.

Dirks et al. Brain Tumor Stem Cells: Bringing Order to the Chaos of Brain Cancer. Journal of Clinical Oncology, 2008, 26(17), 2916-2924.

Lopez-Lazaro. The migration ability of stem cells can explain the existence of cancer of unknown primary site. Rethinking metastasis. Oncoscience, 2015, 2(5), 467-475.

Tran and Rosenthal. Survival comparison between glioblastoma multiforme and other incurable cancers, Journal of Clinical Neuroscience, 2010, 17(4), 417-421.

* cited by examiner

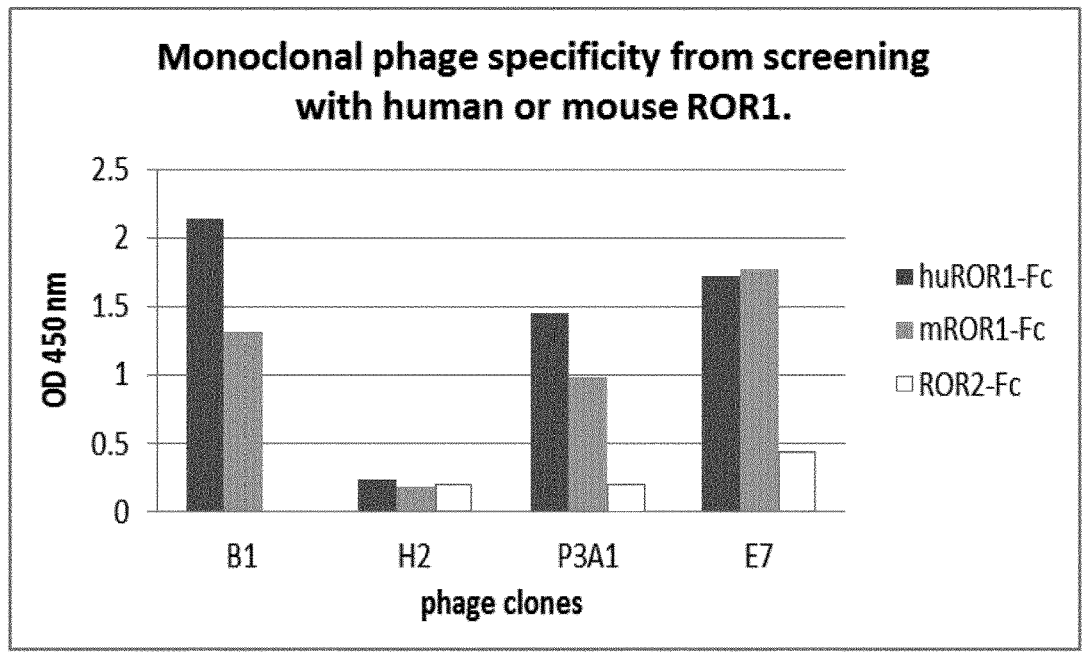

Fig. 1

```
                  10         20         30         40         50         60         70
E7   Protein  - TRVDQTPRTATKETGESLTINCVVTGAKYGLAATYWYRKNPGSSNQERISISGRYVESVNKRTMSFSLRI
CPF7 Protein- TRVDQTPRTATKETGESLTINCVVTGAKYGLFATYWYRKNPGSSNQERISISGRYVESVNKRTMSFSLRI
P3A1 Protein- TRVDQTPRTATKETGESLTINCVLTDTSYGLYSTSWFRKNPGTTDWERMSIGGRYVESVNKGAKSFSLRI
B1   Protein  - ASVNQTPRTATKETGESLTINCVVTGANYGLAATYWYRKNPGSSNQERISISGRYVESVNKRTMSFSLRI
                     80         90        100        110
E7   Protein  - KDLTVADSATYYCKAY----PWAMWG----QWYDGAGTVLTVN  105  SEQ ID NO: 102
CPF7 Protein- KDLTVADSATYYCKAVFMPQHWHPAA----HWYDGAGTVLTVN  109  SEQ ID NO: 103
P3A1 Protein- KDLTVADSATYYCKAR---EARHPWLR---QWYDGAGTVLTVN  107  SEQ ID NO: 47
B1   Protein  - KDLTVADSATYYCKAY----PWGAGAPWLVQWYDGAGTVLTVN  109  SEQ ID NO: 44

10         20         30         40         50         60         70
E7   Protein  - TRVDQTPRTATKETGESLTINCVVTGAKYGLAATYWYRKNPGSSNQERISISGRYVESVNKRTMSFSLRI
CPF7 Protein- TRVDQTPRTATKETGESLTINCVVTGAKYGLFATYWYRKNPGSSNQERISISGRYVESVNKRTMSFSLRI
P3A1 Protein- TRVDQTPRTATKETGESLTINCVLTDTSYGLYSTSWFRKNPGTTDWERMSIGGRYVESVNKGAKSFSLRI
B1   Protein  - ASVNQTPRTATKETGESLTINCVVTGANYGLAATYWYRKNPGSSNQERISISGRYVESVNKRTMSFSLRI
                     80         90        100        110       120       130
E7   Protein  - KDLTVADSATYYCKAY----PWAMWG----QWYDGAGTVLTVNQASGAHHHHHHGAEFEQKLISEEDL    130
CPF7 Protein- KDLTVADSATYYCKAVFMPQHWHPAA----HWYDGAGTVLTVNQASGAHHHHHHGAEFEQKLISEEDL    134
P3A1 Protein- KDLTVADSATYYCKAR---EARHPWLR---QWYDGAGTVLTVNQASGAHHHHHHGAEFEQKLISEEDL    132
B1   Protein  - KDLTVADSATYYCKAY----PWGAGAPWLVQWYDGAGTVLTVNQASGAHHHHHHGAEFEQKLISEEDL    134
```

SEQ ID NO: 104
SEQ ID NO: 105
SEQ ID NO: 106
SEQ ID NO: 107

Fig. 2

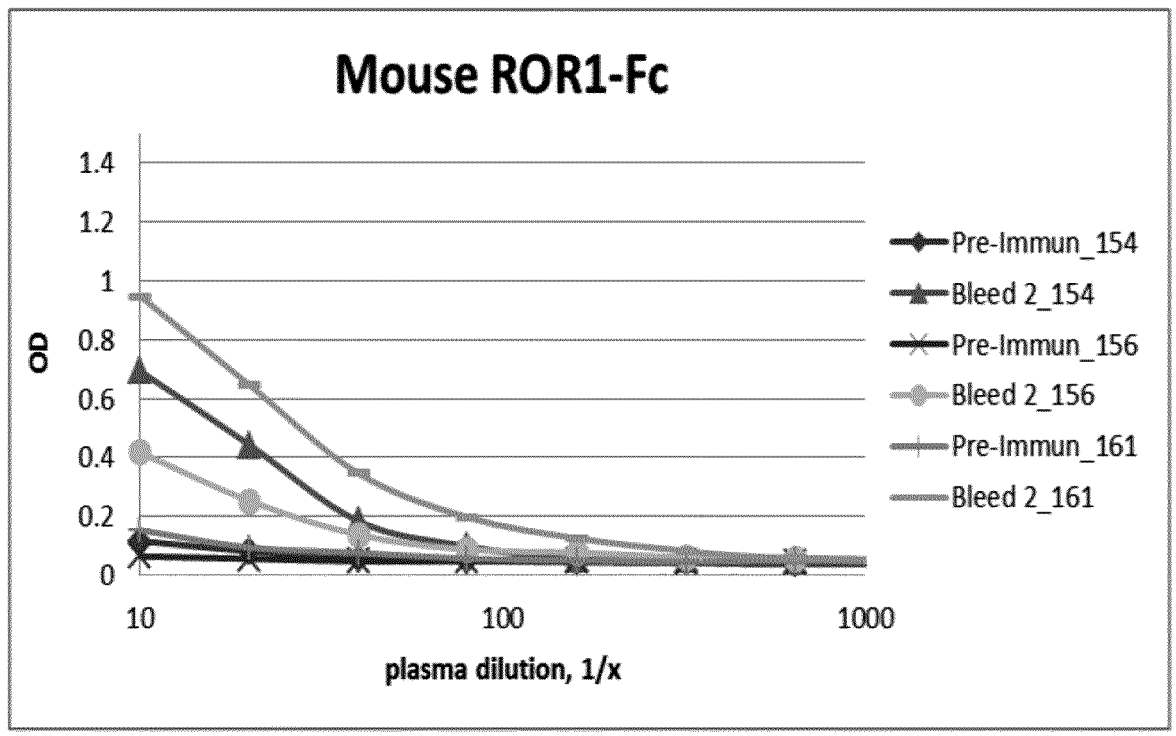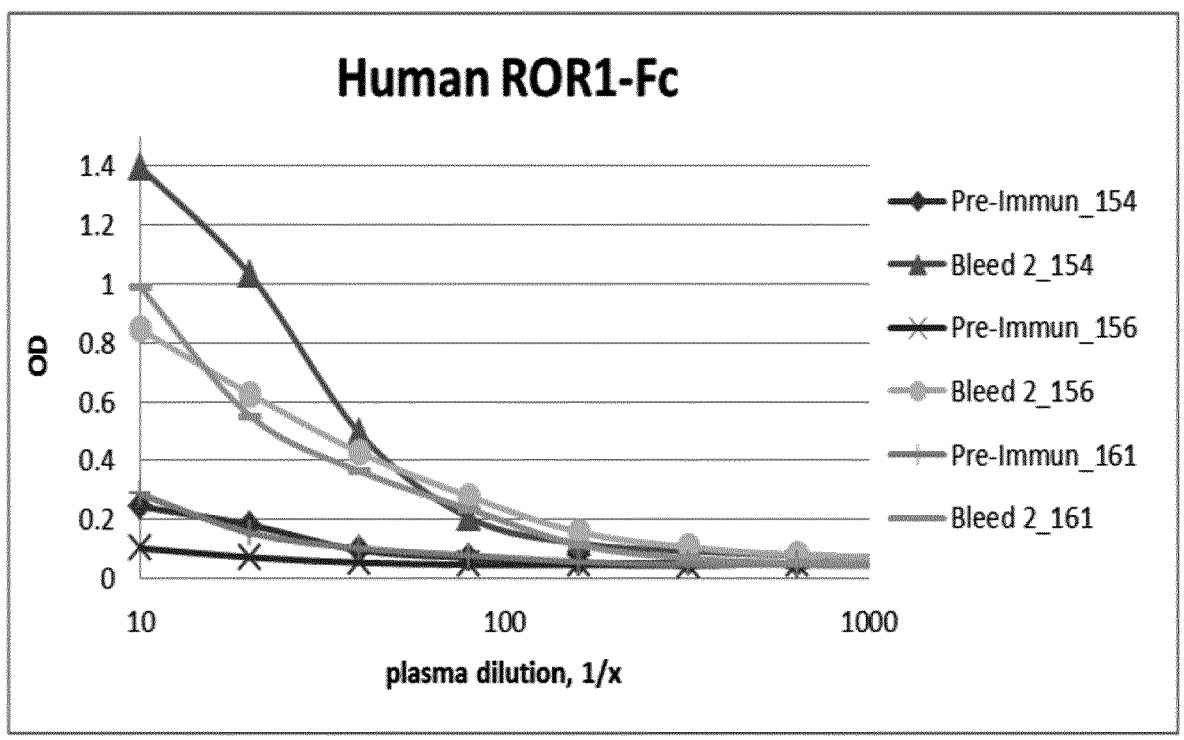
Fig. 3

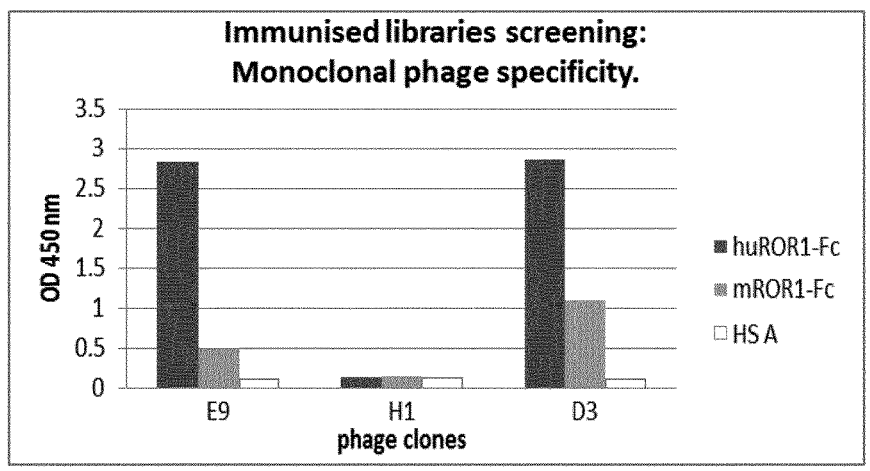

Fig. 4

```
                 10        20        30        40        50        60        70
D3 protein - ASVNQTPRTATKETGESLTINCVLTDTSYGLYSTSWFRKNPGTTDWERMSIGGRYVESVNKRAKSFSLRI
E9 protein - AKVDQTPRTATKETGESLTINCVLTDTSYGLYSTSWFRKNPGTTDWERMSIGGRYVESVNKRAKSFSLRI
                 80        90       100       110
D3 protein - KDLTVADSATYYCKAQSGMAISTGSGHGYNWYDGAGTVLTVN   112   SEQ ID NO: 39
E9 protein - KDLTVADSATYYCKAQSGMAIDIGSGHGYNWYDGAGTVLTVN   112   SEQ ID NO: 40

10        20        30        40        50        60        70
D3 protein - ASVNQTPRTATKETGESLTINCVLTDTSYGLYSTSWFRKNPGTTDWERMSIGGRYVESVNKRAKSFSLRI
E9 protein - AKVDQTPRTATKETGESLTINCVLTDTSYGLYSTSWFRKNPGTTDWERMSIGGRYVESVNKRAKSFSLRI
                 80        90       100       110       120       130
D3 protein - KDLTVADSATYYCKAQSGMAISTGSGHGYNWYDGAGTVLTVNQASGAHHHHHHGAEFEQKLISEEDL   137
E9 protein - KDLTVADSATYYCKAQSGMAIDIGSGHGYNWYDGAGTVLTVNQASGAHHHHHHGAEFEQKLISEEDL   137
                                                                  SEQ ID NO: 108
                                                                  SEQ ID NO: 109
```

Fig. 5

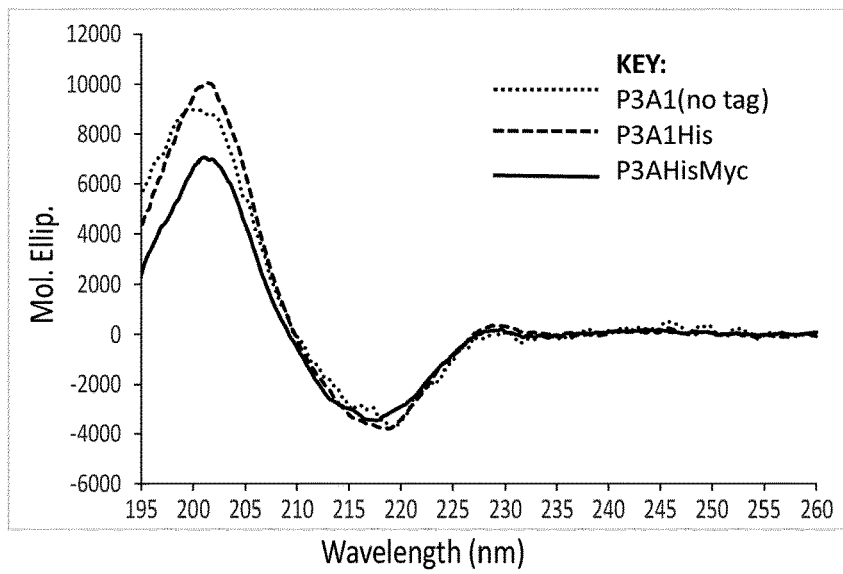

Fig. 6

Linker mouse IgG2a sequence for VNAR fusions

GGGGSGGGGSGGGGSEPRGPTIKPCPPCKCPAPNLLGGPSVFIFPPKIKDVLMISL
SPIVTCVVVDVSEDDPDVQISWFVNNVEVHTAQTQTHREDYNSTLRVVSALPIQ
HQDWMSGKEFKCKVNNKDLPAPIERTISKPKGSVRAPQVYVLPPPEEEMTKKQV
TLTCMVTDFMPEDIYVEWTNNGKTELNYKNTEPVLDSDGSYFMYSKLRVEKKN
WVERNSYSCSVVHEGLHNHHTTKSFSRTPGK (SEQ ID NO 110)

Linker human IgG1 sequences for VNAR fusions

N-terminal VNAR hFc (linker-hFc sequence)

GGGGSGGGGSGGGGSEPKSSDKTHTCPPCPAPELLGGPSVFLFPPKPKDTLMISR
TPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO 111)

Cysteine engineered variants for bioconjugation

GGGGSGGGGSGGGGSEPKSSDKTHTCPPCPAPELLGGPCVFLFPPKPKDTLMIS
RTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO 112)

GGGGSGGGGSGGGGSEPKSSDKTHTCPPCPAPELLGGPSVFLFPPKPKDTLMISR
TPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQ
GNVFSCSVMHEALHNHYTQKSLCLSPGK (SEQ ID NO 113)

C-terminal hFc VNAR (hFc-linker sequence)

DKTHTCPPCPAPELLGGPCVFLFPPKPKDTLMISRTPEVTCVVVDVSHEDPEVKF
NWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHY
TQKSLSLSPGKGGGGSGGGGSGGGGSGGGGSGGGGS (SEQ ID NO 114)

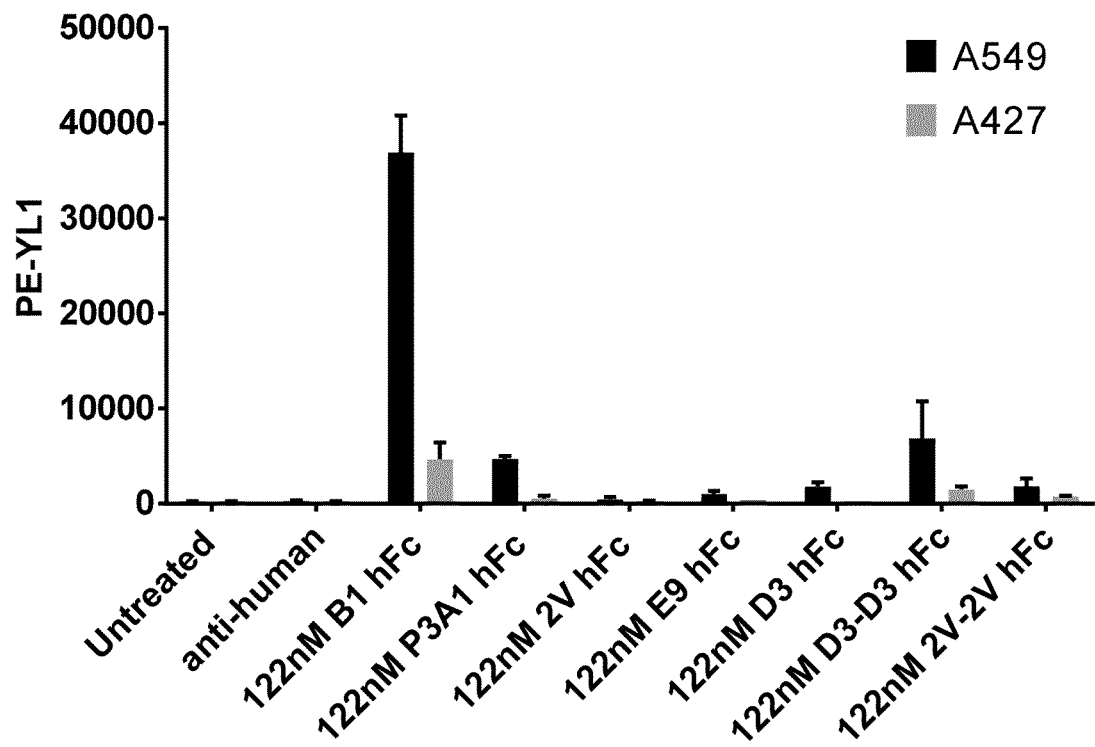
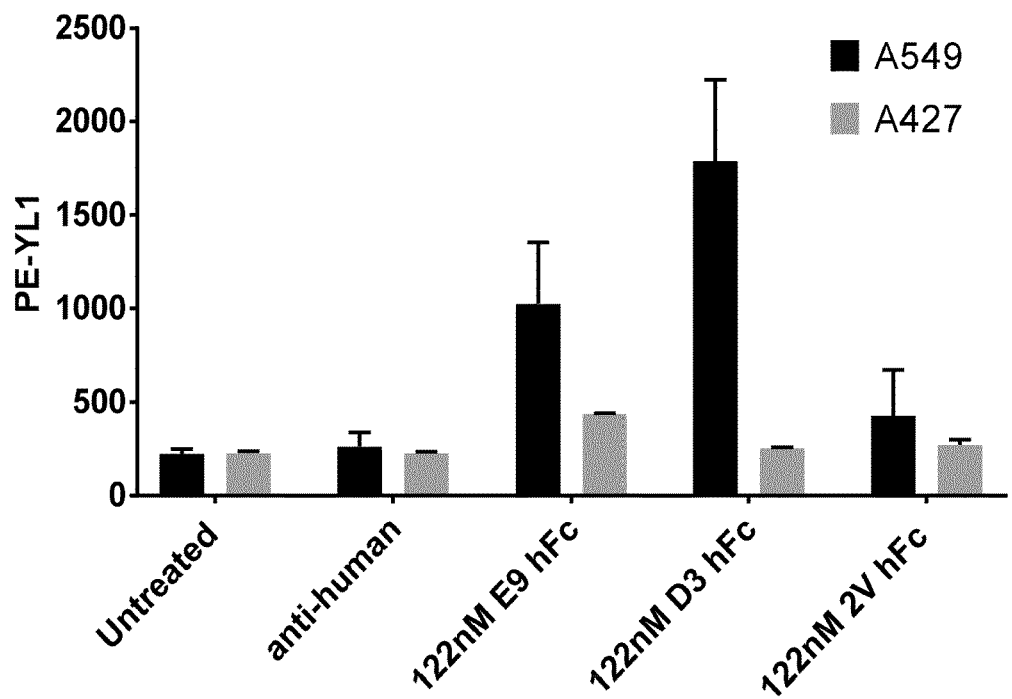
Fig. 15

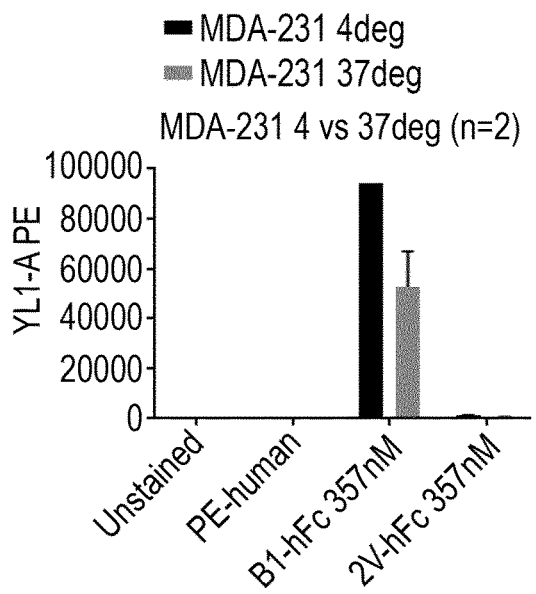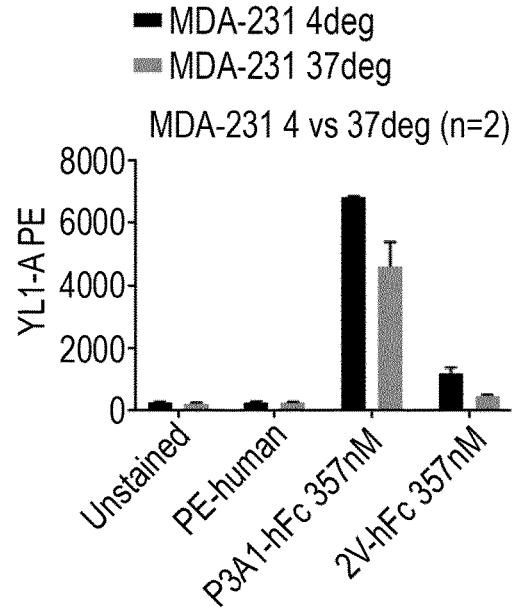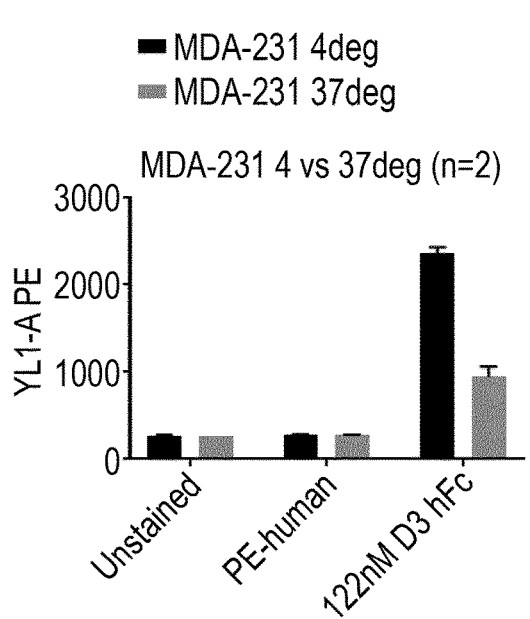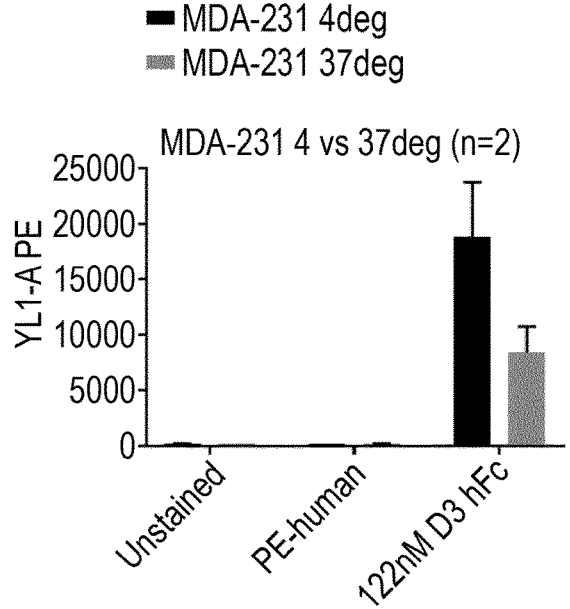
Fig. 16

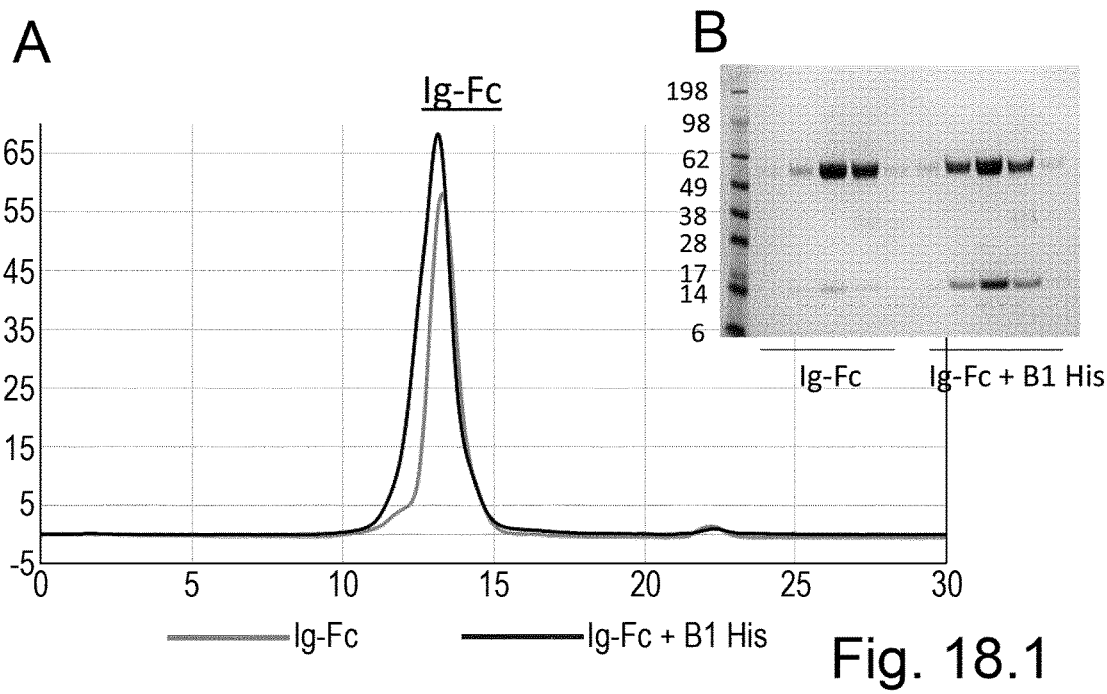
Fig. 18.1
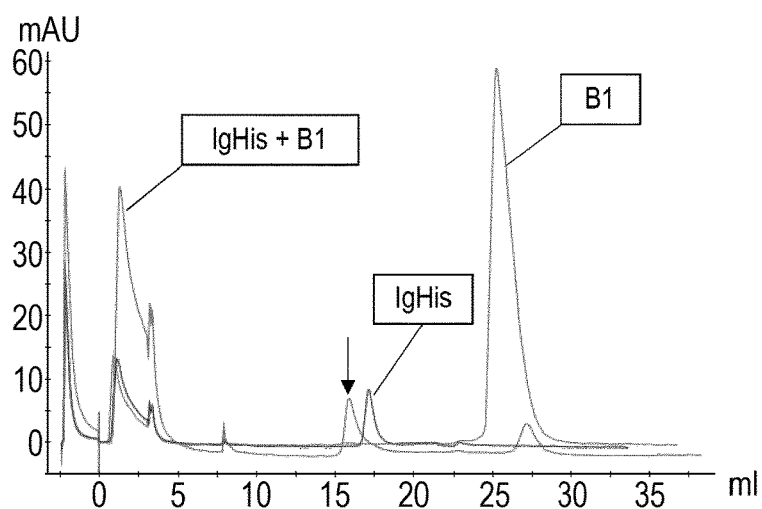
Fig. 18.2
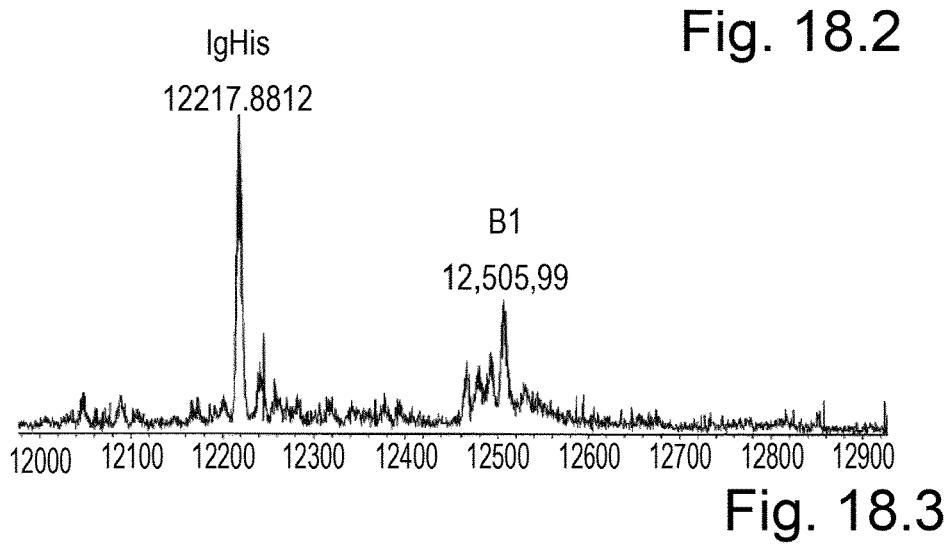
Fig. 18.3

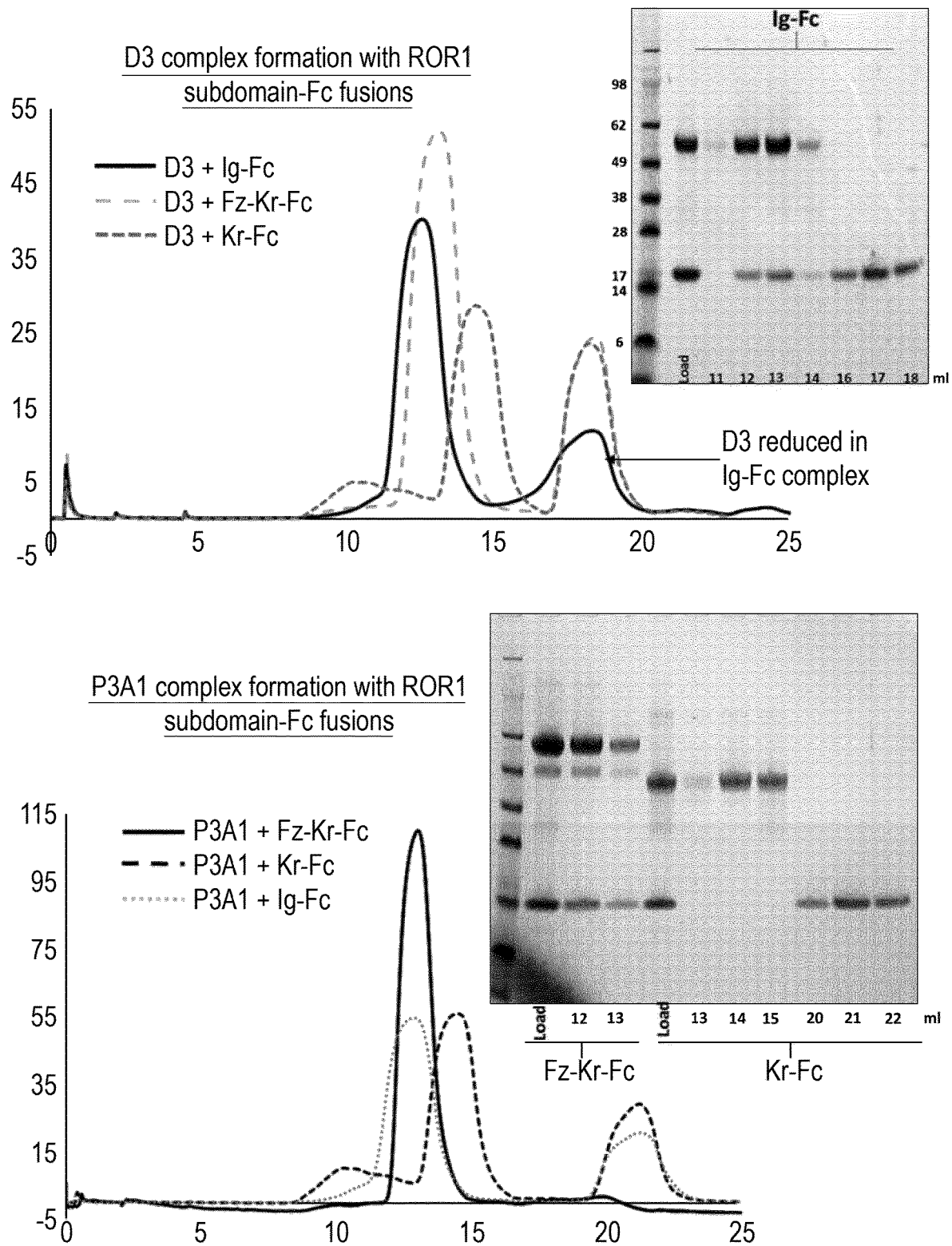
Fig. 18.4

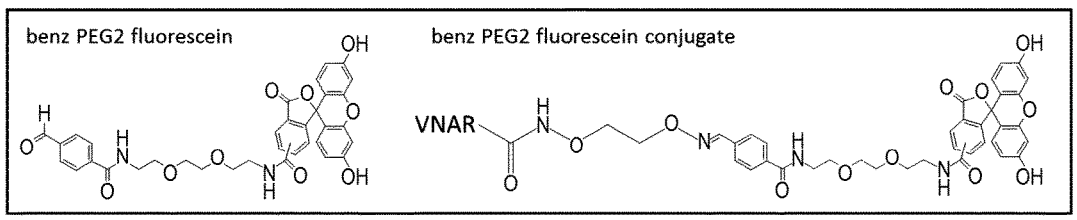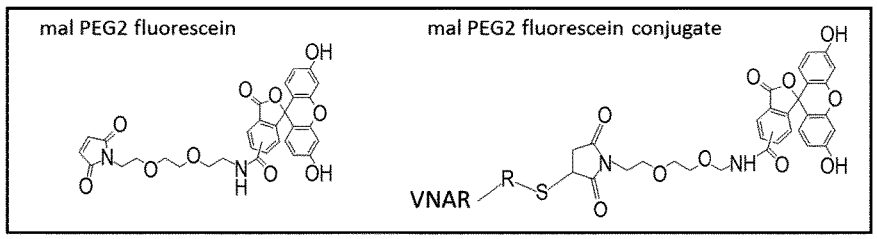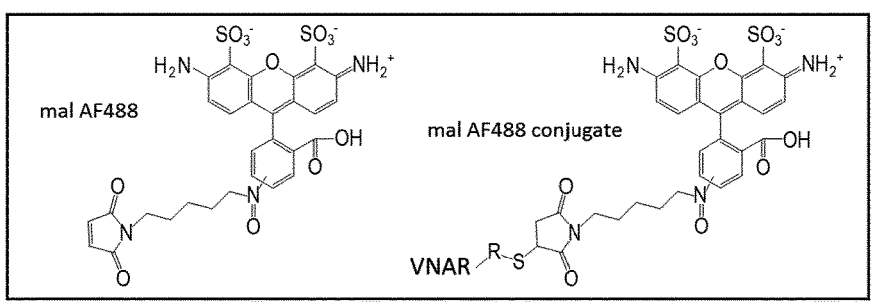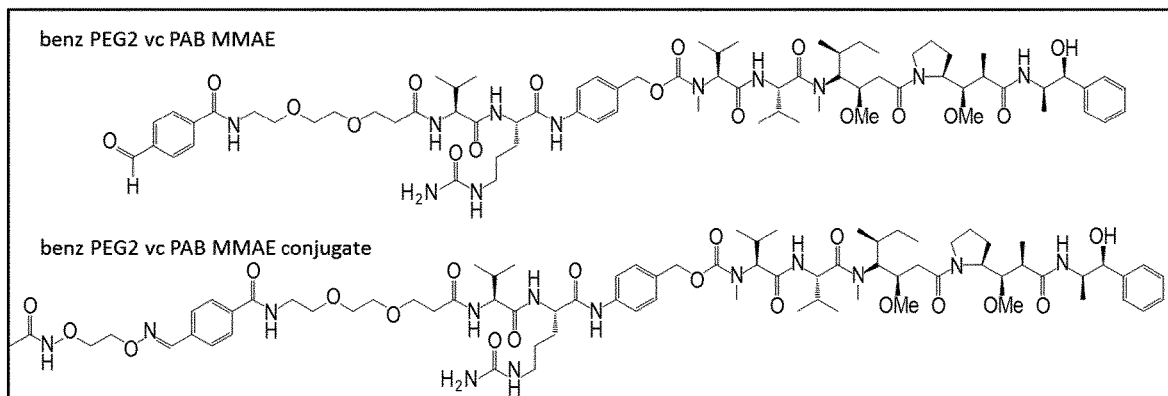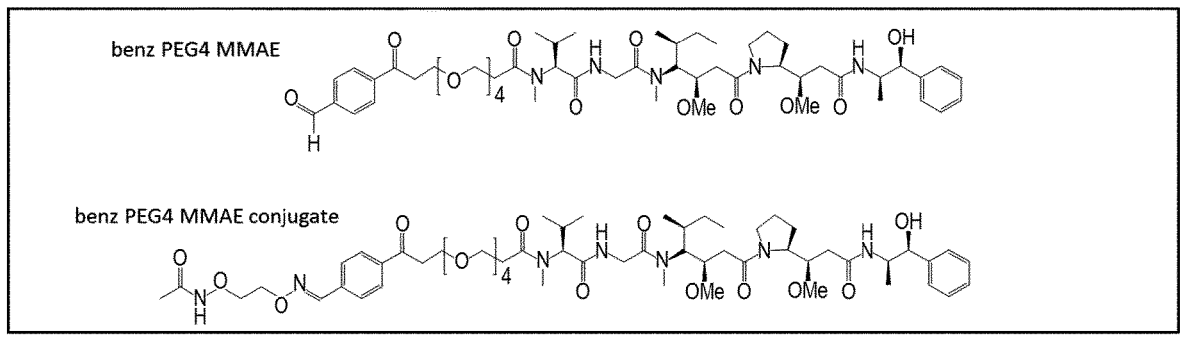
Fig. 28

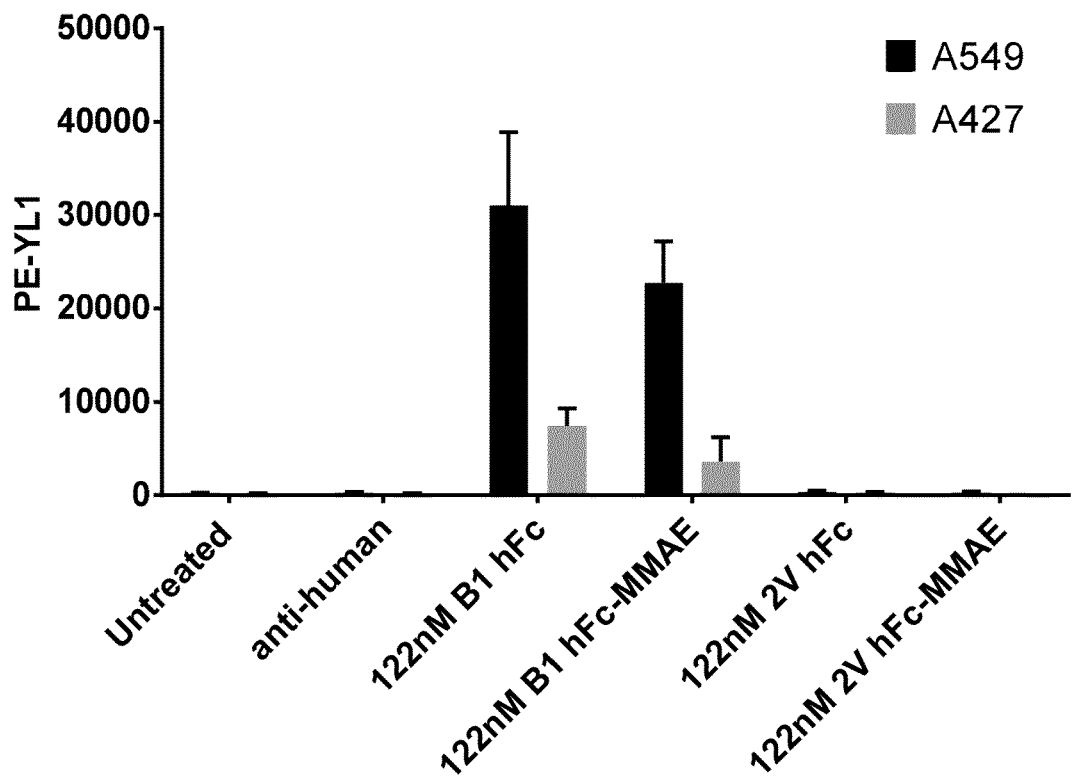
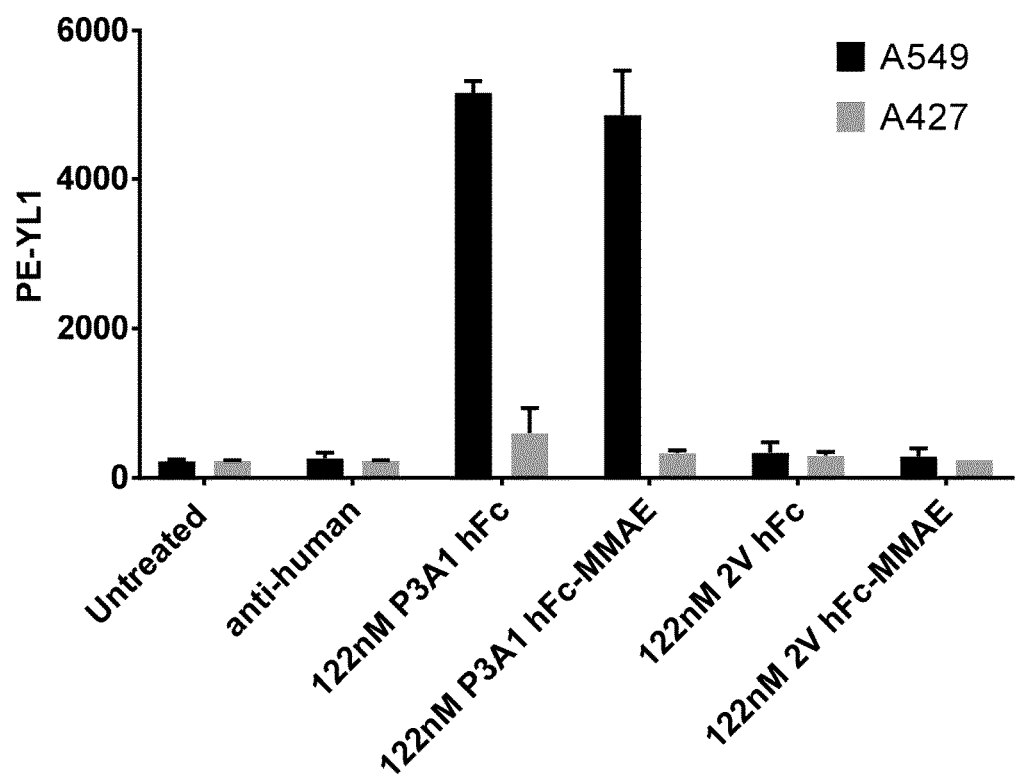
Fig. 30

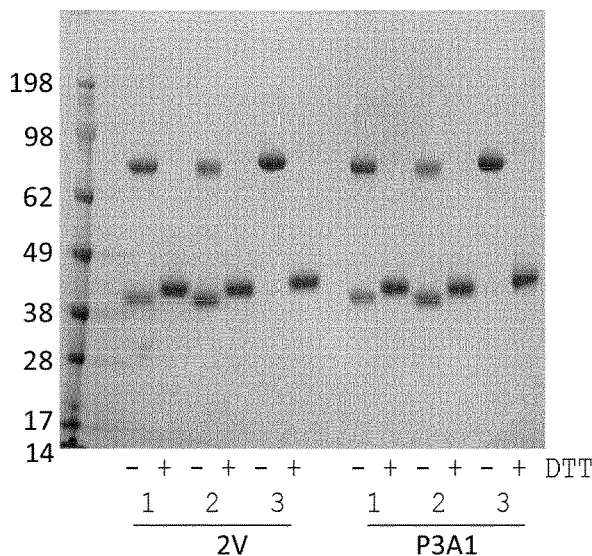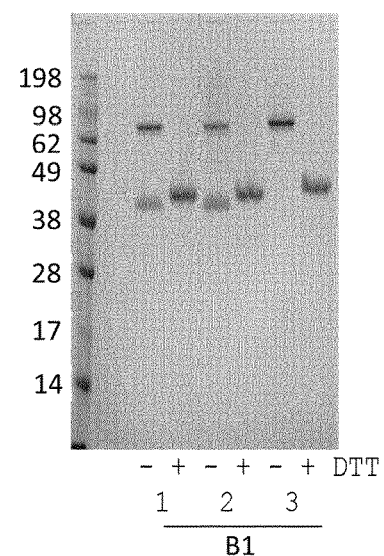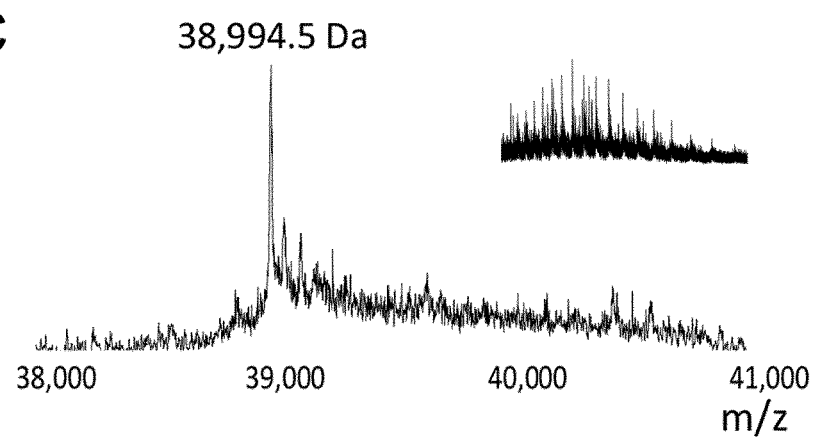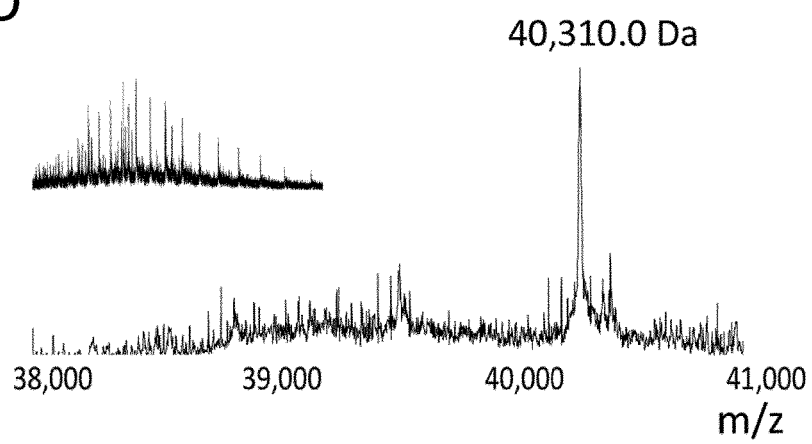
Fig. 31

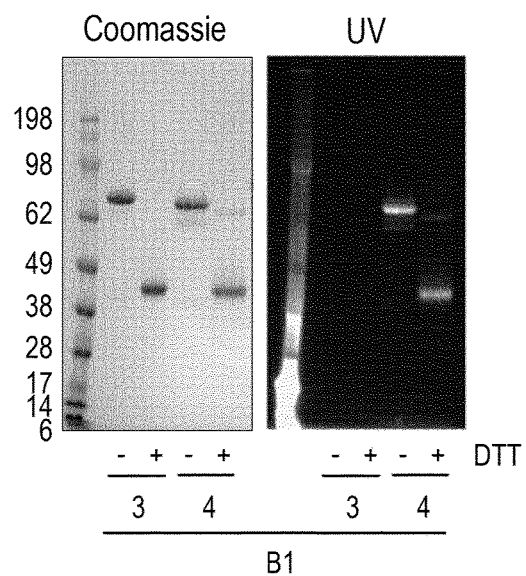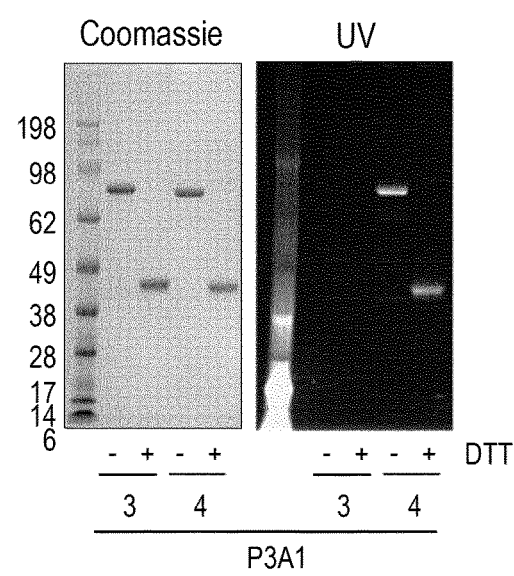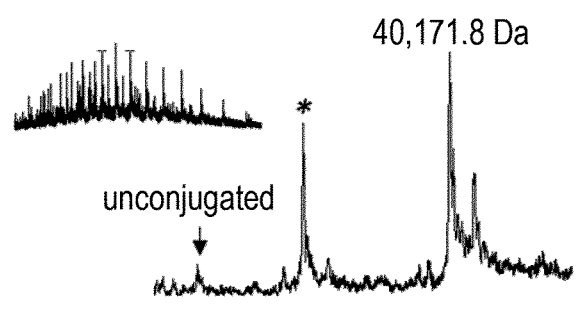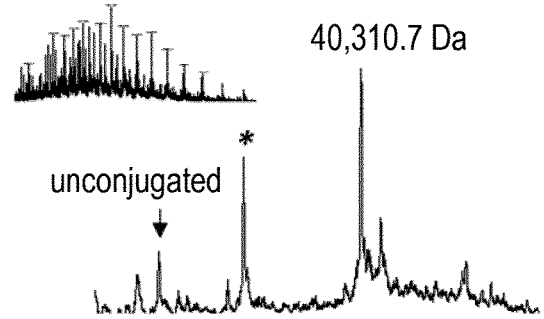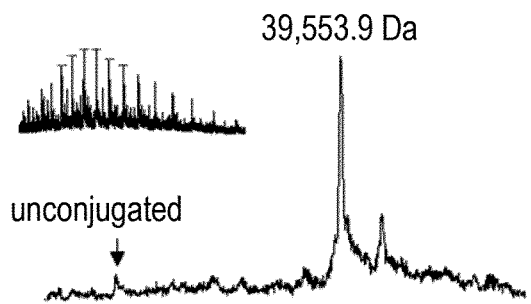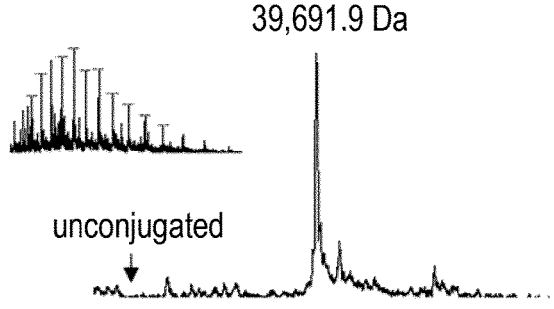
Fig. 31 (continued)

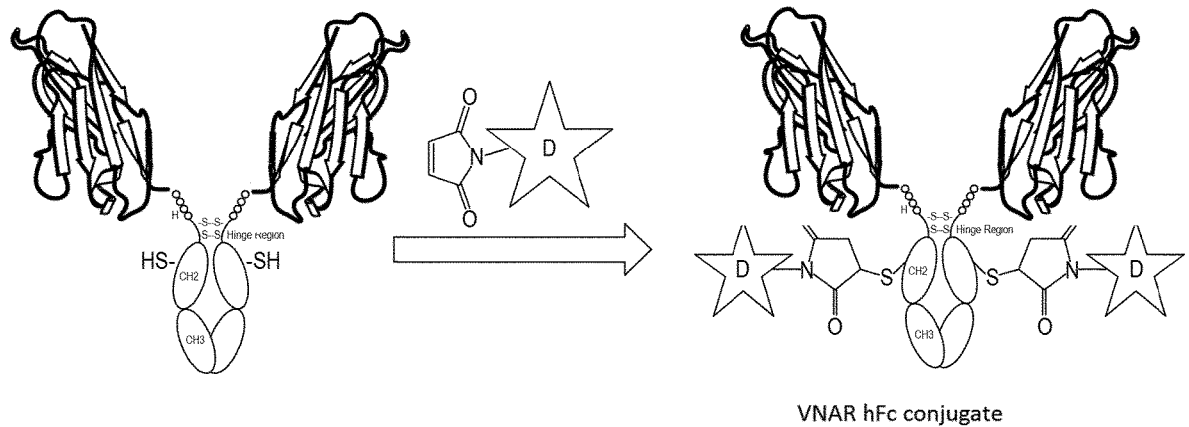
VNAR hFc conjugate
Examples of drug labels (D) and corresponding conjugate:
MA PEG4 va PBD
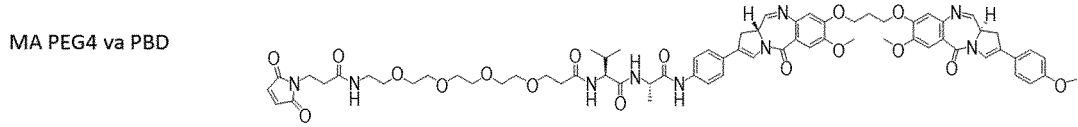
MA PEG4 va PBD conjugate
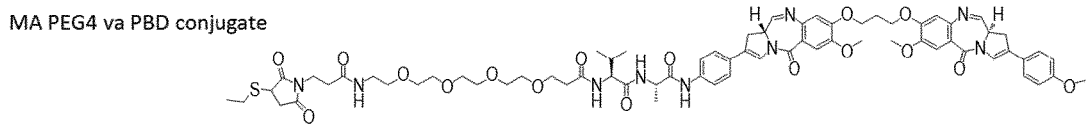
MA PEG8 va PAB SG3199
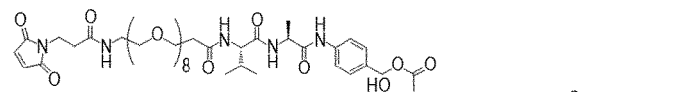
MA PEG8 va PAB SG3199 conjugate
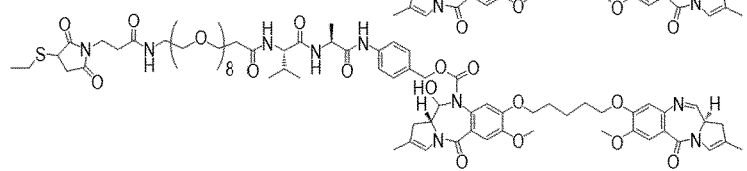
MC vc PAB NHC$_6$ α-amanitin
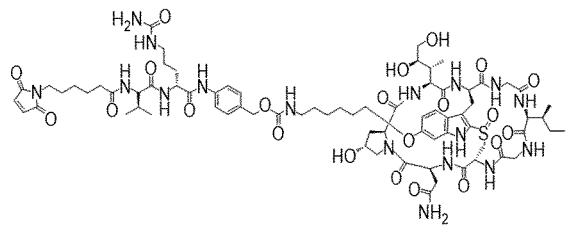
MC vc PAB NHC$_6$ α-amanitin conjugate
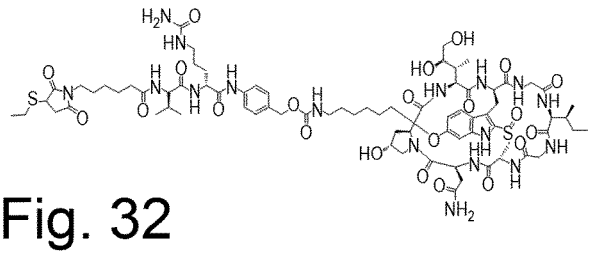
Fig. 32

MA PEG4 vc PAB PNU 159682 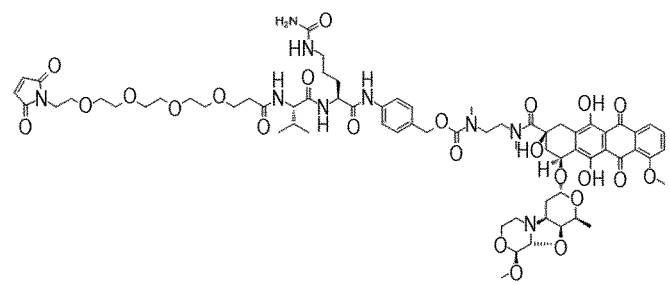
MA PEG4 vc PAB PNU 159682 conjugate 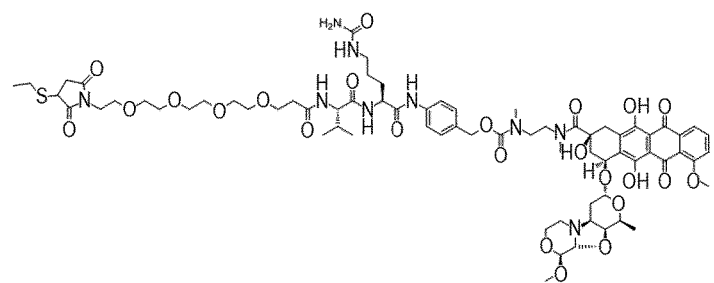
Fig. 32 (continued)

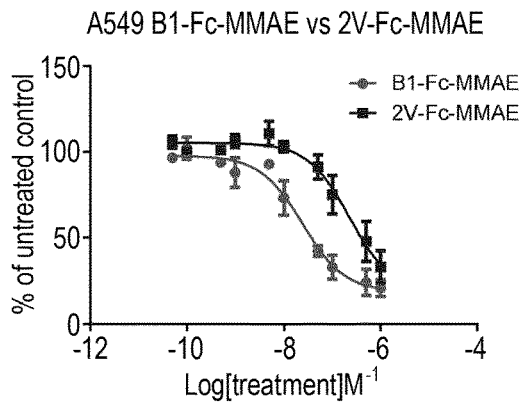
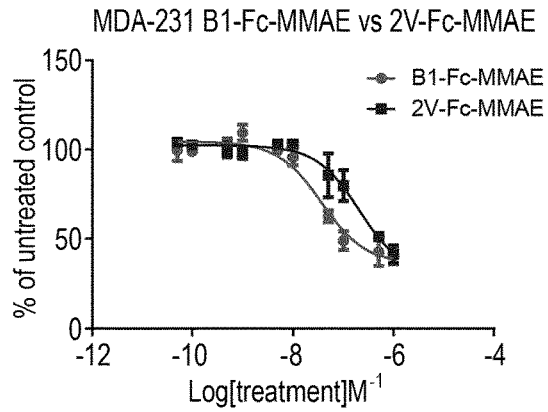
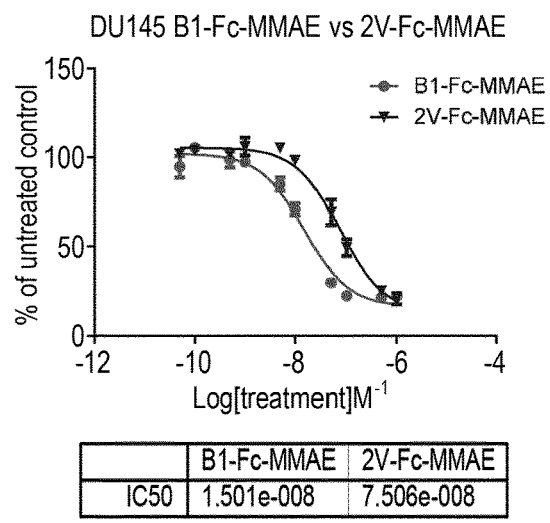
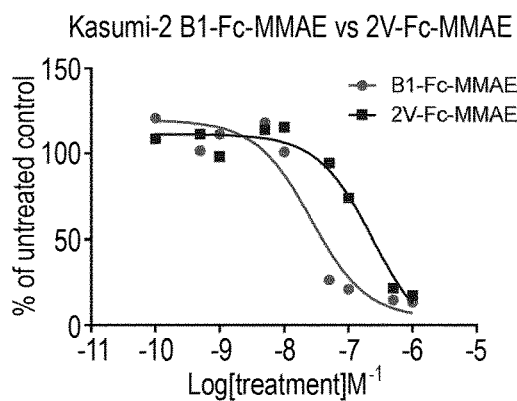
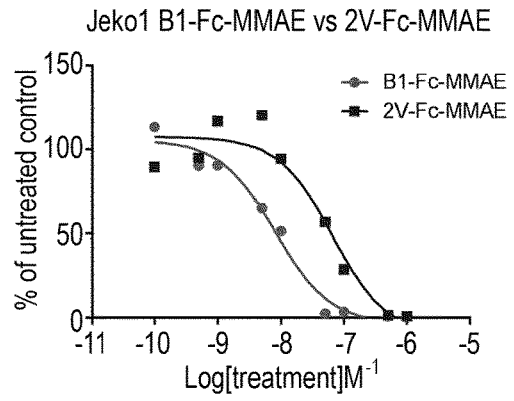
Fig. 33

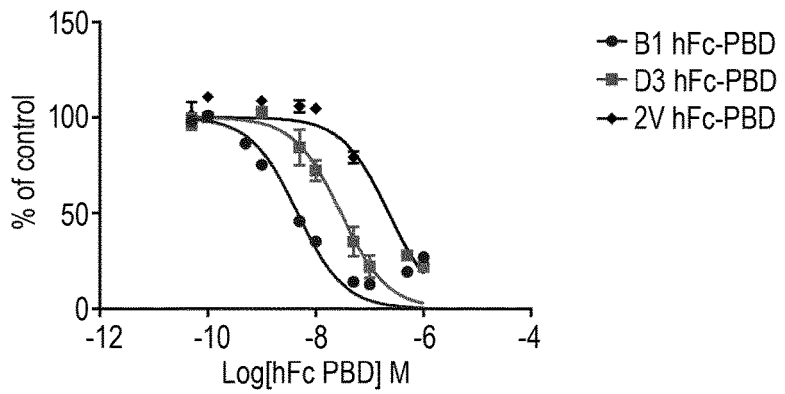
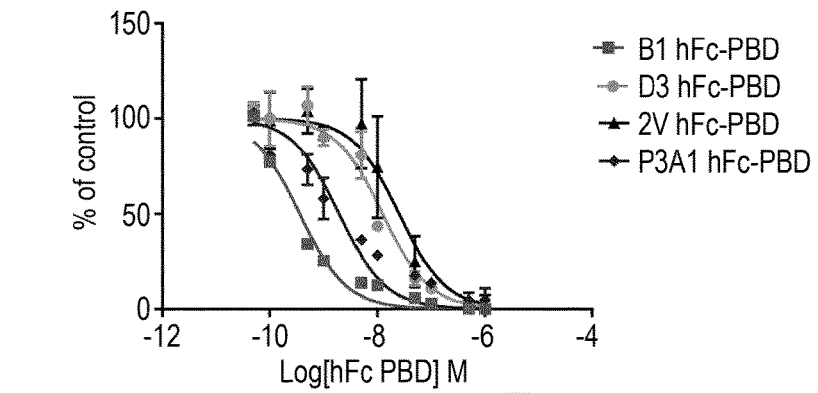
| Cell Line | B1 hFc-PBD IC50 (nM) | P3A1 hFc-PBD IC50 (nM) | D3 hFc-PBD IC50 (nM) | 2V hFc-PBD IC50 (nM) |
|---|---|---|---|---|
| DU145 | 4.6 | / | 29.2 | 226.2 |
| JeKo-1 | 0.36 | 1.9 | 12.6 | 25.4 |
Fig. 34

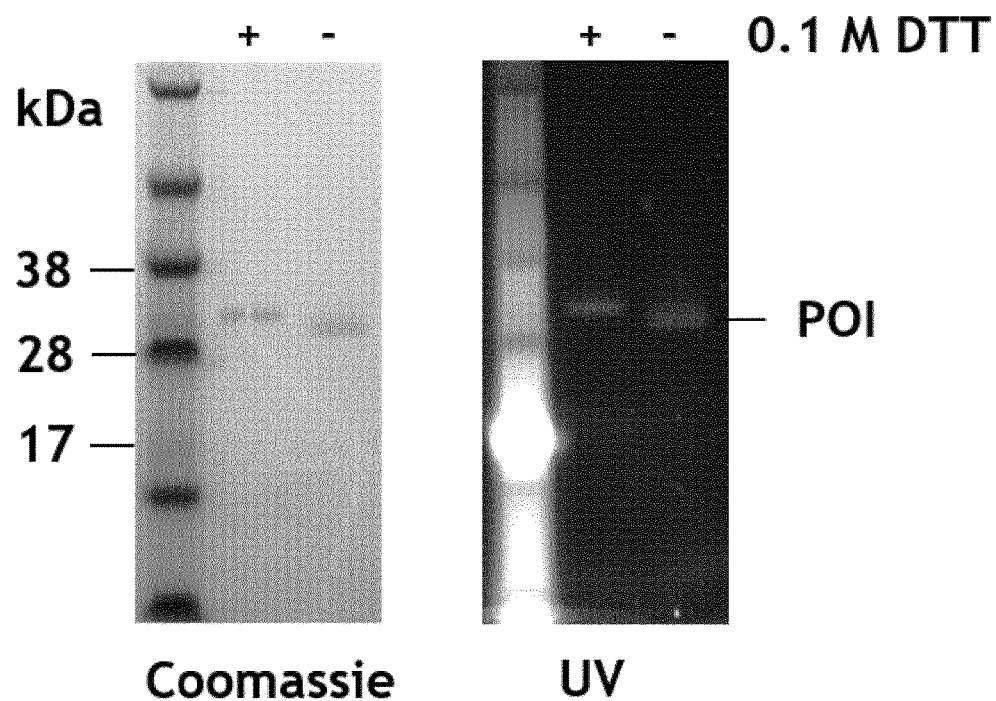
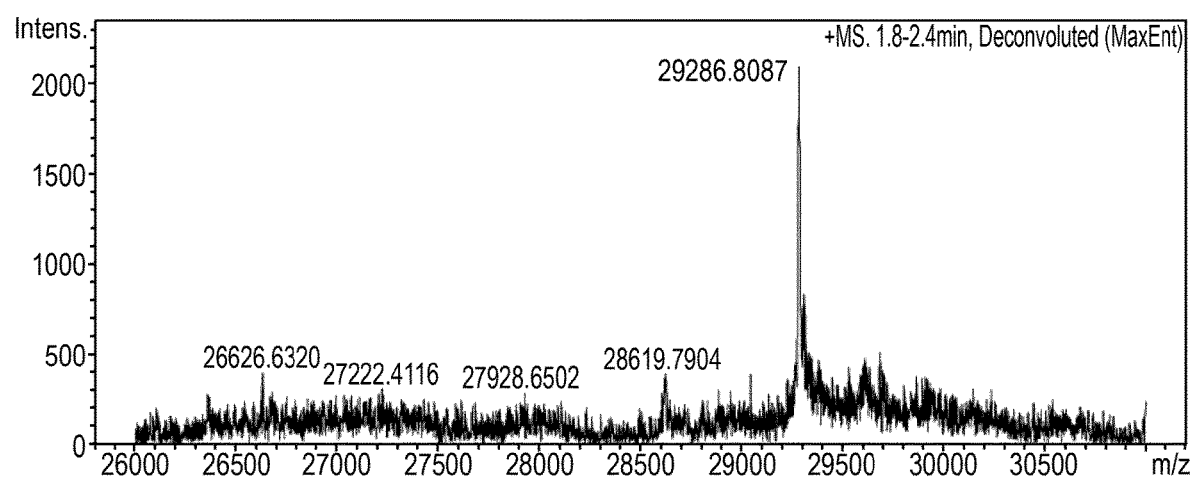
Fig. 36

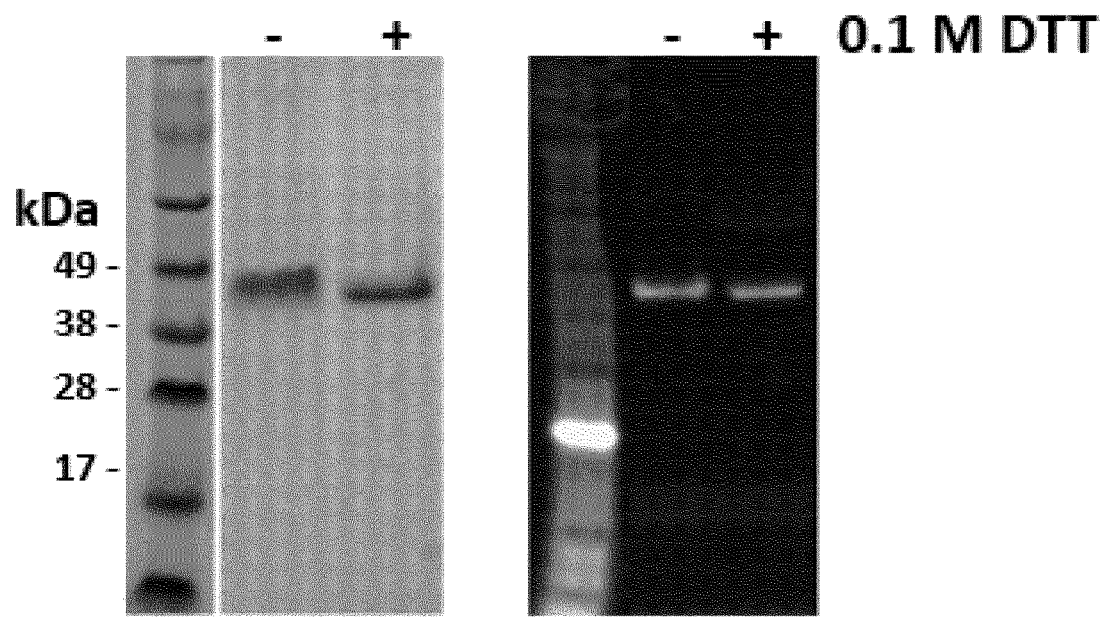
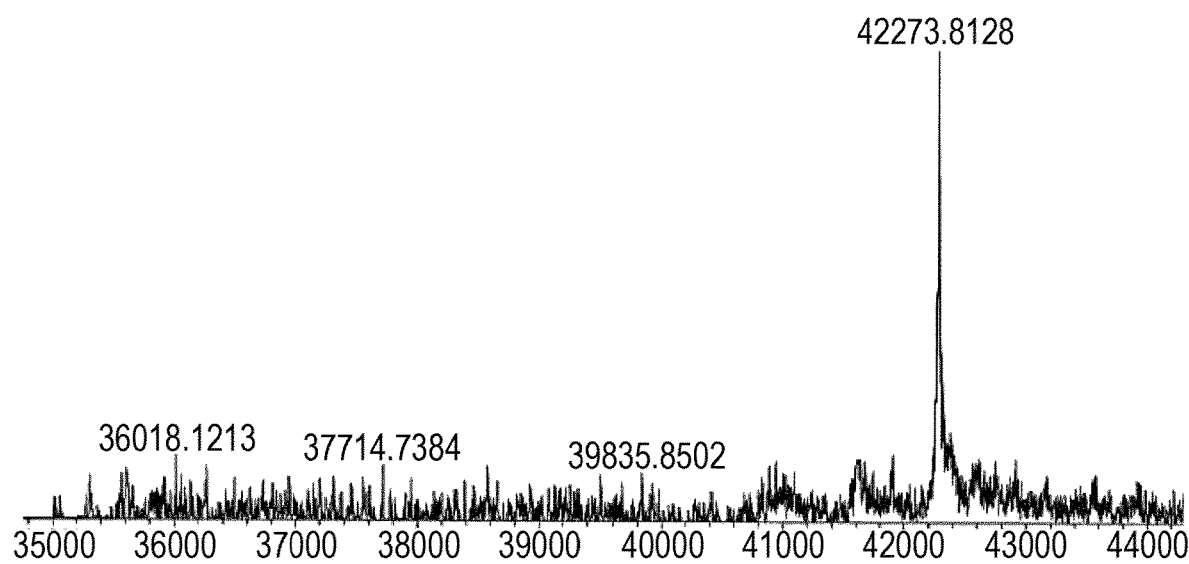
Fig. 37

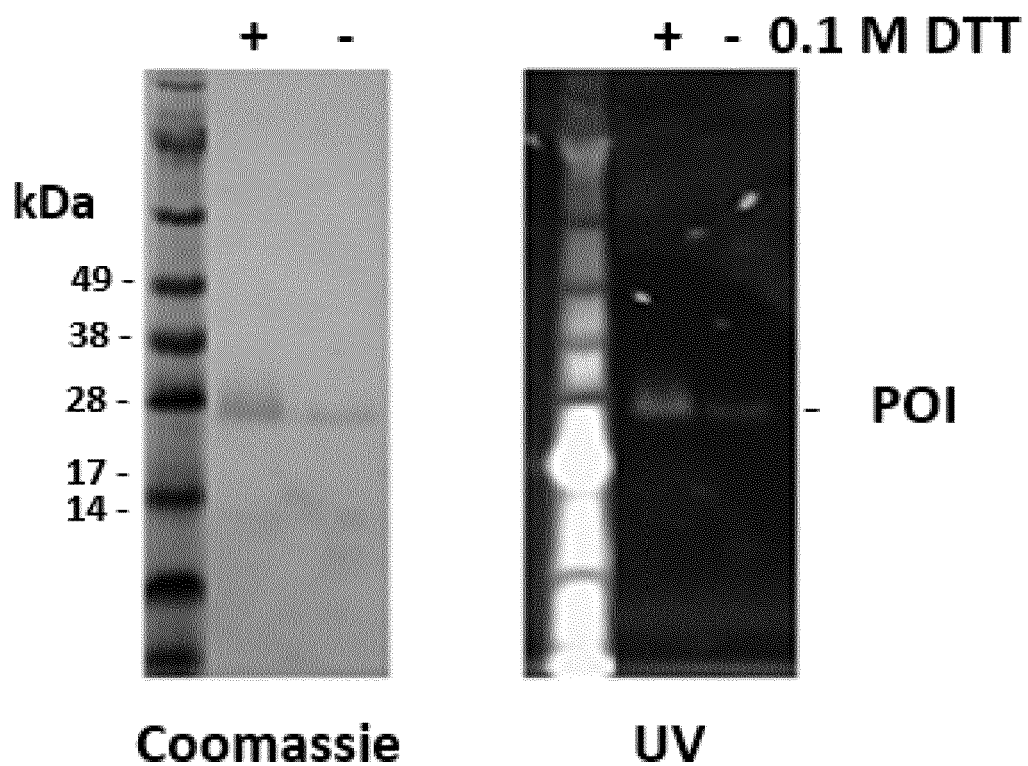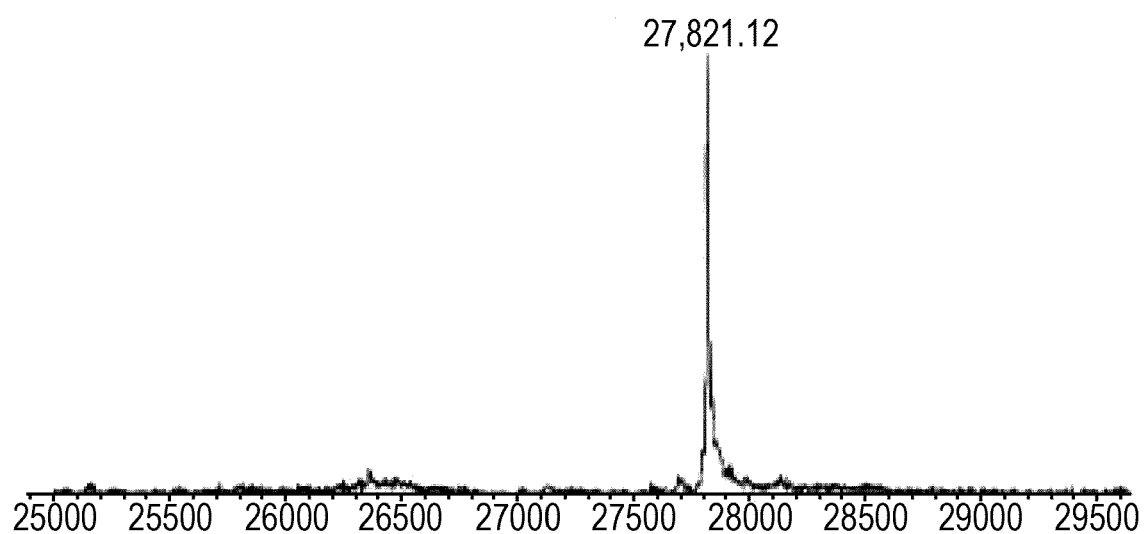
Fig. 38

SEQUENCE LISTING

```
<160> NUMBER OF SEQ ID NOS: 270

<210> SEQ ID NO 1
<211> LENGTH: 8
<212> TYPE: PRT
<213> ORGANISM: Artificial Sequence
<220> FEATURE:
<223> OTHER INFORMATION: Antibody CDR

<400> SEQUENCE: 1

Asp Thr Ser Tyr Gly Leu Tyr Ser
1               5

<210> SEQ ID NO 2
<211> LENGTH: 8
<212> TYPE: PRT
<213> ORGANISM: Artificial Sequence
<220> FEATURE:
<223> OTHER INFORMATION: Antibody CDR

<400> SEQUENCE: 2

Gly Ala Lys Tyr Gly Leu Ala Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Antibody CDR

<400> SEQUENCE: 3

Gly Ala Lys Tyr Gly Leu Phe Ala
1               5

<210> SEQ ID NO 4
<211> LENGTH: 8
<212> TYPE: PRT
```

```
<213> ORGANISM: Artificial Sequence
<220> FEATURE:
<223> OTHER INFORMATION: Antibody CDR

<400> SEQUENCE: 4

Gly Ala Asn Tyr Gly Leu Ala Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Antibody CDR

<400> SEQUENCE: 5

Gly Ala Asn Tyr Gly Leu Ala Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Antibody hypervariable sequence

<400> SEQUENCE: 6

Thr Thr Asp Trp Glu Arg Met Ser Ile Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Antibody hypervariable sequence

<400> SEQUENCE: 7

Ser Ser Asn Gln Glu Arg Ile Ser Ile Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Antibody hypervariable sequence

<400> SEQUENCE: 8

Ser Ser Asn Lys Glu Gln Ile Ser Ile Ser
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Antibody hypervariable sequence

<400> SEQUENCE: 9

Asn Lys Arg Ala Lys
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: Antibody hypervariable sequence

<400> SEQUENCE: 10

Asn Lys Arg Thr Met
1               5

<210> SEQ ID NO 11
<211> LENGTH: 5
<212> TYPE: PRT
<213> ORGANISM: Artificial Sequence
<220> FEATURE:
<223> OTHER INFORMATION: Antibody hypervariable sequence

<400> SEQUENCE: 11

Asn Lys Gly Ala Lys
1               5

<210> SEQ ID NO 12
<211> LENGTH: 5
<212> TYPE: PRT
<213> ORGANISM: Artificial Sequence
<220> FEATURE:
<223> OTHER INFORMATION: Antibody hypervariable sequence

<400> SEQUENCE: 12

Asn Lys Gly Thr Lys
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody CDR sequence

<400> SEQUENCE: 13

Gln Ser Gly Met Ala Ile Ser Thr Gly Ser Gly His Gly Tyr Asn Trp
1               5                   10                  15

Tyr

<210> SEQ ID NO 14
<211> LENGTH: 17
<212> TYPE: PRT
<213> ORGANISM: Artificial Sequence
<220> FEATURE:
<223> OTHER INFORMATION: Antibody CDR sequence

<400> SEQUENCE: 14

Gln Ser Gly Met Ala Ile Asp Ile Gly Ser Gly His Gly Tyr Asn Trp
1               5                   10                  15

Tyr

<210> SEQ ID NO 15
<211> LENGTH: 10
<212> TYPE: PRT
<213> ORGANISM: Artificial Sequence
<220> FEATURE:
<223> OTHER INFORMATION: Antibody CDR sequence

<400> SEQUENCE: 15

Tyr Pro Trp Ala Met Trp Gly Gln Trp Tyr
1               5                   10

<210> SEQ ID NO 16
```

```
<211> LENGTH: 14
<212> TYPE: PRT
<213> ORGANISM: Artificial Sequence
<220> FEATURE:
<223> OTHER INFORMATION: Antibody CDR sequence

<400> SEQUENCE: 16

Val Phe Met Pro Gln His Trp His Pro Ala Ala His Trp Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Antibody CDR sequence

<400> SEQUENCE: 17

Arg Glu Ala Arg His Pro Trp Leu Arg Gln Trp Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Antibody CDR sequence

<400> SEQUENCE: 18

Tyr Pro Trp Gly Ala Gly Ala Pro Trp Leu Val Gln Trp Tyr
1               5                   10

<210> SEQ ID NO 19
<211> LENGTH: 25
<212> TYPE: PRT
<213> ORGANISM: Artificial Sequence
<220> FEATURE:
<223> OTHER INFORMATION: Antibody framework region sequence

<400> SEQUENCE: 19

Ala Ser Val Asn Gln Thr Pro Arg Thr Ala Thr Lys Glu Thr Gly Glu
1               5                   10                  15

Ser Leu Thr Ile Asn Cys Val Leu Thr
            20                  25

<210> SEQ ID NO 20
<211> LENGTH: 25
<212> TYPE: PRT
<213> ORGANISM: Artificial Sequence
<220> FEATURE:
<223> OTHER INFORMATION: Antibody framework region sequence

<400> SEQUENCE: 20

Ala Lys Val Asp Gln Thr Pro Arg Thr Ala Thr Lys Glu Thr Gly Glu
1               5                   10                  15

Ser Leu Thr Ile Asn Cys Val Leu Thr
            20                  25

<210> SEQ ID NO 21
<211> LENGTH: 25
<212> TYPE: PRT
<213> ORGANISM: Artificial Sequence
<220> FEATURE:
<223> OTHER INFORMATION: Antibody framework region sequence

<400> SEQUENCE: 21
```

```
Thr Arg Val Asp Gln Thr Pro Arg Thr Ala Thr Lys Glu Thr Gly Glu
1               5                   10                  15

Ser Leu Thr Ile Asn Cys Val Val Thr
            20                  25
```

<210> SEQ ID NO 22
<211> LENGTH: 25
<212> TYPE: PRT
<213> ORGANISM: Artificial Sequence
<220> FEATURE:
<223> OTHER INFORMATION: Antibody framework region sequence

<400> SEQUENCE: 22

```
Thr Arg Val Asp Gln Thr Pro Arg Thr Ala Thr Lys Glu Thr Gly Glu
1               5                   10                  15

Ser Leu Thr Ile Asn Cys Val Leu Thr
            20                  25
```

<210> SEQ ID NO 23
<211> LENGTH: 25
<212> TYPE: PRT
<213> ORGANISM: Artificial Sequence
<220> FEATURE:
<223> OTHER INFORMATION: Antibody framework region sequence

<400> SEQUENCE: 23

```
Ala Ser Val Asn Gln Thr Pro Arg Thr Ala Thr Lys Glu Thr Gly Glu
1               5                   10                  15

Ser Leu Thr Ile Asn Cys Val Val Thr
            20                  25
```

<210> SEQ ID NO 24
<211> LENGTH: 25
<212> TYPE: PRT
<213> ORGANISM: Artificial Sequence
<220> FEATURE:
<223> OTHER INFORMATION: Antibody framework region sequence

<400> SEQUENCE: 24

```
Thr Arg Val Asp Gln Ser Pro Ser Ser Leu Ser Ala Ser Val Gly Asp
1               5                   10                  15

Arg Val Thr Ile Thr Cys Val Leu Thr
            20                  25
```

<210> SEQ ID NO 25
<211> LENGTH: 9
<212> TYPE: PRT
<213> ORGANISM: Artificial Sequence
<220> FEATURE:
<223> OTHER INFORMATION: Antibody framework region sequence

<400> SEQUENCE: 25

```
Thr Ser Trp Phe Arg Lys Asn Pro Gly
1               5
```

<210> SEQ ID NO 26
<211> LENGTH: 9
<212> TYPE: PRT
<213> ORGANISM: Artificial Sequence
<220> FEATURE:
<223> OTHER INFORMATION: Antibody framework region sequence

<400> SEQUENCE: 26

```
Thr Tyr Trp Tyr Arg Lys Asn Pro Gly
1               5
```

<210> SEQ ID NO 27
<211> LENGTH: 7
<212> TYPE: PRT
<213> ORGANISM: Artificial Sequence
<220> FEATURE:
<223> OTHER INFORMATION: Antibody framework region sequence

<400> SEQUENCE: 27

Gly Arg Tyr Val Glu Ser Val
1               5

<210> SEQ ID NO 28
<211> LENGTH: 7
<212> TYPE: PRT
<213> ORGANISM: Artificial Sequence
<220> FEATURE:
<223> OTHER INFORMATION: Antibody framework region sequence

<400> SEQUENCE: 28

Gly Arg Tyr Ser Glu Ser Val
1               5

<210> SEQ ID NO 29
<211> LENGTH: 21
<212> TYPE: PRT
<213> ORGANISM: Artificial Sequence
<220> FEATURE:
<223> OTHER INFORMATION: Antibody framework region sequence

<400> SEQUENCE: 29

Ser Phe Ser Leu Arg Ile Lys Asp Leu Thr Val Ala Asp Ser Ala Thr
1               5                   10                  15

Tyr Tyr Cys Lys Ala
            20

<210> SEQ ID NO 30
<211> LENGTH: 21
<212> TYPE: PRT
<213> ORGANISM: Artificial Sequence
<220> FEATURE:
<223> OTHER INFORMATION: Antibody framework region sequence

<400> SEQUENCE: 30

Ser Phe Thr Leu Thr Ile Ser Ser Leu Gln Pro Glu Asp Ser Ala Thr
1               5                   10                  15

Tyr Tyr Cys Arg Ala
            20

<210> SEQ ID NO 31
<211> LENGTH: 21
<212> TYPE: PRT
<213> ORGANISM: Artificial Sequence
<220> FEATURE:
<223> OTHER INFORMATION: Antibody framework region sequence

<400> SEQUENCE: 31

Ser Phe Thr Leu Thr Ile Ser Ser Leu Gln Pro Glu Asp Phe Ala Thr
1               5                   10                  15

Tyr Tyr Cys Lys Ala
            20

<210> SEQ ID NO 32
<211> LENGTH: 10
<212> TYPE: PRT

```
<213> ORGANISM: Artificial Sequence
<220> FEATURE:
<223> OTHER INFORMATION: Antibody framework region sequence

<400> SEQUENCE: 32

Asp Gly Ala Gly Thr Val Leu Thr Val Asn
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Antibody framework region sequence

<400> SEQUENCE: 33

Asp Gly Ala Gly Thr Lys Val Glu Ile Lys
1               5                   10

<210> SEQ ID NO 34
<211> LENGTH: 15
<212> TYPE: PRT
<213> ORGANISM: Artificial Sequence
<220> FEATURE:
<223> OTHER INFORMATION: ECD peptide Sequence

<400> SEQUENCE: 34

Tyr Met Glu Ser Leu His Met Gln Gly Glu Ile Glu Asn Gln Ile
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: ECD peptide Sequence

<400> SEQUENCE: 35

Cys Gln Pro Trp Asn Ser Gln Tyr Pro His Thr His Thr Phe Thr Ala
1               5                   10                  15

Leu Arg Phe Pro
            20

<210> SEQ ID NO 36
<211> LENGTH: 23
<212> TYPE: PRT
<213> ORGANISM: Artificial Sequence
<220> FEATURE:
<223> OTHER INFORMATION: ECD peptide Sequence

<400> SEQUENCE: 36

Arg Ser Thr Ile Tyr Gly Ser Arg Leu Arg Ile Arg Asn Leu Asp Thr
1               5                   10                  15

Thr Asp Thr Gly Tyr Phe Gln
            20

<210> SEQ ID NO 37
<211> LENGTH: 36
<212> TYPE: PRT
<213> ORGANISM: Artificial Sequence
<220> FEATURE:
<223> OTHER INFORMATION: ECD peptide Sequence

<400> SEQUENCE: 37

Gln Cys Val Ala Thr Asn Gly Lys Glu Val Val Ser Ser Thr Gly Val
1               5                   10                  15
```

```
Leu Phe Val Lys Phe Gly Pro Pro Thr Ala Ser Pro Gly Tyr Ser
                20                  25                  30

Asp Glu Tyr Glu
        35

<210> SEQ ID NO 38
<211> LENGTH: 22
<212> TYPE: PRT
<213> ORGANISM: Artificial Sequence
<220> FEATURE:
<223> OTHER INFORMATION: ECD peptide Sequence

<400> SEQUENCE: 38

Arg Ser Thr Ile Tyr Gly Ser Arg Leu Arg Ile Asn Leu Asp Thr Thr
1               5                   10                  15

Asp Thr Gly Tyr Phe Gln
            20

<210> SEQ ID NO 39
<211> LENGTH: 112
<212> TYPE: PRT
<213> ORGANISM: Artificial Sequence
<220> FEATURE:
<223> OTHER INFORMATION: Antibody Sequence

<400> SEQUENCE: 39

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: Antibody Sequence

<400> SEQUENCE: 40

Ala Lys Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80
```

Tyr Tyr Cys Lys Ala Gln Ser Gly Met Ala Ile Asp Ile Gly Ser Gly
                85                  90                  95

His Gly Tyr Asn Trp Tyr Asp Gly Ala Gly Thr Val Leu Thr Val Asn
            100                 105                 110

<210> SEQ ID NO 41
<211> LENGTH: 105
<212> TYPE: PRT
<213> ORGANISM: Artificial Sequence
<220> FEATURE:
<223> OTHER INFORMATION: Antibody Sequence

<400> SEQUENCE: 41

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Ala Met Trp Gly Gln Trp Tyr Asp
                85                  90                  95

Gly Ala Gly Thr Val Leu Thr Val Asn
            100                 105

<210> SEQ ID NO 42
<211> LENGTH: 109
<212> TYPE: PRT
<213> ORGANISM: Artificial Sequence
<220> FEATURE:
<223> OTHER INFORMATION: Antibody Sequence

<400> SEQUENCE: 42

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Phe
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Met Pro Gln His Trp His Pro Ala Ala
                85                  90                  95

His Trp Tyr Asp Gly Ala Gly Thr Val Leu Thr Val Asn
            100                 105

<210> SEQ ID NO 43
<211> LENGTH: 107
<212> TYPE: PRT
<213> ORGANISM: Artificial Sequence
<220> FEATURE:
<223> OTHER INFORMATION: Antibody Sequence

<400> SEQUENCE: 43

Thr Arg Val Asp Gln Thr Pro Arg Thr Ala Thr Lys Glu Thr Gly Glu

```
1               5                   10                  15
Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn
                100                 105

<210> SEQ ID NO 44
<211> LENGTH: 109
<212> TYPE: PRT
<213> ORGANISM: Artificial Sequence
<220> FEATURE:
<223> OTHER INFORMATION: Antibody Sequence

<400> SEQUENCE: 44

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
            50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn
                100                 105

<210> SEQ ID NO 45
<211> LENGTH: 109
<212> TYPE: PRT
<213> ORGANISM: Artificial Sequence
<220> FEATURE:
<223> OTHER INFORMATION: Antibody Sequence

<400> SEQUENCE: 45

Thr Arg Val Asp Gln Ser Pro Ser Ser Leu Ser Ala Ser Val Gly Asp
1               5                   10                  15

Arg Val Thr Ile Thr Cys Val Leu Thr Gly Ala Asn Tyr Gly Leu Ala
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
            50                  55                  60

Ser Phe Thr Leu Thr Ile Ser Ser Leu Gln Pro Glu Asp Ser Ala Thr
65                  70                  75                  80

Tyr Tyr Cys Arg Ala Tyr Pro Trp Gly Ala Gly Ala Pro Trp Leu Val
                85                  90                  95
```

```
Gln Trp Tyr Asp Gly Ala Gly Thr Lys Val Glu Ile Lys
            100                 105
```

<210> SEQ ID NO 46
<211> LENGTH: 109
<212> TYPE: PRT
<213> ORGANISM: Artificial Sequence
<220> FEATURE:
<223> OTHER INFORMATION: Antibody Sequence

<400> SEQUENCE: 46

```
Thr Arg Val Asp Gln Ser Pro Ser Ser Leu Ser Ala Ser Val Gly Asp
1               5                   10                  15

Arg Val Thr Ile Thr Cys Val Leu Thr Gly Ala Asn Tyr Gly Leu Ala
            20                  25                  30

Ser Thr Tyr Trp Tyr Arg Lys Asn Pro Gly Ser Ser Asn Gln Glu Arg
        35                  40                  45

Ile Ser Ile Ser Gly Arg Tyr Ser Glu Ser Val Asn Lys Arg Thr Met
    50                  55                  60

Ser Phe Thr Leu Thr Ile Ser Ser Leu Gln Pro Glu Asp Ser Ala Thr
65                  70                  75                  80

Tyr Tyr Cys Arg Ala Tyr Pro Trp Gly Ala Gly Ala Pro Trp Leu Val
                85                  90                  95

Gln Trp Tyr Asp Gly Ala Gly Thr Lys Val Glu Ile Lys
            100                 105
```

<210> SEQ ID NO 47
<211> LENGTH: 107
<212> TYPE: PRT
<213> ORGANISM: Artificial Sequence
<220> FEATURE:
<223> OTHER INFORMATION: Antibody Sequence

<400> SEQUENCE: 47

```
Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Thr Leu Thr Ile Ser Ser Leu Gln Pro Glu Asp Phe Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Lys Val Glu Ile Lys
            100                 105
```

<210> SEQ ID NO 48
<211> LENGTH: 107
<212> TYPE: PRT
<213> ORGANISM: Artificial Sequence
<220> FEATURE:
<223> OTHER INFORMATION: Antibody Sequence

<400> SEQUENCE: 48

```
Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
```

```
                    20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
 50                  55                  60

Ser Phe Thr Leu Thr Ile Ser Ser Leu Gln Pro Glu Asp Ser Ala Thr
 65                  70                  75                  80

Tyr Tyr Cys Arg Ala Arg Glu Ala Arg His Pro Trp Leu Arg Gln Trp
                85                  90                  95

Tyr Asp Gly Ala Gly Thr Lys Val Glu Ile Lys
               100                 105

<210> SEQ ID NO 49
<211> LENGTH: 107
<212> TYPE: PRT
<213> ORGANISM: Artificial Sequence
<220> FEATURE:
<223> OTHER INFORMATION: Antibody Sequence

<400> SEQUENCE: 49

Thr Arg Val Asp Gln Ser Pro Ser Ser Leu Ser Ala Ser Val Gly Asp
 1               5                  10                  15

Arg Val Thr Ile Thr Cys Val Leu Thr Asp Thr Ser Tyr Gly Leu Tyr
                20                  25                  30

Ser Thr Tyr Trp Tyr Arg Lys Asn Pro Gly Thr Thr Asp Trp Glu Arg
            35                  40                  45

Met Ser Ile Gly Gly Arg Tyr Ser Glu Ser Val Asn Lys Gly Ala Lys
 50                  55                  60

Ser Phe Thr Leu Thr Ile Ser Ser Leu Gln Pro Glu Asp Ser Ala Thr
 65                  70                  75                  80

Tyr Tyr Cys Arg Ala Arg Glu Ala Arg His Pro Trp Leu Arg Gln Trp
                85                  90                  95

Tyr Asp Gly Ala Gly Thr Lys Val Glu Ile Lys
               100                 105

<210> SEQ ID NO 50
<211> LENGTH: 112
<212> TYPE: PRT
<213> ORGANISM: Artificial Sequence
<220> FEATURE:
<223> OTHER INFORMATION: Antibody Sequence

<400> SEQUENCE: 50

Ala Ser Val Asn Gln Ser Pro Ser Ser Leu Ser Ala Ser Val Gly Asp
 1               5                  10                  15

Arg Val Thr Ile Thr Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Ser Glu Ser Val Asn Lys Gly Ala Lys
 50                  55                  60

Ser Phe Thr Leu Thr Ile Ser Ser Leu Gln Pro Glu Asp Ser Ala Thr
 65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
               100                 105                 110
```

<210> SEQ ID NO 51
<211> LENGTH: 112
<212> TYPE: PRT
<213> ORGANISM: Artificial Sequence
<220> FEATURE:
<223> OTHER INFORMATION: Antibody Sequence

<400> SEQUENCE: 51

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Ser Glu Ser Val Asn Lys Gly Ala Lys
    50                  55                  60

Ser Phe Thr Leu Thr Ile Ser Ser Leu Gln Pro Glu Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: Antibody Sequence

<400> SEQUENCE: 52

Ala Ser Val Asn Gln Ser Pro Ser Ala Ser Ala Ser Val Gly Asp
1               5                   10                  15

Arg Leu Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Ser Glu Ser Val Asn Lys Gly Ala Lys
    50                  55                  60

Ser Phe Thr Leu Thr Ile Ser Ser Leu Gln Pro Glu Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Leu Glu Val Lys
            100                 105                 110

<210> SEQ ID NO 53
<211> LENGTH: 109
<212> TYPE: PRT
<213> ORGANISM: Artificial Sequence
<220> FEATURE:
<223> OTHER INFORMATION: Antibody Sequence

<400> SEQUENCE: 53

Ala Ser Val Asp Gln Ser Pro Ser Ser Leu Ser Ala Ser Val Gly Asp
1               5                   10                  15

Arg Val Thr Ile Thr Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg

```
                35                  40                  45
Ile Ser Ile Ser Gly Arg Tyr Ser Glu Ser Val Asn Lys Arg Thr Met
 50                  55                  60

Ser Phe Thr Leu Thr Ile Ser Ser Leu Gln Pro Glu Asp Ser Ala Thr
 65                  70                  75                  80

Tyr Tyr Cys Lys Ala Tyr Pro Trp Gly Ala Gly Ala Pro Trp Leu Val
                 85                  90                  95

Gln Trp Tyr Asp Gly Ala Gly Thr Lys Val Glu Ile Lys
                100                 105

<210> SEQ ID NO 54
<211> LENGTH: 109
<212> TYPE: PRT
<213> ORGANISM: Artificial Sequence
<220> FEATURE:
<223> OTHER INFORMATION: Antibody Sequence

<400> SEQUENCE: 54

Ala Ser Val Asp Gln Ser Pro Ser Ala Ser Ala Ser Val Gly Asp
 1               5                  10                  15

Arg Leu Thr Ile Thr Cys Val Val Thr Gly Ala Asn Tyr Gly Leu Ala
                 20                  25                  30

Ala Thr Tyr Trp Tyr Arg Lys Asn Pro Gly Ser Ser Asn Gln Glu Arg
             35                  40                  45

Ile Ser Ile Ser Gly Arg Tyr Ser Glu Ser Val Asn Lys Arg Thr Met
 50                  55                  60

Ser Phe Thr Leu Thr Ile Ser Ser Leu Gln Pro Glu Asp Ser Ala Thr
 65                  70                  75                  80

Tyr Tyr Cys Lys Ala Tyr Pro Trp Gly Ala Gly Ala Pro Trp Leu Val
                 85                  90                  95

Gln Trp Tyr Asp Gly Ala Gly Thr Lys Leu Glu Val Lys
                100                 105

<210> SEQ ID NO 55
<211> LENGTH: 112
<212> TYPE: PRT
<213> ORGANISM: Artificial Sequence
<220> FEATURE:
<223> OTHER INFORMATION: Antibody Sequence

<400> SEQUENCE: 55

Ala Ser Val Asn Gln Ser Pro Ser Ser Leu Ser Ala Ser Val Gly Asp
 1               5                  10                  15

Arg Val Thr Ile Thr Cys Val Leu Thr Asp Thr Ser Tyr Gly Leu Tyr
                 20                  25                  30

Ser Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Arg Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Val Glu Ile Lys
                100                 105                 110

<210> SEQ ID NO 56
<211> LENGTH: 112
```

```
<212> TYPE: PRT
<213> ORGANISM: Artificial Sequence
<220> FEATURE:
<223> OTHER INFORMATION: Antibody Sequence

<400> SEQUENCE: 56

Ala Ser Val Asn Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Thr Leu Thr Ile Ser Ser Leu Gln Pro Glu Asp Phe Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: Antibody Sequence

<400> SEQUENCE: 57

Ala Ser Val Asn Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Phe Ser Gly Ser Gly Ser Lys Arg Ala Lys
    50                  55                  60

Ser Phe Thr Leu Thr Ile Ser Ser Leu Gln Pro Glu Asp Phe Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: Antibody Sequence

<400> SEQUENCE: 58

Ala Ser Val Asn Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Tyr Gln Gln Lys Pro Gly Thr Thr Asp Trp Glu Arg
        35                  40                  45

Met Ser Ile Gly Gly Arg Tyr Val Glu Ser Val Asn Lys Arg Ala Lys
```

```
                50                  55                  60
Ser Phe Thr Leu Thr Ile Ser Ser Leu Gln Pro Glu Asp Phe Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Val Glu Ile Lys
                100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Antibody Sequence

<400> SEQUENCE: 59

Ala Ser Val Asn Gln Ser Pro Ser Ser Leu Ser Ala Ser Val Gly Asp
 1               5                  10                  15

Arg Val Thr Ile Thr Cys Val Leu Thr Asp Thr Ser Tyr Gly Leu Tyr
                 20                  25                  30

Ser Thr Ser Trp Tyr Gln Gln Lys Pro Gly Thr Thr Asp Trp Glu Arg
         35                  40                  45

Met Ser Ile Gly Gly Arg Phe Ser Gly Ser Gly Ser Lys Arg Ala Lys
     50                  55                  60

Ser Phe Thr Leu Thr Ile Ser Ser Leu Gln Pro Glu Asp Phe Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Val Glu Ile Lys
                100                 105                 110

<210> SEQ ID NO 60
<211> LENGTH: 15
<212> TYPE: PRT
<213> ORGANISM: Artificial Sequence
<220> FEATURE:
<223> OTHER INFORMATION: Linker Sequence

<400> SEQUENCE: 60

Gly Gly Gly Gly Ser Gly Gly Gly Gly Ser Gly Gly Gly Gly Ser
 1               5                  10                  15

<210> SEQ ID NO 61
<211> LENGTH: 25
<212> TYPE: PRT
<213> ORGANISM: Artificial Sequence
<220> FEATURE:
<223> OTHER INFORMATION: Linker Sequence

<400> SEQUENCE: 61

Gly Gly Gly Gly Ser Gly Gly Gly Gly Ser Gly Gly Gly Gly Ser Gly
 1               5                  10                  15

Gly Gly Gly Ser Gly Gly Gly Gly Ser
                 20                  25

<210> SEQ ID NO 62
<211> LENGTH: 7
<212> TYPE: PRT
<213> ORGANISM: Artificial Sequence
<220> FEATURE:
<223> OTHER INFORMATION: Linker Sequence
```

```
<400> SEQUENCE: 62

Pro Gly Val Gln Pro Ser Pro
1               5

<210> SEQ ID NO 63
<211> LENGTH: 12
<212> TYPE: PRT
<213> ORGANISM: Artificial Sequence
<220> FEATURE:
<223> OTHER INFORMATION: Linker Sequence

<400> SEQUENCE: 63

Pro Gly Val Gln Pro Ser Pro Gly Gly Gly Gly Ser
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Linker Sequence

<400> SEQUENCE: 64

Pro Gly Val Gln Pro Ala Pro Gly Gly Gly Gly Ser
1               5                   10

<210> SEQ ID NO 65
<211> LENGTH: 107
<212> TYPE: PRT
<213> ORGANISM: Artificial Sequence
<220> FEATURE:
<223> OTHER INFORMATION: Antibody Sequence

<400> SEQUENCE: 65

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn
                100                 105

<210> SEQ ID NO 66
<211> LENGTH: 103
<212> TYPE: PRT
<213> ORGANISM: Artificial Sequence
<220> FEATURE:
<223> OTHER INFORMATION: Antibody Sequence

<400> SEQUENCE: 66

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
```

```
                35                  40                  45
Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys
            100

<210> SEQ ID NO 67
<211> LENGTH: 25
<212> TYPE: PRT
<213> ORGANISM: Artificial Sequence
<220> FEATURE:
<223> OTHER INFORMATION: Tag Sequence

<400> SEQUENCE: 67

Gln Ala Cys Gly Ala His His His His His Gly Ala Glu Phe Glu
1               5                   10                  15

Gln Lys Leu Ile Ser Glu Glu Asp Leu
            20                  25

<210> SEQ ID NO 68
<211> LENGTH: 10
<212> TYPE: PRT
<213> ORGANISM: Artificial Sequence
<220> FEATURE:
<223> OTHER INFORMATION: Tag Sequence

<400> SEQUENCE: 68

Glu Gln Lys Leu Ile Ser Glu Glu Asp Leu
1               5                   10

<210> SEQ ID NO 69
<211> LENGTH: 25
<212> TYPE: PRT
<213> ORGANISM: Artificial Sequence
<220> FEATURE:
<223> OTHER INFORMATION: Tag Sequence

<400> SEQUENCE: 69

Gln Ala Ser Gly Ala His His His His His Gly Ala Glu Phe Glu
1               5                   10                  15

Gln Lys Leu Ile Ser Glu Glu Asp Leu
            20                  25

<210> SEQ ID NO 70
<211> LENGTH: 25
<212> TYPE: PRT
<213> ORGANISM: Artificial Sequence
<220> FEATURE:
<223> OTHER INFORMATION: Tag Sequence

<400> SEQUENCE: 70

Gln Ala Cys Lys Ala His His His His His Gly Ala Glu Phe Glu
1               5                   10                  15

Gln Lys Leu Ile Ser Glu Glu Asp Leu
            20                  25

<210> SEQ ID NO 71
<211> LENGTH: 23
<212> TYPE: PRT
```

<213> ORGANISM: Artificial Sequence
<220> FEATURE:
<223> OTHER INFORMATION: Tag Sequence

<400> SEQUENCE: 71

Ala Ala Ala His His His His His His Gly Ala Glu Phe Glu Gln Lys
1               5                   10                  15

Leu Ile Ser Glu Glu Asp Leu
            20

<210> SEQ ID NO 72
<211> LENGTH: 23
<212> TYPE: PRT
<213> ORGANISM: Artificial Sequence
<220> FEATURE:
<223> OTHER INFORMATION: Tag Sequence

<400> SEQUENCE: 72

Ala Cys Ala His His His His His His Gly Ala Glu Phe Glu Gln Lys
1               5                   10                  15

Leu Ile Ser Glu Glu Asp Leu
            20

<210> SEQ ID NO 73
<211> LENGTH: 11
<212> TYPE: PRT
<213> ORGANISM: Artificial Sequence
<220> FEATURE:
<223> OTHER INFORMATION: Tag Sequence

<400> SEQUENCE: 73

Gln Ala Ser Gly Ala His His His His His His
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Tag Sequence

<400> SEQUENCE: 74

Gln Ala Cys Gly Ala His His His His His His
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Tag Sequence

<400> SEQUENCE: 75

Gln Ala Cys Lys Ala His His His His His His
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Tag Sequence

<400> SEQUENCE: 76

Ala Ala Ala His His His His His His
1               5

```
<210> SEQ ID NO 77
<211> LENGTH: 9
<212> TYPE: PRT
<213> ORGANISM: Artificial Sequence
<220> FEATURE:
<223> OTHER INFORMATION: Tag Sequence

<400> SEQUENCE: 77

Ala Cys Ala His His His His His His
1               5

<210> SEQ ID NO 78
<211> LENGTH: 5
<212> TYPE: PRT
<213> ORGANISM: Artificial Sequence
<220> FEATURE:
<223> OTHER INFORMATION: Tag Sequence

<400> SEQUENCE: 78

Gln Ala Ser Gly Ala
1               5

<210> SEQ ID NO 79
<211> LENGTH: 5
<212> TYPE: PRT
<213> ORGANISM: Artificial Sequence
<220> FEATURE:
<223> OTHER INFORMATION: Tag Sequence

<400> SEQUENCE: 79

Gln Ala Cys Gly Ala
1               5

<210> SEQ ID NO 80
<211> LENGTH: 5
<212> TYPE: PRT
<213> ORGANISM: Artificial Sequence
<220> FEATURE:
<223> OTHER INFORMATION: Tag Sequence

<400> SEQUENCE: 80

Gln Ala Cys Lys Ala
1               5

<210> SEQ ID NO 81
<211> LENGTH: 3
<212> TYPE: PRT
<213> ORGANISM: Artificial Sequence
<220> FEATURE:
<223> OTHER INFORMATION: Tag Sequence

<400> SEQUENCE: 81

Ala Cys Ala
1

<210> SEQ ID NO 82
<211> LENGTH: 5
<212> TYPE: PRT
<213> ORGANISM: Artificial Sequence
<220> FEATURE:
<223> OTHER INFORMATION: Tag Sequence

<400> SEQUENCE: 82

Ser Ala Pro Ser Ala
1               5
```

```
<210> SEQ ID NO 83
<211> LENGTH: 361
<212> TYPE: PRT
<213> ORGANISM: Artificial Sequence
<220> FEATURE:
<223> OTHER INFORMATION: Binding protein Sequence

<400> SEQUENCE: 83

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Asp Ile Lys Leu Gln Gln Ser Gly Ala Glu Leu Ala Arg Pro
        115                 120                 125

Gly Ala Ser Val Lys Met Ser Cys Lys Thr Ser Gly Tyr Thr Phe Thr
130                 135                 140

Arg Tyr Thr Met His Trp Val Lys Gln Arg Pro Gly Gln Gly Leu Glu
145                 150                 155                 160

Trp Ile Gly Tyr Ile Asn Pro Ser Arg Gly Tyr Thr Asn Tyr Asn Gln
                165                 170                 175

Lys Phe Lys Asp Lys Ala Thr Leu Thr Thr Asp Lys Ser Ser Ser Thr
            180                 185                 190

Ala Tyr Met Gln Leu Ser Ser Leu Thr Ser Glu Asp Ser Ala Val Tyr
        195                 200                 205

Tyr Cys Ala Arg Tyr Tyr Asp Asp His Tyr Cys Leu Asp Tyr Trp Gly
210                 215                 220

Gln Gly Thr Thr Leu Thr Val Ser Ser Gly Gly Gly Ser Gly Gly
225                 230                 235                 240

Gly Gly Ser Gly Gly Gly Gly Ser Asp Ile Gln Leu Thr Gln Ser Pro
                245                 250                 255

Ala Ile Met Ser Ala Ser Pro Gly Glu Lys Val Thr Met Thr Cys Arg
            260                 265                 270

Ala Ser Ser Ser Val Ser Tyr Met Asn Trp Tyr Gln Gln Lys Ser Gly
        275                 280                 285

Thr Ser Pro Lys Arg Trp Ile Tyr Asp Thr Ser Lys Val Ala Ser Gly
    290                 295                 300

Val Pro Tyr Arg Phe Ser Gly Ser Gly Ser Gly Thr Ser Tyr Ser Leu
305                 310                 315                 320

Thr Ile Ser Ser Met Glu Ala Glu Asp Ala Ala Thr Tyr Tyr Cys Gln
                325                 330                 335

Gln Trp Ser Ser Asn Pro Leu Thr Phe Gly Ala Gly Thr Lys Leu Glu
            340                 345                 350

Leu Lys Ser His His His His His
        355                 360
```

<210> SEQ ID NO 84
<211> LENGTH: 371
<212> TYPE: PRT
<213> ORGANISM: Artificial Sequence
<220> FEATURE:
<223> OTHER INFORMATION: Binding protein sequence

<400> SEQUENCE: 84

```
Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Gly Gly Gly Gly Ser Gly Gly Gly Ser Asp Ile Lys Leu
            115                 120                 125

Gln Gln Ser Gly Ala Glu Leu Ala Arg Pro Gly Ala Ser Val Lys Met
    130                 135                 140

Ser Cys Lys Thr Ser Gly Tyr Thr Phe Thr Arg Tyr Thr Met His Trp
145                 150                 155                 160

Val Lys Gln Arg Pro Gly Gln Gly Leu Glu Trp Ile Gly Tyr Ile Asn
                165                 170                 175

Pro Ser Arg Gly Tyr Thr Asn Tyr Asn Gln Lys Phe Lys Asp Lys Ala
            180                 185                 190

Thr Leu Thr Thr Asp Lys Ser Ser Thr Ala Tyr Met Gln Leu Ser
    195                 200                 205

Ser Leu Thr Ser Glu Asp Ser Ala Val Tyr Tyr Cys Ala Arg Tyr Tyr
    210                 215                 220

Asp Asp His Tyr Cys Leu Asp Tyr Trp Gly Gln Gly Thr Thr Leu Thr
225                 230                 235                 240

Val Ser Ser Gly Gly Gly Gly Ser Gly Gly Gly Ser Gly Gly Gly
                245                 250                 255

Gly Ser Asp Ile Gln Leu Thr Gln Ser Pro Ala Ile Met Ser Ala Ser
            260                 265                 270

Pro Gly Glu Lys Val Thr Met Thr Cys Arg Ala Ser Ser Ser Val Ser
            275                 280                 285

Tyr Met Asn Trp Tyr Gln Gln Lys Ser Gly Thr Ser Pro Lys Arg Trp
    290                 295                 300

Ile Tyr Asp Thr Ser Lys Val Ala Ser Gly Val Pro Tyr Arg Phe Ser
305                 310                 315                 320

Gly Ser Gly Ser Gly Thr Ser Tyr Ser Leu Thr Ile Ser Ser Met Glu
                325                 330                 335

Ala Glu Asp Ala Ala Thr Tyr Tyr Cys Gln Gln Trp Ser Ser Asn Pro
            340                 345                 350

Leu Thr Phe Gly Ala Gly Thr Lys Leu Glu Leu Lys Ser His His
    355                 360                 365
```

His His His
    370

<210> SEQ ID NO 85
<211> LENGTH: 359
<212> TYPE: PRT
<213> ORGANISM: Artificial Sequence
<220> FEATURE:
<223> OTHER INFORMATION: Binding protein sequence

<400> SEQUENCE: 85

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Ser
            100                 105                 110

Asp Ile Lys Leu Gln Gln Ser Gly Ala Glu Leu Ala Arg Pro Gly Ala
        115                 120                 125

Ser Val Lys Met Ser Cys Lys Thr Ser Gly Tyr Thr Phe Thr Arg Tyr
    130                 135                 140

Thr Met His Trp Val Lys Gln Arg Pro Gly Gln Gly Leu Glu Trp Ile
145                 150                 155                 160

Gly Tyr Ile Asn Pro Ser Arg Gly Tyr Thr Asn Tyr Asn Gln Lys Phe
                165                 170                 175

Lys Asp Lys Ala Thr Leu Thr Thr Asp Lys Ser Ser Ser Thr Ala Tyr
            180                 185                 190

Met Gln Leu Ser Ser Leu Thr Ser Glu Asp Ser Ala Val Tyr Tyr Cys
        195                 200                 205

Ala Arg Tyr Tyr Asp Asp His Tyr Cys Leu Asp Tyr Trp Gly Gln Gly
    210                 215                 220

Thr Thr Leu Thr Val Ser Ser Gly Gly Gly Ser Gly Gly Gly Gly
225                 230                 235                 240

Ser Gly Gly Gly Gly Ser Asp Ile Gln Leu Thr Gln Ser Pro Ala Ile
                245                 250                 255

Met Ser Ala Ser Pro Gly Glu Lys Val Thr Met Thr Cys Arg Ala Ser
            260                 265                 270

Ser Ser Val Ser Tyr Met Asn Trp Tyr Gln Gln Lys Ser Gly Thr Ser
        275                 280                 285

Pro Lys Arg Trp Ile Tyr Asp Thr Ser Lys Val Ala Ser Gly Val Pro
    290                 295                 300

Tyr Arg Phe Ser Gly Ser Gly Ser Gly Thr Ser Tyr Ser Leu Thr Ile
305                 310                 315                 320

Ser Ser Met Glu Ala Glu Asp Ala Ala Thr Tyr Tyr Cys Gln Gln Trp
                325                 330                 335

Ser Ser Asn Pro Leu Thr Phe Gly Ala Gly Thr Lys Leu Glu Leu Lys
            340                 345                 350

Ser His His His His His
        355

<210> SEQ ID NO 86
<211> LENGTH: 369
<212> TYPE: PRT
<213> ORGANISM: Artificial Sequence
<220> FEATURE:
<223> OTHER INFORMATION: Binding protein sequence

<400> SEQUENCE: 86

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Asp Ile Lys Leu Gln Gln
        115                 120                 125

Ser Gly Ala Glu Leu Ala Arg Pro Gly Ala Ser Val Lys Met Ser Cys
    130                 135                 140

Lys Thr Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
210                 215                 220

His Tyr Cys Leu Asp Tyr Trp Gly Gln Gly Thr Thr Leu Thr Val Ser
225                 230                 235                 240

Ser Gly Gly Gly Gly Ser Gly Gly Gly Gly Ser Gly Gly Gly Gly Ser
                245                 250                 255

Asp Ile Gln Leu Thr Gln Ser Pro Ala Ile Met Ser Ala Ser Pro Gly
            260                 265                 270

Glu Lys Val Thr Met Thr Cys Arg Ala Ser Ser Ser Val Ser Tyr Met
        275                 280                 285

Asn Trp Tyr Gln Gln Lys Ser Gly Thr Ser Pro Lys Arg Trp Ile Tyr
    290                 295                 300

Asp Thr Ser Lys Val Ala Ser Gly Val Pro Tyr Arg Phe Ser Gly Ser
305                 310                 315                 320

Gly Ser Gly Thr Ser Tyr Ser Leu Thr Ile Ser Ser Met Glu Ala Glu
                325                 330                 335

Asp Ala Ala Thr Tyr Tyr Cys Gln Gln Trp Ser Ser Asn Pro Leu Thr
            340                 345                 350

```
Phe Gly Ala Gly Thr Lys Leu Glu Leu Lys Ser His His His His
            355                 360                 365
His

<210> SEQ ID NO 87
<211> LENGTH: 491
<212> TYPE: PRT
<213> ORGANISM: Artificial Sequence
<220> FEATURE:
<223> OTHER INFORMATION: Binding protein sequence

<400> SEQUENCE: 87

Thr Arg Val Asp Gln Thr Pro Arg Thr Ala Thr Lys Glu Thr Gly Glu
  1               5                  10                  15

Ser Leu Thr Ile Asn Cys Val Leu Thr Asp Thr Ser Tyr Gly Leu Tyr
             20                  25                  30

Ser Thr Ser Trp Phe Arg Lys Asn Pro Gly Thr Thr Asp Trp Glu Arg
         35                  40                  45

Met Ser Ile Gly Gly Arg Tyr Val Glu Ser Val Asn Lys Gly Ala Lys
     50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Gly Ser Gly
            115                 120                 125

Gly Gly Gly Ser Thr Arg Val Asp Gln Thr Pro Arg Thr Ala Thr Lys
        130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Gly Ala Lys Ser Phe Ser Leu Arg Ile Lys Asp Leu Thr Val Ala
        195                 200                 205

Asp Ser Ala Thr Tyr Tyr Cys Lys Ala Arg Glu Ala Arg His Pro Trp
    210                 215                 220

Leu Arg Gln Trp Tyr Asp Gly Ala Gly Thr Val Leu Thr Val Asn Gly
225                 230                 235                 240

Gly Gly Gly Ser Asp Ile Lys Leu Gln Gln Ser Gly Ala Glu Leu Ala
                245                 250                 255

Arg Pro Gly Ala Ser Val Lys Met Ser Cys Lys Thr Ser Gly Tyr Thr
            260                 265                 270

Phe Thr Arg Tyr Thr Met His Trp Val Lys Gln Arg Pro Gly Gln Gly
        275                 280                 285

Leu Glu Trp Ile Gly Tyr Ile Asn Pro Ser Arg Gly Tyr Thr Asn Tyr
    290                 295                 300

Asn Gln Lys Phe Lys Asp Lys Ala Thr Leu Thr Thr Asp Lys Ser Ser
305                 310                 315                 320

Ser Thr Ala Tyr Met Gln Leu Ser Ser Leu Thr Ser Glu Asp Ser Ala
                325                 330                 335

Val Tyr Tyr Cys Ala Arg Tyr Tyr Asp Asp His Tyr Cys Leu Asp Tyr
```

```
            340                 345                 350
Trp Gly Gln Gly Thr Thr Leu Thr Val Ser Ser Gly Gly Gly Ser
            355                 360                 365
Gly Gly Gly Gly Ser Gly Gly Gly Ser Asp Ile Gln Leu Thr Gln
            370                 375                 380
Ser Pro Ala Ile Met Ser Ala Ser Pro Gly Glu Lys Val Thr Met Thr
385                 390                 395                 400
Cys Arg Ala Ser Ser Val Ser Tyr Met Asn Trp Tyr Gln Gln Lys
            405                 410                 415
Ser Gly Thr Ser Pro Lys Arg Trp Ile Tyr Asp Thr Ser Lys Val Ala
            420                 425                 430
Ser Gly Val Pro Tyr Arg Phe Ser Gly Ser Gly Ser Gly Thr Ser Tyr
            435                 440                 445
Ser Leu Thr Ile Ser Ser Met Glu Ala Glu Asp Ala Ala Thr Tyr Tyr
            450                 455                 460
Cys Gln Gln Trp Ser Ser Asn Pro Leu Thr Phe Gly Ala Gly Thr Lys
465                 470                 475                 480
Leu Glu Leu Lys Ser His His His His His His
            485                 490

<210> SEQ ID NO 88
<211> LENGTH: 501
<212> TYPE: PRT
<213> ORGANISM: Artificial Sequence
<220> FEATURE:
<223> OTHER INFORMATION: Binding protein sequence

<400> SEQUENCE: 88

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
            85                  90                  95

Tyr Asp Gly Ala Gly Thr Val Leu Thr Val Asn Gly Gly Gly Ser
            100                 105                 110

Gly Gly Gly Gly Ser Gly Gly Gly Ser Gly Gly Gly Ser Gly
            115                 120                 125

Gly Gly Ser Thr Arg Val Asp Gln Thr Pro Arg Thr Ala Thr Lys
            130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
            165                 170                 175

Asp Trp Glu Arg Met Ser Ile Gly Gly Arg Tyr Val Glu Ser Val Asn
            180                 185                 190

Lys Gly Ala Lys Ser Phe Ser Leu Arg Ile Lys Asp Leu Thr Val Ala
            195                 200                 205

Asp Ser Ala Thr Tyr Tyr Cys Lys Ala Arg Glu Ala Arg His Pro Trp
```

```
                    210                 215                 220
Leu Arg Gln Trp Tyr Asp Gly Ala Gly Thr Val Leu Thr Val Asn Gly
225                 230                 235                 240

Gly Gly Gly Ser Gly Gly Gly Ser Gly Gly Gly Ser Asp Ile
            245                 250                 255

Lys Leu Gln Gln Ser Gly Ala Glu Leu Ala Arg Pro Gly Ala Ser Val
                260                 265                 270

Lys Met Ser Cys Lys Thr Ser Gly Tyr Thr Phe Thr Arg Tyr Thr Met
            275                 280                 285

His Trp Val Lys Gln Arg Pro Gly Gln Gly Leu Glu Trp Ile Gly Tyr
        290                 295                 300

Ile Asn Pro Ser Arg Gly Tyr Thr Asn Tyr Asn Gln Lys Phe Lys Asp
305                 310                 315                 320

Lys Ala Thr Leu Thr Thr Asp Lys Ser Ser Thr Ala Tyr Met Gln
                325                 330                 335

Leu Ser Ser Leu Thr Ser Glu Asp Ser Ala Val Tyr Tyr Cys Ala Arg
                340                 345                 350

Tyr Tyr Asp Asp His Tyr Cys Leu Asp Tyr Trp Gly Gln Gly Thr Thr
            355                 360                 365

Leu Thr Val Ser Ser Gly Gly Gly Gly Ser Gly Gly Gly Gly Ser Gly
        370                 375                 380

Gly Gly Ser Asp Ile Gln Leu Thr Gln Ser Pro Ala Ile Met Ser
385                 390                 395                 400

Ala Ser Pro Gly Glu Lys Val Thr Met Thr Cys Arg Ala Ser Ser Ser
                405                 410                 415

Val Ser Tyr Met Asn Trp Tyr Gln Gln Lys Ser Gly Thr Ser Pro Lys
            420                 425                 430

Arg Trp Ile Tyr Asp Thr Ser Lys Val Ala Ser Gly Val Pro Tyr Arg
        435                 440                 445

Phe Ser Gly Ser Gly Ser Gly Thr Ser Tyr Ser Leu Thr Ile Ser Ser
    450                 455                 460

Met Glu Ala Glu Asp Ala Ala Thr Tyr Tyr Cys Gln Gln Trp Ser Ser
465                 470                 475                 480

Asn Pro Leu Thr Phe Gly Ala Gly Thr Lys Leu Glu Leu Lys Ser His
                485                 490                 495

His His His His His
            500

<210> SEQ ID NO 89
<211> LENGTH: 480
<212> TYPE: PRT
<213> ORGANISM: Artificial Sequence
<220> FEATURE:
<223> OTHER INFORMATION: Binding protein sequence

<400> SEQUENCE: 89

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
```

```
              65                  70                  75                  80
Tyr Tyr Cys Lys Ala Arg Glu Ala Arg His Pro Trp Leu Arg Gln Trp
                    85                  90                  95
Tyr Asp Gly Ala Gly Thr Val Leu Thr Val Asn Pro Gly Val Gln Pro
                100                 105                 110
Ser Pro Gly Gly Gly Ser Ala Ser Val Asn Gln Thr Pro Arg Thr
            115                 120                 125
Ala Thr Lys Glu Thr Gly Glu Ser Leu Thr Ile Asn Cys Val Val Thr
        130                 135                 140
Gly Ala Asn Tyr Gly Leu Ala Ala Thr Tyr Trp Tyr Arg Lys Asn Pro
145                 150                 155                 160
Gly Ser Ser Asn Gln Glu Arg Ile Ser Ile Ser Gly Arg Tyr Val Glu
                165                 170                 175
Ser Val Asn Lys Arg Thr Met Ser Phe Ser Leu Arg Ile Lys Asp Leu
            180                 185                 190
Thr Val Ala Asp Ser Ala Thr Tyr Tyr Cys Lys Ala Tyr Pro Trp Gly
        195                 200                 205
Ala Gly Ala Pro Trp Leu Val Gln Trp Tyr Asp Gly Ala Gly Thr Val
210                 215                 220
Leu Thr Val Asn Gly Gly Gly Gly Ser Asp Ile Lys Leu Gln Gln Ser
225                 230                 235                 240
Gly Ala Glu Leu Ala Arg Pro Gly Ala Ser Val Lys Met Ser Cys Lys
                245                 250                 255
Thr Ser Gly Tyr Thr Phe Thr Arg Tyr Thr Met His Trp Val Lys Gln
            260                 265                 270
Arg Pro Gly Gln Gly Leu Glu Trp Ile Gly Tyr Ile Asn Pro Ser Arg
        275                 280                 285
Gly Tyr Thr Asn Tyr Asn Gln Lys Phe Lys Asp Lys Ala Thr Leu Thr
        290                 295                 300
Thr Asp Lys Ser Ser Ser Thr Ala Tyr Met Gln Leu Ser Ser Leu Thr
305                 310                 315                 320
Ser Glu Asp Ser Ala Val Tyr Tyr Cys Ala Arg Tyr Tyr Asp Asp His
                325                 330                 335
Tyr Cys Leu Asp Tyr Trp Gly Gln Gly Thr Thr Leu Thr Val Ser Ser
            340                 345                 350
Gly Gly Gly Gly Ser Gly Gly Gly Gly Ser Gly Gly Gly Gly Ser Asp
        355                 360                 365
Ile Gln Leu Thr Gln Ser Pro Ala Ile Met Ser Ala Ser Pro Gly Glu
        370                 375                 380
Lys Val Thr Met Thr Cys Arg Ala Ser Ser Ser Val Ser Tyr Met Asn
385                 390                 395                 400
Trp Tyr Gln Gln Lys Ser Gly Thr Ser Pro Lys Arg Trp Ile Tyr Asp
                405                 410                 415
Thr Ser Lys Val Ala Ser Gly Val Pro Tyr Arg Phe Ser Gly Ser Gly
            420                 425                 430
Ser Gly Thr Ser Tyr Ser Leu Thr Ile Ser Ser Met Glu Ala Glu Asp
        435                 440                 445
Ala Ala Thr Tyr Tyr Cys Gln Gln Trp Ser Ser Asn Pro Leu Thr Phe
    450                 455                 460
Gly Ala Gly Thr Lys Leu Glu Leu Lys Ser His His His His His His
465                 470                 475                 480

<210> SEQ ID NO 90
```

```
<211> LENGTH: 490
<212> TYPE: PRT
<213> ORGANISM: Artificial Sequence
<220> FEATURE:
<223> OTHER INFORMATION: Binding protein sequence

<400> SEQUENCE: 90
```

| | | | | | | | | | | | | | | |
|---|---|---|---|---|---|---|---|---|---|---|---|---|---|---|
| Thr | Arg | Val | Asp | Gln | Thr | Pro | Arg | Thr | Ala | Thr | Lys | Glu | Thr | Gly | Glu |
| 1 | | | | 5 | | | | | 10 | | | | | 15 |

Ser Leu Thr Ile Asn Cys Val Leu Thr Asp Thr Ser Tyr Gly Leu Tyr
              20                 25                30

Ser Thr Ser Trp Phe Arg Lys Asn Pro Gly Thr Thr Asp Trp Glu Arg
     35               40                45

Met Ser Ile Gly Gly Arg Tyr Val Glu Ser Val Asn Lys Gly Ala Lys
     50               55                60

Ser Phe Ser Leu Arg Ile Lys Asp Leu Thr Val Ala Asp Ser Ala Thr
65                  70                75                80

Tyr Tyr Cys Lys Ala Arg Glu Ala Arg His Pro Trp Leu Arg Gln Trp
              85                 90                95

Tyr Asp Gly Ala Gly Thr Val Leu Thr Val Asn Pro Gly Val Gln Pro
           100                105              110

Ser Pro Gly Gly Gly Ser Ala Ser Val Asn Gln Thr Pro Arg Thr
           115                120              125

Ala Thr Lys Glu Thr Gly Glu Ser Leu Thr Ile Asn Cys Val Val Thr
     130               135                140

Gly Ala Asn Tyr Gly Leu Ala Ala Thr Tyr Trp Tyr Arg Lys Asn Pro
145                 150                155              160

Gly Ser Ser Asn Gln Glu Arg Ile Ser Ile Ser Gly Arg Tyr Val Glu
           165                170              175

Ser Val Asn Lys Arg Thr Met Ser Phe Ser Leu Arg Ile Lys Asp Leu
           180                185              190

Thr Val Ala Asp Ser Ala Thr Tyr Tyr Cys Lys Ala Tyr Pro Trp Gly
           195                200              205

Ala Gly Ala Pro Trp Leu Val Gln Trp Tyr Asp Gly Ala Gly Thr Val
     210               215                220

Leu Thr Val Asn Gly Gly Gly Gly Ser Gly Gly Gly Ser Gly Gly
225                 230                235              240

Gly Gly Ser Asp Ile Lys Leu Gln Gln Ser Gly Ala Glu Leu Ala Arg
           245                250              255

Pro Gly Ala Ser Val Lys Met Ser Cys Lys Thr Ser Gly Tyr Thr Phe
     260               265                270

Thr Arg Tyr Thr Met His Trp Val Lys Gln Arg Pro Gly Gln Gly Leu
           275                280              285

Glu Trp Ile Gly Tyr Ile Asn Pro Ser Arg Gly Tyr Thr Asn Tyr Asn
     290               295                300

Gln Lys Phe Lys Asp Lys Ala Thr Leu Thr Thr Asp Lys Ser Ser Ser
305                 310                315              320

Thr Ala Tyr Met Gln Leu Ser Ser Leu Thr Ser Glu Asp Ser Ala Val
                325              330              335

Tyr Tyr Cys Ala Arg Tyr Tyr Asp Asp His Tyr Cys Leu Asp Tyr Trp
           340                345              350

Gly Gln Gly Thr Thr Leu Thr Val Ser Ser Gly Gly Gly Gly Ser Gly
           355                360              365

Gly Gly Gly Ser Gly Gly Gly Gly Ser Asp Ile Gln Leu Thr Gln Ser
     370               375                380

Pro Ala Ile Met Ser Ala Ser Pro Gly Glu Lys Val Thr Met Thr Cys
385                 390                 395                 400

Arg Ala Ser Ser Val Ser Tyr Met Asn Trp Tyr Gln Gln Lys Ser
            405                 410                 415

Gly Thr Ser Pro Lys Arg Trp Ile Tyr Asp Thr Ser Lys Val Ala Ser
            420                 425                 430

Gly Val Pro Tyr Arg Phe Ser Gly Ser Gly Ser Gly Thr Ser Tyr Ser
            435                 440                 445

Leu Thr Ile Ser Ser Met Glu Ala Glu Asp Ala Ala Thr Tyr Tyr Cys
            450                 455                 460

Gln Gln Trp Ser Ser Asn Pro Leu Thr Phe Gly Ala Gly Thr Lys Leu
465                 470                 475                 480

Glu Leu Lys Ser His His His His His His
                485                 490

<210> SEQ ID NO 91
<211> LENGTH: 483
<212> TYPE: PRT
<213> ORGANISM: Artificial Sequence
<220> FEATURE:
<223> OTHER INFORMATION: Binding protein sequence

<400> SEQUENCE: 91

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ala Pro Gly Gly Gly Gly Ser Ala Ser Val Asn Gln Thr Pro Arg Thr
            115                 120                 125

Ala Thr Lys Glu Thr Gly Glu Ser Leu Thr Ile Asn Cys Val Leu Thr
            130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

Ser Val Asn Lys Arg Ala Lys Ser Phe Ser Leu Arg Ile Lys Asp Leu
            180                 185                 190

Thr Val Ala Asp Ser Ala Thr Tyr Tyr Cys Lys Ala Gln Ser Gly Met
            195                 200                 205

Ala Ile Ser Thr Gly Ser Gly His Gly Tyr Asn Trp Tyr Asp Gly Ala
            210                 215                 220

Gly Thr Val Leu Thr Val Asn Gly Gly Gly Ser Asp Ile Lys Leu
225                 230                 235                 240

Gln Gln Ser Gly Ala Glu Leu Ala Arg Pro Gly Ala Ser Val Lys Met
                245                 250                 255

```
Ser Cys Lys Thr Ser Gly Tyr Thr Phe Thr Arg Tyr Thr Met His Trp
            260                 265                 270

Val Lys Gln Arg Pro Gly Gln Gly Leu Glu Trp Ile Gly Tyr Ile Asn
            275                 280                 285

Pro Ser Arg Gly Tyr Thr Asn Tyr Asn Gln Lys Phe Lys Asp Lys Ala
            290                 295                 300

Thr Leu Thr Thr Asp Lys Ser Ser Thr Ala Tyr Met Gln Leu Ser
305                 310                 315                 320

Ser Leu Thr Ser Glu Asp Ser Ala Val Tyr Tyr Cys Ala Arg Tyr Tyr
                325                 330                 335

Asp Asp His Tyr Cys Leu Asp Tyr Trp Gly Gln Gly Thr Thr Leu Thr
            340                 345                 350

Val Ser Ser Gly Gly Gly Gly Ser Gly Gly Gly Gly Ser Gly Gly Gly
            355                 360                 365

Gly Ser Asp Ile Gln Leu Thr Gln Ser Pro Ala Ile Met Ser Ala Ser
            370                 375                 380

Pro Gly Glu Lys Val Thr Met Thr Cys Arg Ala Ser Ser Ser Val Ser
385                 390                 395                 400

Tyr Met Asn Trp Tyr Gln Gln Lys Ser Gly Thr Ser Pro Lys Arg Trp
                405                 410                 415

Ile Tyr Asp Thr Ser Lys Val Ala Ser Gly Val Pro Tyr Arg Phe Ser
                420                 425                 430

Gly Ser Gly Ser Gly Thr Ser Tyr Ser Leu Thr Ile Ser Ser Met Glu
            435                 440                 445

Ala Glu Asp Ala Ala Thr Tyr Tyr Cys Gln Gln Trp Ser Ser Asn Pro
            450                 455                 460

Leu Thr Phe Gly Ala Gly Thr Lys Leu Glu Leu Lys Ser His His His
465                 470                 475                 480

His His His

<210> SEQ ID NO 92
<211> LENGTH: 493
<212> TYPE: PRT
<213> ORGANISM: Artificial Sequence
<220> FEATURE:
<223> OTHER INFORMATION: Binding protein sequence

<400> SEQUENCE: 92

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ala Pro Gly Gly Gly Ser Ala Ser Val Asn Gln Thr Pro Arg Thr
            115                 120                 125
```

```
Ala Thr Lys Glu Thr Gly Glu Ser Leu Thr Ile Asn Cys Val Leu Thr
130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

Ser Val Asn Lys Arg Ala Lys Ser Phe Ser Leu Arg Ile Lys Asp Leu
            180                 185                 190

Thr Val Ala Asp Ser Ala Thr Tyr Tyr Cys Lys Ala Gln Ser Gly Met
        195                 200                 205

Ala Ile Ser Thr Gly Ser Gly His Gly Tyr Asn Trp Tyr Asp Gly Ala
210                 215                 220

Gly Thr Val Leu Thr Val Asn Gly Gly Gly Ser Gly Gly Gly Gly
225                 230                 235                 240

Ser Gly Gly Gly Gly Ser Asp Ile Lys Leu Gln Gln Ser Gly Ala Glu
                245                 250                 255

Leu Ala Arg Pro Gly Ala Ser Val Lys Met Ser Cys Lys Thr Ser Gly
            260                 265                 270

Tyr Thr Phe Thr Arg Tyr Thr Met His Trp Val Lys Gln Arg Pro Gly
        275                 280                 285

Gln Gly Leu Glu Trp Ile Gly Tyr Ile Asn Pro Ser Arg Gly Tyr Thr
290                 295                 300

Asn Tyr Asn Gln Lys Phe Lys Asp Lys Ala Thr Leu Thr Thr Asp Lys
305                 310                 315                 320

Ser Ser Ser Thr Ala Tyr Met Gln Leu Ser Ser Leu Thr Ser Glu Asp
                325                 330                 335

Ser Ala Val Tyr Tyr Cys Ala Arg Tyr Tyr Asp Asp His Tyr Cys Leu
            340                 345                 350

Asp Tyr Trp Gly Gln Gly Thr Thr Leu Thr Val Ser Ser Gly Gly Gly
        355                 360                 365

Gly Ser Gly Gly Gly Gly Ser Gly Gly Gly Gly Ser Asp Ile Gln Leu
370                 375                 380

Thr Gln Ser Pro Ala Ile Met Ser Ala Ser Pro Gly Glu Lys Val Thr
385                 390                 395                 400

Met Thr Cys Arg Ala Ser Ser Val Ser Tyr Met Asn Trp Tyr Gln
                405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
        435                 440                 445

Ser Tyr Ser Leu Thr Ile Ser Ser Met Glu Ala Glu Asp Ala Ala Thr
450                 455                 460

Tyr Tyr Cys Gln Gln Trp Ser Ser Asn Pro Leu Thr Phe Gly Ala Gly
465                 470                 475                 480

Thr Lys Leu Glu Leu Lys Ser His His His His His
                485                 490

<210> SEQ ID NO 93
<211> LENGTH: 496
<212> TYPE: PRT
<213> ORGANISM: Artificial Sequence
<220> FEATURE:
<223> OTHER INFORMATION: Binding protein sequence

<400> SEQUENCE: 93
```

-continued

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Gly Ser Gly
        115                 120                 125

Gly Gly Gly Ser Ala Ser Val Asn Gln Thr Pro Arg Thr Ala Thr Lys
    130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Arg Ala Lys Ser Phe Ser Leu Arg Ile Lys Asp Leu Thr Val Ala
        195                 200                 205

Asp Ser Ala Thr Tyr Tyr Cys Lys Ala Gln Ser Gly Met Ala Ile Ser
    210                 215                 220

Thr Gly Ser Gly His Gly Tyr Asn Trp Tyr Asp Gly Ala Gly Thr Val
225                 230                 235                 240

Leu Thr Val Asn Gly Gly Gly Ser Asp Ile Lys Leu Gln Gln Ser
                245                 250                 255

Gly Ala Glu Leu Ala Arg Pro Gly Ala Ser Val Lys Met Ser Cys Lys
            260                 265                 270

Thr Ser Gly Tyr Thr Phe Thr Arg Tyr Thr Met His Trp Val Lys Gln
        275                 280                 285

Arg Pro Gly Gln Gly Leu Glu Trp Ile Gly Tyr Ile Asn Pro Ser Arg
    290                 295                 300

Gly Tyr Thr Asn Tyr Asn Gln Lys Phe Lys Asp Lys Ala Thr Leu Thr
305                 310                 315                 320

Thr Asp Lys Ser Ser Ser Thr Ala Tyr Met Gln Leu Ser Ser Leu Thr
                325                 330                 335

Ser Glu Asp Ser Ala Val Tyr Tyr Cys Ala Arg Tyr Tyr Asp Asp His
            340                 345                 350

Tyr Cys Leu Asp Tyr Trp Gly Gln Gly Thr Thr Leu Thr Val Ser Ser
        355                 360                 365

Gly Gly Gly Gly Ser Gly Gly Gly Gly Ser Gly Gly Gly Gly Ser Asp
    370                 375                 380

Ile Gln Leu Thr Gln Ser Pro Ala Ile Met Ser Ala Ser Pro Gly Glu
385                 390                 395                 400

Lys Val Thr Met Thr Cys Arg Ala Ser Ser Ser Val Ser Tyr Met Asn
                405                 410                 415

Trp Tyr Gln Gln Lys Ser Gly Thr Ser Pro Lys Arg Trp Ile Tyr Asp
```

-continued

```
                420             425             430
Thr Ser Lys Val Ala Ser Gly Val Pro Tyr Arg Phe Ser Gly Ser Gly
        435             440             445
Ser Gly Thr Ser Tyr Ser Leu Thr Ile Ser Ser Met Glu Ala Glu Asp
        450             455             460
Ala Ala Thr Tyr Tyr Cys Gln Gln Trp Ser Ser Asn Pro Leu Thr Phe
465             470             475             480
Gly Ala Gly Thr Lys Leu Glu Leu Lys Ser His His His His His His
            485             490             495
```

<210> SEQ ID NO 94
<211> LENGTH: 506
<212> TYPE: PRT
<213> ORGANISM: Artificial Sequence
<220> FEATURE:
<223> OTHER INFORMATION: Binding protein sequence

<400> SEQUENCE: 94

```
Thr Arg Val Asp Gln Thr Pro Arg Thr Ala Thr Lys Glu Thr Gly Glu
1               5               10              15
Ser Leu Thr Ile Asn Cys Val Leu Thr Asp Thr Ser Tyr Gly Leu Tyr
            20              25              30
Ser Thr Ser Trp Phe Arg Lys Asn Pro Gly Thr Thr Asp Trp Glu Arg
        35              40              45
Met Ser Ile Gly Gly Arg Tyr Val Glu Ser Val Asn Lys Gly Ala Lys
    50              55              60
Ser Phe Ser Leu Arg Ile Lys Asp Leu Thr Val Ala Asp Ser Ala Thr
65              70              75              80
Tyr Tyr Cys Lys Ala Arg Glu Ala Arg His Pro Trp Leu Arg Gln Trp
                85              90              95
Tyr Asp Gly Ala Gly Thr Val Leu Thr Val Asn Gly Gly Gly Gly Ser
            100             105             110
Gly Gly Gly Gly Ser Gly Gly Gly Ser Gly Gly Gly Gly Ser Gly
        115             120             125
Gly Gly Gly Ser Ala Ser Val Asn Gln Thr Pro Arg Thr Ala Thr Lys
    130             135             140
Glu Thr Gly Glu Ser Leu Thr Ile Asn Cys Val Leu Thr Asp Thr Ser
145             150             155             160
Tyr Gly Leu Tyr Ser Thr Ser Trp Phe Arg Lys Asn Pro Gly Thr Thr
                165             170             175
Asp Trp Glu Arg Met Ser Ile Gly Gly Arg Tyr Val Glu Ser Val Asn
            180             185             190
Lys Arg Ala Lys Ser Phe Ser Leu Arg Ile Lys Asp Leu Thr Val Ala
        195             200             205
Asp Ser Ala Thr Tyr Tyr Cys Lys Ala Gln Ser Gly Met Ala Ile Ser
    210             215             220
Thr Gly Ser Gly His Gly Tyr Asn Trp Tyr Asp Gly Ala Gly Thr Val
225             230             235             240
Leu Thr Val Asn Gly Gly Gly Ser Gly Gly Gly Gly Ser Gly Gly
                245             250             255
Gly Gly Ser Asp Ile Lys Leu Gln Gln Ser Gly Ala Glu Leu Ala Arg
            260             265             270
Pro Gly Ala Ser Val Lys Met Ser Cys Lys Thr Ser Gly Tyr Thr Phe
        275             280             285
Thr Arg Tyr Thr Met His Trp Val Lys Gln Arg Pro Gly Gln Gly Leu
```

```
                290             295             300
Glu Trp Ile Gly Tyr Ile Asn Pro Ser Arg Gly Tyr Thr Asn Tyr Asn
305                     310                 315                 320

Gln Lys Phe Lys Asp Lys Ala Thr Leu Thr Thr Asp Lys Ser Ser Ser
                    325                 330                 335

Thr Ala Tyr Met Gln Leu Ser Ser Leu Thr Ser Glu Asp Ser Ala Val
                340                 345                 350

Tyr Tyr Cys Ala Arg Tyr Tyr Asp Asp His Tyr Cys Leu Asp Tyr Trp
                355                 360                 365

Gly Gln Gly Thr Thr Leu Thr Val Ser Ser Gly Gly Gly Gly Ser Gly
            370                 375                 380

Gly Gly Gly Ser Gly Gly Gly Ser Asp Ile Gln Leu Thr Gln Ser
385                 390                 395                 400

Pro Ala Ile Met Ser Ala Ser Pro Gly Glu Lys Val Thr Met Thr Cys
                    405                 410                 415

Arg Ala Ser Ser Ser Val Ser Tyr Met Asn Trp Tyr Gln Gln Lys Ser
                420                 425                 430

Gly Thr Ser Pro Lys Arg Trp Ile Tyr Asp Thr Ser Lys Val Ala Ser
                435                 440                 445

Gly Val Pro Tyr Arg Phe Ser Gly Ser Gly Ser Gly Thr Ser Tyr Ser
450                 455                 460

Leu Thr Ile Ser Ser Met Glu Ala Glu Asp Ala Ala Thr Tyr Tyr Cys
465                 470                 475                 480

Gln Gln Trp Ser Ser Asn Pro Leu Thr Phe Gly Ala Gly Thr Lys Leu
                485                 490                 495

Glu Leu Lys Ser His His His His His His
                500                 505

<210> SEQ ID NO 95
<211> LENGTH: 233
<212> TYPE: PRT
<213> ORGANISM: Artificial Sequence
<220> FEATURE:
<223> OTHER INFORMATION: Fc Domain Sequence

<400> SEQUENCE: 95

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
                20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
                100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Pro Glu Glu Glu Met
            130                 135                 140

Thr Lys Lys Gln Val Thr Leu Thr Cys Met Val Thr Asp Phe Met Pro
```

```
                  145                 150                 155                 160
Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
                180                 185                 190

Tyr Ser Lys Leu Arg Val Glu Lys Asn Trp Val Glu Arg Asn Ser
                195                 200                 205

Tyr Ser Cys Ser Val Val His Glu Gly Leu His Asn His His Thr Thr
                210                 215                 220

Lys Ser Phe Ser Arg Thr Pro Gly Lys
225                 230

<210> SEQ ID NO 96
<211> LENGTH: 232
<212> TYPE: PRT
<213> ORGANISM: Artificial Sequence
<220> FEATURE:
<223> OTHER INFORMATION: Fc Domain Sequence

<400> SEQUENCE: 96

Glu Pro Lys Ser Ser Asp Lys Thr His Thr Cys Pro Pro Cys Pro Ala
1                   5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
                130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 97
<211> LENGTH: 26
<212> TYPE: PRT
<213> ORGANISM: Artificial Sequence
<220> FEATURE:
<223> OTHER INFORMATION: Tag Sequence
```

<400> SEQUENCE: 97

Gln Ala Ser Gly Ala His His His His His Gly Ala Glu Phe Glu
1               5                   10                  15

Gln Lys Leu Ile Ser Glu Glu Asp Leu Gly
            20                  25

<210> SEQ ID NO 98
<211> LENGTH: 446
<212> TYPE: PRT
<213> ORGANISM: Artificial Sequence
<220> FEATURE:
<223> OTHER INFORMATION: Antibody Heavy Chain Sequence

<400> SEQUENCE: 98

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 99
<211> LENGTH: 214
<212> TYPE: PRT
<213> ORGANISM: Artificial Sequence
<220> FEATURE:
<223> OTHER INFORMATION: Antibody Light Chain Sequence

<400> SEQUENCE: 99

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Thr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 100
<211> LENGTH: 241
```

<212> TYPE: PRT
<213> ORGANISM: Artificial Sequence
<220> FEATURE:
<223> OTHER INFORMATION: Binding Protein Sequence

<400> SEQUENCE: 100

```
Asp Ile Lys Leu Gln Gln Ser Gly Ala Glu Leu Ala Arg Pro Gly Ala
1               5                  10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly
        115                 120                 125

Ser Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser
```

<210> SEQ ID NO 101
<211> LENGTH: 245
<212> TYPE: PRT
<213> ORGANISM: Artificial Sequence
<220> FEATURE:
<223> OTHER INFORMATION: Antibody Sequence

<400> SEQUENCE: 101

```
Met Asp Ile Gln Met Thr Gln Thr Thr Ser Ser Leu Ser Ala Ser Leu
1               5                  10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80
```

```
Gln Glu Asp Ile Ala Thr Tyr Phe Cys Gln Gln Gly Asn Thr Leu Pro
                85                  90                  95
Trp Thr Phe Ala Gly Gly Thr Lys Leu Glu Ile Lys Gly Gly Gly Gly
            100                 105                 110
Ser Gly Gly Gly Gly Ser Gly Gly Gly Ser Glu Val Gln Leu Gln
        115                 120                 125
Gln Ser Gly Pro Glu Leu Val Lys Pro Gly Ala Ser Met Lys Ile Ser
    130                 135                 140
Cys Lys Ala Ser Gly Tyr Ser Phe Thr Gly Tyr Thr Met Asn Trp Val
145                 150                 155                 160
Lys Gln Ser His Gly Lys Asn Leu Glu Trp Met Gly Leu Ile Asn Pro
                165                 170                 175
Tyr Lys Gly Val Ser Thr Tyr Asn Gln Lys Phe Lys Asp Lys Ala Thr
            180                 185                 190
Leu Thr Val Asp Lys Ser Ser Ser Thr Ala Tyr Met Glu Leu Leu Ser
        195                 200                 205
Leu Thr Ser Glu Asp Ser Ala Val Tyr Tyr Cys Ala Arg Ser Gly Tyr
    210                 215                 220
Tyr Gly Asp Ser Asp Trp Tyr Phe Asp Val Trp Gly Gln Gly Thr Thr
225                 230                 235                 240
Leu Thr Val Phe Ser
                245

<210> SEQ ID NO 102
<211> LENGTH: 105
<212> TYPE: PRT
<213> ORGANISM: Artificial Sequence
<220> FEATURE:
<223> OTHER INFORMATION: E7 Protein Sequence

<400> SEQUENCE: 102

Thr Arg Val Asp Gln Thr Pro Arg Thr Ala Thr Lys Glu Thr Gly Glu
1               5                   10                  15
Ser Leu Thr Ile Asn Cys Val Val Thr Gly Ala Lys Tyr Gly Leu Ala
            20                  25                  30
Ala Thr Tyr Trp Tyr Arg Lys Asn Pro Gly Ser Ser Asn Gln Glu Arg
        35                  40                  45
Ile Ser Ile Ser Gly Arg Tyr Val Glu Ser Val Asn Lys Arg Thr Met
    50                  55                  60
Ser Phe Ser Leu Arg Ile Lys Asp Leu Thr Val Ala Asp Ser Ala Thr
65                  70                  75                  80
Tyr Tyr Cys Lys Ala Tyr Pro Trp Ala Met Trp Gly Gln Trp Tyr Asp
                85                  90                  95
Gly Ala Gly Thr Val Leu Thr Val Asn
            100                 105

<210> SEQ ID NO 103
<211> LENGTH: 109
<212> TYPE: PRT
<213> ORGANISM: Artificial Sequence
<220> FEATURE:
<223> OTHER INFORMATION: CPF7 Protein Sequence

<400> SEQUENCE: 103

Thr Arg Val Asp Gln Thr Pro Arg Thr Ala Thr Lys Glu Thr Gly Glu
1               5                   10                  15
Ser Leu Thr Ile Asn Cys Val Val Thr Gly Ala Lys Tyr Gly Leu Phe
            20                  25                  30
```

```
Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Met Pro Gln His Trp His Pro Ala Ala
                85                  90                  95

His Trp Tyr Asp Gly Ala Gly Thr Val Leu Thr Val Asn
                100                 105

<210> SEQ ID NO 104
<211> LENGTH: 130
<212> TYPE: PRT
<213> ORGANISM: Artificial Sequence
<220> FEATURE:
<223> OTHER INFORMATION: E7 Protein Sequence

<400> SEQUENCE: 104

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Ala
            20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Ala Met Trp Gly Gln Trp Tyr Asp
                85                  90                  95

Gly Ala Gly Thr Val Leu Thr Val Asn Gln Ala Ser Gly Ala His His
                100                 105                 110

His His His His Gly Ala Glu Phe Glu Gln Lys Leu Ile Ser Glu Glu
        115                 120                 125

Asp Leu
    130

<210> SEQ ID NO 105
<211> LENGTH: 134
<212> TYPE: PRT
<213> ORGANISM: Artificial Sequence
<220> FEATURE:
<223> OTHER INFORMATION: CPF7 Protein Sequence

<400> SEQUENCE: 105

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Phe
            20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Met Pro Gln His Trp His Pro Ala Ala
```

```
                    85                  90                  95

His Trp Tyr Asp Gly Ala Gly Thr Val Leu Thr Val Asn Gln Ala Ser
                100                 105                 110

Gly Ala His His His His His Gly Ala Glu Phe Glu Gln Lys Leu
            115                 120                 125

Ile Ser Glu Glu Asp Leu
        130

<210> SEQ ID NO 106
<211> LENGTH: 132
<212> TYPE: PRT
<213> ORGANISM: Artificial Sequence
<220> FEATURE:
<223> OTHER INFORMATION: P3A1 Sequence

<400> SEQUENCE: 106

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gln Ala Ser Gly Ala
                100                 105                 110

His His His His His His Gly Ala Glu Phe Glu Gln Lys Leu Ile Ser
            115                 120                 125

Glu Glu Asp Leu
        130

<210> SEQ ID NO 107
<211> LENGTH: 134
<212> TYPE: PRT
<213> ORGANISM: Artificial Sequence
<220> FEATURE:
<223> OTHER INFORMATION: B1 Protein Sequence

<400> SEQUENCE: 107

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Ser
                100                 105                 110
```

Gly Ala His His His His His Gly Ala Glu Phe Glu Gln Lys Leu
            115                 120                 125

Ile Ser Glu Glu Asp Leu
    130

<210> SEQ ID NO 108
<211> LENGTH: 137
<212> TYPE: PRT
<213> ORGANISM: Artificial Sequence
<220> FEATURE:
<223> OTHER INFORMATION: D3 Protein Sequence

<400> SEQUENCE: 108

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gln Ala Ser Gly Ala His His His His His Gly Ala Glu Phe Glu
            115                 120                 125

Gln Lys Leu Ile Ser Glu Glu Asp Leu
            130                 135

<210> SEQ ID NO 109
<211> LENGTH: 137
<212> TYPE: PRT
<213> ORGANISM: Artificial Sequence
<220> FEATURE:
<223> OTHER INFORMATION: E9 Protein Sequence

<400> SEQUENCE: 109

Ala Lys Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Asp Ile Gly Ser Gly
                85                  90                  95

His Gly Tyr Asn Trp Tyr Asp Gly Ala Gly Thr Val Leu Thr Val Asn
            100                 105                 110

Gln Ala Ser Gly Ala His His His His His Gly Ala Glu Phe Glu
            115                 120                 125

Gln Lys Leu Ile Ser Glu Glu Asp Leu
            130                 135

<210> SEQ ID NO 110
<211> LENGTH: 248
<212> TYPE: PRT
<213> ORGANISM: Artificial Sequence
<220> FEATURE:
<223> OTHER INFORMATION: Linker mouse IgG2a Sequence

<400> SEQUENCE: 110

Gly Gly Gly Gly Ser Gly Gly Gly Ser Gly Gly Gly Gly Ser Glu
1               5                   10                  15

Pro Arg Gly Pro Thr Ile Lys Pro Cys Pro Pro Cys Lys Cys Pro Ala
            20                  25                  30

Pro Asn Leu Leu Gly Gly Pro Ser Val Phe Ile Phe Pro Pro Lys Ile
        35                  40                  45

Lys Asp Val Leu Met Ile Ser Leu Ser Pro Ile Val Thr Cys Val Val
    50                  55                  60

Val Asp Val Ser Glu Asp Asp Pro Asp Val Gln Ile Ser Trp Phe Val
65                  70                  75                  80

Asn Asn Val Glu Val His Thr Ala Gln Thr Gln Thr His Arg Glu Asp
                85                  90                  95

Tyr Asn Ser Thr Leu Arg Val Val Ser Ala Leu Pro Ile Gln His Gln
            100                 105                 110

Asp Trp Met Ser Gly Lys Glu Phe Lys Cys Lys Val Asn Asn Lys Asp
        115                 120                 125

Leu Pro Ala Pro Ile Glu Arg Thr Ile Ser Lys Pro Lys Gly Ser Val
    130                 135                 140

Arg Ala Pro Gln Val Tyr Val Leu Pro Pro Pro Glu Glu Glu Met Thr
145                 150                 155                 160

Lys Lys Gln Val Thr Leu Thr Cys Met Val Thr Asp Phe Met Pro Glu
                165                 170                 175

Asp Ile Tyr Val Glu Trp Thr Asn Asn Gly Lys Thr Glu Leu Asn Tyr
            180                 185                 190

Lys Asn Thr Glu Pro Val Leu Asp Ser Asp Gly Ser Tyr Phe Met Tyr
        195                 200                 205

Ser Lys Leu Arg Val Glu Lys Lys Asn Trp Val Glu Arg Asn Ser Tyr
    210                 215                 220

Ser Cys Ser Val Val His Glu Gly Leu His Asn His Thr Thr Lys
225                 230                 235                 240

Ser Phe Ser Arg Thr Pro Gly Lys
                245

<210> SEQ ID NO 111
<211> LENGTH: 247
<212> TYPE: PRT
<213> ORGANISM: Artificial Sequence
<220> FEATURE:
<223> OTHER INFORMATION: Linker human IgG1 Sequence

<400> SEQUENCE: 111

Gly Gly Gly Gly Ser Gly Gly Gly Gly Ser Gly Gly Gly Gly Ser Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val

```
                    50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                     85                  90                  95

Asn Ser Thr Tyr Arg Val Val Ser Val Leu Thr Val Leu His Gln Asp
                    100                 105                 110

Trp Leu Asn Gly Lys Glu Tyr Lys Cys Lys Val Ser Asn Lys Ala Leu
                115                 120                 125

Pro Ala Pro Ile Glu Lys Thr Ile Ser Lys Ala Lys Gly Gln Pro Arg
            130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 112
<211> LENGTH: 247
<212> TYPE: PRT
<213> ORGANISM: Artificial Sequence
<220> FEATURE:
<223> OTHER INFORMATION: Linker human IgG1 Sequence

<400> SEQUENCE: 112

Gly Gly Gly Gly Ser Gly Gly Gly Ser Gly Gly Gly Gly Ser Glu
 1               5                  10                  15

Pro Lys Ser Ser Asp Lys Thr His Thr Cys Pro Pro Cys Pro Ala Pro
                 20                  25                  30

Glu Leu Leu Gly Gly Pro Cys Val Phe Leu Phe Pro Pro Lys Pro Lys
             35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                     85                  90                  95

Asn Ser Thr Tyr Arg Val Val Ser Val Leu Thr Val Leu His Gln Asp
                    100                 105                 110

Trp Leu Asn Gly Lys Glu Tyr Lys Cys Lys Val Ser Asn Lys Ala Leu
                115                 120                 125

Pro Ala Pro Ile Glu Lys Thr Ile Ser Lys Ala Lys Gly Gln Pro Arg
            130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
```

```
            165                 170                 175
Ile Ala Val Glu Trp Glu Ser Asn Gly Gln Pro Glu Asn Asn Tyr Lys
        180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 113
<211> LENGTH: 247
<212> TYPE: PRT
<213> ORGANISM: Artificial Sequence
<220> FEATURE:
<223> OTHER INFORMATION: Linker human IgG1 Sequence

<400> SEQUENCE: 113

Gly Gly Gly Gly Ser Gly Gly Gly Ser Gly Gly Gly Gly Ser Glu
1               5                   10                  15

Pro Lys Ser Ser Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Cys Leu Ser Pro Gly Lys
                245

<210> SEQ ID NO 114
<211> LENGTH: 252
<212> TYPE: PRT
```

-continued

<213> ORGANISM: Artificial Sequence
<220> FEATURE:
<223> OTHER INFORMATION: Linker human IgG1 Sequence

<400> SEQUENCE: 114

Asp Lys Thr His Thr Cys Pro Pro Cys Pro Ala Pro Glu Leu Leu Gly
1               5                   10                  15

Gly Pro Cys Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Gly Gly Gly Gly Ser Gly Gly Gly Ser
                245                 250

<210> SEQ ID NO 115
<211> LENGTH: 253
<212> TYPE: PRT
<213> ORGANISM: Artificial Sequence
<220> FEATURE:
<223> OTHER INFORMATION: Antibody Sequence

<400> SEQUENCE: 115

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

```
Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Pro Gly Val
            100                 105                 110

Gln Pro Ser Pro Gly Gly Gly Ser Thr Arg Val Asp Gln Thr Pro
            115                 120                 125

Arg Thr Ala Thr Lys Glu Thr Gly Glu Ser Leu Thr Ile Asn Cys Val
            130                 135                 140

Leu Thr Asp Thr Ser Tyr Gly Leu Tyr Ser Thr Ser Trp Phe Arg Lys
145                 150                 155                 160

Asn Pro Gly Thr Thr Asp Trp Glu Arg Met Ser Ile Gly Gly Arg Tyr
                165                 170                 175

Val Glu Ser Val Asn Lys Gly Ala Lys Ser Phe Ser Leu Arg Ile Lys
            180                 185                 190

Asp Leu Thr Val Ala Asp Ser Ala Thr Tyr Tyr Cys Lys Ala Arg Glu
            195                 200                 205

Ala Arg His Pro Trp Leu Arg Gln Trp Tyr Asp Gly Ala Gly Thr Val
            210                 215                 220

Leu Thr Val Asn Gln Ala Cys Lys Ala His His His His His Gly
225                 230                 235                 240

Ala Glu Phe Glu Gln Lys Leu Ile Ser Glu Glu Asp Leu
                245                 250

<210> SEQ ID NO 116
<211> LENGTH: 253
<212> TYPE: PRT
<213> ORGANISM: Artificial Sequence
<220> FEATURE:
<223> OTHER INFORMATION: Antibody Sequence

<400> SEQUENCE: 116

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ser Pro Gly Gly Gly Gly Ser Ala Ser Val Asn Gln Thr Pro Arg Thr
            115                 120                 125

Ala Thr Lys Glu Thr Gly Glu Ser Leu Thr Ile Asn Cys Val Val Thr
            130                 135                 140

Gly Ala Asn Tyr Gly Leu Ala Ala Thr Tyr Trp Tyr Arg Lys Asn Pro
145                 150                 155                 160

Gly Ser Ser Asn Gln Glu Arg Ile Ser Ile Ser Gly Arg Tyr Val Glu
                165                 170                 175

Ser Val Asn Lys Arg Thr Met Ser Phe Ser Leu Arg Ile Lys Asp Leu
            180                 185                 190
```

```
Thr Val Ala Asp Ser Ala Thr Tyr Tyr Cys Lys Ala Tyr Pro Trp Gly
            195                 200                 205

Ala Gly Ala Pro Trp Leu Val Gln Trp Tyr Asp Gly Ala Gly Thr Val
        210                 215                 220

Leu Thr Val Asn Gln Ala Cys Lys Ala His His His His His Gly
225                 230                 235                 240

Ala Glu Phe Glu Gln Lys Leu Ile Ser Glu Glu Asp Leu
                245                 250

<210> SEQ ID NO 117
<211> LENGTH: 256
<212> TYPE: PRT
<213> ORGANISM: Artificial Sequence
<220> FEATURE:
<223> OTHER INFORMATION: Antibody Sequence

<400> SEQUENCE: 117

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Pro Gly Val Gln Pro Ser Pro Gly Gly Gly Ser Thr Arg Val Asp
        115                 120                 125

Gln Thr Pro Arg Thr Ala Thr Lys Glu Thr Gly Glu Ser Leu Thr Ile
    130                 135                 140

Asn Cys Val Leu Thr Asp Thr Ser Tyr Gly Leu Tyr Ser Thr Ser Trp
145                 150                 155                 160

Phe Arg Lys Asn Pro Gly Thr Thr Asp Trp Glu Arg Met Ser Ile Gly
                165                 170                 175

Gly Arg Tyr Val Glu Ser Val Asn Lys Gly Ala Lys Ser Phe Ser Leu
            180                 185                 190

Arg Ile Lys Asp Leu Thr Val Ala Asp Ser Ala Thr Tyr Tyr Cys Lys
        195                 200                 205

Ala Arg Glu Ala Arg His Pro Trp Leu Arg Gln Trp Tyr Asp Gly Ala
    210                 215                 220

Gly Thr Val Leu Thr Val Asn Gln Ala Cys Lys Ala His His His
225                 230                 235                 240

His His Gly Ala Glu Phe Glu Gln Lys Leu Ile Ser Glu Glu Asp Leu
                245                 250                 255

<210> SEQ ID NO 118
<211> LENGTH: 256
<212> TYPE: PRT
<213> ORGANISM: Artificial Sequence
<220> FEATURE:
<223> OTHER INFORMATION: Antibody Sequence

<400> SEQUENCE: 118
```

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
                100                 105                 110

Ser Pro Gly Gly Gly Ser Ala Ser Val Asn Gln Thr Pro Arg Thr
            115                 120                 125

Ala Thr Lys Glu Thr Gly Glu Ser Leu Thr Ile Asn Cys Val Leu Thr
    130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

Ser Val Asn Lys Arg Ala Lys Ser Phe Ser Leu Arg Ile Lys Asp Leu
                180                 185                 190

Thr Val Ala Asp Ser Ala Thr Tyr Tyr Cys Lys Ala Gln Ser Gly Met
                195                 200                 205

Ala Ile Ser Thr Gly Ser Gly His Gly Tyr Asn Trp Tyr Asp Gly Ala
    210                 215                 220

Gly Thr Val Leu Thr Val Asn Gln Ala Cys Lys Ala His His His His
225                 230                 235                 240

His His Gly Ala Glu Phe Glu Gln Lys Leu Ile Ser Glu Glu Asp Leu
                245                 250                 255

<210> SEQ ID NO 119
<211> LENGTH: 258
<212> TYPE: PRT
<213> ORGANISM: Artificial Sequence
<220> FEATURE:
<223> OTHER INFORMATION: Antibody Sequence

<400> SEQUENCE: 119

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Pro Gly Val
                100                 105                 110

Gln Pro Ser Pro Gly Gly Gly Ser Ala Ser Val Asn Gln Thr Pro
                115                 120                 125

Arg Thr Ala Thr Lys Glu Thr Gly Glu Ser Leu Thr Ile Asn Cys Val
            130                 135                 140

Leu Thr Asp Thr Ser Tyr Gly Leu Tyr Ser Thr Ser Trp Phe Arg Lys
145                 150                 155                 160

Asn Pro Gly Thr Thr Asp Trp Glu Arg Met Ser Ile Gly Gly Arg Tyr
                165                 170                 175

Val Glu Ser Val Asn Lys Arg Ala Lys Ser Phe Ser Leu Arg Ile Lys
                180                 185                 190

Asp Leu Thr Val Ala Asp Ser Ala Thr Tyr Tyr Cys Lys Ala Gln Ser
                195                 200                 205

Gly Met Ala Ile Ser Thr Gly Ser Gly His Gly Tyr Asn Trp Tyr Asp
            210                 215                 220

Gly Ala Gly Thr Val Leu Thr Val Asn Gln Ala Cys Lys Ala His His
225                 230                 235                 240

His His His His Gly Ala Glu Phe Glu Gln Lys Leu Ile Ser Glu Glu
                245                 250                 255

Asp Leu

<210> SEQ ID NO 120
<211> LENGTH: 368
<212> TYPE: PRT
<213> ORGANISM: Artificial Sequence
<220> FEATURE:
<223> OTHER INFORMATION: Antibody Sequence

<400> SEQUENCE: 120

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Pro Gly Val
                100                 105                 110

Gln Pro Ser Pro Gly Gly Gly Ser Thr Arg Val Asp Gln Ser Pro
                115                 120                 125

Ser Ser Leu Ser Ala Ser Val Gly Asp Arg Val Thr Ile Thr Cys Val
            130                 135                 140

Leu Thr Asp Thr Ser Tyr Pro Leu Tyr Ser Thr Tyr Trp Tyr Arg Lys
145                 150                 155                 160

Asn Pro Gly Ser Ser Asn Lys Glu Gln Ile Ser Ile Ser Gly Arg Tyr
                165                 170                 175

Ser Glu Ser Val Asn Lys Gly Thr Lys Ser Phe Thr Leu Thr Ile Ser
                180                 185                 190

Ser Leu Gln Pro Glu Asp Ser Ala Thr Tyr Tyr Cys Arg Ala Met Ser
            195                 200                 205

Thr Asn Ile Trp Thr Gly Asp Gly Ala Gly Thr Lys Val Glu Ile Lys
210                 215                 220

Pro Gly Val Gln Pro Ser Pro Gly Gly Gly Ser Thr Arg Val Asp
225                 230                 235                 240

Gln Thr Pro Arg Thr Ala Thr Lys Glu Thr Gly Glu Ser Leu Thr Ile
            245                 250                 255

Asn Cys Val Leu Thr Asp Thr Ser Tyr Gly Leu Tyr Ser Thr Ser Trp
                260                 265                 270

Phe Arg Lys Asn Pro Gly Thr Thr Asp Trp Glu Arg Met Ser Ile Gly
            275                 280                 285

Gly Arg Tyr Val Glu Ser Val Asn Lys Gly Ala Lys Ser Phe Ser Leu
290                 295                 300

Arg Ile Lys Asp Leu Thr Val Ala Asp Ser Ala Thr Tyr Tyr Cys Lys
305                 310                 315                 320

Ala Arg Glu Ala Arg His Pro Trp Leu Arg Gln Trp Tyr Asp Gly Ala
                325                 330                 335

Gly Thr Val Leu Thr Val Asn Gln Ala Cys Lys Ala His His His His
            340                 345                 350

His His Gly Ala Glu Phe Glu Gln Lys Leu Ile Ser Glu Glu Asp Leu
355                 360                 365

<210> SEQ ID NO 121
<211> LENGTH: 368
<212> TYPE: PRT
<213> ORGANISM: Artificial Sequence
<220> FEATURE:
<223> OTHER INFORMATION: Antibody Sequence

<400> SEQUENCE: 121

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Pro Gly Val Gln Pro Ser Pro Gly Gly
            100                 105                 110

Gly Gly Ser Ala Ser Val Asn Gln Thr Pro Arg Thr Ala Thr Lys Glu
        115                 120                 125

Thr Gly Glu Ser Leu Thr Ile Asn Cys Val Val Thr Gly Ala Asn Tyr
130                 135                 140

Gly Leu Ala Ala Thr Tyr Trp Tyr Arg Lys Asn Pro Gly Ser Ser Asn
145                 150                 155                 160

Gln Glu Arg Ile Ser Ile Ser Gly Arg Tyr Val Glu Ser Val Asn Lys
                165                 170                 175

Arg Thr Met Ser Phe Ser Leu Arg Ile Lys Asp Leu Thr Val Ala Asp
            180                 185                 190

Ser Ala Thr Tyr Tyr Cys Lys Ala Tyr Pro Trp Gly Ala Gly Ala Pro
        195                 200                 205

```
Trp Leu Val Gln Trp Tyr Asp Gly Ala Gly Thr Val Leu Thr Val Asn
    210                 215                 220

Pro Gly Val Gln Pro Ser Pro Gly Gly Gly Ser Thr Arg Val Asp
225                 230                 235                 240

Gln Thr Pro Arg Thr Ala Thr Lys Glu Thr Gly Glu Ser Leu Thr Ile
                245                 250                 255

Asn Cys Val Leu Thr Asp Thr Ser Tyr Gly Leu Tyr Ser Thr Ser Trp
                260                 265                 270

Phe Arg Lys Asn Pro Gly Thr Thr Asp Trp Glu Arg Met Ser Ile Gly
                275                 280                 285

Gly Arg Tyr Val Glu Ser Val Asn Lys Gly Ala Lys Ser Phe Ser Leu
            290                 295                 300

Arg Ile Lys Asp Leu Thr Val Ala Asp Ser Ala Thr Tyr Tyr Cys Lys
305                 310                 315                 320

Ala Arg Glu Ala Arg His Pro Trp Leu Arg Gln Trp Tyr Asp Gly Ala
                325                 330                 335

Gly Thr Val Leu Thr Val Asn Gln Ala Cys Lys Ala His His His His
                340                 345                 350

His His Gly Ala Glu Phe Glu Gln Lys Leu Ile Ser Glu Glu Asp Leu
            355                 360                 365

<210> SEQ ID NO 122
<211> LENGTH: 368
<212> TYPE: PRT
<213> ORGANISM: Artificial Sequence
<220> FEATURE:
<223> OTHER INFORMATION: Antibody Sequence

<400> SEQUENCE: 122

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ser Pro Gly Gly Gly Ser Thr Arg Val Asp Gln Ser Pro Ser Ser
            115                 120                 125

Leu Ser Ala Ser Val Gly Asp Arg Val Thr Ile Thr Cys Val Leu Thr
    130                 135                 140

Asp Thr Ser Tyr Pro Leu Tyr Ser Thr Ser Tyr Trp Tyr Arg Lys Asn Pro
145                 150                 155                 160

Gly Ser Ser Asn Lys Glu Gln Ile Ser Ile Ser Gly Arg Tyr Ser Glu
                165                 170                 175

Ser Val Asn Lys Gly Thr Lys Ser Phe Thr Leu Thr Ile Ser Ser Leu
            180                 185                 190

Gln Pro Glu Asp Ser Ala Thr Tyr Tyr Cys Arg Ala Met Ser Thr Asn
    195                 200                 205
```

Ile Trp Thr Gly Asp Gly Ala Gly Thr Lys Val Glu Ile Lys Pro Gly
210                 215                 220

Val Gln Pro Ser Pro Gly Gly Gly Ser Ala Ser Val Asn Gln Thr
225                 230                 235                 240

Pro Arg Thr Ala Thr Lys Glu Thr Gly Glu Ser Leu Thr Ile Asn Cys
                245                 250                 255

Val Val Thr Gly Ala Asn Tyr Gly Leu Ala Thr Tyr Trp Tyr Arg
                260                 265                 270

Lys Asn Pro Gly Ser Ser Asn Gln Glu Arg Ile Ser Ile Ser Gly Arg
                275                 280                 285

Tyr Val Glu Ser Val Asn Lys Arg Thr Met Ser Phe Ser Leu Arg Ile
290                 295                 300

Lys Asp Leu Thr Val Ala Asp Ser Ala Thr Tyr Tyr Cys Lys Ala Tyr
305                 310                 315                 320

Pro Trp Gly Ala Gly Ala Pro Trp Leu Val Gln Trp Tyr Asp Gly Ala
                325                 330                 335

Gly Thr Val Leu Thr Val Asn Gln Ala Cys Lys Ala His His His
                340                 345                 350

His His Gly Ala Glu Phe Glu Gln Lys Leu Ile Ser Glu Glu Asp Leu
                355                 360                 365

<210> SEQ ID NO 123
<211> LENGTH: 371
<212> TYPE: PRT
<213> ORGANISM: Artificial Sequence
<220> FEATURE:
<223> OTHER INFORMATION: Antibody Sequence

<400> SEQUENCE: 123

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
                35                  40                  45

Met Ser Ile Gly Gly Arg Tyr Val Glu Ser Val Asn Lys Arg Ala Lys
                50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
                100                 105                 110

Pro Gly Val Gln Pro Ser Pro Gly Gly Gly Ser Thr Arg Val Asp
                115                 120                 125

Gln Thr Pro Arg Thr Ala Thr Lys Glu Thr Gly Glu Ser Leu Thr Ile
130                 135                 140

Asn Cys Val Leu Thr Asp Thr Ser Tyr Gly Leu Tyr Ser Thr Ser Trp
145                 150                 155                 160

Phe Arg Lys Asn Pro Gly Thr Thr Asp Trp Glu Arg Met Ser Ile Gly
                165                 170                 175

Gly Arg Tyr Val Glu Ser Val Asn Lys Gly Ala Lys Ser Phe Ser Leu
                180                 185                 190

Arg Ile Lys Asp Leu Thr Val Ala Asp Ser Ala Thr Tyr Tyr Cys Lys
                195                 200                 205

Ala Arg Glu Ala Arg His Pro Trp Leu Arg Gln Trp Tyr Asp Gly Ala
            210                 215                 220

Gly Thr Val Leu Thr Val Asn Pro Gly Val Gln Pro Ser Pro Gly Gly
225                 230                 235                 240

Gly Gly Ser Thr Arg Val Asp Gln Ser Pro Ser Ser Leu Ser Ala Ser
                245                 250                 255

Val Gly Asp Arg Val Thr Ile Thr Cys Val Leu Thr Asp Thr Ser Tyr
                260                 265                 270

Pro Leu Tyr Ser Thr Tyr Trp Tyr Arg Lys Asn Pro Gly Ser Ser Asn
            275                 280                 285

Lys Glu Gln Ile Ser Ile Ser Gly Arg Tyr Ser Glu Ser Val Asn Lys
290                 295                 300

Gly Thr Lys Ser Phe Thr Leu Thr Ile Ser Ser Leu Gln Pro Glu Asp
305                 310                 315                 320

Ser Ala Thr Tyr Tyr Cys Arg Ala Met Ser Thr Asn Ile Trp Thr Gly
                325                 330                 335

Asp Gly Ala Gly Thr Lys Val Glu Ile Lys Gln Ala Cys Lys Ala His
                340                 345                 350

His His His His Gly Ala Glu Phe Glu Gln Lys Leu Ile Ser Glu
            355                 360                 365

Glu Asp Leu
    370

<210> SEQ ID NO 124
<211> LENGTH: 371
<212> TYPE: PRT
<213> ORGANISM: Artificial Sequence
<220> FEATURE:
<223> OTHER INFORMATION: Antibody Sequence

<400> SEQUENCE: 124

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Pro Gly Val Gln Pro Ser Pro Gly Gly Gly Ser Thr Arg Val Asp
            115                 120                 125

Gln Ser Pro Ser Ser Leu Ser Ala Ser Val Gly Asp Arg Val Thr Ile
            130                 135                 140

Thr Cys Val Leu Thr Asp Thr Ser Tyr Pro Leu Tyr Ser Thr Tyr Trp
145                 150                 155                 160

Tyr Arg Lys Asn Pro Gly Ser Ser Asn Lys Glu Gln Ile Ser Ile Ser
                165                 170                 175

Gly Arg Tyr Ser Glu Ser Val Asn Lys Gly Thr Lys Ser Phe Thr Leu
            180                 185                 190

```
Thr Ile Ser Ser Leu Gln Pro Glu Asp Ser Ala Thr Tyr Tyr Cys Arg
            195                 200                 205

Ala Met Ser Thr Asn Ile Trp Thr Gly Asp Gly Ala Gly Thr Lys Val
210                 215                 220

Glu Ile Lys Pro Gly Val Gln Pro Ser Pro Gly Gly Gly Gly Ser Thr
225                 230                 235                 240

Arg Val Asp Gln Thr Pro Arg Thr Ala Thr Lys Glu Thr Gly Glu Ser
                245                 250                 255

Leu Thr Ile Asn Cys Val Leu Thr Asp Thr Ser Tyr Gly Leu Tyr Ser
            260                 265                 270

Thr Ser Trp Phe Arg Lys Asn Pro Gly Thr Thr Asp Trp Glu Arg Met
        275                 280                 285

Ser Ile Gly Gly Arg Tyr Val Glu Ser Val Asn Lys Gly Ala Lys Ser
290                 295                 300

Phe Ser Leu Arg Ile Lys Asp Leu Thr Val Ala Asp Ser Ala Thr Tyr
305                 310                 315                 320

Tyr Cys Lys Ala Arg Glu Ala Arg His Pro Trp Leu Arg Gln Trp Tyr
                325                 330                 335

Asp Gly Ala Gly Thr Val Leu Thr Val Asn Gln Ala Cys Lys Ala His
            340                 345                 350

His His His His Gly Ala Glu Phe Glu Gln Lys Leu Ile Ser Glu
        355                 360                 365

Glu Asp Leu
    370

<210> SEQ ID NO 125
<211> LENGTH: 371
<212> TYPE: PRT
<213> ORGANISM: Artificial Sequence
<220> FEATURE:
<223> OTHER INFORMATION: Antibody Sequence

<400> SEQUENCE: 125

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ser Pro Gly Gly Gly Gly Ser Thr Arg Val Asp Gln Ser Pro Ser Ser
        115                 120                 125

Leu Ser Ala Ser Val Gly Asp Arg Val Thr Ile Thr Cys Val Leu Thr
    130                 135                 140

Asp Thr Ser Tyr Pro Leu Tyr Ser Thr Tyr Trp Tyr Arg Lys Asn Pro
145                 150                 155                 160

Gly Ser Ser Asn Lys Glu Gln Ile Ser Ile Ser Gly Arg Tyr Ser Glu
                165                 170                 175
```

```
Ser Val Asn Lys Gly Thr Lys Ser Phe Thr Leu Thr Ile Ser Ser Leu
            180                 185                 190

Gln Pro Glu Asp Ser Ala Thr Tyr Tyr Cys Arg Ala Met Ser Thr Asn
        195                 200                 205

Ile Trp Thr Gly Asp Gly Ala Gly Thr Lys Val Glu Ile Lys Pro Gly
    210                 215                 220

Val Gln Pro Ser Pro Gly Gly Gly Ser Ala Ser Val Asn Gln Thr
225                 230                 235                 240

Pro Arg Thr Ala Thr Lys Glu Thr Gly Glu Ser Leu Thr Ile Asn Cys
                245                 250                 255

Val Leu Thr Asp Thr Ser Tyr Gly Leu Tyr Ser Thr Ser Trp Phe Arg
                260                 265                 270

Lys Asn Pro Gly Thr Thr Asp Trp Glu Arg Met Ser Ile Gly Gly Arg
                275                 280                 285

Tyr Val Glu Ser Val Asn Lys Arg Ala Lys Ser Phe Ser Leu Arg Ile
            290                 295                 300

Lys Asp Leu Thr Val Ala Asp Ser Ala Thr Tyr Tyr Cys Lys Ala Gln
305                 310                 315                 320

Ser Gly Met Ala Ile Ser Thr Gly Ser Gly His Gly Tyr Asn Trp Tyr
                325                 330                 335

Asp Gly Ala Gly Thr Val Leu Thr Val Asn Gln Ala Cys Lys Ala His
                340                 345                 350

His His His His Gly Ala Glu Phe Glu Gln Lys Leu Ile Ser Glu
                355                 360                 365

Glu Asp Leu
    370

<210> SEQ ID NO 126
<211> LENGTH: 371
<212> TYPE: PRT
<213> ORGANISM: Artificial Sequence
<220> FEATURE:
<223> OTHER INFORMATION: Antibody Sequence

<400> SEQUENCE: 126

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ser Pro Gly Gly Gly Gly Ser Ala Ser Val Asn Gln Thr Pro Arg Thr
        115                 120                 125

Ala Thr Lys Glu Thr Gly Glu Ser Leu Thr Ile Asn Cys Val Leu Thr
    130                 135                 140

Asp Thr Ser Tyr Gly Leu Tyr Ser Thr Ser Trp Phe Arg Lys Asn Pro
145                 150                 155                 160
```

Gly Thr Thr Asp Trp Glu Arg Met Ser Ile Gly Gly Arg Tyr Val Glu
            165                 170                 175

Ser Val Asn Lys Arg Ala Lys Ser Phe Ser Leu Arg Ile Lys Asp Leu
        180                 185                 190

Thr Val Ala Asp Ser Ala Thr Tyr Tyr Cys Lys Ala Gln Ser Gly Met
    195                 200                 205

Ala Ile Ser Thr Gly Ser Gly His Gly Tyr Asn Trp Tyr Asp Gly Ala
210                 215                 220

Gly Thr Val Leu Thr Val Asn Pro Gly Val Gln Pro Ser Pro Gly Gly
225                 230                 235                 240

Gly Gly Ser Thr Arg Val Asp Gln Ser Pro Ser Ser Leu Ser Ala Ser
            245                 250                 255

Val Gly Asp Arg Val Thr Ile Thr Cys Val Leu Thr Asp Thr Ser Tyr
        260                 265                 270

Pro Leu Tyr Ser Thr Tyr Trp Tyr Arg Lys Asn Pro Gly Ser Ser Asn
    275                 280                 285

Lys Glu Gln Ile Ser Ile Ser Gly Arg Tyr Ser Glu Ser Val Asn Lys
290                 295                 300

Gly Thr Lys Ser Phe Thr Leu Thr Ile Ser Ser Leu Gln Pro Glu Asp
305                 310                 315                 320

Ser Ala Thr Tyr Tyr Cys Arg Ala Met Ser Thr Asn Ile Trp Thr Gly
            325                 330                 335

Asp Gly Ala Gly Thr Lys Val Glu Ile Lys Gln Ala Cys Lys Ala His
        340                 345                 350

His His His His Gly Ala Glu Phe Glu Gln Lys Leu Ile Ser Glu
    355                 360                 365

Glu Asp Leu
    370

<210> SEQ ID NO 127
<211> LENGTH: 373
<212> TYPE: PRT
<213> ORGANISM: Artificial Sequence
<220> FEATURE:
<223> OTHER INFORMATION: Antibody Sequence

<400> SEQUENCE: 127

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
            85                  90                  95

Gln Trp Tyr Asp Gly Ala Gly Thr Val Leu Thr Val Asn Pro Gly Val
        100                 105                 110

Gln Pro Ser Pro Gly Gly Gly Ser Thr Arg Val Asp Gln Ser Pro
    115                 120                 125

Ser Ser Leu Ser Ala Ser Val Gly Asp Arg Val Thr Ile Thr Cys Val
130                 135                 140

```
Leu Thr Asp Thr Ser Tyr Pro Leu Tyr Ser Thr Tyr Trp Tyr Arg Lys
145                 150                 155                 160

Asn Pro Gly Ser Ser Asn Lys Glu Gln Ile Ser Ile Ser Gly Arg Tyr
                165                 170                 175

Ser Glu Ser Val Asn Lys Gly Thr Lys Ser Phe Thr Leu Thr Ile Ser
            180                 185                 190

Ser Leu Gln Pro Glu Asp Ser Ala Thr Tyr Tyr Cys Arg Ala Met Ser
        195                 200                 205

Thr Asn Ile Trp Thr Gly Asp Gly Ala Gly Thr Lys Val Glu Ile Lys
    210                 215                 220

Pro Gly Val Gln Pro Ser Pro Gly Gly Gly Ser Ala Ser Val Asn
225                 230                 235                 240

Gln Thr Pro Arg Thr Ala Thr Lys Glu Thr Gly Glu Ser Leu Thr Ile
                245                 250                 255

Asn Cys Val Leu Thr Asp Thr Ser Tyr Gly Leu Tyr Ser Thr Ser Trp
            260                 265                 270

Phe Arg Lys Asn Pro Gly Thr Thr Asp Trp Glu Arg Met Ser Ile Gly
        275                 280                 285

Gly Arg Tyr Val Glu Ser Val Asn Lys Arg Ala Lys Ser Phe Ser Leu
    290                 295                 300

Arg Ile Lys Asp Leu Thr Val Ala Asp Ser Ala Thr Tyr Tyr Cys Lys
305                 310                 315                 320

Ala Gln Ser Gly Met Ala Ile Ser Thr Gly Ser Gly His Gly Tyr Asn
                325                 330                 335

Trp Tyr Asp Gly Ala Gly Thr Val Leu Thr Val Asn Gln Ala Cys Lys
            340                 345                 350

Ala His His His His His Gly Ala Glu Phe Glu Gln Lys Leu Ile
        355                 360                 365

Ser Glu Glu Asp Leu
370

<210> SEQ ID NO 128
<211> LENGTH: 373
<212> TYPE: PRT
<213> ORGANISM: Artificial Sequence
<220> FEATURE:
<223> OTHER INFORMATION: Antibody Sequence

<400> SEQUENCE: 128

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Pro Gly Val Gln Pro Ser Pro Gly Gly
            100                 105                 110

Gly Gly Ser Ala Ser Val Asn Gln Thr Pro Arg Thr Ala Thr Lys Glu
        115                 120                 125
```

Thr Gly Glu Ser Leu Thr Ile Asn Cys Val Val Gly Ala Asn Tyr
            130                 135                 140

Gly Leu Ala Ala Thr Tyr Trp Tyr Arg Lys Asn Pro Gly Ser Ser Asn
145                 150                 155                 160

Gln Glu Arg Ile Ser Ile Ser Gly Arg Tyr Val Glu Ser Val Asn Lys
                165                 170                 175

Arg Thr Met Ser Phe Ser Leu Arg Ile Lys Asp Leu Thr Val Ala Asp
            180                 185                 190

Ser Ala Thr Tyr Tyr Cys Lys Ala Tyr Pro Trp Gly Ala Gly Ala Pro
        195                 200                 205

Trp Leu Val Gln Trp Tyr Asp Gly Ala Gly Thr Val Leu Thr Val Asn
    210                 215                 220

Pro Gly Val Gln Pro Ser Pro Gly Gly Gly Ser Ala Ser Val Asn
225                 230                 235                 240

Gln Thr Pro Arg Thr Ala Thr Lys Glu Thr Gly Glu Ser Leu Thr Ile
                245                 250                 255

Asn Cys Val Leu Thr Asp Thr Ser Tyr Gly Leu Tyr Ser Thr Ser Trp
            260                 265                 270

Phe Arg Lys Asn Pro Gly Thr Thr Asp Trp Glu Arg Met Ser Ile Gly
        275                 280                 285

Gly Arg Tyr Val Glu Ser Val Asn Lys Arg Ala Lys Ser Phe Ser Leu
    290                 295                 300

Arg Ile Lys Asp Leu Thr Val Ala Asp Ser Ala Thr Tyr Tyr Cys Lys
305                 310                 315                 320

Ala Gln Ser Gly Met Ala Ile Ser Thr Gly Ser Gly His Gly Tyr Asn
                325                 330                 335

Trp Tyr Asp Gly Ala Gly Thr Val Leu Thr Val Asn Gln Ala Cys Lys
            340                 345                 350

Ala His His His His His Gly Ala Glu Phe Glu Gln Lys Leu Ile
        355                 360                 365

Ser Glu Glu Asp Leu
    370

<210> SEQ ID NO 129
<211> LENGTH: 373
<212> TYPE: PRT
<213> ORGANISM: Artificial Sequence
<220> FEATURE:
<223> OTHER INFORMATION: Antibody Sequence

<400> SEQUENCE: 129

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

```
Pro Gly Val Gln Pro Ser Pro Gly Gly Gly Ser Thr Arg Val Asp
        115                 120                 125

Gln Ser Pro Ser Ser Leu Ser Ala Ser Val Gly Asp Arg Val Thr Ile
130                 135                 140

Thr Cys Val Leu Thr Asp Thr Ser Tyr Pro Leu Tyr Ser Thr Tyr Trp
145                 150                 155                 160

Tyr Arg Lys Asn Pro Gly Ser Ser Asn Lys Glu Gln Ile Ser Ile Ser
                165                 170                 175

Gly Arg Tyr Ser Glu Ser Val Asn Lys Gly Thr Lys Ser Phe Thr Leu
                180                 185                 190

Thr Ile Ser Ser Leu Gln Pro Glu Asp Ser Ala Thr Tyr Tyr Cys Arg
        195                 200                 205

Ala Met Ser Thr Asn Ile Trp Thr Gly Asp Gly Ala Gly Thr Lys Val
        210                 215                 220

Glu Ile Lys Pro Gly Val Gln Pro Ser Pro Gly Gly Gly Ser Ala
225                 230                 235                 240

Ser Val Asn Gln Thr Pro Arg Thr Ala Thr Lys Glu Thr Gly Glu Ser
                245                 250                 255

Leu Thr Ile Asn Cys Val Val Thr Gly Ala Asn Tyr Gly Leu Ala Ala
                260                 265                 270

Thr Tyr Trp Tyr Arg Lys Asn Pro Gly Ser Ser Asn Gln Glu Arg Ile
        275                 280                 285

Ser Ile Ser Gly Arg Tyr Val Glu Ser Val Asn Lys Arg Thr Met Ser
        290                 295                 300

Phe Ser Leu Arg Ile Lys Asp Leu Thr Val Ala Asp Ser Ala Thr Tyr
305                 310                 315                 320

Tyr Cys Lys Ala Tyr Pro Trp Gly Ala Gly Ala Pro Trp Leu Val Gln
                325                 330                 335

Trp Tyr Asp Gly Ala Gly Thr Val Leu Thr Val Asn Gln Ala Cys Lys
                340                 345                 350

Ala His His His His His His Gly Ala Glu Phe Glu Gln Lys Leu Ile
        355                 360                 365

Ser Glu Glu Asp Leu
    370

<210> SEQ ID NO 130
<211> LENGTH: 256
<212> TYPE: PRT
<213> ORGANISM: Artificial Sequence
<220> FEATURE:
<223> OTHER INFORMATION: Antibody Sequence

<400> SEQUENCE: 130

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95
```

His Gly Tyr Asn Trp Tyr Asp Gly Ala Gly Thr Val Leu Thr Val Asn
                100                 105                 110

Pro Gly Val Gln Pro Ala Pro Gly Gly Gly Ser Thr Arg Val Asp
            115                 120                 125

Gln Thr Pro Arg Thr Ala Thr Lys Glu Thr Gly Glu Ser Leu Thr Ile
    130                 135                 140

Asn Cys Val Leu Thr Asp Thr Ser Tyr Gly Leu Tyr Ser Thr Ser Trp
145                 150                 155                 160

Phe Arg Lys Asn Pro Gly Thr Thr Asp Trp Glu Arg Met Ser Ile Gly
                165                 170                 175

Gly Arg Tyr Val Glu Ser Val Asn Lys Gly Ala Lys Ser Phe Ser Leu
            180                 185                 190

Arg Ile Lys Asp Leu Thr Val Ala Asp Ser Ala Thr Tyr Tyr Cys Lys
    195                 200                 205

Ala Arg Glu Ala Arg His Pro Trp Leu Arg Gln Trp Tyr Asp Gly Ala
        210                 215                 220

Gly Thr Val Leu Thr Val Asn Gln Ala Cys Lys Ala His His His
225                 230                 235                 240

His His Gly Ala Glu Phe Glu Gln Lys Leu Ile Ser Glu Glu Asp Leu
                245                 250                 255

<210> SEQ ID NO 131
<211> LENGTH: 371
<212> TYPE: PRT
<213> ORGANISM: Artificial Sequence
<220> FEATURE:
<223> OTHER INFORMATION: Antibody Sequence

<400> SEQUENCE: 131

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
                100                 105                 110

Pro Gly Val Gln Pro Ala Pro Gly Gly Gly Ser Thr Arg Val Asp
            115                 120                 125

Gln Thr Pro Arg Thr Ala Thr Lys Glu Thr Gly Glu Ser Leu Thr Ile
    130                 135                 140

Asn Cys Val Leu Thr Asp Thr Ser Tyr Gly Leu Tyr Ser Thr Ser Trp
145                 150                 155                 160

Phe Arg Lys Asn Pro Gly Thr Thr Asp Trp Glu Arg Met Ser Ile Gly
                165                 170                 175

Gly Arg Tyr Val Glu Ser Val Asn Lys Gly Ala Lys Ser Phe Ser Leu
            180                 185                 190

Arg Ile Lys Asp Leu Thr Val Ala Asp Ser Ala Thr Tyr Tyr Cys Lys
    195                 200                 205

```
Ala Arg Glu Ala Arg His Pro Trp Leu Arg Gln Trp Tyr Asp Gly Ala
    210                 215                 220

Gly Thr Val Leu Thr Val Asn Pro Gly Val Gln Pro Ala Pro Gly Gly
225                 230                 235                 240

Gly Gly Ser Thr Arg Val Asp Gln Ser Pro Ser Ser Leu Ser Ala Ser
                245                 250                 255

Val Gly Asp Arg Val Thr Ile Thr Cys Val Leu Thr Asp Thr Ser Tyr
                260                 265                 270

Pro Leu Tyr Ser Thr Tyr Trp Tyr Arg Lys Asn Pro Gly Ser Ser Asn
            275                 280                 285

Lys Glu Gln Ile Ser Ile Ser Gly Arg Tyr Ser Glu Ser Val Asn Lys
    290                 295                 300

Gly Thr Lys Ser Phe Thr Leu Thr Ile Ser Ser Leu Gln Pro Glu Asp
305                 310                 315                 320

Ser Ala Thr Tyr Tyr Cys Arg Ala Met Ser Thr Asn Ile Trp Thr Gly
                325                 330                 335

Asp Gly Ala Gly Thr Lys Val Glu Ile Lys Ala Cys Lys Ala His
            340                 345                 350

His His His His Gly Ala Glu Phe Glu Gln Lys Leu Ile Ser Glu
        355                 360                 365

Glu Asp Leu
    370

<210> SEQ ID NO 132
<211> LENGTH: 371
<212> TYPE: PRT
<213> ORGANISM: Artificial Sequence
<220> FEATURE:
<223> OTHER INFORMATION: Antibody Sequence

<400> SEQUENCE: 132

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Pro Gly Val Gln Pro Ala Pro Gly Gly Gly Ser Thr Arg Val Asp
        115                 120                 125

Gln Ser Pro Ser Ser Leu Ser Ala Ser Val Gly Asp Arg Val Thr Ile
    130                 135                 140

Thr Cys Val Leu Thr Asp Thr Ser Tyr Pro Leu Tyr Ser Thr Tyr Trp
145                 150                 155                 160

Tyr Arg Lys Asn Pro Gly Ser Ser Asn Lys Glu Gln Ile Ser Ile Ser
                165                 170                 175

Gly Arg Tyr Ser Glu Ser Val Asn Lys Gly Thr Lys Ser Phe Thr Leu
            180                 185                 190
```

-continued

Thr Ile Ser Ser Leu Gln Pro Glu Asp Ser Ala Thr Tyr Tyr Cys Arg
            195                 200                 205

Ala Met Ser Thr Asn Ile Trp Thr Gly Asp Gly Ala Gly Thr Lys Val
    210                 215                 220

Glu Ile Lys Pro Gly Val Gln Pro Ala Pro Gly Gly Gly Ser Thr
225                 230                 235                 240

Arg Val Asp Gln Thr Pro Arg Thr Ala Thr Lys Glu Thr Gly Glu Ser
                245                 250                 255

Leu Thr Ile Asn Cys Val Leu Thr Asp Thr Ser Tyr Gly Leu Tyr Ser
            260                 265                 270

Thr Ser Trp Phe Arg Lys Asn Pro Gly Thr Thr Asp Trp Glu Arg Met
        275                 280                 285

Ser Ile Gly Gly Arg Tyr Val Glu Ser Val Asn Lys Gly Ala Lys Ser
    290                 295                 300

Phe Ser Leu Arg Ile Lys Asp Leu Thr Val Ala Asp Ser Ala Thr Tyr
305                 310                 315                 320

Tyr Cys Lys Ala Arg Glu Ala Arg His Pro Trp Leu Arg Gln Trp Tyr
                325                 330                 335

Asp Gly Ala Gly Thr Val Leu Thr Val Asn Gln Ala Cys Lys Ala His
            340                 345                 350

His His His His Gly Ala Glu Phe Glu Gln Lys Leu Ile Ser Glu
        355                 360                 365

Glu Asp Leu
    370

<210> SEQ ID NO 133
<211> LENGTH: 256
<212> TYPE: PRT
<213> ORGANISM: Artificial Sequence
<220> FEATURE:
<223> OTHER INFORMATION: Antibody Sequence

<400> SEQUENCE: 133

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ala Pro Gly Gly Gly Ser Ala Ser Val Asn Gln Thr Pro Arg Thr
        115                 120                 125

Ala Thr Lys Glu Thr Gly Glu Ser Leu Thr Ile Asn Cys Val Leu Thr
    130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

```
Ser Val Asn Lys Arg Ala Lys Ser Phe Ser Leu Arg Ile Lys Asp Leu
            180                 185                 190

Thr Val Ala Asp Ser Ala Thr Tyr Tyr Cys Lys Ala Gln Ser Gly Met
        195                 200                 205

Ala Ile Ser Thr Gly Ser Gly His Gly Tyr Asn Trp Tyr Asp Gly Ala
    210                 215                 220

Gly Thr Val Leu Thr Val Asn Gln Ala Cys Lys Ala His His His His
225                 230                 235                 240

His His Gly Ala Glu Phe Glu Gln Lys Leu Ile Ser Glu Glu Asp Leu
                245                 250                 255

<210> SEQ ID NO 134
<211> LENGTH: 371
<212> TYPE: PRT
<213> ORGANISM: Artificial Sequence
<220> FEATURE:
<223> OTHER INFORMATION: Antibody Sequence

<400> SEQUENCE: 134

Thr Arg Val Asp Gln Thr Pro Arg Thr Ala Thr Lys Glu Thr Gly Glu
1               5                   10                  15

Ser Leu Thr Ile Asn Cys Val Leu Thr Asp Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ala Pro Gly Gly Gly Ser Thr Arg Val Asp Gln Ser Pro Ser Ser
        115                 120                 125

Leu Ser Ala Ser Val Gly Asp Arg Val Thr Ile Thr Cys Val Leu Thr
    130                 135                 140

Asp Thr Ser Tyr Pro Leu Tyr Ser Thr Tyr Trp Tyr Arg Lys Asn Pro
145                 150                 155                 160

Gly Ser Ser Asn Lys Glu Gln Ile Ser Ile Ser Gly Arg Tyr Ser Glu
                165                 170                 175

Ser Val Asn Lys Gly Thr Lys Ser Phe Thr Leu Thr Ile Ser Ser Leu
            180                 185                 190

Gln Pro Glu Asp Ser Ala Thr Tyr Tyr Cys Arg Ala Met Ser Thr Asn
        195                 200                 205

Ile Trp Thr Gly Asp Gly Ala Gly Thr Lys Val Glu Ile Lys Pro Gly
    210                 215                 220

Val Gln Pro Ala Pro Gly Gly Gly Ser Ala Ser Val Asn Gln Thr
225                 230                 235                 240

Pro Arg Thr Ala Thr Lys Glu Thr Gly Glu Ser Leu Thr Ile Asn Cys
                245                 250                 255

Val Leu Thr Asp Thr Ser Tyr Gly Leu Tyr Ser Thr Ser Trp Phe Arg
            260                 265                 270

Lys Asn Pro Gly Thr Thr Asp Trp Glu Arg Met Ser Ile Gly Gly Arg
        275                 280                 285
```

```
Tyr Val Glu Ser Val Asn Lys Arg Ala Lys Ser Phe Ser Leu Arg Ile
    290                 295                 300

Lys Asp Leu Thr Val Ala Asp Ser Ala Thr Tyr Tyr Cys Lys Ala Gln
305                 310                 315                 320

Ser Gly Met Ala Ile Ser Thr Gly Ser Gly His Gly Tyr Asn Trp Tyr
                325                 330                 335

Asp Gly Ala Gly Thr Val Leu Thr Val Asn Gln Ala Cys Lys Ala His
                340                 345                 350

His His His His His Gly Ala Glu Phe Glu Gln Lys Leu Ile Ser Glu
                355                 360                 365

Glu Asp Leu
    370

<210> SEQ ID NO 135
<211> LENGTH: 371
<212> TYPE: PRT
<213> ORGANISM: Artificial Sequence
<220> FEATURE:
<223> OTHER INFORMATION: Antibody Sequence

<400> SEQUENCE: 135

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
                100                 105                 110

Ala Pro Gly Gly Gly Gly Ser Ala Ser Val Asn Gln Thr Pro Arg Thr
            115                 120                 125

Ala Thr Lys Glu Thr Gly Glu Ser Leu Thr Ile Asn Cys Val Leu Thr
130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

Ser Val Asn Lys Arg Ala Lys Ser Phe Ser Leu Arg Ile Lys Asp Leu
                180                 185                 190

Thr Val Ala Asp Ser Ala Thr Tyr Tyr Cys Lys Ala Gln Ser Gly Met
            195                 200                 205

Ala Ile Ser Thr Gly Ser Gly His Gly Tyr Asn Trp Tyr Asp Gly Ala
            210                 215                 220

Gly Thr Val Leu Thr Val Asn Pro Gly Val Gln Pro Ala Pro Gly Gly
225                 230                 235                 240

Gly Gly Ser Thr Arg Val Asp Gln Ser Pro Ser Ser Leu Ser Ala Ser
                245                 250                 255

Val Gly Asp Arg Val Thr Ile Thr Cys Val Leu Thr Asp Thr Ser Tyr
                260                 265                 270
```

```
Pro Leu Tyr Ser Thr Tyr Trp Tyr Arg Lys Asn Pro Gly Ser Ser Asn
            275                 280                 285

Lys Glu Gln Ile Ser Ile Ser Gly Arg Tyr Ser Glu Ser Val Asn Lys
        290                 295                 300

Gly Thr Lys Ser Phe Thr Leu Thr Ile Ser Ser Leu Gln Pro Glu Asp
305                 310                 315                 320

Ser Ala Thr Tyr Tyr Cys Arg Ala Met Ser Thr Asn Ile Trp Thr Gly
                325                 330                 335

Asp Gly Ala Gly Thr Lys Val Glu Ile Lys Gln Ala Cys Lys Ala His
            340                 345                 350

His His His His His Gly Ala Glu Phe Glu Gln Lys Leu Ile Ser Glu
            355                 360                 365

Glu Asp Leu
    370

<210> SEQ ID NO 136
<211> LENGTH: 366
<212> TYPE: PRT
<213> ORGANISM: Artificial Sequence
<220> FEATURE:
<223> OTHER INFORMATION: Antibody Sequence

<400> SEQUENCE: 136

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ser Pro Gly Gly Gly Gly Ser Thr Arg Val Asp Gln Ser Pro Ser Ser
        115                 120                 125

Leu Ser Ala Ser Val Gly Asp Arg Val Thr Ile Thr Cys Val Leu Thr
130                 135                 140

Asp Thr Ser Tyr Pro Leu Tyr Ser Thr Tyr Trp Tyr Arg Lys Asn Pro
145                 150                 155                 160

Gly Ser Ser Asn Lys Glu Gln Ile Ser Ile Ser Gly Arg Tyr Ser Glu
                165                 170                 175

Ser Val Asn Lys Gly Thr Lys Ser Phe Thr Leu Thr Ile Ser Ser Leu
            180                 185                 190

Gln Pro Glu Asp Ser Ala Thr Tyr Tyr Cys Arg Ala Met Ser Thr Asn
        195                 200                 205

Ile Trp Thr Gly Asp Gly Ala Gly Thr Lys Val Glu Ile Lys Pro Gly
    210                 215                 220

Val Gln Pro Ser Pro Gly Gly Gly Ser Thr Arg Val Asp Gln Thr
225                 230                 235                 240

Pro Arg Thr Ala Thr Lys Glu Thr Gly Glu Ser Leu Thr Ile Asn Cys
                245                 250                 255
```

```
Val Leu Thr Asp Thr Ser Tyr Gly Leu Tyr Ser Thr Ser Trp Phe Arg
                260                 265                 270

Lys Asn Pro Gly Thr Thr Asp Trp Glu Arg Met Ser Ile Gly Gly Arg
                275                 280                 285

Tyr Val Glu Ser Val Asn Lys Gly Ala Lys Ser Phe Ser Leu Arg Ile
                290                 295                 300

Lys Asp Leu Thr Val Ala Asp Ser Ala Thr Tyr Tyr Cys Lys Ala Arg
305                 310                 315                 320

Glu Ala Arg His Pro Trp Leu Arg Gln Trp Tyr Asp Gly Ala Gly Thr
                325                 330                 335

Val Leu Thr Val Asn Gln Ala Cys Lys Ala His His His His His His
                340                 345                 350

Gly Ala Glu Phe Glu Gln Lys Leu Ile Ser Glu Glu Asp Leu
                355                 360                 365

<210> SEQ ID NO 137
<211> LENGTH: 366
<212> TYPE: PRT
<213> ORGANISM: Artificial Sequence
<220> FEATURE:
<223> OTHER INFORMATION: Antibody Sequence

<400> SEQUENCE: 137

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
                35                  40                  45

Ile Ser Ile Ser Gly Arg Tyr Ser Glu Ser Val Asn Lys Gly Thr Lys
            50                  55                  60

Ser Phe Thr Leu Thr Ile Ser Ser Leu Gln Pro Glu Asp Ser Ala Thr
65              70                  75                  80

Tyr Tyr Cys Arg Ala Met Ser Thr Asn Ile Trp Thr Gly Asp Gly Ala
                85                  90                  95

Gly Thr Lys Val Glu Ile Lys Pro Gly Val Gln Pro Ser Pro Gly Gly
                100                 105                 110

Gly Gly Ser Thr Arg Val Asp Gln Thr Pro Arg Thr Ala Thr Lys Glu
            115                 120                 125

Thr Gly Glu Ser Leu Thr Ile Asn Cys Val Leu Thr Asp Thr Ser Tyr
130                 135                 140

Gly Leu Tyr Ser Thr Ser Trp Phe Arg Lys Asn Pro Gly Thr Thr Asp
145                 150                 155                 160

Trp Glu Arg Met Ser Ile Gly Gly Arg Tyr Val Glu Ser Val Asn Lys
                165                 170                 175

Gly Ala Lys Ser Phe Ser Leu Arg Ile Lys Asp Leu Thr Val Ala Asp
                180                 185                 190

Ser Ala Thr Tyr Tyr Cys Lys Ala Arg Glu Ala Arg His Pro Trp Leu
                195                 200                 205

Arg Gln Trp Tyr Asp Gly Ala Gly Thr Val Leu Thr Val Asn Pro Gly
                210                 215                 220

Val Gln Pro Ser Pro Gly Gly Gly Ser Thr Arg Val Asp Gln Thr
225                 230                 235                 240

Pro Arg Thr Ala Thr Lys Glu Thr Gly Glu Ser Leu Thr Ile Asn Cys
                245                 250                 255
```

Val Leu Thr Asp Thr Ser Tyr Gly Leu Tyr Ser Thr Ser Trp Phe Arg
            260                 265                 270

Lys Asn Pro Gly Thr Thr Asp Trp Glu Arg Met Ser Ile Gly Gly Arg
            275                 280                 285

Tyr Val Glu Ser Val Asn Lys Gly Ala Lys Ser Phe Ser Leu Arg Ile
            290                 295                 300

Lys Asp Leu Thr Val Ala Asp Ser Ala Thr Tyr Tyr Cys Lys Ala Arg
305                 310                 315                 320

Glu Ala Arg His Pro Trp Leu Arg Gln Trp Tyr Asp Gly Ala Gly Thr
            325                 330                 335

Val Leu Thr Val Asn Gln Ala Cys Lys Ala His His His His His His
            340                 345                 350

Gly Ala Glu Phe Glu Gln Lys Leu Ile Ser Glu Glu Asp Leu
            355                 360                 365

<210> SEQ ID NO 138
<211> LENGTH: 251
<212> TYPE: PRT
<213> ORGANISM: Artificial Sequence
<220> FEATURE:
<223> OTHER INFORMATION: Antibody Sequence

<400> SEQUENCE: 138

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
            85                  90                  95

Tyr Asp Gly Ala Gly Thr Val Leu Thr Val Asn Pro Gly Val Gln Pro
            100                 105                 110

Ser Pro Gly Gly Gly Ser Thr Arg Val Asp Gln Thr Pro Arg Thr
            115                 120                 125

Ala Thr Lys Glu Thr Gly Glu Ser Leu Thr Ile Asn Cys Val Leu Thr
        130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
            165                 170                 175

Ser Val Asn Lys Gly Ala Lys Ser Phe Ser Leu Arg Ile Lys Asp Leu
            180                 185                 190

Thr Val Ala Asp Ser Ala Thr Tyr Tyr Cys Lys Ala Gln Ser Leu Ala
            195                 200                 205

Ile Ser Thr Arg Ser Tyr Trp Tyr Asp Gly Ala Gly Thr Val Leu Thr
            210                 215                 220

Val Asn Gln Ala Cys Lys Ala His His His His His His Gly Ala Glu
225                 230                 235                 240

Phe Glu Gln Lys Leu Ile Ser Glu Glu Asp Leu
            245                 250

<210> SEQ ID NO 139
<211> LENGTH: 366
<212> TYPE: PRT
<213> ORGANISM: Artificial Sequence
<220> FEATURE:
<223> OTHER INFORMATION: Antibody Sequence

<400> SEQUENCE: 139

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn Pro Gly Val Gln Pro
            100                 105                 110

Ser Pro Gly Gly Gly Gly Ser Thr Arg Val Asp Gln Ser Pro Ser Ser
        115                 120                 125

Leu Ser Ala Ser Val Gly Asp Arg Val Thr Ile Thr Cys Val Leu Thr
130                 135                 140

Asp Thr Ser Tyr Pro Leu Tyr Ser Thr Tyr Trp Tyr Arg Lys Asn Pro
145                 150                 155                 160

Gly Ser Ser Asn Lys Glu Gln Ile Ser Ile Ser Gly Arg Tyr Ser Glu
                165                 170                 175

Ser Val Asn Lys Gly Thr Lys Ser Phe Thr Leu Thr Ile Ser Ser Leu
            180                 185                 190

Gln Pro Glu Asp Ser Ala Thr Tyr Tyr Cys Arg Ala Met Ser Thr Asn
        195                 200                 205

Ile Trp Thr Gly Asp Gly Ala Gly Thr Lys Val Glu Ile Lys Pro Gly
    210                 215                 220

Val Gln Pro Ser Pro Gly Gly Gly Gly Ser Thr Arg Val Asp Gln Thr
225                 230                 235                 240

Pro Arg Thr Ala Thr Lys Glu Thr Gly Glu Ser Leu Thr Ile Asn Cys
                245                 250                 255

Val Leu Thr Asp Thr Ser Tyr Gly Leu Tyr Ser Thr Ser Trp Phe Arg
            260                 265                 270

Lys Asn Pro Gly Thr Thr Asp Trp Glu Arg Met Ser Ile Gly Gly Arg
        275                 280                 285

Tyr Val Glu Ser Val Asn Lys Gly Ala Lys Ser Phe Ser Leu Arg Ile
    290                 295                 300

Lys Asp Leu Thr Val Ala Asp Ser Ala Thr Tyr Tyr Cys Lys Ala Gln
305                 310                 315                 320

Ser Leu Ala Ile Ser Thr Arg Ser Tyr Trp Tyr Asp Gly Ala Gly Thr
                325                 330                 335

Val Leu Thr Val Asn Gln Ala Cys Lys Ala His His His His His His
            340                 345                 350

Gly Ala Glu Phe Glu Gln Lys Leu Ile Ser Glu Glu Asp Leu
        355                 360                 365
```

```
<210> SEQ ID NO 140
<211> LENGTH: 250
<212> TYPE: PRT
<213> ORGANISM: Artificial Sequence
<220> FEATURE:
<223> OTHER INFORMATION: Antibody Sequence

<400> SEQUENCE: 140

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Ser Ala Thr
65              70                  75                  80

Tyr Tyr Cys Arg Ala Met Ser Thr Asn Ile Trp Thr Gly Asp Gly Ala
                85                  90                  95

Gly Thr Lys Val Glu Ile Lys Pro Gly Val Gln Pro Ser Pro Gly Gly
            100                 105                 110

Gly Gly Gly Ser Ala Ser Val Asn Gln Thr Pro Arg Thr Ala Thr Lys
        115                 120                 125

Glu Thr Gly Glu Ser Leu Thr Ile Asn Cys Val Val Thr Gly Ala Asn
130             135                 140

Tyr Gly Leu Ala Ala Thr Tyr Trp Tyr Arg Lys Asn Pro Gly Ser Ser
145             150                 155                 160

Asn Gln Glu Arg Ile Ser Ile Ser Gly Arg Tyr Val Glu Ser Val Asn
                165                 170                 175

Lys Arg Thr Met Ser Phe Ser Leu Arg Ile Lys Asp Leu Thr Val Ala
            180                 185                 190

Asp Ser Ala Thr Tyr Tyr Cys Lys Ala Tyr Pro Trp Gly Ala Gly Ala
        195                 200                 205

Pro Trp Leu Val Gln Trp Tyr Asp Gly Ala Gly Thr Val Leu Thr Val
    210                 215                 220

Asn Gln Ala Cys Gly Ala His His His His His Gly Ala Glu Phe
225             230                 235                 240

Glu Gln Lys Leu Ile Ser Glu Glu Asp Leu
                245                 250

<210> SEQ ID NO 141
<211> LENGTH: 250
<212> TYPE: PRT
<213> ORGANISM: Artificial Sequence
<220> FEATURE:
<223> OTHER INFORMATION: Antibody Sequence

<400> SEQUENCE: 141

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60
```

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Pro Gly Val Gln Pro Ala Pro Gly Gly
            100                 105                 110

Gly Gly Gly Ser Ala Ser Val Asn Gln Thr Pro Arg Thr Ala Thr Lys
        115                 120                 125

Glu Thr Gly Glu Ser Leu Thr Ile Asn Cys Val Val Thr Gly Ala Asn
    130                 135                 140

Tyr Gly Leu Ala Ala Thr Tyr Trp Tyr Arg Lys Asn Pro Gly Ser Ser
145                 150                 155                 160

Asn Gln Glu Arg Ile Ser Ile Ser Gly Arg Tyr Val Glu Ser Val Asn
                165                 170                 175

Lys Arg Thr Met Ser Phe Ser Leu Arg Ile Lys Asp Leu Thr Val Ala
            180                 185                 190

Asp Ser Ala Thr Tyr Tyr Cys Lys Ala Tyr Pro Trp Gly Ala Gly Ala
        195                 200                 205

Pro Trp Leu Val Gln Trp Tyr Asp Gly Ala Gly Thr Val Leu Thr Val
    210                 215                 220

Asn Gln Ala Cys Gly Ala His His His His His Gly Ala Glu Phe
225                 230                 235                 240

Glu Gln Lys Leu Ile Ser Glu Glu Asp Leu
                245                 250

<210> SEQ ID NO 142
<211> LENGTH: 250
<212> TYPE: PRT
<213> ORGANISM: Artificial Sequence
<220> FEATURE:
<223> OTHER INFORMATION: Antibody Sequence

<400> SEQUENCE: 142

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Pro Gly Val Gln Pro Ser Pro Gly Gly
            100                 105                 110

Gly Gly Gly Ser Ala Ser Val Asn Gln Thr Pro Arg Thr Ala Thr Lys
        115                 120                 125

Glu Thr Gly Glu Ser Leu Thr Ile Asn Cys Val Val Thr Gly Ala Asn
    130                 135                 140

Tyr Gly Leu Ala Ala Thr Tyr Trp Tyr Arg Lys Asn Pro Gly Ser Ser
145                 150                 155                 160

Asn Gln Glu Arg Ile Ser Ile Ser Gly Arg Tyr Val Glu Ser Val Asn
                165                 170                 175

```
Lys Arg Thr Met Ser Phe Ser Leu Arg Ile Lys Asp Leu Thr Val Ala
            180                 185                 190

Asp Ser Ala Thr Tyr Tyr Cys Lys Ala Tyr Pro Trp Gly Ala Gly Ala
            195                 200                 205

Pro Trp Leu Val Gln Trp Tyr Asp Gly Ala Gly Thr Val Leu Thr Val
            210                 215                 220

Asn Gln Ala Ser Gly Ala His His His His His Gly Ala Glu Phe
225             230                 235                 240

Glu Gln Lys Leu Ile Ser Glu Glu Asp Leu
                245                 250

<210> SEQ ID NO 143
<211> LENGTH: 250
<212> TYPE: PRT
<213> ORGANISM: Artificial Sequence
<220> FEATURE:
<223> OTHER INFORMATION: Antibody Sequence

<400> SEQUENCE: 143

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
            85                  90                  95

Gly Thr Lys Val Glu Ile Lys Pro Gly Val Gln Pro Ala Pro Gly Gly
            100                 105                 110

Gly Gly Gly Ser Ala Ser Val Asn Gln Thr Pro Arg Thr Ala Thr Lys
            115                 120                 125

Glu Thr Gly Glu Ser Leu Thr Ile Asn Cys Val Val Thr Gly Ala Asn
            130                 135                 140

Tyr Gly Leu Ala Ala Thr Tyr Trp Tyr Arg Lys Asn Pro Gly Ser Ser
145                 150                 155                 160

Asn Gln Glu Arg Ile Ser Ile Ser Gly Arg Tyr Val Glu Ser Val Asn
            165                 170                 175

Lys Arg Thr Met Ser Phe Ser Leu Arg Ile Lys Asp Leu Thr Val Ala
            180                 185                 190

Asp Ser Ala Thr Tyr Tyr Cys Lys Ala Tyr Pro Trp Gly Ala Gly Ala
            195                 200                 205

Pro Trp Leu Val Gln Trp Tyr Asp Gly Ala Gly Thr Val Leu Thr Val
            210                 215                 220

Asn Gln Ala Ser Gly Ala His His His His His Gly Ala Glu Phe
225             230                 235                 240

Glu Gln Lys Leu Ile Ser Glu Glu Asp Leu
                245                 250

<210> SEQ ID NO 144
<211> LENGTH: 271
<212> TYPE: PRT
<213> ORGANISM: Artificial Sequence
```

<220> FEATURE:
<223> OTHER INFORMATION: Antibody Sequence

<400> SEQUENCE: 144

```
Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Gly Gly Gly Gly Ser Gly Gly Gly Gly Ser Gly Gly Gly Gly
        115                 120                 125

Ser Gly Gly Gly Gly Ser Ala Ser Val Asn Gln Thr Pro Arg Thr Ala
    130                 135                 140

Thr Lys Glu Thr Gly Glu Ser Leu Thr Ile Asn Cys Val Leu Thr Asp
145                 150                 155                 160

Thr Ser Tyr Gly Leu Tyr Ser Thr Ser Trp Phe Arg Lys Asn Pro Gly
                165                 170                 175

Thr Thr Asp Trp Glu Arg Met Ser Ile Gly Gly Arg Tyr Val Glu Ser
            180                 185                 190

Val Asn Lys Arg Ala Lys Ser Phe Ser Leu Arg Ile Lys Asp Leu Thr
        195                 200                 205

Val Ala Asp Ser Ala Thr Tyr Tyr Cys Lys Ala Gln Ser Gly Met Ala
    210                 215                 220

Ile Ser Thr Gly Ser Gly His Gly Tyr Asn Trp Tyr Asp Gly Ala Gly
225                 230                 235                 240

Thr Val Leu Thr Val Asn Gln Ala Ser Gly Ala His His His His His
                245                 250                 255

His Gly Ala Glu Phe Glu Gln Lys Leu Ile Ser Glu Glu Asp Leu
            260                 265                 270
```

<210> SEQ ID NO 145
<211> LENGTH: 269
<212> TYPE: PRT
<213> ORGANISM: Artificial Sequence
<220> FEATURE:
<223> OTHER INFORMATION: Antibody Sequence

<400> SEQUENCE: 145

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
```

```
                65                  70                  75                  80
Tyr Tyr Cys Lys Ala Gln Ser Gly Met Ala Ile Ser Thr Gly Ser Gly
                    85                  90                  95

His Gly Tyr Asn Trp Tyr Asp Gly Ala Gly Thr Val Leu Thr Val Asn
                100                 105                 110

Gly Gly Gly Gly Ser Gly Gly Gly Ser Gly Gly Gly Ser Gly
            115                 120                 125

Gly Gly Gly Ser Gly Gly Gly Ser Thr Arg Val Asp Gln Thr Pro
        130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
                180                 185                 190

Val Glu Ser Val Asn Lys Gly Ala Lys Ser Phe Ser Leu Arg Ile Lys
                195                 200                 205

Asp Leu Thr Val Ala Asp Ser Ala Thr Tyr Tyr Cys Lys Ala Arg Glu
            210                 215                 220

Ala Arg His Pro Trp Leu Arg Gln Trp Tyr Asp Gly Ala Gly Thr Val
225                 230                 235                 240

Leu Thr Val Asn Gln Ala Ser Gly Ala His His His His His Gly
                245                 250                 255

Ala Glu Phe Glu Gln Lys Leu Ile Ser Glu Glu Asp Leu
                260                 265
```

<210> SEQ ID NO 146
<211> LENGTH: 269
<212> TYPE: PRT
<213> ORGANISM: Artificial Sequence
<220> FEATURE:
<223> OTHER INFORMATION: Antibody Sequence

<400> SEQUENCE: 146

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
                35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
                100                 105                 110

Gly Gly Gly Gly Ser Gly Gly Gly Gly Ser Gly Gly Gly Gly Ser Gly
            115                 120                 125

Gly Gly Ser Ala Ser Val Asn Gln Thr Pro Arg Thr Ala Thr Lys
        130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
```

```
                165                 170                 175
Asp Trp Glu Arg Met Ser Ile Gly Gly Arg Tyr Val Glu Ser Val Asn
            180                 185                 190

Lys Arg Ala Lys Ser Phe Ser Leu Arg Ile Lys Asp Leu Thr Val Ala
        195                 200                 205

Asp Ser Ala Thr Tyr Tyr Cys Lys Ala Gln Ser Gly Met Ala Ile Ser
    210                 215                 220

Thr Gly Ser Gly His Gly Tyr Asn Trp Tyr Asp Gly Ala Gly Thr Val
225                 230                 235                 240

Leu Thr Val Asn Gln Ala Ser Gly Ala His His His His His His Gly
                245                 250                 255

Ala Glu Phe Glu Gln Lys Leu Ile Ser Glu Glu Asp Leu
            260                 265

<210> SEQ ID NO 147
<211> LENGTH: 271
<212> TYPE: PRT
<213> ORGANISM: Artificial Sequence
<220> FEATURE:
<223> OTHER INFORMATION: Antibody Sequence

<400> SEQUENCE: 147

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Gly Ser Gly
        115                 120                 125

Gly Gly Gly Ser Gly Gly Gly Ser Ala Ser Val Asn Gln Thr Pro
    130                 135                 140

Arg Thr Ala Thr Lys Glu Thr Gly Glu Ser Leu Thr Ile Asn Cys Val
145                 150                 155                 160

Val Thr Gly Ala Asn Tyr Gly Leu Ala Ala Thr Tyr Trp Tyr Arg Lys
                165                 170                 175

Asn Pro Gly Ser Ser Asn Gln Glu Arg Ile Ser Ile Ser Gly Arg Tyr
            180                 185                 190

Val Glu Ser Val Asn Lys Arg Thr Met Ser Phe Ser Leu Arg Ile Lys
        195                 200                 205

Asp Leu Thr Val Ala Asp Ser Ala Thr Tyr Tyr Cys Lys Ala Tyr Pro
    210                 215                 220

Trp Gly Ala Gly Ala Pro Trp Leu Val Gln Trp Tyr Asp Gly Ala Gly
225                 230                 235                 240

Thr Val Leu Thr Val Asn Gln Ala Cys Gly Ala His His His His
                245                 250                 255

His Gly Ala Glu Phe Glu Gln Lys Leu Ile Ser Glu Glu Asp Leu
```

<210> SEQ ID NO 148
<211> LENGTH: 271
<212> TYPE: PRT
<213> ORGANISM: Artificial Sequence
<220> FEATURE:
<223> OTHER INFORMATION: Antibody Sequence

<400> SEQUENCE: 148

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Gly Gly Gly Gly Ser Gly Gly Gly Gly Ser Gly Gly Gly Gly
            115                 120                 125

Ser Gly Gly Gly Gly Ser Ala Ser Val Asn Gln Thr Pro Arg Thr Ala
        130                 135                 140

Thr Lys Glu Thr Gly Glu Ser Leu Thr Ile Asn Cys Val Leu Thr Asp
145                 150                 155                 160

Thr Ser Tyr Gly Leu Tyr Ser Thr Ser Trp Phe Arg Lys Asn Pro Gly
                165                 170                 175

Thr Thr Asp Trp Glu Arg Met Ser Ile Gly Gly Arg Tyr Val Glu Ser
            180                 185                 190

Val Asn Lys Arg Ala Lys Ser Phe Ser Leu Arg Ile Lys Asp Leu Thr
        195                 200                 205

Val Ala Asp Ser Ala Thr Tyr Tyr Cys Lys Ala Gln Ser Gly Met Ala
    210                 215                 220

Ile Ser Thr Gly Ser Gly His Gly Tyr Asn Trp Tyr Asp Gly Ala Gly
225                 230                 235                 240

Thr Val Leu Thr Val Asn Gln Ala Cys Gly Ala His His His His
                245                 250                 255

His Gly Ala Glu Phe Glu Gln Lys Leu Ile Ser Glu Glu Asp Leu
            260                 265                 270

<210> SEQ ID NO 149
<211> LENGTH: 269
<212> TYPE: PRT
<213> ORGANISM: Artificial Sequence
<220> FEATURE:
<223> OTHER INFORMATION: Antibody Sequence

<400> SEQUENCE: 149

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

```
Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Val Leu Thr Val Asn
                100                 105                 110

Gly Gly Gly Gly Ser Gly Gly Gly Ser Gly Gly Gly Ser Gly
            115                 120                 125

Gly Gly Gly Ser Gly Gly Gly Ser Thr Arg Val Asp Gln Thr Pro
            130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
                180                 185                 190

Val Glu Ser Val Asn Lys Gly Ala Lys Ser Phe Ser Leu Arg Ile Lys
                195                 200                 205

Asp Leu Thr Val Ala Asp Ser Ala Thr Tyr Tyr Cys Lys Ala Arg Glu
            210                 215                 220

Ala Arg His Pro Trp Leu Arg Gln Trp Tyr Asp Gly Ala Gly Thr Val
225                 230                 235                 240

Leu Thr Val Asn Gln Ala Cys Gly Ala His His His His His His Gly
                245                 250                 255

Ala Glu Phe Glu Gln Lys Leu Ile Ser Glu Glu Asp Leu
            260                 265

<210> SEQ ID NO 150
<211> LENGTH: 269
<212> TYPE: PRT
<213> ORGANISM: Artificial Sequence
<220> FEATURE:
<223> OTHER INFORMATION: Antibody Sequence

<400> SEQUENCE: 150

Thr Arg Val Asp Gln Thr Pro Arg Thr Ala Thr Lys Glu Thr Gly Glu
 1                   5                  10                  15

Ser Leu Thr Ile Asn Cys Val Leu Thr Asp Thr Ser Tyr Gly Leu Tyr
                 20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Gly Gly Gly Gly Ser
                100                 105                 110

Gly Gly Gly Gly Ser Gly Gly Gly Ser Gly Gly Gly Gly Ser Gly
            115                 120                 125
```

```
Gly Gly Gly Ser Ala Ser Val Asn Gln Thr Pro Arg Thr Ala Thr Lys
        130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                    165                 170                 175

Asp Trp Glu Arg Met Ser Ile Gly Gly Arg Tyr Val Glu Ser Val Asn
                180                 185                 190

Lys Arg Ala Lys Ser Phe Ser Leu Arg Ile Lys Asp Leu Thr Val Ala
                195                 200                 205

Asp Ser Ala Thr Tyr Tyr Cys Lys Ala Gln Ser Gly Met Ala Ile Ser
210                 215                 220

Thr Gly Ser Gly His Gly Tyr Asn Trp Tyr Asp Gly Ala Gly Thr Val
225                 230                 235                 240

Leu Thr Val Asn Gln Ala Cys Gly Ala His His His His His His Gly
                    245                 250                 255

Ala Glu Phe Glu Gln Lys Leu Ile Ser Glu Glu Asp Leu
                260                 265

<210> SEQ ID NO 151
<211> LENGTH: 394
<212> TYPE: PRT
<213> ORGANISM: Artificial Sequence
<220> FEATURE:
<223> OTHER INFORMATION: Antibody Sequence

<400> SEQUENCE: 151

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
                100                 105                 110

Gly Ser Gly Gly Gly Ser Gly Gly Gly Ser Gly Gly Gly
            115                 120                 125

Ser Gly Gly Gly Gly Ser Thr Arg Val Asp Gln Ser Pro Ser Ser Leu
        130                 135                 140

Ser Ala Ser Val Gly Asp Arg Val Thr Ile Thr Cys Val Leu Thr Asp
145                 150                 155                 160

Thr Ser Tyr Pro Leu Tyr Ser Thr Ser Trp Tyr Arg Lys Asn Pro Gly
                    165                 170                 175

Ser Ser Asn Lys Glu Gln Ile Ser Ile Ser Gly Arg Tyr Ser Glu Ser
                180                 185                 190

Val Asn Lys Gly Thr Lys Ser Phe Thr Leu Thr Ile Ser Ser Leu Gln
                195                 200                 205

Pro Glu Asp Ser Ala Thr Tyr Tyr Cys Arg Ala Met Ser Thr Asn Ile
210                 215                 220
```

Trp Thr Gly Asp Gly Ala Gly Thr Lys Val Glu Ile Lys Gly Gly Gly
225                 230                 235                 240

Gly Ser Gly Gly Gly Ser Gly Gly Gly Ser Gly Gly Gly
            245                 250                 255

Ser Gly Gly Gly Ser Thr Arg Val Asp Gln Thr Pro Arg Thr Ala
            260                 265                 270

Thr Lys Glu Thr Gly Glu Ser Leu Thr Ile Asn Cys Val Leu Thr Asp
            275                 280                 285

Thr Ser Tyr Gly Leu Tyr Ser Thr Ser Trp Phe Arg Lys Asn Pro Gly
            290                 295                 300

Thr Thr Asp Trp Glu Arg Met Ser Ile Gly Gly Arg Tyr Val Glu Ser
305                 310                 315                 320

Val Asn Lys Gly Ala Lys Ser Phe Ser Leu Arg Ile Lys Asp Leu Thr
                325                 330                 335

Val Ala Asp Ser Ala Thr Tyr Tyr Cys Lys Ala Arg Glu Ala Arg His
                340                 345                 350

Pro Trp Leu Arg Gln Trp Tyr Asp Gly Ala Gly Thr Val Leu Thr Val
            355                 360                 365

Asn Gln Ala Ser Gly Ala His His His His His Gly Ala Glu Phe
            370                 375                 380

Glu Gln Lys Leu Ile Ser Glu Glu Asp Leu
385                 390

<210> SEQ ID NO 152
<211> LENGTH: 399
<212> TYPE: PRT
<213> ORGANISM: Artificial Sequence
<220> FEATURE:
<223> OTHER INFORMATION: Antibody Sequence

<400> SEQUENCE: 152

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Gly Gly Gly Gly Ser Gly Gly Gly Ser Gly Gly Gly Gly
            115                 120                 125

Ser Gly Gly Gly Gly Ser Thr Arg Val Asp Gln Ser Pro Ser Ser Leu
            130                 135                 140

Ser Ala Ser Val Gly Asp Arg Val Thr Ile Thr Cys Val Leu Thr Asp
145                 150                 155                 160

Thr Ser Tyr Pro Leu Tyr Ser Thr Tyr Trp Tyr Arg Lys Asn Pro Gly
            165                 170                 175

Ser Ser Asn Lys Glu Gln Ile Ser Ile Ser Gly Arg Tyr Ser Glu Ser
            180                 185                 190

```
Val Asn Lys Gly Thr Lys Ser Phe Thr Leu Thr Ile Ser Ser Leu Gln
            195                 200                 205

Pro Glu Asp Ser Ala Thr Tyr Tyr Cys Arg Ala Met Ser Thr Asn Ile
    210                 215                 220

Trp Thr Gly Asp Gly Ala Gly Thr Lys Val Glu Ile Lys Gly Gly Gly
225                 230                 235                 240

Gly Ser Gly Gly Gly Ser Gly Gly Gly Ser Gly Gly Gly Gly
                245                 250                 255

Ser Gly Gly Gly Ser Ala Ser Val Asn Gln Thr Pro Arg Thr Ala
                260                 265                 270

Thr Lys Glu Thr Gly Glu Ser Leu Thr Ile Asn Cys Val Leu Thr Asp
        275                 280                 285

Thr Ser Tyr Gly Leu Tyr Ser Thr Ser Trp Phe Arg Lys Asn Pro Gly
        290                 295                 300

Thr Thr Asp Trp Glu Arg Met Ser Ile Gly Gly Arg Tyr Val Glu Ser
305                 310                 315                 320

Val Asn Lys Arg Ala Lys Ser Phe Ser Leu Arg Ile Lys Asp Leu Thr
                325                 330                 335

Val Ala Asp Ser Ala Thr Tyr Tyr Cys Lys Ala Gln Ser Gly Met Ala
                340                 345                 350

Ile Ser Thr Gly Ser Gly His Gly Tyr Asn Trp Tyr Asp Gly Ala Gly
            355                 360                 365

Thr Val Leu Thr Val Asn Gln Ala Ser Gly Ala His His His His
            370                 375                 380

His Gly Ala Glu Phe Glu Gln Lys Leu Ile Ser Glu Glu Asp Leu
385                 390                 395

<210> SEQ ID NO 153
<211> LENGTH: 399
<212> TYPE: PRT
<213> ORGANISM: Artificial Sequence
<220> FEATURE:
<223> OTHER INFORMATION: Antibody Sequence

<400> SEQUENCE: 153

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Gly Ser Gly
            115                 120                 125

Gly Gly Ser Gly Gly Gly Ser Thr Arg Val Asp Gln Ser Pro
    130                 135                 140

Ser Ser Leu Ser Ala Ser Val Gly Asp Arg Val Thr Ile Thr Cys Val
145                 150                 155                 160
```

-continued

```
Leu Thr Asp Thr Ser Tyr Pro Leu Tyr Ser Thr Tyr Trp Tyr Arg Lys
                165                 170                 175

Asn Pro Gly Ser Ser Asn Lys Glu Gln Ile Ser Ile Ser Gly Arg Tyr
            180                 185                 190

Ser Glu Ser Val Asn Lys Gly Thr Lys Ser Phe Thr Leu Thr Ile Ser
        195                 200                 205

Ser Leu Gln Pro Glu Asp Ser Ala Thr Tyr Tyr Cys Arg Ala Met Ser
    210                 215                 220

Thr Asn Ile Trp Thr Gly Asp Gly Ala Gly Thr Lys Val Glu Ile Lys
225                 230                 235                 240

Gly Gly Gly Gly Ser Gly Gly Gly Ser Gly Gly Gly Gly Ser Gly
                245                 250                 255

Gly Gly Gly Ser Gly Gly Gly Ser Ala Ser Val Asn Gln Thr Pro
                260                 265                 270

Arg Thr Ala Thr Lys Glu Thr Gly Glu Ser Leu Thr Ile Asn Cys Val
            275                 280                 285

Val Thr Gly Ala Asn Tyr Gly Leu Ala Ala Thr Tyr Trp Tyr Arg Lys
        290                 295                 300

Asn Pro Gly Ser Ser Asn Gln Glu Arg Ile Ser Ile Ser Gly Arg Tyr
305                 310                 315                 320

Val Glu Ser Val Asn Lys Arg Thr Met Ser Phe Ser Leu Arg Ile Lys
                325                 330                 335

Asp Leu Thr Val Ala Asp Ser Ala Thr Tyr Tyr Cys Lys Ala Tyr Pro
            340                 345                 350

Trp Gly Ala Gly Ala Pro Trp Leu Val Gln Trp Tyr Asp Gly Ala Gly
        355                 360                 365

Thr Val Leu Thr Val Asn Gln Ala Cys Gly Ala His His His His His
    370                 375                 380

His Gly Ala Glu Phe Glu Gln Lys Leu Ile Ser Glu Glu Asp Leu
385                 390                 395
```

<210> SEQ ID NO 154
<211> LENGTH: 399
<212> TYPE: PRT
<213> ORGANISM: Artificial Sequence
<220> FEATURE:
<223> OTHER INFORMATION: Antibody Sequence

<400> SEQUENCE: 154

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Gly Ser Gly
            115                 120                 125
```

Gly Gly Gly Ser Gly Gly Gly Ser Thr Arg Val Asp Gln Ser Pro
130                 135                 140

Ser Ser Leu Ser Ala Ser Val Gly Asp Arg Val Thr Ile Thr Cys Val
145                 150                 155                 160

Leu Thr Asp Thr Ser Tyr Pro Leu Tyr Ser Thr Tyr Trp Tyr Arg Lys
            165                 170                 175

Asn Pro Gly Ser Ser Asn Lys Glu Gln Ile Ser Ile Ser Gly Arg Tyr
            180                 185                 190

Ser Glu Ser Val Asn Lys Gly Thr Lys Ser Phe Thr Leu Thr Ile Ser
        195                 200                 205

Ser Leu Gln Pro Glu Asp Ser Ala Thr Tyr Tyr Cys Arg Ala Met Ser
210                 215                 220

Thr Asn Ile Trp Thr Gly Asp Gly Ala Gly Thr Lys Val Glu Ile Lys
225                 230                 235                 240

Gly Gly Gly Gly Ser Gly Gly Gly Ser Gly Gly Gly Ser Gly
                    245                 250                 255

Gly Gly Gly Ser Gly Gly Gly Ser Ala Ser Val Asn Gln Thr Pro
            260                 265                 270

Arg Thr Ala Thr Lys Glu Thr Gly Glu Ser Leu Thr Ile Asn Cys Val
        275                 280                 285

Val Thr Gly Ala Asn Tyr Gly Leu Ala Ala Thr Tyr Trp Tyr Arg Lys
290                 295                 300

Asn Pro Gly Ser Ser Asn Gln Glu Arg Ile Ser Ile Ser Gly Arg Tyr
305                 310                 315                 320

Val Glu Ser Val Asn Lys Arg Thr Met Ser Phe Ser Leu Arg Ile Lys
            325                 330                 335

Asp Leu Thr Val Ala Asp Ser Ala Thr Tyr Tyr Cys Lys Ala Tyr Pro
            340                 345                 350

Trp Gly Ala Gly Ala Pro Trp Leu Val Gln Trp Tyr Asp Gly Ala Gly
        355                 360                 365

Thr Val Leu Thr Val Asn Gln Ala Ser Gly Ala His His His His
370                 375                 380

His Gly Ala Glu Phe Glu Gln Lys Leu Ile Ser Glu Glu Asp Leu
385                 390                 395

<210> SEQ ID NO 155
<211> LENGTH: 397
<212> TYPE: PRT
<213> ORGANISM: Artificial Sequence
<220> FEATURE:
<223> OTHER INFORMATION: Antibody Sequence

<400> SEQUENCE: 155

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Ser Gly
            115                 120                 125

Gly Gly Gly Ser Gly Gly Gly Ser Thr Arg Val Asp Gln Ser Pro
130                 135                 140

Ser Ser Leu Ser Ala Ser Val Gly Asp Arg Val Thr Ile Thr Cys Val
145                 150                 155                 160

Leu Thr Asp Thr Ser Tyr Pro Leu Tyr Ser Thr Tyr Trp Tyr Arg Lys
            165                 170                 175

Asn Pro Gly Ser Ser Asn Lys Glu Gln Ile Ser Ile Ser Gly Arg Tyr
            180                 185                 190

Ser Glu Ser Val Asn Lys Gly Thr Lys Ser Phe Thr Leu Thr Ile Ser
            195                 200                 205

Ser Leu Gln Pro Glu Asp Ser Ala Thr Tyr Tyr Cys Arg Ala Met Ser
210                 215                 220

Thr Asn Ile Trp Thr Gly Asp Gly Ala Gly Thr Lys Val Glu Ile Lys
225                 230                 235                 240

Gly Gly Gly Gly Ser Gly Gly Gly Ser Gly Gly Gly Ser Gly
            245                 250                 255

Gly Gly Gly Ser Gly Gly Gly Ser Thr Arg Val Asp Gln Thr Pro
            260                 265                 270

Arg Thr Ala Thr Lys Glu Thr Gly Glu Ser Leu Thr Ile Asn Cys Val
            275                 280                 285

Leu Thr Asp Thr Ser Tyr Gly Leu Tyr Ser Thr Ser Trp Phe Arg Lys
            290                 295                 300

Asn Pro Gly Thr Thr Asp Trp Glu Arg Met Ser Ile Gly Gly Arg Tyr
305                 310                 315                 320

Val Glu Ser Val Asn Lys Gly Ala Lys Ser Phe Ser Leu Arg Ile Lys
            325                 330                 335

Asp Leu Thr Val Ala Asp Ser Ala Thr Tyr Tyr Cys Lys Ala Arg Glu
            340                 345                 350

Ala Arg His Pro Trp Leu Arg Gln Trp Tyr Asp Gly Ala Gly Thr Val
            355                 360                 365

Leu Thr Val Asn Gln Ala Ser Gly Ala His His His His His His Gly
            370                 375                 380

Ala Glu Phe Glu Gln Lys Leu Ile Ser Glu Glu Asp Leu
385                 390                 395

<210> SEQ ID NO 156
<211> LENGTH: 397
<212> TYPE: PRT
<213> ORGANISM: Artificial Sequence
<220> FEATURE:
<223> OTHER INFORMATION: Antibody Sequence

<400> SEQUENCE: 156

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Ser Gly
        115                 120                 125

Gly Gly Gly Ser Thr Arg Val Asp Gln Ser Pro Ser Ser Leu Ser Ala
        130                 135                 140

Ser Val Gly Asp Arg Val Thr Ile Thr Cys Val Leu Thr Asp Thr Ser
145                 150                 155                 160

Tyr Pro Leu Tyr Ser Thr Tyr Trp Tyr Arg Lys Asn Pro Gly Ser Ser
                165                 170                 175

Asn Lys Glu Gln Ile Ser Ile Ser Gly Arg Tyr Ser Glu Ser Val Asn
            180                 185                 190

Lys Gly Thr Lys Ser Phe Thr Leu Thr Ile Ser Ser Leu Gln Pro Glu
        195                 200                 205

Asp Ser Ala Thr Tyr Tyr Cys Arg Ala Met Ser Thr Asn Ile Trp Thr
210                 215                 220

Gly Asp Gly Ala Gly Thr Lys Val Glu Ile Lys Gly Gly Gly Gly Ser
225                 230                 235                 240

Gly Gly Gly Gly Ser Gly Gly Gly Ser Gly Gly Gly Ser Gly
            245                 250                 255

Gly Gly Gly Ser Ala Ser Val Asn Gln Thr Pro Arg Thr Ala Thr Lys
        260                 265                 270

Glu Thr Gly Glu Ser Leu Thr Ile Asn Cys Val Leu Thr Asp Thr Ser
        275                 280                 285

Tyr Gly Leu Tyr Ser Thr Ser Trp Phe Arg Lys Asn Pro Gly Thr Thr
        290                 295                 300

Asp Trp Glu Arg Met Ser Ile Gly Gly Arg Tyr Val Glu Ser Val Asn
305                 310                 315                 320

Lys Arg Ala Lys Ser Phe Ser Leu Arg Ile Lys Asp Leu Thr Val Ala
                325                 330                 335

Asp Ser Ala Thr Tyr Tyr Cys Lys Ala Gln Ser Gly Met Ala Ile Ser
            340                 345                 350

Thr Gly Ser Gly His Gly Tyr Asn Trp Tyr Asp Gly Ala Gly Thr Val
        355                 360                 365

Leu Thr Val Asn Gln Ala Cys Gly Ala His His His His His His Gly
        370                 375                 380

Ala Glu Phe Glu Gln Lys Leu Ile Ser Glu Glu Asp Leu
385                 390                 395

<210> SEQ ID NO 157
<211> LENGTH: 397
<212> TYPE: PRT
<213> ORGANISM: Artificial Sequence
<220> FEATURE:
<223> OTHER INFORMATION: Antibody Sequence

<400> SEQUENCE: 157

Thr Arg Val Asp Gln Thr Pro Arg Thr Ala Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Asp Trp Glu Arg
         35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Gly Gly Gly Ser
                100                 105                 110

Gly Gly Gly Gly Ser Gly Gly Gly Ser Gly Gly Gly Ser Gly
             115                 120                 125

Gly Gly Gly Ser Thr Arg Val Asp Gln Ser Pro Ser Ser Leu Ser Ala
     130                 135                 140

Ser Val Gly Asp Arg Val Thr Ile Thr Cys Val Leu Thr Asp Thr Ser
145                 150                 155                 160

Tyr Pro Leu Tyr Ser Thr Tyr Trp Tyr Arg Lys Asn Pro Gly Ser Ser
                165                 170                 175

Asn Lys Glu Gln Ile Ser Ile Ser Gly Arg Tyr Ser Glu Ser Val Asn
            180                 185                 190

Lys Gly Thr Lys Ser Phe Thr Leu Thr Ile Ser Ser Leu Gln Pro Glu
        195                 200                 205

Asp Ser Ala Thr Tyr Tyr Cys Arg Ala Met Ser Thr Asn Ile Trp Thr
    210                 215                 220

Gly Asp Gly Ala Gly Thr Lys Val Glu Ile Lys Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Ala Ser Val Asn Gln Thr Pro Arg Thr Ala Thr Lys
                260                 265                 270

Glu Thr Gly Glu Ser Leu Thr Ile Asn Cys Val Leu Thr Asp Thr Ser
            275                 280                 285

Tyr Gly Leu Tyr Ser Thr Ser Trp Phe Arg Lys Asn Pro Gly Thr Thr
        290                 295                 300

Asp Trp Glu Arg Met Ser Ile Gly Gly Arg Tyr Val Glu Ser Val Asn
305                 310                 315                 320

Lys Arg Ala Lys Ser Phe Ser Leu Arg Ile Lys Asp Leu Thr Val Ala
                325                 330                 335

Asp Ser Ala Thr Tyr Tyr Cys Lys Ala Gln Ser Gly Met Ala Ile Ser
            340                 345                 350

Thr Gly Ser Gly His Gly Tyr Asn Trp Tyr Asp Gly Ala Gly Thr Val
        355                 360                 365

Leu Thr Val Asn Gln Ala Ser Gly Ala His His His His His His Gly
    370                 375                 380

Ala Glu Phe Glu Gln Lys Leu Ile Ser Glu Glu Asp Leu
385                 390                 395

<210> SEQ ID NO 158
<211> LENGTH: 266
<212> TYPE: PRT
<213> ORGANISM: Artificial Sequence
<220> FEATURE:
<223> OTHER INFORMATION: Antibody Sequence

<400> SEQUENCE: 158

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Gly Ser Gly
            115                 120                 125

Gly Gly Gly Ser Ala Ser Val Asn Gln Thr Pro Arg Thr Ala Thr Lys
        130                 135                 140

Glu Thr Gly Glu Ser Leu Thr Ile Asn Cys Val Val Thr Gly Ala Asn
145                 150                 155                 160

Tyr Gly Leu Ala Ala Thr Tyr Trp Tyr Arg Lys Asn Pro Gly Ser Ser
                165                 170                 175

Asn Gln Glu Arg Ile Ser Ile Ser Gly Arg Tyr Val Glu Ser Val Asn
            180                 185                 190

Lys Arg Thr Met Ser Phe Ser Leu Arg Ile Lys Asp Leu Thr Val Ala
        195                 200                 205

Asp Ser Ala Thr Tyr Tyr Cys Lys Ala Tyr Pro Trp Gly Ala Gly Ala
    210                 215                 220

Pro Trp Leu Val Gln Trp Tyr Asp Gly Ala Gly Thr Val Leu Thr Val
225                 230                 235                 240

Asn Gln Ala Ser Gly Ala His His His His His Gly Ala Glu Phe
            245                 250                 255

Glu Gln Lys Leu Ile Ser Glu Glu Asp Leu
        260                 265

<210> SEQ ID NO 159
<211> LENGTH: 255
<212> TYPE: PRT
<213> ORGANISM: Artificial Sequence
<220> FEATURE:
<223> OTHER INFORMATION: Antibody Sequence

<400> SEQUENCE: 159

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95
```

Tyr Asp Gly Ala Gly Thr Val Leu Thr Val Asn Gly Gly Gly Ser
            100                 105                 110

Gly Gly Gly Gly Ser Gly Gly Gly Ser Gly Gly Gly Gly Ser Gly
            115                 120                 125

Gly Gly Gly Ser Ala Ser Val Asn Gln Thr Pro Arg Thr Ala Thr Lys
            130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Arg Ala Lys Ser Phe Ser Leu Arg Ile Lys Asp Leu Thr Val Ala
            195                 200                 205

Asp Ser Ala Thr Tyr Tyr Cys Lys Ala Gln Ser Gly Met Ala Ile Ser
            210                 215                 220

Thr Gly Ser Gly His Gly Tyr Asn Trp Tyr Asp Gly Ala Gly Thr Val
225                 230                 235                 240

Leu Thr Val Asn Gln Ala Ser Gly Ala His His His His His
            245                 250                 255

<210> SEQ ID NO 160
<211> LENGTH: 246
<212> TYPE: PRT
<213> ORGANISM: Artificial Sequence
<220> FEATURE:
<223> OTHER INFORMATION: Antibody Sequence

<400> SEQUENCE: 160

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Gly Ser Gly
            115                 120                 125

Gly Gly Gly Ser Ala Ser Val Asn Gln Thr Pro Arg Thr Ala Thr Lys
            130                 135                 140

Glu Thr Gly Glu Ser Leu Thr Ile Asn Cys Val Val Thr Gly Ala Asn
145                 150                 155                 160

Tyr Gly Leu Ala Ala Thr Tyr Trp Tyr Arg Lys Asn Pro Gly Ser Ser
                165                 170                 175

Asn Gln Glu Arg Ile Ser Ile Ser Gly Arg Tyr Val Glu Ser Val Asn
            180                 185                 190

Lys Arg Thr Met Ser Phe Ser Leu Arg Ile Lys Asp Leu Thr Val Ala
            195                 200                 205

```
Asp Ser Ala Thr Tyr Tyr Cys Lys Ala Tyr Pro Trp Gly Ala Gly Ala
    210                 215                 220

Pro Trp Leu Val Gln Trp Tyr Asp Gly Ala Gly Thr Val Leu Thr Val
225                 230                 235                 240

Asn Ser Ala Pro Ser Ala
            245

<210> SEQ ID NO 161
<211> LENGTH: 260
<212> TYPE: PRT
<213> ORGANISM: Artificial Sequence
<220> FEATURE:
<223> OTHER INFORMATION: Antibody Sequence

<400> SEQUENCE: 161

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Gly Ser Gly
        115                 120                 125

Gly Gly Gly Ser Thr Arg Val Asp Gln Ser Pro Ser Ser Leu Ser Ala
    130                 135                 140

Ser Val Gly Asp Arg Val Thr Ile Thr Cys Val Leu Thr Asp Thr Ser
145                 150                 155                 160

Tyr Pro Leu Tyr Ser Thr Tyr Trp Tyr Arg Lys Asn Pro Gly Ser Ser
                165                 170                 175

Asn Lys Glu Gln Ile Ser Ile Ser Gly Arg Tyr Ser Glu Ser Val Asn
            180                 185                 190

Lys Gly Thr Lys Ser Phe Thr Leu Thr Ile Ser Ser Leu Gln Pro Glu
        195                 200                 205

Asp Ser Ala Thr Tyr Tyr Cys Arg Ala Met Ser Thr Asn Ile Trp Thr
    210                 215                 220

Gly Asp Gly Ala Gly Thr Lys Val Glu Ile Lys Gln Ala Cys Gly Ala
225                 230                 235                 240

His His His His His His Gly Ala Glu Phe Glu Gln Lys Leu Ile Ser
                245                 250                 255

Glu Glu Asp Leu
            260

<210> SEQ ID NO 162
<211> LENGTH: 260
<212> TYPE: PRT
<213> ORGANISM: Artificial Sequence
<220> FEATURE:
<223> OTHER INFORMATION: Antibody Sequence

<400> SEQUENCE: 162
```

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn Gly Gly Gly Ser
            100                 105                 110

Gly Gly Gly Gly Ser Gly Gly Gly Ser Gly Gly Gly Gly Ser Gly
            115                 120                 125

Gly Gly Gly Ser Thr Arg Val Asp Gln Ser Pro Ser Ser Leu Ser Ala
        130                 135                 140

Ser Val Gly Asp Arg Val Thr Ile Thr Cys Val Leu Thr Asp Thr Ser
145                 150                 155                 160

Tyr Pro Leu Tyr Ser Thr Tyr Trp Tyr Arg Lys Asn Pro Gly Ser Ser
                165                 170                 175

Asn Lys Glu Gln Ile Ser Ile Ser Gly Arg Tyr Ser Glu Ser Val Asn
            180                 185                 190

Lys Gly Thr Lys Ser Phe Thr Leu Thr Ile Ser Ser Leu Gln Pro Glu
        195                 200                 205

Asp Ser Ala Thr Tyr Tyr Cys Arg Ala Met Ser Thr Asn Ile Trp Thr
    210                 215                 220

Gly Asp Gly Ala Gly Thr Lys Val Glu Ile Lys Gln Ala Ser Gly Ala
225                 230                 235                 240

His His His His His His Gly Ala Glu Phe Glu Gln Lys Leu Ile Ser
                245                 250                 255

Glu Glu Asp Leu
            260

<210> SEQ ID NO 163
<211> LENGTH: 260
<212> TYPE: PRT
<213> ORGANISM: Artificial Sequence
<220> FEATURE:
<223> OTHER INFORMATION: Antibody Sequence

<400> SEQUENCE: 163

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Gly Gly Gly Ser Gly Gly Gly Gly
            100                 105                 110

Ser Gly Gly Gly Gly Ser Gly Gly Gly Ser Gly Gly Gly Gly Ser
            115                 120                 125

Thr Arg Val Asp Gln Thr Pro Arg Thr Ala Thr Lys Glu Thr Gly Glu
            130                 135                 140

Ser Leu Thr Ile Asn Cys Val Leu Thr Asp Thr Ser Tyr Gly Leu Tyr
145                 150                 155                 160

Ser Thr Ser Trp Phe Arg Lys Asn Pro Gly Thr Thr Asp Trp Glu Arg
                165                 170                 175

Met Ser Ile Gly Gly Arg Tyr Val Glu Ser Val Asn Lys Gly Ala Lys
            180                 185                 190

Ser Phe Ser Leu Arg Ile Lys Asp Leu Thr Val Ala Asp Ser Ala Thr
            195                 200                 205

Tyr Tyr Cys Lys Ala Gln Ser Leu Ala Ile Ser Thr Arg Ser Tyr Trp
            210                 215                 220

Tyr Asp Gly Ala Gly Thr Val Leu Thr Val Asn Gln Ala Ser Gly Ala
225                 230                 235                 240

His His His His His His Gly Ala Glu Phe Glu Gln Lys Leu Ile Ser
                245                 250                 255

Glu Glu Asp Leu
            260

<210> SEQ ID NO 164
<211> LENGTH: 402
<212> TYPE: PRT
<213> ORGANISM: Artificial Sequence
<220> FEATURE:
<223> OTHER INFORMATION: Antibody Sequence

<400> SEQUENCE: 164

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Gly Ser Gly Gly Gly Ser Gly
            115                 120                 125

Gly Gly Gly Ser Gly Gly Gly Gly Ser Ala Ser Val Asn Gln Thr Pro
            130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
            180                 185                 190

```
Val Glu Ser Val Asn Lys Arg Ala Lys Ser Phe Ser Leu Arg Ile Lys
            195                 200                 205

Asp Leu Thr Val Ala Asp Ser Ala Thr Tyr Tyr Cys Lys Ala Gln Ser
        210                 215                 220

Gly Met Ala Ile Ser Thr Gly Ser Gly His Gly Tyr Asn Trp Tyr Asp
225                 230                 235                 240

Gly Ala Gly Thr Val Leu Thr Val Asn Gly Gly Gly Ser Gly Gly
            245                 250                 255

Gly Gly Ser Gly Gly Gly Ser Gly Gly Gly Ser Gly Gly
            260                 265                 270

Gly Ser Thr Arg Val Asp Gln Ser Pro Ser Ser Leu Ser Ala Ser Val
            275                 280                 285

Gly Asp Arg Val Thr Ile Thr Cys Val Leu Thr Asp Thr Ser Tyr Pro
        290                 295                 300

Leu Tyr Ser Thr Tyr Trp Tyr Arg Lys Asn Pro Gly Ser Ser Asn Lys
305                 310                 315                 320

Glu Gln Ile Ser Ile Ser Gly Arg Tyr Ser Glu Ser Val Asn Lys Gly
            325                 330                 335

Thr Lys Ser Phe Thr Leu Thr Ile Ser Ser Leu Gln Pro Glu Asp Ser
        340                 345                 350

Ala Thr Tyr Tyr Cys Arg Ala Met Ser Thr Asn Ile Trp Thr Gly Asp
        355                 360                 365

Gly Ala Gly Thr Lys Val Glu Ile Lys Gln Ala Ser Gly Ala His His
        370                 375                 380

His His His His Gly Ala Glu Phe Glu Gln Lys Leu Ile Ser Glu Glu
385                 390                 395                 400

Asp Leu

<210> SEQ ID NO 165
<211> LENGTH: 402
<212> TYPE: PRT
<213> ORGANISM: Artificial Sequence
<220> FEATURE:
<223> OTHER INFORMATION: Antibody Sequence

<400> SEQUENCE: 165

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
            85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Gly Ser Gly
            115                 120                 125

Gly Gly Gly Ser Gly Gly Gly Ser Ala Ser Val Asn Gln Thr Pro
        130                 135                 140
```

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
            165                 170                 175

Asn Pro Gly Thr Thr Asp Trp Glu Arg Met Ser Ile Gly Gly Arg Tyr
            180                 185                 190

Val Glu Ser Val Asn Lys Arg Ala Lys Ser Phe Ser Leu Arg Ile Lys
            195                 200                 205

Asp Leu Thr Val Ala Asp Ser Ala Thr Tyr Tyr Cys Lys Ala Gln Ser
210                 215                 220

Gly Met Ala Ile Ser Thr Gly Ser Gly His Gly Tyr Asn Trp Tyr Asp
225                 230                 235                 240

Gly Ala Gly Thr Val Leu Thr Val Asn Gly Gly Gly Ser Gly Gly
            245                 250                 255

Gly Gly Ser Gly Gly Gly Ser Gly Gly Gly Ser Gly Gly
            260                 265                 270

Gly Ser Thr Arg Val Asp Gln Ser Pro Ser Ser Leu Ser Ala Ser Val
            275                 280                 285

Gly Asp Arg Val Thr Ile Thr Cys Val Leu Thr Asp Thr Ser Tyr Pro
290                 295                 300

Leu Tyr Ser Thr Tyr Trp Tyr Arg Lys Asn Pro Gly Ser Ser Asn Lys
305                 310                 315                 320

Glu Gln Ile Ser Ile Ser Gly Arg Tyr Ser Glu Ser Val Asn Lys Gly
            325                 330                 335

Thr Lys Ser Phe Thr Leu Thr Ile Ser Ser Leu Gln Pro Glu Asp Ser
            340                 345                 350

Ala Thr Tyr Tyr Cys Arg Ala Met Ser Thr Asn Ile Trp Thr Gly Asp
            355                 360                 365

Gly Ala Gly Thr Lys Val Glu Ile Lys Gln Ala Cys Gly Ala His His
370                 375                 380

His His His His Gly Ala Glu Phe Glu Gln Lys Leu Ile Ser Glu Glu
385                 390                 395                 400

Asp Leu

<210> SEQ ID NO 166
<211> LENGTH: 402
<212> TYPE: PRT
<213> ORGANISM: Artificial Sequence
<220> FEATURE:
<223> OTHER INFORMATION: Antibody Sequence

<400> SEQUENCE: 166

Ala Lys Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Asp Ile Gly Ser Gly
            85                  90                  95

His Gly Tyr Asn Trp Tyr Asp Gly Ala Gly Thr Val Leu Thr Val Asn

```
                100             105             110
Gly Gly Gly Gly Ser Gly Gly Gly Ser Gly Gly Gly Ser Gly
            115             120             125

Gly Gly Gly Ser Gly Gly Gly Ser Thr Arg Val Asp Gln Ser Pro
            130             135             140

Ser Ser Leu Ser Ala Ser Val Gly Asp Arg Val Thr Ile Thr Cys Val
145             150             155             160

Leu Thr Asp Thr Ser Tyr Pro Leu Tyr Ser Thr Tyr Trp Tyr Arg Lys
            165             170             175

Asn Pro Gly Ser Ser Asn Lys Glu Gln Ile Ser Ile Ser Gly Arg Tyr
            180             185             190

Ser Glu Ser Val Asn Lys Gly Thr Lys Ser Phe Thr Leu Thr Ile Ser
            195             200             205

Ser Leu Gln Pro Glu Asp Ser Ala Thr Tyr Tyr Cys Arg Ala Met Ser
210             215             220

Thr Asn Ile Trp Thr Gly Asp Gly Ala Gly Thr Lys Val Glu Ile Lys
225             230             235             240

Gly Gly Gly Gly Ser Gly Gly Gly Ser Gly Gly Gly Ser Gly
            245             250             255

Gly Gly Gly Ser Gly Gly Gly Ser Ala Lys Val Asp Gln Thr Pro
            260             265             270

Arg Thr Ala Thr Lys Glu Thr Gly Glu Ser Leu Thr Ile Asn Cys Val
            275             280             285

Leu Thr Asp Thr Ser Tyr Gly Leu Tyr Ser Thr Ser Trp Phe Arg Lys
            290             295             300

Asn Pro Gly Thr Thr Asp Trp Glu Arg Met Ser Ile Gly Gly Arg Tyr
305             310             315             320

Val Glu Ser Val Asn Lys Arg Ala Lys Ser Phe Ser Leu Arg Ile Lys
            325             330             335

Asp Leu Thr Val Ala Asp Ser Ala Thr Tyr Tyr Cys Lys Ala Gln Ser
            340             345             350

Gly Met Ala Ile Asp Ile Gly Ser Gly His Gly Tyr Asn Trp Tyr Asp
            355             360             365

Gly Ala Gly Thr Val Leu Thr Val Asn Gln Ala Ser Gly Ala His His
            370             375             380

His His His His Gly Ala Glu Phe Glu Gln Lys Leu Ile Ser Glu Glu
385             390             395             400

Asp Leu

<210> SEQ ID NO 167
<211> LENGTH: 402
<212> TYPE: PRT
<213> ORGANISM: Artificial Sequence
<220> FEATURE:
<223> OTHER INFORMATION: Antibody Sequence

<400> SEQUENCE: 167

Ala Ser Val Asn Gln Thr Pro Arg Thr Ala Thr Lys Glu Thr Gly Glu
1               5               10              15

Ser Leu Thr Ile Asn Cys Val Leu Thr Asp Thr Ser Tyr Gly Leu Tyr
            20              25              30

Ser Thr Ser Trp Phe Arg Lys Asn Pro Gly Thr Thr Asp Trp Glu Arg
        35              40              45

Met Ser Ile Gly Gly Arg Tyr Val Glu Ser Val Asn Lys Arg Ala Lys
50              55              60
```

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
            85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Gly Ser Gly
        115                 120                 125

Gly Gly Gly Ser Gly Gly Gly Ser Thr Arg Val Asp Gln Ser Pro
    130                 135                 140

Ser Ser Leu Ser Ala Ser Val Gly Asp Arg Val Thr Ile Thr Cys Val
145                 150                 155                 160

Leu Thr Asp Thr Ser Tyr Pro Leu Tyr Ser Thr Tyr Trp Tyr Arg Lys
                165                 170                 175

Asn Pro Gly Ser Ser Asn Lys Glu Gln Ile Ser Ile Ser Gly Arg Tyr
            180                 185                 190

Ser Glu Ser Val Asn Lys Gly Thr Lys Ser Phe Thr Leu Thr Ile Ser
            195                 200                 205

Ser Leu Gln Pro Glu Asp Ser Ala Thr Tyr Tyr Cys Arg Ala Met Ser
210                 215                 220

Thr Asn Ile Trp Thr Gly Asp Gly Ala Gly Thr Lys Val Glu Ile Lys
225                 230                 235                 240

Gly Gly Gly Gly Ser Gly Gly Gly Ser Gly Gly Gly Gly Ser Gly
            245                 250                 255

Gly Gly Gly Ser Gly Gly Gly Ser Ala Ser Val Asn Gln Thr Pro
        260                 265                 270

Arg Thr Ala Thr Lys Glu Thr Gly Glu Ser Leu Thr Ile Asn Cys Val
        275                 280                 285

Leu Thr Asp Thr Ser Tyr Gly Leu Tyr Ser Thr Ser Trp Phe Arg Lys
290                 295                 300

Asn Pro Gly Thr Thr Asp Trp Glu Arg Met Ser Ile Gly Gly Arg Tyr
305                 310                 315                 320

Val Glu Ser Val Asn Lys Arg Ala Lys Ser Phe Ser Leu Arg Ile Lys
                325                 330                 335

Asp Leu Thr Val Ala Asp Ser Ala Thr Tyr Tyr Cys Lys Ala Gln Ser
            340                 345                 350

Gly Met Ala Ile Ser Thr Gly Ser Gly His Gly Tyr Asn Trp Tyr Asp
        355                 360                 365

Gly Ala Gly Thr Val Leu Thr Val Asn Gln Ala Ser Gly Ala His His
    370                 375                 380

His His His His Gly Ala Glu Phe Glu Gln Lys Leu Ile Ser Glu Glu
385                 390                 395                 400

Asp Leu

<210> SEQ ID NO 168
<211> LENGTH: 392
<212> TYPE: PRT
<213> ORGANISM: Artificial Sequence
<220> FEATURE:
<223> OTHER INFORMATION: Antibody Sequence

<400> SEQUENCE: 168

Thr Arg Val Asp Gln Thr Pro Arg Thr Ala Thr Lys Glu Thr Gly Glu
1               5                   10                  15

-continued

Ser Leu Thr Ile Asn Cys Val Leu Thr Asp Thr Ser Tyr Gly Leu Tyr
              20                  25                  30

Ser Thr Ser Trp Phe Arg Lys Asn Pro Gly Thr Thr Asp Trp Glu Arg
         35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
             85                  90                  95

Tyr Asp Gly Ala Gly Thr Val Leu Thr Val Asn Gly Gly Gly Ser
            100                 105                 110

Gly Gly Gly Gly Ser Gly Gly Gly Ser Gly Gly Gly Ser Gly
            115                 120                 125

Gly Gly Gly Ser Thr Arg Val Asp Gln Ser Pro Ser Ser Leu Ser Ala
            130                 135                 140

Ser Val Gly Asp Arg Val Thr Ile Thr Cys Val Leu Thr Asp Thr Ser
145                 150                 155                 160

Tyr Pro Leu Tyr Ser Thr Tyr Trp Tyr Arg Lys Asn Pro Gly Ser Ser
                165                 170                 175

Asn Lys Glu Gln Ile Ser Ile Ser Gly Arg Tyr Ser Glu Ser Val Asn
            180                 185                 190

Lys Gly Thr Lys Ser Phe Thr Leu Thr Ile Ser Ser Leu Gln Pro Glu
            195                 200                 205

Asp Ser Ala Thr Tyr Tyr Cys Arg Ala Met Ser Thr Asn Ile Trp Thr
210                 215                 220

Gly Asp Gly Ala Gly Thr Lys Val Glu Ile Lys Gly Gly Gly Ser
225                 230                 235                 240

Gly Gly Gly Gly Ser Gly Gly Gly Ser Gly Gly Gly Ser Gly
                245                 250                 255

Gly Gly Gly Ser Thr Arg Val Asp Gln Thr Pro Arg Thr Ala Thr Lys
            260                 265                 270

Glu Thr Gly Glu Ser Leu Thr Ile Asn Cys Val Leu Thr Asp Thr Ser
            275                 280                 285

Tyr Gly Leu Tyr Ser Thr Ser Trp Phe Arg Lys Asn Pro Gly Thr Thr
            290                 295                 300

Asp Trp Glu Arg Met Ser Ile Gly Gly Arg Tyr Val Glu Ser Val Asn
305                 310                 315                 320

Lys Gly Ala Lys Ser Phe Ser Leu Arg Ile Lys Asp Leu Thr Val Ala
                325                 330                 335

Asp Ser Ala Thr Tyr Tyr Cys Lys Ala Arg Glu Ala Arg His Pro Trp
            340                 345                 350

Leu Arg Gln Trp Tyr Asp Gly Ala Gly Thr Val Leu Thr Val Asn Gln
            355                 360                 365

Ala Ser Gly Ala His His His His His Gly Ala Glu Phe Glu Gln
            370                 375                 380

Lys Leu Ile Ser Glu Glu Asp Leu
385                 390

<210> SEQ ID NO 169
<211> LENGTH: 262
<212> TYPE: PRT
<213> ORGANISM: Artificial Sequence
<220> FEATURE:
<223> OTHER INFORMATION: Antibody Sequence

<400> SEQUENCE: 169

```
Thr Arg Val Asp Gln Ser Pro Ser Ser Leu Ser Ala Ser Val Gly Asp
1               5                   10                  15
Arg Val Thr Ile Thr Cys Val Leu Thr Asp Thr Ser Tyr Pro Leu Tyr
            20                  25                  30
Ser Thr Tyr Trp Tyr Arg Lys Asn Pro Gly Ser Ser Asn Lys Glu Gln
        35                  40                  45
Ile Ser Ile Ser Gly Arg Tyr Ser Glu Ser Val Asn Lys Gly Thr Lys
    50                  55                  60
Ser Phe Thr Leu Thr Ile Ser Ser Leu Gln Pro Glu Asp Ser Ala Thr
65                  70                  75                  80
Tyr Tyr Cys Arg Ala Met Ser Thr Asn Ile Trp Thr Gly Asp Gly Ala
                85                  90                  95
Gly Thr Lys Val Glu Ile Lys Gly Gly Gly Ser Gly Gly Gly Gly
            100                 105                 110
Ser Gly Gly Gly Gly Ser Gly Gly Gly Ser Gly Gly Gly Gly Ser
        115                 120                 125
Ala Ser Val Asn Gln Thr Pro Arg Thr Ala Thr Lys Glu Thr Gly Glu
130                 135                 140
Ser Leu Thr Ile Asn Cys Val Val Thr Gly Ala Asn Tyr Gly Leu Ala
145                 150                 155                 160
Ala Thr Tyr Trp Tyr Arg Lys Asn Pro Gly Ser Ser Asn Gln Glu Arg
                165                 170                 175
Ile Ser Ile Ser Gly Arg Tyr Val Glu Ser Val Asn Lys Arg Thr Met
            180                 185                 190
Ser Phe Ser Leu Arg Ile Lys Asp Leu Thr Val Ala Asp Ser Ala Thr
        195                 200                 205
Tyr Tyr Cys Lys Ala Tyr Pro Trp Gly Ala Gly Ala Pro Trp Leu Val
    210                 215                 220
Gln Trp Tyr Asp Gly Ala Gly Thr Val Leu Thr Val Asn Gln Ala Ser
225                 230                 235                 240
Gly Ala His His His His His Gly Ala Glu Phe Glu Gln Lys Leu
                245                 250                 255
Ile Ser Glu Glu Asp Leu
                260
```

<210> SEQ ID NO 170
<211> LENGTH: 249
<212> TYPE: PRT
<213> ORGANISM: Artificial Sequence
<220> FEATURE:
<223> OTHER INFORMATION: Antibody Sequence

<400> SEQUENCE: 170

```
Ala Ser Val Asn Gln Thr Pro Arg Thr Ala Thr Lys Glu Thr Gly Glu
1               5                   10                  15
Ser Leu Thr Ile Asn Cys Val Val Thr Gly Ala Asn Tyr Gly Leu Ala
            20                  25                  30
Ala Thr Tyr Trp Tyr Arg Lys Asn Pro Gly Ser Ser Asn Gln Glu Arg
        35                  40                  45
Ile Ser Ile Ser Gly Arg Tyr Val Glu Ser Val Asn Lys Arg Thr Met
    50                  55                  60
Ser Phe Ser Leu Arg Ile Lys Asp Leu Thr Val Ala Asp Ser Ala Thr
65                  70                  75                  80
```

```
Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Ser Pro Ser
            100                 105                 110

Thr Pro Pro Thr Pro Ser Pro Thr Pro Ala Thr Arg Val Asp Gln
        115                 120                 125

Ser Pro Ser Ser Leu Ser Ala Ser Val Gly Asp Arg Val Thr Ile Thr
        130                 135                 140

Cys Val Leu Thr Asp Thr Ser Tyr Pro Leu Tyr Ser Thr Tyr Trp Tyr
145                 150                 155                 160

Arg Lys Asn Pro Gly Ser Ser Asn Lys Glu Gln Ile Ser Ile Ser Gly
                165                 170                 175

Arg Tyr Ser Glu Ser Val Asn Lys Gly Thr Lys Ser Phe Thr Leu Thr
            180                 185                 190

Ile Ser Ser Leu Gln Pro Glu Asp Ser Ala Thr Tyr Tyr Cys Arg Ala
        195                 200                 205

Met Ser Thr Asn Ile Trp Thr Gly Asp Gly Ala Gly Thr Lys Val Glu
        210                 215                 220

Ile Lys Ala Cys Ala His His His His His Gly Ala Glu Phe Glu
225                 230                 235                 240

Gln Lys Leu Ile Ser Glu Glu Asp Leu
                245

<210> SEQ ID NO 171
<211> LENGTH: 251
<212> TYPE: PRT
<213> ORGANISM: Artificial Sequence
<220> FEATURE:
<223> OTHER INFORMATION: Antibody Sequence

<400> SEQUENCE: 171

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Ser Pro Ser Thr Pro Thr Pro Ser
            100                 105                 110

Pro Thr Pro Pro Ala Ala Ser Val Asn Gln Thr Pro Arg Thr Ala Thr
        115                 120                 125

Lys Glu Thr Gly Glu Ser Leu Thr Ile Asn Cys Val Thr Gly Ala
    130                 135                 140

Asn Tyr Gly Leu Ala Ala Thr Tyr Trp Tyr Arg Lys Asn Pro Gly Ser
145                 150                 155                 160

Ser Asn Gln Glu Arg Ile Ser Ile Ser Gly Arg Tyr Val Glu Ser Val
                165                 170                 175

Asn Lys Arg Thr Met Ser Phe Ser Leu Arg Ile Lys Asp Leu Thr Val
            180                 185                 190
```

```
Ala Asp Ser Ala Thr Tyr Tyr Cys Lys Ala Tyr Pro Trp Gly Ala Gly
            195                 200                 205

Ala Pro Trp Leu Val Gln Trp Tyr Asp Gly Ala Gly Thr Val Leu Thr
    210                 215                 220

Val Asn Gln Ala Cys Gly Ala His His His His His Gly Ala Glu
225                 230                 235                 240

Phe Glu Gln Lys Leu Ile Ser Glu Glu Asp Leu
                245                 250

<210> SEQ ID NO 172
<211> LENGTH: 283
<212> TYPE: PRT
<213> ORGANISM: Artificial Sequence
<220> FEATURE:
<223> OTHER INFORMATION: Antibody Sequence

<400> SEQUENCE: 172

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Ala Glu Ala Ala Lys Glu Ala Ala
            100                 105                 110

Ala Lys Glu Ala Ala Lys Glu Ala Ala Lys Ala Leu Glu Ala
        115                 120                 125

Glu Ala Ala Ala Lys Glu Ala Ala Lys Glu Ala Ala Ala Lys Glu
    130                 135                 140

Ala Ala Ala Lys Ala Ala Ser Val Asn Gln Thr Pro Arg Thr Ala Thr
145                 150                 155                 160

Lys Glu Thr Gly Glu Ser Leu Thr Ile Asn Cys Val Val Thr Gly Ala
                165                 170                 175

Asn Tyr Gly Leu Ala Ala Thr Tyr Trp Tyr Arg Lys Asn Pro Gly Ser
            180                 185                 190

Ser Asn Gln Glu Arg Ile Ser Ile Ser Gly Arg Tyr Val Glu Ser Val
        195                 200                 205

Asn Lys Arg Thr Met Ser Phe Ser Leu Arg Ile Lys Asp Leu Thr Val
    210                 215                 220

Ala Asp Ser Ala Thr Tyr Tyr Cys Lys Ala Tyr Pro Trp Gly Ala Gly
225                 230                 235                 240

Ala Pro Trp Leu Val Gln Trp Tyr Asp Gly Ala Gly Thr Val Leu Thr
                245                 250                 255

Val Asn Gln Ala Cys Gly Ala His His His His His Gly Ala Glu
            260                 265                 270

Phe Glu Gln Lys Leu Ile Ser Glu Glu Asp Leu
        275                 280

<210> SEQ ID NO 173
<211> LENGTH: 264
```

```
<212> TYPE: PRT
<213> ORGANISM: Artificial Sequence
<220> FEATURE:
<223> OTHER INFORMATION: Antibody Sequence

<400> SEQUENCE: 173

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Ser Pro Ser Thr Pro Pro Thr Pro Ser
            100                 105                 110

Pro Thr Pro Pro Ser Pro Ser Thr Pro Pro Thr Pro Ser Pro Thr Pro
            115                 120                 125

Pro Ala Ala Ser Val Asn Gln Thr Pro Arg Thr Ala Thr Lys Glu Thr
130                 135                 140

Gly Glu Ser Leu Thr Ile Asn Cys Val Val Thr Gly Ala Asn Tyr Gly
145                 150                 155                 160

Leu Ala Ala Thr Tyr Trp Tyr Arg Lys Asn Pro Gly Ser Ser Asn Gln
                165                 170                 175

Glu Arg Ile Ser Ile Ser Gly Arg Tyr Val Glu Ser Val Asn Lys Arg
            180                 185                 190

Thr Met Ser Phe Ser Leu Arg Ile Lys Asp Leu Thr Val Ala Asp Ser
        195                 200                 205

Ala Thr Tyr Tyr Cys Lys Ala Tyr Pro Trp Gly Ala Gly Ala Pro Trp
210                 215                 220

Leu Val Gln Trp Tyr Asp Gly Ala Gly Thr Val Leu Thr Val Asn Gln
225                 230                 235                 240

Ala Cys Gly Ala His His His His His Gly Ala Glu Phe Glu Gln
                245                 250                 255

Lys Leu Ile Ser Glu Glu Asp Leu
                260

<210> SEQ ID NO 174
<211> LENGTH: 249
<212> TYPE: PRT
<213> ORGANISM: Artificial Sequence
<220> FEATURE:
<223> OTHER INFORMATION: Antibody Sequence

<400> SEQUENCE: 174

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60
```

```
Ser Phe Ser Leu Arg Ile Lys Asp Leu Thr Val Ala Asp Ser Ala Thr
 65                  70                  75                  80

Tyr Tyr Cys Lys Ala Tyr Pro Trp Gly Ala Gly Ala Pro Trp Leu Val
                 85                  90                  95

Gln Trp Tyr Asp Gly Ala Gly Thr Val Leu Thr Val Asn Ser Pro Ser
            100                 105                 110

Thr Pro Pro Thr Pro Ser Pro Thr Pro Pro Ala Thr Arg Val Asp Gln
        115                 120                 125

Ser Pro Ser Ser Leu Ser Ala Ser Val Gly Asp Arg Val Thr Ile Thr
    130                 135                 140

Cys Val Leu Thr Asp Thr Ser Tyr Pro Leu Tyr Ser Thr Tyr Trp Tyr
145                 150                 155                 160

Arg Lys Asn Pro Gly Ser Ser Asn Lys Glu Gln Ile Ser Ile Ser Gly
                165                 170                 175

Arg Tyr Ser Glu Ser Val Asn Lys Gly Thr Lys Ser Phe Thr Leu Thr
            180                 185                 190

Ile Ser Ser Leu Gln Pro Glu Asp Ser Ala Thr Tyr Tyr Cys Arg Ala
        195                 200                 205

Met Ser Thr Asn Ile Trp Thr Gly Asp Gly Ala Gly Thr Lys Val Glu
    210                 215                 220

Ile Lys Ala Cys Ala His His His His His His Gly Ala Glu Phe Glu
225                 230                 235                 240

Gln Lys Leu Ile Ser Glu Glu Asp Leu
                245

<210> SEQ ID NO 175
<211> LENGTH: 251
<212> TYPE: PRT
<213> ORGANISM: Artificial Sequence
<220> FEATURE:
<223> OTHER INFORMATION: Antibody Sequence

<400> SEQUENCE: 175

Thr Arg Val Asp Gln Ser Pro Ser Ser Leu Ser Ala Ser Val Gly Asp
 1               5                  10                  15

Arg Val Thr Ile Thr Cys Val Leu Thr Asp Thr Ser Tyr Pro Leu Tyr
                 20                  25                  30

Ser Thr Tyr Trp Tyr Arg Lys Asn Pro Gly Ser Ser Asn Lys Glu Gln
             35                  40                  45

Ile Ser Ile Ser Gly Arg Tyr Ser Glu Ser Val Asn Lys Gly Thr Lys
 50                  55                  60

Ser Phe Thr Leu Thr Ile Ser Ser Leu Gln Pro Glu Asp Ser Ala Thr
 65                  70                  75                  80

Tyr Tyr Cys Arg Ala Met Ser Thr Asn Ile Trp Thr Gly Asp Gly Ala
                 85                  90                  95

Gly Thr Lys Val Glu Ile Lys Ser Pro Ser Thr Pro Pro Thr Pro Ser
            100                 105                 110

Pro Thr Pro Pro Ala Ala Ser Val Asn Gln Thr Pro Arg Thr Ala Thr
        115                 120                 125

Lys Glu Thr Gly Glu Ser Leu Thr Ile Asn Cys Val Val Thr Gly Ala
    130                 135                 140

Asn Tyr Gly Leu Ala Ala Thr Tyr Trp Tyr Arg Lys Asn Pro Gly Ser
145                 150                 155                 160

Ser Asn Gln Glu Arg Ile Ser Ile Ser Gly Arg Tyr Val Glu Ser Val
                165                 170                 175
```

```
Asn Lys Arg Thr Met Ser Phe Ser Leu Arg Ile Lys Asp Leu Thr Val
            180                 185                 190

Ala Asp Ser Ala Thr Tyr Tyr Cys Lys Ala Tyr Pro Trp Gly Ala Gly
        195                 200                 205

Ala Pro Trp Leu Val Gln Trp Tyr Asp Gly Ala Gly Thr Val Leu Thr
    210                 215                 220

Val Asn Gln Ala Cys Gly Ala His His His His His Gly Ala Glu
225                 230                 235                 240

Phe Glu Gln Lys Leu Ile Ser Glu Glu Asp Leu
                245                 250

<210> SEQ ID NO 176
<211> LENGTH: 283
<212> TYPE: PRT
<213> ORGANISM: Artificial Sequence
<220> FEATURE:
<223> OTHER INFORMATION: Antibody Sequence

<400> SEQUENCE: 176

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Ala Glu Ala Ala Lys Glu Ala Ala
            100                 105                 110

Ala Lys Glu Ala Ala Lys Glu Ala Ala Lys Ala Leu Glu Ala
        115                 120                 125

Glu Ala Ala Ala Lys Glu Ala Ala Lys Glu Ala Ala Ala Lys Glu
    130                 135                 140

Ala Ala Ala Lys Ala Ala Ser Val Asn Gln Thr Pro Arg Thr Ala Thr
145                 150                 155                 160

Lys Glu Thr Gly Glu Ser Leu Thr Ile Asn Cys Val Val Thr Gly Ala
                165                 170                 175

Asn Tyr Gly Leu Ala Ala Thr Tyr Trp Tyr Arg Lys Asn Pro Gly Ser
            180                 185                 190

Ser Asn Gln Glu Arg Ile Ser Ile Ser Gly Arg Tyr Val Glu Ser Val
        195                 200                 205

Asn Lys Arg Thr Met Ser Phe Ser Leu Arg Ile Lys Asp Leu Thr Val
    210                 215                 220

Ala Asp Ser Ala Thr Tyr Tyr Cys Lys Ala Tyr Pro Trp Gly Ala Gly
225                 230                 235                 240

Ala Pro Trp Leu Val Gln Trp Tyr Asp Gly Ala Gly Thr Val Leu Thr
                245                 250                 255

Val Asn Gln Ala Cys Gly Ala His His His His His Gly Ala Glu
            260                 265                 270

Phe Glu Gln Lys Leu Ile Ser Glu Glu Asp Leu
        275                 280
```

<210> SEQ ID NO 177
<211> LENGTH: 264
<212> TYPE: PRT
<213> ORGANISM: Artificial Sequence
<220> FEATURE:
<223> OTHER INFORMATION: Antibody Sequence

<400> SEQUENCE: 177

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Ser Pro Ser Thr Pro Pro Thr Pro Ser
            100                 105                 110

Pro Thr Pro Pro Ser Pro Ser Thr Pro Pro Thr Pro Ser Pro Thr Pro
        115                 120                 125

Pro Ala Ala Ser Val Asn Gln Thr Pro Arg Thr Ala Thr Lys Glu Thr
130                 135                 140

Gly Glu Ser Leu Thr Ile Asn Cys Val Val Thr Gly Ala Asn Tyr Gly
145                 150                 155                 160

Leu Ala Ala Thr Tyr Trp Tyr Arg Lys Asn Pro Gly Ser Ser Asn Gln
                165                 170                 175

Glu Arg Ile Ser Ile Ser Gly Arg Tyr Val Glu Ser Val Asn Lys Arg
            180                 185                 190

Thr Met Ser Phe Ser Leu Arg Ile Lys Asp Leu Thr Val Ala Asp Ser
        195                 200                 205

Ala Thr Tyr Tyr Cys Lys Ala Tyr Pro Trp Gly Ala Gly Ala Pro Trp
    210                 215                 220

Leu Val Gln Trp Tyr Asp Gly Ala Gly Thr Val Leu Thr Val Asn Gln
225                 230                 235                 240

Ala Cys Gly Ala His His His His His Gly Ala Glu Phe Glu Gln
                245                 250                 255

Lys Leu Ile Ser Glu Glu Asp Leu
            260

<210> SEQ ID NO 178
<211> LENGTH: 256
<212> TYPE: PRT
<213> ORGANISM: Artificial Sequence
<220> FEATURE:
<223> OTHER INFORMATION: Antibody Sequence

<400> SEQUENCE: 178

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg

```
                35                  40                  45
Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Gly Gly Gly Gly Ser
                100                 105                 110

Gly Gly Gly Gly Ser Gly Gly Gly Ser Ala Ser Val Asn Gln Thr
                115                 120                 125

Pro Arg Thr Ala Thr Lys Glu Thr Gly Glu Ser Leu Thr Ile Asn Cys
                130                 135                 140

Val Val Thr Gly Ala Asn Tyr Gly Leu Ala Ala Thr Tyr Trp Tyr Arg
145                 150                 155                 160

Lys Asn Pro Gly Ser Ser Asn Gln Glu Arg Ile Ser Ile Ser Gly Arg
                165                 170                 175

Tyr Val Glu Ser Val Asn Lys Arg Thr Met Ser Phe Ser Leu Arg Ile
                180                 185                 190

Lys Asp Leu Thr Val Ala Asp Ser Ala Thr Tyr Tyr Cys Lys Ala Tyr
                195                 200                 205

Pro Trp Gly Ala Gly Ala Pro Trp Leu Val Gln Trp Tyr Asp Gly Ala
                210                 215                 220

Gly Thr Val Leu Thr Val Asn Gln Ala Ser Gly Ala His His His His
225                 230                 235                 240

His His Gly Ala Glu Phe Glu Gln Lys Leu Ile Ser Glu Glu Asp Leu
                245                 250                 255

<210> SEQ ID NO 179
<211> LENGTH: 276
<212> TYPE: PRT
<213> ORGANISM: Artificial Sequence
<220> FEATURE:
<223> OTHER INFORMATION: Antibody Sequence

<400> SEQUENCE: 179

Thr Arg Val Asp Gln Thr Pro Arg Thr Ala Thr Lys Glu Thr Gly Glu
 1                   5                  10                  15

Ser Leu Thr Ile Asn Cys Val Leu Thr Asp Thr Ser Tyr Gly Leu Tyr
                 20                  25                  30

Ser Thr Ser Trp Phe Arg Lys Asn Pro Gly Thr Thr Asp Trp Glu Arg
                 35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Gly Gly Gly Gly Ser
                100                 105                 110

Gly Gly Gly Gly Ser Gly Gly Gly Gly Ser Gly Gly Gly Gly Ser Gly
                115                 120                 125

Gly Gly Ser Gly Gly Gly Ser Gly Gly Gly Ser Ala Ser
                130                 135                 140

Val Asn Gln Thr Pro Arg Thr Ala Thr Lys Glu Thr Gly Glu Ser Leu
```

```
                145                 150                 155                 160
Thr Ile Asn Cys Val Val Thr Gly Ala Asn Tyr Gly Leu Ala Ala Thr
                165                 170                 175

Tyr Trp Tyr Arg Lys Asn Pro Gly Ser Ser Asn Gln Glu Arg Ile Ser
            180                 185                 190

Ile Ser Gly Arg Tyr Val Glu Ser Val Asn Lys Arg Thr Met Ser Phe
        195                 200                 205

Ser Leu Arg Ile Lys Asp Leu Thr Val Ala Asp Ser Ala Thr Tyr Tyr
    210                 215                 220

Cys Lys Ala Tyr Pro Trp Gly Ala Gly Ala Pro Trp Leu Val Gln Trp
225                 230                 235                 240

Tyr Asp Gly Ala Gly Thr Val Leu Thr Val Asn Gln Ala Ser Gly Ala
                245                 250                 255

His His His His His His Gly Ala Glu Phe Glu Gln Lys Leu Ile Ser
                260                 265                 270

Glu Glu Asp Leu
            275

<210> SEQ ID NO 180
<211> LENGTH: 252
<212> TYPE: PRT
<213> ORGANISM: Artificial Sequence
<220> FEATURE:
<223> OTHER INFORMATION: Antibody Sequence

<400> SEQUENCE: 180

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                85                  90                  95

Gly Thr Lys Val Glu Ile Lys Gly Gly Gly Ser Gly Gly Gly Gly
            100                 105                 110

Ser Gly Gly Gly Gly Ser Ala Ser Val Asn Gln Thr Pro Arg Thr Ala
        115                 120                 125

Thr Lys Glu Thr Gly Glu Ser Leu Thr Ile Asn Cys Val Val Thr Gly
    130                 135                 140

Ala Asn Tyr Gly Leu Ala Ala Thr Tyr Trp Tyr Arg Lys Asn Pro Gly
145                 150                 155                 160

Ser Ser Asn Gln Glu Arg Ile Ser Ile Ser Gly Arg Tyr Val Glu Ser
                165                 170                 175

Val Asn Lys Arg Thr Met Ser Phe Ser Leu Arg Ile Lys Asp Leu Thr
            180                 185                 190

Val Ala Asp Ser Ala Thr Tyr Tyr Cys Lys Ala Tyr Pro Trp Gly Ala
        195                 200                 205

Gly Ala Pro Trp Leu Val Gln Trp Tyr Asp Gly Ala Gly Thr Val Leu
    210                 215                 220

Thr Val Asn Gln Ala Cys Gly Ala His His His His His Gly Ala
```

```
                225                 230                 235                 240

Glu Phe Glu Gln Lys Leu Ile Ser Glu Glu Asp Leu
                245                 250

<210> SEQ ID NO 181
<211> LENGTH: 107
<212> TYPE: PRT
<213> ORGANISM: Artificial Sequence
<220> FEATURE:
<223> OTHER INFORMATION: Antibody Sequence

<400> SEQUENCE: 181

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn
                100                 105

<210> SEQ ID NO 182
<211> LENGTH: 134
<212> TYPE: PRT
<213> ORGANISM: Artificial Sequence
<220> FEATURE:
<223> OTHER INFORMATION: Antibody Sequence

<400> SEQUENCE: 182

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Ser
            100                 105                 110

Gly Ala His His His His His His Gly Ala Glu Phe Glu Gln Lys Leu
        115                 120                 125

Ile Ser Glu Glu Asp Leu
    130

<210> SEQ ID NO 183
<211> LENGTH: 120
<212> TYPE: PRT
<213> ORGANISM: Artificial Sequence
<220> FEATURE:
```

<223> OTHER INFORMATION: Antibody Sequence

<400> SEQUENCE: 183

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Ser
            100                 105                 110

Gly Ala His His His His His His
        115                 120

<210> SEQ ID NO 184
<211> LENGTH: 114
<212> TYPE: PRT
<213> ORGANISM: Artificial Sequence
<220> FEATURE:
<223> OTHER INFORMATION: Antibody Sequence

<400> SEQUENCE: 184

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Ser
            100                 105                 110

Gly Ala

<210> SEQ ID NO 185
<211> LENGTH: 120
<212> TYPE: PRT
<213> ORGANISM: Artificial Sequence
<220> FEATURE:
<223> OTHER INFORMATION: Antibody Sequence

<400> SEQUENCE: 185

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Cys
                100                 105                 110

Gly Ala His His His His His His
            115                 120

<210> SEQ ID NO 186
<211> LENGTH: 120
<212> TYPE: PRT
<213> ORGANISM: Artificial Sequence
<220> FEATURE:
<223> OTHER INFORMATION: Antibody Sequence

<400> SEQUENCE: 186

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Cys
                100                 105                 110

Lys Ala His His His His His His
            115                 120

<210> SEQ ID NO 187
<211> LENGTH: 114
<212> TYPE: PRT
<213> ORGANISM: Artificial Sequence
<220> FEATURE:
<223> OTHER INFORMATION: Antibody Sequence

<400> SEQUENCE: 187

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Ser Ala Pro

Ser Ala

<210> SEQ ID NO 188
<211> LENGTH: 123
<212> TYPE: PRT
<213> ORGANISM: Artificial Sequence
<220> FEATURE:
<223> OTHER INFORMATION: Antibody Sequence

<400> SEQUENCE: 188

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Ser Pro Ser
            100                 105                 110

Thr Pro Pro Thr Pro Ser Pro Thr Pro Ala
        115                 120

<210> SEQ ID NO 189
<211> LENGTH: 134
<212> TYPE: PRT
<213> ORGANISM: Artificial Sequence
<220> FEATURE:
<223> OTHER INFORMATION: Antibody Sequence

<400> SEQUENCE: 189

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gln Ala Ser
            100                 105                 110

Gly Ala His His His His His His Gly Ala Glu Phe Glu Gln Lys Leu
        115                 120                 125

Ile Ser Glu Glu Asp Leu
        130

<210> SEQ ID NO 190
<211> LENGTH: 132
<212> TYPE: PRT

-continued

```
<213> ORGANISM: Artificial Sequence
<220> FEATURE:
<223> OTHER INFORMATION: Antibody Sequence

<400> SEQUENCE: 190

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gln Ala Ser Gly Ala
            100                 105                 110

His His His His His His Gly Ala Glu Phe Glu Gln Lys Leu Ile Ser
        115                 120                 125

Glu Glu Asp Leu
        130

<210> SEQ ID NO 191
<211> LENGTH: 119
<212> TYPE: PRT
<213> ORGANISM: Artificial Sequence
<220> FEATURE:
<223> OTHER INFORMATION: Antibody Sequence

<400> SEQUENCE: 191

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gln Ala Ser Gly Ala
            100                 105                 110

His His His His His His His
        115

<210> SEQ ID NO 192
<211> LENGTH: 107
<212> TYPE: PRT
<213> ORGANISM: Artificial Sequence
<220> FEATURE:
<223> OTHER INFORMATION: Antibody Sequence

<400> SEQUENCE: 192

Thr Arg Val Asp Gln Thr Pro Arg Thr Ala Thr Lys Glu Thr Gly Glu
1               5                   10                  15
```

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn
            100                 105

<210> SEQ ID NO 193
<211> LENGTH: 137
<212> TYPE: PRT
<213> ORGANISM: Artificial Sequence
<220> FEATURE:
<223> OTHER INFORMATION: Antibody Sequence

<400> SEQUENCE: 193

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gln Ala Ser Gly Ala His His His His His Gly Ala Glu Phe Glu
        115                 120                 125

Gln Lys Leu Ile Ser Glu Glu Asp Leu
    130                 135

<210> SEQ ID NO 194
<211> LENGTH: 137
<212> TYPE: PRT
<213> ORGANISM: Artificial Sequence
<220> FEATURE:
<223> OTHER INFORMATION: Antibody Sequence

<400> SEQUENCE: 194

Ala Lys Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
 50                  55                  60

Ser Phe Ser Leu Arg Ile Lys Asp Leu Thr Val Ala Asp Ser Ala Thr

```
                65                  70                  75                  80
Tyr Tyr Cys Lys Ala Gln Ser Gly Met Ala Ile Asp Ile Gly Ser Gly
                    85                  90                  95

His Gly Tyr Asn Trp Tyr Asp Gly Ala Gly Thr Val Leu Thr Val Asn
                100                 105                 110

Gln Ala Ser Gly Ala His His His His His Gly Ala Glu Phe Glu
                115                 120                 125

Gln Lys Leu Ile Ser Glu Glu Asp Leu
            130                 135

<210> SEQ ID NO 195
<211> LENGTH: 130
<212> TYPE: PRT
<213> ORGANISM: Artificial Sequence
<220> FEATURE:
<223> OTHER INFORMATION: Antibody Sequence

<400> SEQUENCE: 195

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Ala
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Ala Met Trp Gly Gln Trp Tyr Asp
                85                  90                  95

Gly Ala Gly Thr Val Leu Thr Val Asn Gln Ala Ser Gly Ala His His
                100                 105                 110

His His His His Gly Ala Glu Phe Glu Gln Lys Leu Ile Ser Glu Glu
            115                 120                 125

Asp Leu
    130

<210> SEQ ID NO 196
<211> LENGTH: 134
<212> TYPE: PRT
<213> ORGANISM: Artificial Sequence
<220> FEATURE:
<223> OTHER INFORMATION: Antibody Sequence

<400> SEQUENCE: 196

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Phe
                20                  25                  30

Ala Thr Tyr Trp Tyr Arg Lys Asn Pro Gly Ser Ser Asn Gln Glu Arg
            35                  40                  45

Ile Ser Ile Ser Gly Arg Tyr Val Glu Ser Val Asn Lys Arg Thr Met
        50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Met Pro Gln His Trp Pro Ala Ala
                85                  90                  95
```

His Trp Tyr Asp Gly Ala Gly Thr Val Leu Thr Val Asn Gln Ala Ser
            100                 105                 110

Gly Ala His His His His His Gly Ala Glu Phe Glu Gln Lys Leu
        115                 120                 125

Ile Ser Glu Glu Asp Leu
    130

<210> SEQ ID NO 197
<211> LENGTH: 103
<212> TYPE: PRT
<213> ORGANISM: Artificial Sequence
<220> FEATURE:
<223> OTHER INFORMATION: Antibody Sequence

<400> SEQUENCE: 197

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Gly Asp Gly Ala
                85                  90                  95

Gly Thr Lys Val Glu Ile Lys
            100

<210> SEQ ID NO 198
<211> LENGTH: 134
<212> TYPE: PRT
<213> ORGANISM: Artificial Sequence
<220> FEATURE:
<223> OTHER INFORMATION: Antibody Sequence

<400> SEQUENCE: 198

Thr Arg Val Asp Gln Ser Pro Ser Ser Leu Ser Ala Ser Val Gly Asp
1               5                   10                  15

Arg Val Thr Ile Thr Cys Val Leu Thr Gly Ala Asn Tyr Gly Leu Ala
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Tyr Pro Trp Gly Ala Gly Ala Pro Trp Leu Val
                85                  90                  95

Gln Trp Tyr Asp Gly Ala Gly Thr Lys Val Glu Ile Lys Gln Ala Ser
            100                 105                 110

Gly Ala His His His His His Gly Ala Glu Phe Glu Gln Lys Leu
        115                 120                 125

Ile Ser Glu Glu Asp Leu
    130

<210> SEQ ID NO 199

```
<211> LENGTH: 134
<212> TYPE: PRT
<213> ORGANISM: Artificial Sequence
<220> FEATURE:
<223> OTHER INFORMATION: Antibody Sequence

<400> SEQUENCE: 199

Thr Arg Val Asp Gln Ser Pro Ser Ser Leu Ser Ala Ser Val Gly Asp
1               5                   10                  15

Arg Val Thr Ile Thr Cys Val Leu Thr Gly Ala Asn Tyr Gly Leu Ala
            20                  25                  30

Ser Thr Tyr Trp Tyr Arg Lys Asn Pro Gly Ser Ser Asn Gln Glu Arg
        35                  40                  45

Ile Ser Ile Ser Gly Arg Tyr Ser Glu Ser Val Asn Lys Arg Thr Met
50                  55                  60

Ser Phe Thr Leu Thr Ile Ser Ser Leu Gln Pro Glu Asp Ser Ala Thr
65                  70                  75                  80

Tyr Tyr Cys Arg Ala Tyr Pro Trp Gly Ala Gly Ala Pro Trp Leu Val
                85                  90                  95

Gln Trp Tyr Asp Gly Ala Gly Thr Lys Val Glu Ile Lys Gln Ala Ser
            100                 105                 110

Gly Ala His His His His His His Gly Ala Glu Phe Glu Gln Lys Leu
        115                 120                 125

Ile Ser Glu Glu Asp Leu
    130

<210> SEQ ID NO 200
<211> LENGTH: 134
<212> TYPE: PRT
<213> ORGANISM: Artificial Sequence
<220> FEATURE:
<223> OTHER INFORMATION: Antibody Sequence

<400> SEQUENCE: 200

Ala Ser Val Asn Gln Ser Pro Ser Ser Leu Ser Ala Ser Val Gly Asp
1               5                   10                  15

Arg Val Thr Ile Thr Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Thr Leu Thr Ile Ser Ser Leu Gln Pro Glu Asp Phe Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Lys Val Glu Ile Lys Gln Ala Ser
            100                 105                 110

Gly Ala His His His His His His Gly Ala Glu Phe Glu Gln Lys Leu
        115                 120                 125

Ile Ser Glu Glu Asp Leu
    130

<210> SEQ ID NO 201
<211> LENGTH: 134
<212> TYPE: PRT
<213> ORGANISM: Artificial Sequence
<220> FEATURE:
<223> OTHER INFORMATION: Antibody Sequence
```

<400> SEQUENCE: 201

Ala Ser Val Asp Gln Ser Pro Ser Ser Leu Ser Ala Ser Val Gly Asp
1               5                   10                  15

Arg Val Thr Ile Thr Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Ser Glu Ser Val Asn Lys Arg Thr Met
50                  55                  60

Ser Phe Thr Leu Thr Ile Ser Ser Leu Gln Pro Glu Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Lys Val Glu Ile Lys Gln Ala Ser
            100                 105                 110

Gly Ala His His His His His His Gly Ala Glu Phe Glu Gln Lys Leu
        115                 120                 125

Ile Ser Glu Glu Asp Leu
    130

<210> SEQ ID NO 202
<211> LENGTH: 134
<212> TYPE: PRT
<213> ORGANISM: Artificial Sequence
<220> FEATURE:
<223> OTHER INFORMATION: Antibody Sequence

<400> SEQUENCE: 202

Ala Ser Val Asp Gln Ser Pro Ser Ala Ser Ala Ser Val Gly Asp
1               5                   10                  15

Arg Leu Thr Ile Thr Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Ser Glu Ser Val Asn Lys Arg Thr Met
50                  55                  60

Ser Phe Thr Leu Thr Ile Ser Ser Leu Gln Pro Glu Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Lys Leu Glu Val Lys Gln Ala Ser
            100                 105                 110

Gly Ala His His His His His Gly Ala Glu Phe Glu Gln Lys Leu
        115                 120                 125

Ile Ser Glu Glu Asp Leu
    130

<210> SEQ ID NO 203
<211> LENGTH: 137
<212> TYPE: PRT
<213> ORGANISM: Artificial Sequence
<220> FEATURE:
<223> OTHER INFORMATION: Antibody Sequence

<400> SEQUENCE: 203

Ala Ser Val Asn Gln Ser Pro Ser Ser Leu Ser Ala Ser Val Gly Asp
1               5                   10                  15

```
Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Ser Glu Ser Val Asn Lys Gly Ala Lys
    50                  55                  60

Ser Phe Thr Leu Thr Ile Ser Ser Leu Gln Pro Glu Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

Gln Ala Ser Gly Ala His His His His His Gly Ala Glu Phe Glu
            115                 120                 125

Gln Lys Leu Ile Ser Glu Glu Asp Leu
            130                 135

<210> SEQ ID NO 204
<211> LENGTH: 137
<212> TYPE: PRT
<213> ORGANISM: Artificial Sequence
<220> FEATURE:
<223> OTHER INFORMATION: Antibody Sequence

<400> SEQUENCE: 204

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Ser Glu Ser Val Asn Lys Gly Ala Lys
    50                  55                  60

Ser Phe Thr Leu Thr Ile Ser Ser Leu Gln Pro Glu Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

Gln Ala Ser Gly Ala His His His His His Gly Ala Glu Phe Glu
            115                 120                 125

Gln Lys Leu Ile Ser Glu Glu Asp Leu
            130                 135

<210> SEQ ID NO 205
<211> LENGTH: 137
<212> TYPE: PRT
<213> ORGANISM: Artificial Sequence
<220> FEATURE:
<223> OTHER INFORMATION: Antibody Sequence

<400> SEQUENCE: 205

Ala Ser Val Asn Gln Ser Pro Ser Ser Ala Ser Ala Ser Val Gly Asp
1               5                   10                  15

Arg Leu Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
```

```
                35                  40                  45
Met Ser Ile Gly Gly Arg Tyr Ser Glu Ser Val Asn Lys Gly Ala Lys
        50                  55                  60

Ser Phe Thr Leu Thr Ile Ser Ser Leu Gln Pro Glu Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Leu Glu Val Lys
            100                 105                 110

Gln Ala Ser Gly Ala His His His His His Gly Ala Glu Phe Glu
        115                 120                 125

Gln Lys Leu Ile Ser Glu Glu Asp Leu
        130                 135

<210> SEQ ID NO 206
<211> LENGTH: 137
<212> TYPE: PRT
<213> ORGANISM: Artificial Sequence
<220> FEATURE:
<223> OTHER INFORMATION: Antibody Sequence

<400> SEQUENCE: 206

Ala Ser Val Asn Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

Gln Ala Ser Gly Ala His His His His His Gly Ala Glu Phe Glu
        115                 120                 125

Gln Lys Leu Ile Ser Glu Glu Asp Leu
        130                 135

<210> SEQ ID NO 207
<211> LENGTH: 137
<212> TYPE: PRT
<213> ORGANISM: Artificial Sequence
<220> FEATURE:
<223> OTHER INFORMATION: Antibody Sequence

<400> SEQUENCE: 207

Ala Ser Val Asn Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
        50                  55                  60
```

```
Ser Phe Thr Leu Thr Ile Ser Ser Leu Gln Pro Glu Asp Phe Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Val Glu Ile Lys
            100                 105                 110

Gln Ala Ser Gly Ala His His His His His Gly Ala Glu Phe Glu
        115                 120                 125

Gln Lys Leu Ile Ser Glu Glu Asp Leu
        130                 135
```

<210> SEQ ID NO 208
<211> LENGTH: 137
<212> TYPE: PRT
<213> ORGANISM: Artificial Sequence
<220> FEATURE:
<223> OTHER INFORMATION: Antibody Sequence

<400> SEQUENCE: 208

```
Ala Ser Val Asn Gln Ser Pro Ser Ser Leu Ser Ala Ser Val Gly Asp
 1               5                  10                  15

Arg Val Thr Ile Thr Cys Val Leu Thr Asp Thr Ser Tyr Gly Leu Tyr
                 20                  25                  30

Ser Thr Ser Trp Phe Arg Lys Asn Pro Gly Thr Thr Asp Trp Glu Arg
             35                  40                  45

Met Ser Ile Gly Gly Arg Phe Ser Gly Ser Gly Ser Lys Arg Ala Lys
         50                  55                  60

Ser Phe Thr Leu Thr Ile Ser Ser Leu Gln Pro Glu Asp Phe Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Val Glu Ile Lys
            100                 105                 110

Gln Ala Ser Gly Ala His His His His His Gly Ala Glu Phe Glu
        115                 120                 125

Gln Lys Leu Ile Ser Glu Glu Asp Leu
        130                 135
```

<210> SEQ ID NO 209
<211> LENGTH: 137
<212> TYPE: PRT
<213> ORGANISM: Artificial Sequence
<220> FEATURE:
<223> OTHER INFORMATION: Antibody Sequence

<400> SEQUENCE: 209

```
Ala Ser Val Asn Gln Ser Pro Ser Ser Leu Ser Ala Ser Val Gly Asp
 1               5                  10                  15

Arg Val Thr Ile Thr Cys Val Leu Thr Asp Thr Ser Tyr Gly Leu Tyr
                 20                  25                  30

Ser Thr Ser Trp Tyr Gln Gln Lys Pro Gly Thr Thr Asp Trp Glu Arg
             35                  40                  45

Met Ser Ile Gly Gly Arg Tyr Val Glu Ser Val Asn Lys Arg Ala Lys
         50                  55                  60

Ser Phe Thr Leu Thr Ile Ser Ser Leu Gln Pro Glu Asp Phe Ala Thr
 65                  70                  75                  80

Tyr Tyr Cys Lys Ala Gln Ser Gly Met Ala Ile Ser Thr Gly Ser Gly
                 85                  90                  95
```

His Gly Tyr Asn Trp Tyr Asp Gly Ala Gly Thr Lys Val Glu Ile Lys
                100                 105                 110

Gln Ala Ser Gly Ala His His His His His Gly Ala Glu Phe Glu
            115                 120                 125

Gln Lys Leu Ile Ser Glu Glu Asp Leu
        130                 135

<210> SEQ ID NO 210
<211> LENGTH: 137
<212> TYPE: PRT
<213> ORGANISM: Artificial Sequence
<220> FEATURE:
<223> OTHER INFORMATION: Antibody Sequence

<400> SEQUENCE: 210

Ala Ser Val Asn Gln Ser Pro Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Tyr Gln Gln Lys Pro Gly Thr Thr Asp Trp Glu Arg
        35                  40                  45

Met Ser Ile Gly Gly Arg Phe Ser Gly Ser Gly Ser Lys Arg Ala Lys
    50                  55                  60

Ser Phe Thr Leu Thr Ile Ser Ser Leu Gln Pro Glu Asp Phe Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
                100                 105                 110

Gln Ala Ser Gly Ala His His His His His Gly Ala Glu Phe Glu
            115                 120                 125

Gln Lys Leu Ile Ser Glu Glu Asp Leu
        130                 135

<210> SEQ ID NO 211
<211> LENGTH: 264
<212> TYPE: PRT
<213> ORGANISM: Artificial Sequence
<220> FEATURE:
<223> OTHER INFORMATION: Antibody Sequence

<400> SEQUENCE: 211

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Ser
            100                 105                 110

Gly Gly Gly Gly Ser Gly Gly Gly Gly Ser Gly Gly Gly Gly Ser Gly

```
            115                 120                 125
Gly Gly Gly Ser Thr Arg Val Asp Gln Thr Pro Arg Thr Ala Thr Lys
        130                 135                 140
Glu Thr Gly Glu Ser Leu Thr Ile Asn Cys Val Leu Thr Asp Thr Ser
145                 150                 155                 160
Tyr Gly Leu Tyr Ser Thr Ser Trp Phe Arg Lys Asn Pro Gly Thr Thr
                165                 170                 175
Asp Trp Glu Arg Met Ser Ile Gly Gly Arg Tyr Val Glu Ser Val Asn
            180                 185                 190
Lys Gly Ala Lys Ser Phe Ser Leu Arg Ile Lys Asp Leu Thr Val Ala
        195                 200                 205
Asp Ser Ala Thr Tyr Tyr Cys Lys Ala Arg Glu Ala Arg His Pro Trp
    210                 215                 220
Leu Arg Gln Trp Tyr Asp Gly Ala Gly Thr Val Leu Thr Val Asn Gln
225                 230                 235                 240
Ala Ser Gly Ala His His His His His Gly Ala Glu Phe Glu Gln
                245                 250                 255
Lys Leu Ile Ser Glu Glu Asp Leu
            260

<210> SEQ ID NO 212
<211> LENGTH: 250
<212> TYPE: PRT
<213> ORGANISM: Artificial Sequence
<220> FEATURE:
<223> OTHER INFORMATION: Antibody Sequence

<400> SEQUENCE: 212

Thr Arg Val Asp Gln Thr Pro Arg Thr Ala Thr Lys Glu Thr Gly Glu
1               5                   10                  15
Ser Leu Thr Ile Asn Cys Val Leu Thr Asp Thr Ser Tyr Gly Leu Tyr
            20                  25                  30
Ser Thr Ser Trp Phe Arg Lys Asn Pro Gly Thr Thr Asp Trp Glu Arg
        35                  40                  45
Met Ser Ile Gly Gly Arg Tyr Val Glu Ser Val Asn Lys Gly Ala Lys
    50                  55                  60
Ser Phe Ser Leu Arg Ile Lys Asp Leu Thr Val Ala Asp Ser Ala Thr
65                  70                  75                  80
Tyr Tyr Cys Lys Ala Arg Glu Ala Arg His Pro Trp Leu Arg Gln Trp
                85                  90                  95
Tyr Asp Gly Ala Gly Thr Val Leu Thr Val Asn Gly Gly Gly Gly Ser
            100                 105                 110
Gly Gly Gly Gly Ser Gly Gly Gly Ser Gly Gly Gly Gly Ser Gly
        115                 120                 125
Gly Gly Gly Ser Thr Arg Val Asp Gln Thr Pro Arg Thr Ala Thr Lys
    130                 135                 140
Glu Thr Gly Glu Ser Leu Thr Ile Asn Cys Val Leu Thr Asp Thr Ser
145                 150                 155                 160
Tyr Gly Leu Tyr Ser Thr Ser Trp Phe Arg Lys Asn Pro Gly Thr Thr
                165                 170                 175
Asp Trp Glu Arg Met Ser Ile Gly Gly Arg Tyr Val Glu Ser Val Asn
            180                 185                 190
Lys Gly Ala Lys Ser Phe Ser Leu Arg Ile Lys Asp Leu Thr Val Ala
        195                 200                 205
Asp Ser Ala Thr Tyr Tyr Cys Lys Ala Arg Glu Ala Arg His Pro Trp
```

```
                    210                 215                 220

Leu Arg Gln Trp Tyr Asp Gly Ala Gly Thr Val Leu Thr Val Asn Gln
225                 230                 235                 240

Ala Ser Gly Ala His His His His His His
                245                 250

<210> SEQ ID NO 213
<211> LENGTH: 244
<212> TYPE: PRT
<213> ORGANISM: Artificial Sequence
<220> FEATURE:
<223> OTHER INFORMATION: Antibody Sequence

<400> SEQUENCE: 213

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Ser
            100                 105                 110

Gly Gly Gly Gly Ser Gly Gly Gly Ser Gly Gly Gly Ser Gly
        115                 120                 125

Gly Gly Ser Thr Arg Val Asp Gln Thr Pro Arg Thr Ala Thr Lys
    130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Gly Ala Lys Ser Phe Ser Leu Arg Ile Lys Asp Leu Thr Val Ala
        195                 200                 205

Asp Ser Ala Thr Tyr Tyr Cys Lys Ala Arg Glu Ala Arg His Pro Trp
    210                 215                 220

Leu Arg Gln Trp Tyr Asp Gly Ala Gly Thr Val Leu Thr Val Asn Ser
225                 230                 235                 240

Ala Pro Ser Ala

<210> SEQ ID NO 214
<211> LENGTH: 274
<212> TYPE: PRT
<213> ORGANISM: Artificial Sequence
<220> FEATURE:
<223> OTHER INFORMATION: Antibody Sequence

<400> SEQUENCE: 214

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
```

```
                    20                  25                  30
Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
                100                 105                 110

Gly Gly Gly Gly Ser Gly Gly Gly Ser Gly Gly Gly Gly Ser Gly
            115                 120                 125

Gly Gly Gly Ser Gly Gly Gly Ser Ala Ser Val Asn Gln Thr Pro
        130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
                180                 185                 190

Val Glu Ser Val Asn Lys Arg Ala Lys Ser Phe Ser Leu Arg Ile Lys
                195                 200                 205

Asp Leu Thr Val Ala Asp Ser Ala Thr Tyr Tyr Cys Lys Ala Gln Ser
                210                 215                 220

Gly Met Ala Ile Ser Thr Gly Ser Gly His Gly Tyr Asn Trp Tyr Asp
225                 230                 235                 240

Gly Ala Gly Thr Val Leu Thr Val Asn Gln Ala Ser Gly Ala His His
                245                 250                 255

His His His His Gly Ala Glu Phe Glu Gln Lys Leu Ile Ser Glu Glu
                260                 265                 270

Asp Leu

<210> SEQ ID NO 215
<211> LENGTH: 260
<212> TYPE: PRT
<213> ORGANISM: Artificial Sequence
<220> FEATURE:
<223> OTHER INFORMATION: Antibody Sequence

<400> SEQUENCE: 215

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
                100                 105                 110
```

Gly Gly Gly Gly Ser Gly Gly Gly Ser Gly Gly Gly Ser Gly
            115                 120                 125

Gly Gly Gly Ser Gly Gly Gly Ser Ala Ser Val Asn Gln Thr Pro
        130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
            180                 185                 190

Val Glu Ser Val Asn Lys Arg Ala Lys Ser Phe Ser Leu Arg Ile Lys
        195                 200                 205

Asp Leu Thr Val Ala Asp Ser Ala Thr Tyr Tyr Cys Lys Ala Gln Ser
    210                 215                 220

Gly Met Ala Ile Ser Thr Gly Ser Gly His Gly Tyr Asn Trp Tyr Asp
225                 230                 235                 240

Gly Ala Gly Thr Val Leu Thr Val Asn Gln Ala Ser Gly Ala His His
                245                 250                 255

His His His His
        260

<210> SEQ ID NO 216
<211> LENGTH: 268
<212> TYPE: PRT
<213> ORGANISM: Artificial Sequence
<220> FEATURE:
<223> OTHER INFORMATION: Antibody Sequence

<400> SEQUENCE: 216

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Lys Tyr Gly Leu Phe
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Met Pro Gln His Trp His Pro Ala Ala
                85                  90                  95

His Trp Tyr Asp Gly Ala Gly Thr Val Leu Thr Val Asn Gly Gly Gly
            100                 105                 110

Gly Ser Gly Gly Gly Gly Ser Gly Gly Gly Ser Gly Gly Gly
        115                 120                 125

Ser Gly Gly Gly Gly Ser Thr Arg Val Asp Gln Thr Pro Arg Thr Ala
        130                 135                 140

Thr Lys Glu Thr Gly Glu Ser Leu Thr Ile Asn Cys Val Val Thr Gly
145                 150                 155                 160

Ala Lys Tyr Gly Leu Phe Ala Thr Tyr Trp Tyr Arg Lys Asn Pro Gly
                165                 170                 175

Ser Ser Asn Gln Glu Arg Ile Ser Ile Ser Gly Arg Tyr Val Glu Ser
            180                 185                 190

Val Asn Lys Arg Thr Met Ser Phe Ser Leu Arg Ile Lys Asp Leu Thr
        195                 200                 205

```
Val Ala Asp Ser Ala Thr Tyr Tyr Cys Lys Ala Val Phe Met Pro Gln
            210                 215                 220

His Trp His Pro Ala Ala His Trp Tyr Asp Gly Ala Gly Thr Val Leu
225                 230                 235                 240

Thr Val Asn Gln Ala Ser Gly Ala His His His His His Gly Ala
                245                 250                 255

Glu Phe Glu Gln Lys Leu Ile Ser Glu Glu Asp Leu
                260                 265

<210> SEQ ID NO 217
<211> LENGTH: 254
<212> TYPE: PRT
<213> ORGANISM: Artificial Sequence
<220> FEATURE:
<223> OTHER INFORMATION: Antibody Sequence

<400> SEQUENCE: 217

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
                100                 105                 110

Gly Gly Gly Gly Ser Gly Gly Gly Ser Gly Gly Gly Gly Ser Gly
            115                 120                 125

Gly Gly Ser Gly Gly Gly Ser Ala Ser Val Asn Gln Thr Pro
        130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
            180                 185                 190

Val Glu Ser Val Asn Lys Arg Ala Lys Ser Phe Ser Leu Arg Ile Lys
        195                 200                 205

Asp Leu Thr Val Ala Asp Ser Ala Thr Tyr Tyr Cys Lys Ala Gln Ser
    210                 215                 220

Gly Met Ala Ile Ser Thr Gly Ser Gly His Gly Tyr Asn Trp Tyr Asp
225                 230                 235                 240

Gly Ala Gly Thr Val Leu Thr Val Asn Gln Ala Cys Gly Ala
                245                 250

<210> SEQ ID NO 218
<211> LENGTH: 260
<212> TYPE: PRT
<213> ORGANISM: Artificial Sequence
<220> FEATURE:
<223> OTHER INFORMATION: Antibody Sequence
```

<400> SEQUENCE: 218

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Ser Gly
        115                 120                 125

Gly Gly Gly Ser Gly Gly Gly Ser Ala Ser Val Asn Gln Thr Pro
        130                 135                 140

Arg Thr Ala Thr Lys Glu Thr Gly Glu Ser Leu Thr Ile Asn Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
            180                 185                 190

Val Glu Ser Val Asn Lys Arg Ala Lys Ser Phe Ser Leu Arg Ile Lys
        195                 200                 205

Asp Leu Thr Val Ala Asp Ser Ala Thr Tyr Tyr Cys Lys Ala Gln Ser
    210                 215                 220

Gly Met Ala Ile Ser Thr Gly Ser Gly His Gly Tyr Asn Trp Tyr Asp
225                 230                 235                 240

Gly Ala Gly Thr Val Leu Thr Val Asn Gln Ala Cys Gly Ala His His
                245                 250                 255

His His His His
        260
```

<210> SEQ ID NO 219
<211> LENGTH: 264
<212> TYPE: PRT
<213> ORGANISM: Artificial Sequence
<220> FEATURE:
<223> OTHER INFORMATION: Antibody Sequence

<400> SEQUENCE: 219

```
Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Thr Leu Thr Ile Ser Ser Leu Gln Pro Glu Asp Phe Ala Thr
65                  70                  75                  80

Tyr Tyr Cys Lys Ala Arg Glu Ala Arg His Pro Trp Leu Arg Gln Trp
```

85                  90                  95
Tyr Asp Gly Ala Gly Thr Lys Val Glu Ile Lys Gly Gly Gly Ser
                    100                 105                 110

Gly Gly Gly Gly Ser Gly Gly Gly Ser Gly Gly Gly Ser Gly
            115                 120                 125

Gly Gly Gly Ser Thr Arg Val Asp Gln Ser Pro Ser Ser Leu Ser Ala
        130                 135                 140

Ser Val Gly Asp Arg Val Thr Ile Thr Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Gly Ala Lys Ser Phe Thr Leu Thr Ile Ser Ser Leu Gln Pro Glu
        195                 200                 205

Asp Phe Ala Thr Tyr Tyr Cys Lys Ala Arg Glu Ala Arg His Pro Trp
    210                 215                 220

Leu Arg Gln Trp Tyr Asp Gly Ala Gly Thr Lys Val Glu Ile Lys Gln
225                 230                 235                 240

Ala Ser Gly Ala His His His His Gly Ala Glu Phe Glu Gln
                245                 250                 255

Lys Leu Ile Ser Glu Glu Asp Leu
            260

<210> SEQ ID NO 220
<211> LENGTH: 264
<212> TYPE: PRT
<213> ORGANISM: Artificial Sequence
<220> FEATURE:
<223> OTHER INFORMATION: Antibody Sequence

<400> SEQUENCE: 220

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Arg Glu Ala Arg His Pro Trp Leu Arg Gln Trp
                85                  90                  95

Tyr Asp Gly Ala Gly Thr Lys Val Glu Ile Lys Gly Gly Gly Gly Ser
                    100                 105                 110

Gly Gly Gly Gly Ser Gly Gly Gly Ser Gly Gly Gly Gly Ser Gly
            115                 120                 125

Gly Gly Gly Ser Thr Arg Val Asp Gln Ser Pro Ser Ser Leu Ser Ala
        130                 135                 140

Ser Val Gly Asp Arg Val Thr Ile Thr Cys Val Leu Thr Asp Thr Ser
145                 150                 155                 160

Tyr Gly Leu Tyr Ser Thr Tyr Trp Tyr Arg Lys Asn Pro Gly Ser Ser
                165                 170                 175

Asn Lys Glu Gln Ile Ser Ile Ser Gly Arg Tyr Ser Glu Ser Val Asn

```
            180                 185                 190
Lys Gly Thr Lys Ser Phe Thr Leu Thr Ile Ser Ser Leu Gln Pro Glu
            195                 200                 205

Asp Ser Ala Thr Tyr Tyr Cys Arg Ala Arg Glu Ala Arg His Pro Trp
        210                 215                 220

Leu Arg Gln Trp Tyr Asp Gly Ala Gly Thr Lys Val Glu Ile Lys Gln
225                 230                 235                 240

Ala Ser Gly Ala His His His His His Gly Ala Glu Phe Glu Gln
                245                 250                 255

Lys Leu Ile Ser Glu Glu Asp Leu
            260

<210> SEQ ID NO 221
<211> LENGTH: 264
<212> TYPE: PRT
<213> ORGANISM: Artificial Sequence
<220> FEATURE:
<223> OTHER INFORMATION: Antibody Sequence

<400> SEQUENCE: 221

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Tyr Trp Tyr Arg Lys Asn Pro Gly Thr Thr Asp Trp Glu Arg
        35                  40                  45

Met Ser Ile Gly Gly Arg Tyr Ser Glu Ser Val Asn Lys Gly Ala Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Arg Glu Ala Arg His Pro Trp Leu Arg Gln Trp
                85                  90                  95

Tyr Asp Gly Ala Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Thr Arg Val Asp Gln Ser Pro Ser Ser Leu Ser Ala
    130                 135                 140

Ser Val Gly Asp Arg Val Thr Ile Thr Cys Val Leu Thr Asp Thr Ser
145                 150                 155                 160

Tyr Gly Leu Tyr Ser Thr Tyr Trp Tyr Arg Lys Asn Pro Gly Thr Thr
                165                 170                 175

Asp Trp Glu Arg Met Ser Ile Gly Gly Arg Tyr Ser Glu Ser Val Asn
            180                 185                 190

Lys Gly Ala Lys Ser Phe Thr Leu Thr Ile Ser Ser Leu Gln Pro Glu
        195                 200                 205

Asp Ser Ala Thr Tyr Tyr Cys Arg Ala Arg Glu Ala Arg His Pro Trp
    210                 215                 220

Leu Arg Gln Trp Tyr Asp Gly Ala Gly Thr Lys Val Glu Ile Lys Gln
225                 230                 235                 240

Ala Ser Gly Ala His His His His His Gly Ala Glu Phe Glu Gln
                245                 250                 255

Lys Leu Ile Ser Glu Glu Asp Leu
            260
```

```
<210> SEQ ID NO 222
<211> LENGTH: 274
<212> TYPE: PRT
<213> ORGANISM: Artificial Sequence
<220> FEATURE:
<223> OTHER INFORMATION: Antibody Sequence

<400> SEQUENCE: 222

Ala Ser Val Asn Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Ser Glu Ser Val Asn Lys Gly Ala Lys
    50                  55                  60

Ser Phe Thr Leu Thr Ile Ser Ser Leu Gln Pro Glu Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Lys Val Glu Ile Lys
            100                 105                 110

Gly Gly Gly Gly Ser Gly Gly Gly Ser Gly Gly Gly Gly Ser Gly
            115                 120                 125

Gly Gly Gly Ser Gly Gly Gly Ser Ala Ser Val Asn Gln Ser Pro
        130                 135                 140

Ser Ser Leu Ser Ala Ser Val Gly Asp Arg Val Thr Ile Thr Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
            180                 185                 190

Ser Glu Ser Val Asn Lys Gly Ala Lys Ser Phe Thr Leu Thr Ile Ser
        195                 200                 205

Ser Leu Gln Pro Glu Asp Ser Ala Thr Tyr Tyr Cys Lys Ala Gln Ser
    210                 215                 220

Gly Met Ala Ile Ser Thr Gly Ser Gly His Gly Tyr Asn Trp Tyr Asp
225                 230                 235                 240

Gly Ala Gly Thr Lys Val Glu Ile Lys Gln Ala Ser Gly Ala His His
                245                 250                 255

His His His His Gly Ala Glu Phe Glu Gln Lys Leu Ile Ser Glu Glu
            260                 265                 270

Asp Leu

<210> SEQ ID NO 223
<211> LENGTH: 274
<212> TYPE: PRT
<213> ORGANISM: Artificial Sequence
<220> FEATURE:
<223> OTHER INFORMATION: Antibody Sequence

<400> SEQUENCE: 223

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
```

```
                    35                  40                  45
Met Ser Ile Gly Gly Arg Tyr Ser Glu Ser Val Asn Lys Gly Ala Lys
 50                  55                  60

Ser Phe Thr Leu Thr Ile Ser Ser Leu Gln Pro Glu Asp Ser Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Val Glu Ile Lys
                100                 105                 110

Gly Gly Gly Gly Ser Gly Gly Gly Ser Gly Gly Gly Ser Gly
                115                 120                 125

Gly Gly Ser Gly Gly Gly Ser Thr Arg Val Asp Gln Ser Pro
        130                 135                 140

Ser Ser Leu Ser Ala Ser Val Gly Asp Arg Val Thr Ile Thr Cys Val
145                 150                 155                 160

Leu Thr Asp Thr Ser Tyr Gly Leu Tyr Ser Thr Ser Trp Phe Arg Lys
                165                 170                 175

Asn Pro Gly Thr Thr Asp Trp Glu Arg Met Ser Ile Gly Gly Arg Tyr
                180                 185                 190

Ser Glu Ser Val Asn Lys Gly Ala Lys Ser Phe Thr Leu Thr Ile Ser
                195                 200                 205

Ser Leu Gln Pro Glu Asp Ser Ala Thr Tyr Tyr Cys Lys Ala Gln Ser
        210                 215                 220

Gly Met Ala Ile Ser Thr Gly Ser Gly His Gly Tyr Asn Trp Tyr Asp
225                 230                 235                 240

Gly Ala Gly Thr Lys Val Glu Ile Lys Gln Ala Ser Gly Ala His His
                245                 250                 255

His His His His Gly Ala Glu Phe Glu Gln Lys Leu Ile Ser Glu Glu
                260                 265                 270

Asp Leu

<210> SEQ ID NO 224
<211> LENGTH: 274
<212> TYPE: PRT
<213> ORGANISM: Artificial Sequence
<220> FEATURE:
<223> OTHER INFORMATION: Antibody Sequence

<400> SEQUENCE: 224

Ala Ser Val Asn Gln Ser Pro Ser Ser Ala Ser Ala Ser Val Gly Asp
 1                   5                  10                  15

Arg Leu Thr Ile Thr Cys Val Leu Thr Asp Thr Ser Tyr Gly Leu Tyr
                 20                  25                  30

Ser Thr Ser Trp Phe Arg Lys Asn Pro Gly Thr Thr Asp Trp Glu Arg
                 35                  40                  45

Met Ser Ile Gly Gly Arg Tyr Ser Glu Ser Val Asn Lys Gly Ala Lys
 50                  55                  60

Ser Phe Thr Leu Thr Ile Ser Ser Leu Gln Pro Glu Asp Ser Ala Thr
 65                  70                  75                  80

Tyr Tyr Cys Lys Ala Gln Ser Gly Met Ala Ile Ser Thr Gly Ser Gly
                 85                  90                  95

His Gly Tyr Asn Trp Tyr Asp Gly Ala Gly Thr Lys Leu Glu Val Lys
                100                 105                 110

Gly Gly Gly Gly Ser Gly Gly Gly Ser Gly Gly Gly Ser Gly
                115                 120                 125
```

Gly Gly Gly Ser Gly Gly Gly Ser Ala Ser Val Asn Gln Ser Pro
            130             135             140

Ser Ser Ala Ser Ala Ser Val Gly Asp Arg Leu Thr Ile Thr Cys Val
145             150             155             160

Leu Thr Asp Thr Ser Tyr Gly Leu Tyr Ser Thr Ser Trp Phe Arg Lys
                165             170             175

Asn Pro Gly Thr Thr Asp Trp Glu Arg Met Ser Ile Gly Gly Arg Tyr
            180             185             190

Ser Glu Ser Val Asn Lys Gly Ala Lys Ser Phe Thr Leu Thr Ile Ser
            195             200             205

Ser Leu Gln Pro Glu Asp Ser Ala Thr Tyr Tyr Cys Lys Ala Gln Ser
            210             215             220

Gly Met Ala Ile Ser Thr Gly Ser Gly His Gly Tyr Asn Trp Tyr Asp
225             230             235             240

Gly Ala Gly Thr Lys Leu Glu Val Lys Gln Ala Ser Gly Ala His His
                245             250             255

His His His His Gly Ala Glu Phe Glu Gln Lys Leu Ile Ser Glu Glu
            260             265             270

Asp Leu

<210> SEQ ID NO 225
<211> LENGTH: 268
<212> TYPE: PRT
<213> ORGANISM: Artificial Sequence
<220> FEATURE:
<223> OTHER INFORMATION: Antibody Sequence

<400> SEQUENCE: 225

Thr Arg Val Asp Gln Ser Pro Ser Ser Leu Ser Ala Ser Val Gly Asp
1               5                   10                  15

Arg Val Thr Ile Thr Cys Val Leu Thr Gly Ala Asn Tyr Gly Leu Ala
            20                  25                  30

Ser Thr Tyr Trp Tyr Arg Lys Asn Pro Gly Ser Ser Asn Gln Glu Arg
        35                  40                  45

Ile Ser Ile Ser Gly Arg Tyr Ser Glu Ser Val Asn Lys Arg Thr Met
    50                  55                  60

Ser Phe Thr Leu Thr Ile Ser Ser Leu Gln Pro Glu Asp Ser Ala Thr
65                  70                  75                  80

Tyr Tyr Cys Arg Ala Tyr Pro Trp Gly Ala Gly Ala Pro Trp Leu Val
                85                  90                  95

Gln Trp Tyr Asp Gly Ala Gly Thr Lys Val Glu Ile Lys Gly Gly Gly
            100             105             110

Gly Ser Gly Gly Gly Gly Ser Gly Gly Gly Ser Gly Gly Gly Gly
        115             120             125

Ser Gly Gly Gly Gly Ser Thr Arg Val Asp Gln Ser Pro Ser Ser Leu
    130             135             140

Ser Ala Ser Val Gly Asp Arg Val Thr Ile Thr Cys Val Leu Thr Gly
145             150             155             160

Ala Asn Tyr Gly Leu Ala Ser Thr Tyr Trp Tyr Arg Lys Asn Pro Gly
                165             170             175

Ser Ser Asn Gln Glu Arg Ile Ser Ile Ser Gly Arg Tyr Ser Glu Ser
            180             185             190

Val Asn Lys Arg Thr Met Ser Phe Thr Leu Thr Ile Ser Ser Leu Gln
        195             200             205

```
Pro Glu Asp Ser Ala Thr Tyr Tyr Cys Arg Ala Tyr Pro Trp Gly Ala
    210                 215                 220

Gly Ala Pro Trp Leu Val Gln Trp Tyr Asp Gly Ala Gly Thr Lys Val
225                 230                 235                 240

Glu Ile Lys Gln Ala Ser Gly Ala His His His His His Gly Ala
            245                 250                 255

Glu Phe Glu Gln Lys Leu Ile Ser Glu Glu Asp Leu
            260                 265
```

<210> SEQ ID NO 226
<211> LENGTH: 268
<212> TYPE: PRT
<213> ORGANISM: Artificial Sequence
<220> FEATURE:
<223> OTHER INFORMATION: Antibody Sequence

<400> SEQUENCE: 226

```
Thr Arg Val Asp Gln Ser Pro Ser Ser Leu Ser Ala Ser Val Gly Asp
1               5                   10                  15

Arg Val Thr Ile Thr Cys Val Leu Thr Gly Ala Asn Tyr Gly Leu Ala
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Ser Ala Thr
65                  70                  75                  80

Tyr Tyr Cys Arg Ala Tyr Pro Trp Gly Ala Gly Ala Pro Trp Leu Val
                85                  90                  95

Gln Trp Tyr Asp Gly Ala Gly Thr Lys Val Glu Ile Lys Gly Gly Gly
            100                 105                 110

Gly Ser Gly Gly Gly Gly Ser Gly Gly Gly Ser Gly Gly Gly Gly
            115                 120                 125

Ser Gly Gly Gly Gly Ser Thr Arg Val Asp Gln Ser Pro Ser Ser Leu
    130                 135                 140

Ser Ala Ser Val Gly Asp Arg Val Thr Ile Thr Cys Val Leu Thr Gly
145                 150                 155                 160

Ala Asn Tyr Gly Leu Ala Ser Thr Tyr Trp Tyr Arg Lys Asn Pro Gly
                165                 170                 175

Ser Ser Asn Lys Glu Gln Ile Ser Ile Ser Gly Arg Tyr Ser Glu Ser
            180                 185                 190

Val Asn Lys Gly Thr Lys Ser Phe Thr Leu Thr Ile Ser Ser Leu Gln
        195                 200                 205

Pro Glu Asp Ser Ala Thr Tyr Tyr Cys Arg Ala Tyr Pro Trp Gly Ala
    210                 215                 220

Gly Ala Pro Trp Leu Val Gln Trp Tyr Asp Gly Ala Gly Thr Lys Val
225                 230                 235                 240

Glu Ile Lys Gln Ala Ser Gly Ala His His His His His Gly Ala
            245                 250                 255

Glu Phe Glu Gln Lys Leu Ile Ser Glu Glu Asp Leu
            260                 265
```

<210> SEQ ID NO 227
<211> LENGTH: 357
<212> TYPE: PRT
<213> ORGANISM: Artificial Sequence
<220> FEATURE:

<223> OTHER INFORMATION: Antibody Sequence

<400> SEQUENCE: 227

```
Ala Ser Val Asn Gln Thr Pro Arg Thr Ala Thr Lys Glu Thr Gly Glu
1               5                   10                  15
Ser Leu Thr Ile Asn Cys Val Val Thr Gly Ala Asn Tyr Gly Leu Ala
            20                  25                  30
Ala Thr Tyr Trp Tyr Arg Lys Asn Pro Gly Ser Ser Asn Gln Glu Arg
        35                  40                  45
Ile Ser Ile Ser Gly Arg Tyr Val Glu Ser Val Asn Lys Arg Thr Met
    50                  55                  60
Ser Phe Ser Leu Arg Ile Lys Asp Leu Thr Val Ala Asp Ser Ala Thr
65                  70                  75                  80
Tyr Tyr Cys Lys Ala Tyr Pro Gly Ala Gly Ala Pro Trp Leu Val
                85                  90                  95
Gln Trp Tyr Asp Gly Ala Gly Thr Val Leu Thr Val Asn Gly Gly Gly
                100                 105                 110
Gly Ser Gly Gly Gly Gly Ser Gly Gly Gly Ser Glu Pro Arg Gly
            115                 120                 125
Pro Thr Ile Lys Pro Cys Pro Cys Lys Cys Pro Ala Pro Asn Leu
    130                 135                 140
Leu Gly Gly Pro Ser Val Phe Ile Phe Pro Pro Lys Ile Lys Asp Val
145                 150                 155                 160
Leu Met Ile Ser Leu Ser Pro Ile Val Thr Cys Val Val Asp Val
                165                 170                 175
Ser Glu Asp Asp Pro Asp Val Gln Ile Ser Trp Phe Val Asn Asn Val
                180                 185                 190
Glu Val His Thr Ala Gln Thr Gln Thr His Arg Glu Asp Tyr Asn Ser
                195                 200                 205
Thr Leu Arg Val Val Ser Ala Leu Pro Ile Gln His Gln Asp Trp Met
    210                 215                 220
Ser Gly Lys Glu Phe Lys Cys Lys Val Asn Asn Lys Asp Leu Pro Ala
225                 230                 235                 240
Pro Ile Glu Arg Thr Ile Ser Lys Pro Lys Gly Ser Val Arg Ala Pro
                245                 250                 255
Gln Val Tyr Val Leu Pro Pro Glu Glu Glu Met Thr Lys Lys Gln
                260                 265                 270
Val Thr Leu Thr Cys Met Val Thr Asp Phe Met Pro Glu Asp Ile Tyr
    275                 280                 285
Val Glu Trp Thr Asn Asn Gly Lys Thr Glu Leu Asn Tyr Lys Asn Thr
    290                 295                 300
Glu Pro Val Leu Asp Ser Asp Gly Ser Tyr Phe Met Tyr Ser Lys Leu
305                 310                 315                 320
Arg Val Glu Lys Lys Asn Trp Val Glu Arg Asn Ser Tyr Ser Cys Ser
                325                 330                 335
Val Val His Glu Gly Leu His Asn His His Thr Lys Ser Phe Ser
                340                 345                 350
Arg Thr Pro Gly Lys
        355
```

<210> SEQ ID NO 228
<211> LENGTH: 355
<212> TYPE: PRT
<213> ORGANISM: Artificial Sequence
<220> FEATURE:

<223> OTHER INFORMATION: Antibody Sequence

<400> SEQUENCE: 228

Thr Arg Val Asp Gln Thr Pro Arg Thr Ala Thr Lys Glu Thr Gly Glu
1               5                   10                  15
Ser Leu Thr Ile Asn Cys Val Leu Thr Asp Thr Ser Tyr Gly Leu Tyr
            20                  25                  30
Ser Thr Ser Trp Phe Arg Lys Asn Pro Gly Thr Asp Trp Glu Arg
        35                  40                  45
Met Ser Ile Gly Gly Arg Tyr Val Glu Ser Val Asn Lys Gly Ala Lys
    50                  55                  60
Ser Phe Ser Leu Arg Ile Lys Asp Leu Thr Val Ala Asp Ser Ala Thr
65                  70                  75                  80
Tyr Tyr Cys Lys Ala Gln Ser Leu Ala Ile Ser Thr Arg Ser Tyr Trp
                85                  90                  95
Tyr Asp Gly Ala Gly Thr Val Leu Thr Val Asn Gly Gly Gly Ser
            100                 105                 110
Gly Gly Gly Gly Ser Gly Gly Gly Ser Glu Pro Arg Gly Pro Thr
            115                 120                 125
Ile Lys Pro Cys Pro Pro Cys Lys Cys Pro Ala Pro Asn Leu Leu Gly
    130                 135                 140
Gly Pro Ser Val Phe Ile Phe Pro Pro Lys Ile Lys Asp Val Leu Met
145                 150                 155                 160
Ile Ser Leu Ser Pro Ile Val Thr Cys Val Val Asp Val Ser Glu
                165                 170                 175
Asp Asp Pro Asp Val Gln Ile Ser Trp Phe Val Asn Asn Val Glu Val
            180                 185                 190
His Thr Ala Gln Thr Gln Thr His Arg Glu Asp Tyr Asn Ser Thr Leu
        195                 200                 205
Arg Val Val Ser Ala Leu Pro Ile Gln His Gln Asp Trp Met Ser Gly
    210                 215                 220
Lys Glu Phe Lys Cys Lys Val Asn Asn Lys Asp Leu Pro Ala Pro Ile
225                 230                 235                 240
Glu Arg Thr Ile Ser Lys Pro Lys Gly Ser Val Arg Ala Pro Gln Val
                245                 250                 255
Tyr Val Leu Pro Pro Pro Glu Glu Glu Met Thr Lys Lys Gln Val Thr
            260                 265                 270
Leu Thr Cys Met Val Thr Asp Phe Met Pro Glu Asp Ile Tyr Val Glu
        275                 280                 285
Trp Thr Asn Asn Gly Lys Thr Glu Leu Asn Tyr Lys Asn Thr Glu Pro
    290                 295                 300
Val Leu Asp Ser Asp Gly Ser Tyr Phe Met Tyr Ser Lys Leu Arg Val
305                 310                 315                 320
Glu Lys Lys Asn Trp Val Glu Arg Asn Ser Tyr Ser Cys Ser Val Val
                325                 330                 335
His Glu Gly Leu His Asn His His Thr Thr Lys Ser Phe Ser Arg Thr
            340                 345                 350
Pro Gly Lys
        355

<210> SEQ ID NO 229
<211> LENGTH: 356
<212> TYPE: PRT
<213> ORGANISM: Artificial Sequence
<220> FEATURE:

<223> OTHER INFORMATION: Antibody Sequence

<400> SEQUENCE: 229

```
Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Gly Gly Gly Ser Gly Gly Gly Ser Glu Pro Lys Ser
        115                 120                 125

Ser Asp Lys Thr His Thr Cys Pro Pro Cys Pro Ala Pro Glu Leu Leu
130                 135                 140

Gly Gly Pro Cys Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355
```

<210> SEQ ID NO 230
<211> LENGTH: 356
<212> TYPE: PRT
<213> ORGANISM: Artificial Sequence
<220> FEATURE:

<223> OTHER INFORMATION: Antibody Sequence

<400> SEQUENCE: 230

```
Thr Arg Val Asp Gln Ser Pro Ser Ser Leu Ser Ala Ser Val Gly Asp
1               5                   10                  15
Arg Val Thr Ile Thr Cys Val Leu Thr Gly Ala Asn Tyr Gly Leu Ala
            20                  25                  30
Ser Thr Tyr Trp Tyr Arg Lys Asn Pro Gly Ser Ser Asn Lys Glu Gln
        35                  40                  45
Ile Ser Ile Ser Gly Arg Tyr Ser Glu Ser Val Asn Lys Gly Thr Lys
    50                  55                  60
Ser Phe Thr Leu Thr Ile Ser Ser Leu Gln Pro Glu Asp Ser Ala Thr
65                  70                  75                  80
Tyr Tyr Cys Arg Ala Tyr Pro Trp Gly Ala Gly Ala Pro Trp Leu Val
                85                  90                  95
Gln Trp Tyr Asp Gly Ala Gly Thr Lys Val Glu Ile Lys Gly Gly Gly
            100                 105                 110
Gly Ser Gly Gly Gly Ser Gly Gly Gly Ser Glu Pro Lys Ser
            115                 120                 125
Ser Asp Lys Thr His Thr Cys Pro Pro Cys Pro Ala Pro Glu Leu Leu
    130                 135                 140
Gly Gly Pro Cys Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
His Glu Asp Pro Glu Val Lys Phe Asn Trp Tyr Val Asp Gly Val Glu
            180                 185                 190
Val His Asn Ala Lys Thr Lys Pro Arg Glu Glu Gln Tyr Asn Ser Thr
        195                 200                 205
Tyr Arg Val Val Ser Val Leu Thr Val Leu His Gln Asp Trp Leu Asn
    210                 215                 220
Gly Lys Glu Tyr Lys Cys Lys Val Ser Asn Lys Ala Leu Pro Ala Pro
225                 230                 235                 240
Ile Glu Lys Thr Ile Ser Lys Ala Lys Gly Gln Pro Arg Glu Pro Gln
                245                 250                 255
Val Tyr Thr Leu Pro Pro Ser Arg Asp Glu Leu Thr Lys Asn Gln Val
            260                 265                 270
Ser Leu Thr Cys Leu Val Lys Gly Phe Tyr Pro Ser Asp Ile Ala Val
        275                 280                 285
Glu Trp Glu Ser Asn Gly Gln Pro Glu Asn Asn Tyr Lys Thr Thr Pro
    290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Ser Leu
            340                 345                 350
Ser Pro Gly Lys
        355

<210> SEQ ID NO 231
<211> LENGTH: 356
<212> TYPE: PRT
<213> ORGANISM: Artificial Sequence
<220> FEATURE:
```

<223> OTHER INFORMATION: Antibody Sequence

<400> SEQUENCE: 231

```
Thr Arg Val Asp Gln Ser Pro Ser Ser Leu Ser Ala Ser Val Gly Asp
1               5                   10                  15
Arg Val Thr Ile Thr Cys Val Leu Thr Gly Ala Asn Tyr Gly Leu Ala
            20                  25                  30
Ser Thr Tyr Trp Tyr Arg Lys Asn Pro Gly Ser Ser Asn Gln Glu Arg
        35                  40                  45
Ile Ser Ile Ser Gly Arg Tyr Ser Glu Ser Val Asn Lys Arg Thr Met
    50                  55                  60
Ser Phe Thr Leu Thr Ile Ser Ser Leu Gln Pro Glu Asp Ser Ala Thr
65                  70                  75                  80
Tyr Tyr Cys Arg Ala Tyr Pro Trp Gly Ala Gly Ala Pro Trp Leu Val
                85                  90                  95
Gln Trp Tyr Asp Gly Ala Gly Thr Lys Val Glu Ile Lys Gly Gly Gly
                100                 105                 110
Gly Ser Gly Gly Gly Ser Gly Gly Gly Ser Glu Pro Lys Ser
                115                 120                 125
Ser Asp Lys Thr His Thr Cys Pro Pro Cys Pro Ala Pro Glu Leu Leu
    130                 135                 140
Gly Gly Pro Cys Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
His Glu Asp Pro Glu Val Lys Phe Asn Trp Tyr Val Asp Gly Val Glu
                180                 185                 190
Val His Asn Ala Lys Thr Lys Pro Arg Glu Glu Gln Tyr Asn Ser Thr
            195                 200                 205
Tyr Arg Val Val Ser Val Leu Thr Val Leu His Gln Asp Trp Leu Asn
    210                 215                 220
Gly Lys Glu Tyr Lys Cys Lys Val Ser Asn Lys Ala Leu Pro Ala Pro
225                 230                 235                 240
Ile Glu Lys Thr Ile Ser Lys Ala Lys Gly Gln Pro Arg Glu Pro Gln
                245                 250                 255
Val Tyr Thr Leu Pro Pro Ser Arg Asp Glu Leu Thr Lys Asn Gln Val
            260                 265                 270
Ser Leu Thr Cys Leu Val Lys Gly Phe Tyr Pro Ser Asp Ile Ala Val
    275                 280                 285
Glu Trp Glu Ser Asn Gly Gln Pro Glu Asn Asn Tyr Lys Thr Thr Pro
290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Ser Leu
                340                 345                 350
Ser Pro Gly Lys
        355
```

<210> SEQ ID NO 232
<211> LENGTH: 356
<212> TYPE: PRT
<213> ORGANISM: Artificial Sequence
<220> FEATURE:

<223> OTHER INFORMATION: Antibody Sequence

<400> SEQUENCE: 232

```
Ala Ser Val Asn Gln Thr Pro Arg Thr Ala Thr Lys Glu Thr Gly Glu
1               5                   10                  15
Ser Leu Thr Ile Asn Cys Val Val Thr Gly Ala Asn Tyr Gly Leu Ala
            20                  25                  30
Ala Thr Tyr Trp Tyr Arg Lys Asn Pro Gly Ser Ser Asn Gln Glu Arg
        35                  40                  45
Ile Ser Ile Ser Gly Arg Tyr Val Glu Ser Val Asn Lys Arg Thr Met
    50                  55                  60
Ser Phe Ser Leu Arg Ile Lys Asp Leu Thr Val Ala Asp Ser Ala Thr
65                  70                  75                  80
Tyr Tyr Cys Lys Ala Tyr Pro Trp Gly Ala Gly Ala Pro Trp Leu Val
                85                  90                  95
Gln Trp Tyr Asp Gly Ala Gly Thr Val Leu Thr Val Asn Gly Gly Gly
            100                 105                 110
Gly Ser Gly Gly Gly Gly Ser Gly Gly Gly Ser Glu Pro Lys Ser
        115                 120                 125
Ser Asp Lys Thr His Thr Cys Pro Pro Cys Pro Ala Pro Glu Leu Leu
    130                 135                 140
Gly Gly Pro Ser Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
His Glu Asp Pro Glu Val Lys Phe Asn Trp Tyr Val Asp Gly Val Glu
            180                 185                 190
Val His Asn Ala Lys Thr Lys Pro Arg Glu Glu Gln Tyr Asn Ser Thr
        195                 200                 205
Tyr Arg Val Val Ser Val Leu Thr Val Leu His Gln Asp Trp Leu Asn
    210                 215                 220
Gly Lys Glu Tyr Lys Cys Lys Val Ser Asn Lys Ala Leu Pro Ala Pro
225                 230                 235                 240
Ile Glu Lys Thr Ile Ser Lys Ala Lys Gly Gln Pro Arg Glu Pro Gln
                245                 250                 255
Val Tyr Thr Leu Pro Pro Ser Arg Asp Glu Leu Thr Lys Asn Gln Val
            260                 265                 270
Ser Leu Thr Cys Leu Val Lys Gly Phe Tyr Pro Ser Asp Ile Ala Val
        275                 280                 285
Glu Trp Glu Ser Asn Gly Gln Pro Glu Asn Asn Tyr Lys Thr Thr Pro
    290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Cys Leu
            340                 345                 350
Ser Pro Gly Lys
        355
```

<210> SEQ ID NO 233
<211> LENGTH: 354
<212> TYPE: PRT
<213> ORGANISM: Artificial Sequence
<220> FEATURE:

<223> OTHER INFORMATION: Antibody Sequence

<400> SEQUENCE: 233

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Ser
            100                 105                 110

Gly Gly Gly Gly Ser Gly Gly Gly Ser Glu Pro Lys Ser Ser Asp
            115                 120                 125

Lys Thr His Thr Cys Pro Pro Cys Pro Ala Pro Glu Leu Leu Gly Gly
    130                 135                 140

Pro Cys Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 234
<211> LENGTH: 359
<212> TYPE: PRT
<213> ORGANISM: Artificial Sequence
<220> FEATURE:
<223> OTHER INFORMATION: Antibody Sequence

<400> SEQUENCE: 234

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Leu | Leu | Gly |
| 1 | | | | 5 | | | | | 10 | | | | | 15 | |
| Gly | Pro | Cys | Val | Phe | Leu | Phe | Pro | Pro | Lys | Pro | Lys | Asp | Thr | Leu | Met |
| | | | 20 | | | | | 25 | | | | | 30 | | |
| Ile | Ser | Arg | Thr | Pro | Glu | Val | Thr | Cys | Val | Val | Val | Asp | Val | Ser | His |
| | | 35 | | | | | 40 | | | | | 45 | | | |
| Glu | Asp | Pro | Glu | Val | Lys | Phe | Asn | Trp | Tyr | Val | Asp | Gly | Val | Glu | Val |
| | 50 | | | | | 55 | | | | | 60 | | | | |
| His | Asn | Ala | Lys | Thr | Lys | Pro | Arg | Glu | Glu | Gln | Tyr | Asn | Ser | Thr | Tyr |
| 65 | | | | | 70 | | | | | 75 | | | | | 80 |
| Arg | Val | Val | Ser | Val | Leu | Thr | Val | Leu | His | Gln | Asp | Trp | Leu | Asn | Gly |
| | | | | 85 | | | | | 90 | | | | | 95 | |
| Lys | Glu | Tyr | Lys | Cys | Lys | Val | Ser | Asn | Lys | Ala | Leu | Pro | Ala | Pro | Ile |
| | | | 100 | | | | | 105 | | | | | 110 | | |
| Glu | Lys | Thr | Ile | Ser | Lys | Ala | Lys | Gly | Gln | Pro | Arg | Glu | Pro | Gln | Val |
| | | 115 | | | | | 120 | | | | | 125 | | | |
| Tyr | Thr | Leu | Pro | Pro | Ser | Arg | Asp | Glu | Leu | Thr | Lys | Asn | Gln | Val | Ser |
| | 130 | | | | | 135 | | | | | 140 | | | | |
| Leu | Thr | Cys | Leu | Val | Lys | Gly | Phe | Tyr | Pro | Ser | Asp | Ile | Ala | Val | Glu |
| 145 | | | | | 150 | | | | | 155 | | | | | 160 |
| Trp | Glu | Ser | Asn | Gly | Gln | Pro | Glu | Asn | Asn | Tyr | Lys | Thr | Thr | Pro | Pro |
| | | | | 165 | | | | | 170 | | | | | 175 | |
| Val | Leu | Asp | Ser | Asp | Gly | Ser | Phe | Phe | Leu | Tyr | Ser | Lys | Leu | Thr | Val |
| | | | 180 | | | | | 185 | | | | | 190 | | |
| Asp | Lys | Ser | Arg | Trp | Gln | Gln | Gly | Asn | Val | Phe | Ser | Cys | Ser | Val | Met |
| | | 195 | | | | | 200 | | | | | 205 | | | |
| His | Glu | Ala | Leu | His | Asn | His | Tyr | Thr | Gln | Lys | Ser | Leu | Ser | Leu | Ser |
| | 210 | | | | | 215 | | | | | 220 | | | | |
| Pro | Gly | Lys | Gly | Gly | Gly | Gly | Ser | Gly | Gly | Gly | Gly | Ser | Gly | Gly | Gly |
| 225 | | | | | 230 | | | | | 235 | | | | | 240 |
| Gly | Ser | Gly | Gly | Gly | Gly | Ser | Gly | Gly | Gly | Gly | Ser | Thr | Arg | Val | Asp |
| | | | | 245 | | | | | 250 | | | | | 255 | |
| Gln | Thr | Pro | Arg | Thr | Ala | Thr | Lys | Glu | Thr | Gly | Glu | Ser | Leu | Thr | Ile |
| | | | 260 | | | | | 265 | | | | | 270 | | |
| Asn | Cys | Val | Leu | Thr | Asp | Thr | Ser | Tyr | Gly | Leu | Tyr | Ser | Thr | Ser | Trp |
| | | 275 | | | | | 280 | | | | | 285 | | | |
| Phe | Arg | Lys | Asn | Pro | Gly | Thr | Thr | Asp | Trp | Glu | Arg | Met | Ser | Ile | Gly |
| | 290 | | | | | 295 | | | | | 300 | | | | |
| Gly | Arg | Tyr | Val | Glu | Ser | Val | Asn | Lys | Gly | Ala | Lys | Ser | Phe | Ser | Leu |
| 305 | | | | | 310 | | | | | 315 | | | | | 320 |
| Arg | Ile | Lys | Asp | Leu | Thr | Val | Ala | Asp | Ser | Ala | Thr | Tyr | Tyr | Cys | Lys |
| | | | | 325 | | | | | 330 | | | | | 335 | |
| Ala | Arg | Glu | Ala | Arg | His | Pro | Trp | Leu | Arg | Gln | Trp | Tyr | Asp | Gly | Ala |
| | | | 340 | | | | | 345 | | | | | 350 | | |
| Gly | Thr | Val | Leu | Thr | Val | Asn | | | | | | | | | |
| | | | | 355 | | | | | | | | | | | |

<210> SEQ ID NO 235
<211> LENGTH: 354
<212> TYPE: PRT
<213> ORGANISM: Artificial Sequence
<220> FEATURE:
<223> OTHER INFORMATION: Antibody Sequence

<400> SEQUENCE: 235

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Glu Pro Lys Ser Ser Asp
            115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys
```

<210> SEQ ID NO 236
<211> LENGTH: 359
<212> TYPE: PRT
<213> ORGANISM: Artificial Sequence
<220> FEATURE:
<223> OTHER INFORMATION: Antibody Sequence

<400> SEQUENCE: 236

```
Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Arg Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Ser Thr Gly Ser Gly
                85                  90                  95

His Gly Tyr Asn Trp Tyr Asp Gly Ala Gly Thr Val Leu Thr Val Asn
            100                 105                 110

Gly Gly Gly Gly Ser Gly Gly Gly Ser Gly Gly Gly Gly Ser Glu
        115                 120                 125

Pro Lys Ser Ser Asp Lys Thr His Thr Cys Pro Pro Cys Pro Ala Pro
    130                 135                 140

Glu Leu Leu Gly Gly Pro Cys Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
            355
```

<210> SEQ ID NO 237
<211> LENGTH: 364
<212> TYPE: PRT
<213> ORGANISM: Artificial Sequence
<220> FEATURE:
<223> OTHER INFORMATION: Antibody Sequence

<400> SEQUENCE: 237

Asp Lys Thr His Thr Cys Pro Cys Pro Ala Pro Glu Leu Leu Gly
1               5                   10                  15

Gly Pro Cys Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Ser Gly Gly Gly
225                 230                 235                 240

Gly Ser Gly Gly Gly Ser Gly Gly Gly Ser Ala Ser Val Asn
                245                 250                 255

Gln Thr Pro Arg Thr Ala Thr Lys Glu Thr Gly Glu Ser Leu Thr Ile
            260                 265                 270

Asn Cys Val Leu Thr Asp Thr Ser Tyr Gly Leu Tyr Ser Thr Ser Trp
            275                 280                 285

Phe Arg Lys Asn Pro Gly Thr Thr Asp Trp Glu Arg Met Ser Ile Gly
290                 295                 300

Gly Arg Tyr Val Glu Ser Val Asn Lys Arg Ala Lys Ser Phe Ser Leu
305                 310                 315                 320

Arg Ile Lys Asp Leu Thr Val Ala Asp Ser Ala Thr Tyr Tyr Cys Lys
                325                 330                 335

Ala Gln Ser Gly Met Ala Ile Ser Thr Gly Ser Gly His Gly Tyr Asn
            340                 345                 350

Trp Tyr Asp Gly Ala Gly Thr Val Leu Thr Val Asn
            355                 360

<210> SEQ ID NO 238
<211> LENGTH: 496
<212> TYPE: PRT
<213> ORGANISM: Artificial Sequence
<220> FEATURE:
<223> OTHER INFORMATION: Antibody Sequence

<400> SEQUENCE: 238

```
Ala Ser Val Asn Gln Thr Pro Arg Thr Ala Thr Lys Glu Thr Gly Glu
1               5                   10                  15
Ser Leu Thr Ile Asn Cys Val Leu Thr Asp Thr Ser Tyr Gly Leu Tyr
            20                  25                  30
Ser Thr Ser Trp Phe Arg Lys Asn Pro Gly Thr Thr Asp Trp Glu Arg
        35                  40                  45
Met Ser Ile Gly Gly Arg Tyr Val Glu Ser Val Asn Lys Arg Ala Lys
    50                  55                  60
Ser Phe Ser Leu Arg Ile Lys Asp Leu Thr Val Ala Asp Ser Ala Thr
65                  70                  75                  80
Tyr Tyr Cys Lys Ala Gln Ser Gly Met Ala Ile Ser Thr Gly Ser Gly
                85                  90                  95
His Gly Tyr Asn Trp Tyr Asp Gly Ala Gly Thr Val Leu Thr Val Asn
            100                 105                 110
Gly Gly Gly Gly Ser Gly Gly Gly Ser Gly Gly Gly Ser Gly
        115                 120                 125
Gly Gly Ser Gly Gly Gly Ser Ala Ser Val Asn Gln Thr Pro
    130                 135                 140
Arg Thr Ala Thr Lys Glu Thr Gly Glu Ser Leu Thr Ile Asn Cys Val
145                 150                 155                 160
Leu Thr Asp Thr Ser Tyr Gly Leu Tyr Ser Thr Ser Trp Phe Arg Lys
                165                 170                 175
Asn Pro Gly Thr Thr Asp Trp Glu Arg Met Ser Ile Gly Gly Arg Tyr
            180                 185                 190
Val Glu Ser Val Asn Lys Arg Ala Lys Ser Phe Ser Leu Arg Ile Lys
        195                 200                 205
Asp Leu Thr Val Ala Asp Ser Ala Thr Tyr Tyr Cys Lys Ala Gln Ser
    210                 215                 220
Gly Met Ala Ile Ser Thr Gly Ser Gly His Gly Tyr Asn Trp Tyr Asp
225                 230                 235                 240
Gly Ala Gly Thr Val Leu Thr Val Asn Gly Gly Gly Ser Gly Gly
                245                 250                 255
Gly Gly Ser Gly Gly Gly Ser Glu Pro Lys Ser Ser Asp Lys Thr
            260                 265                 270
His Thr Cys Pro Pro Cys Pro Ala Pro Glu Leu Leu Gly Gly Pro Cys
            275                 280                 285
Val Phe Leu Phe Pro Pro Lys Pro Lys Asp Thr Leu Met Ile Ser Arg
    290                 295                 300
Thr Pro Glu Val Thr Cys Val Val Asp Val Ser His Glu Asp Pro
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
            340                 345                 350
Ser Val Leu Thr Val Leu His Gln Asp Trp Leu Asn Gly Lys Glu Tyr
        355                 360                 365
Lys Cys Lys Val Ser Asn Lys Ala Leu Pro Ala Pro Ile Glu Lys Thr
    370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
                405                 410                 415
```

```
Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 239
<211> LENGTH: 501
<212> TYPE: PRT
<213> ORGANISM: Artificial Sequence
<220> FEATURE:
<223> OTHER INFORMATION: Antibody Sequence

<400> SEQUENCE: 239

Asp Lys Thr His Thr Cys Pro Pro Cys Pro Ala Pro Glu Leu Leu Gly
1               5                   10                  15

Gly Pro Cys Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Gly Gly Gly Gly Ser Gly Gly Gly Gly Ser Ala Ser Val Asn
                245                 250                 255

Gln Thr Pro Arg Thr Ala Thr Lys Glu Thr Gly Glu Ser Leu Thr Ile
            260                 265                 270

Asn Cys Val Leu Thr Asp Thr Ser Tyr Gly Leu Tyr Ser Thr Ser Trp
        275                 280                 285
```

Phe Arg Lys Asn Pro Gly Thr Thr Asp Trp Glu Arg Met Ser Ile Gly
    290                 295                 300

Gly Arg Tyr Val Glu Ser Val Asn Lys Arg Ala Lys Ser Phe Ser Leu
305                 310                 315                 320

Arg Ile Lys Asp Leu Thr Val Ala Asp Ser Ala Thr Tyr Tyr Cys Lys
                325                 330                 335

Ala Gln Ser Gly Met Ala Ile Ser Thr Gly Ser Gly His Gly Tyr Asn
                340                 345                 350

Trp Tyr Asp Gly Ala Gly Thr Val Leu Thr Val Asn Gly Gly Gly Gly
            355                 360                 365

Ser Gly Gly Gly Gly Ser Gly Gly Gly Gly Ser Gly Gly Gly Gly Ser
370                 375                 380

Gly Gly Gly Gly Ser Ala Ser Val Asn Gln Thr Pro Arg Thr Ala Thr
385                 390                 395                 400

Lys Glu Thr Gly Glu Ser Leu Thr Ile Asn Cys Val Leu Thr Asp Thr
                405                 410                 415

Ser Tyr Gly Leu Tyr Ser Thr Ser Trp Phe Arg Lys Asn Pro Gly Thr
                420                 425                 430

Thr Asp Trp Glu Arg Met Ser Ile Gly Gly Arg Tyr Val Glu Ser Val
            435                 440                 445

Asn Lys Arg Ala Lys Ser Phe Ser Leu Arg Ile Lys Asp Leu Thr Val
450                 455                 460

Ala Asp Ser Ala Thr Tyr Tyr Cys Lys Ala Gln Ser Gly Met Ala Ile
465                 470                 475                 480

Ser Thr Gly Ser Gly His Gly Tyr Asn Trp Tyr Asp Gly Ala Gly Thr
                485                 490                 495

Val Leu Thr Val Asn
            500

<210> SEQ ID NO 240
<211> LENGTH: 359
<212> TYPE: PRT
<213> ORGANISM: Artificial Sequence
<220> FEATURE:
<223> OTHER INFORMATION: Antibody Sequence

<400> SEQUENCE: 240

Ala Lys Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Arg Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Gly Met Ala Ile Asp Ile Gly Ser Gly
                85                  90                  95

His Gly Tyr Asn Trp Tyr Asp Gly Ala Gly Thr Val Leu Thr Val Asn
                100                 105                 110

Gly Gly Gly Gly Ser Gly Gly Gly Gly Ser Gly Gly Gly Gly Ser Glu
            115                 120                 125

Pro Lys Ser Ser Asp Lys Thr His Thr Cys Pro Pro Cys Pro Ala Pro
130                 135                 140

Glu Leu Leu Gly Gly Pro Cys Val Phe Leu Phe Pro Pro Lys Pro Lys
145                 150                 155                 160

Asp Thr Leu Met Ile Ser Arg Thr Pro Glu Val Thr Cys Val Val Val
            165                 170                 175

Asp Val Ser His Glu Asp Pro Glu Val Lys Phe Asn Trp Tyr Val Asp
        180                 185                 190

Gly Val Glu Val His Asn Ala Lys Thr Lys Pro Arg Glu Glu Gln Tyr
    195                 200                 205

Asn Ser Thr Tyr Arg Val Val Ser Val Leu Thr Val Leu His Gln Asp
210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
            245                 250                 255

Glu Pro Gln Val Tyr Thr Leu Pro Pro Ser Arg Asp Glu Leu Thr Lys
        260                 265                 270

Asn Gln Val Ser Leu Thr Cys Leu Val Lys Gly Phe Tyr Pro Ser Asp
    275                 280                 285

Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
            325                 330                 335

Cys Ser Val Met His Glu Ala Leu His Asn His Tyr Thr Gln Lys Ser
        340                 345                 350

Leu Ser Leu Ser Pro Gly Lys
        355

<210> SEQ ID NO 241
<211> LENGTH: 353
<212> TYPE: PRT
<213> ORGANISM: Artificial Sequence
<220> FEATURE:
<223> OTHER INFORMATION: Antibody Sequence

<400> SEQUENCE: 241

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
            85                  90                  95

Tyr Asp Gly Ala Gly Thr Val Leu Thr Val Asn Gly Gly Gly Ser
        100                 105                 110

Gly Gly Gly Gly Ser Gly Gly Gly Ser Glu Pro Lys Ser Ser Asp
    115                 120                 125

Lys Thr His Thr Cys Pro Pro Cys Pro Ala Pro Glu Leu Leu Gly Gly
130                 135                 140

```
Pro Cys Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
            165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
            195                 200                 205

Val Val Ser Val Leu Thr Val Leu His Gln Asp Trp Leu Asn Gly Lys
            210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
            245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
            275                 280                 285

Glu Ser Asn Gly Gln Pro Glu Asn Asn Tyr Lys Thr Thr Pro Pro Val
290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
            325                 330                 335

Glu Ala Leu His Asn His Tyr Thr Gln Lys Ser Leu Ser Leu Ser Pro
            340                 345                 350

Gly

<210> SEQ ID NO 242
<211> LENGTH: 353
<212> TYPE: PRT
<213> ORGANISM: Artificial Sequence
<220> FEATURE:
<223> OTHER INFORMATION: Antibody Sequence

<400> SEQUENCE: 242

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Ser Leu Ala Ile Ser Thr Arg Ser Tyr Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Gly Ser Glu Pro Lys Ser Ser Asp
        115                 120                 125

Lys Thr His Thr Cys Pro Pro Cys Pro Ala Pro Glu Leu Leu Gly Gly
    130                 135                 140
```

```
Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Cys Leu Ser Pro
            340                 345                 350

Gly

<210> SEQ ID NO 243
<211> LENGTH: 376
<212> TYPE: PRT
<213> ORGANISM: Artificial Sequence
<220> FEATURE:
<223> OTHER INFORMATION: Antibody Sequence

<400> SEQUENCE: 243

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
```

```
                145                 150                 155                 160
        Glu Ser Leu His Met Gln Gly Glu Ile Glu Asn Gln Ile Thr Ala Ala
                            165                 170                 175

Phe Thr Met Ile Gly Thr Ser Ser His Leu Ser Asp Lys Cys Ser Gln
                        180                 185                 190

Phe Ala Ile Pro Ser Leu Cys His Tyr Ala Phe Pro Tyr Cys Asp Glu
                        195                 200                 205

Thr Ser Ser Val Pro Lys Pro Arg Asp Leu Cys Arg Asp Glu Cys Glu
                    210                 215                 220

Ile Leu Glu Asn Val Leu Cys Gln Thr Glu Tyr Ile Phe Ala Arg Ser
        225                 230                 235                 240

Asn Pro Met Ile Leu Met Arg Leu Lys Leu Pro Asn Cys Glu Asp Leu
                            245                 250                 255

Pro Gln Pro Glu Ser Pro Glu Ala Ala Asn Cys Ile Arg Ile Gly Ile
                        260                 265                 270

Pro Met Ala Asp Pro Ile Asn Lys Asn His Lys Cys Tyr Asn Ser Thr
                    275                 280                 285

Gly Val Asp Tyr Arg Gly Thr Val Ser Val Thr Lys Ser Gly Arg Gln
                290                 295                 300

Cys Gln Pro Trp Asn Ser Gln Tyr Pro His Thr His Thr Phe Thr Ala
        305                 310                 315                 320

Leu Arg Phe Pro Glu Leu Asn Gly Gly His Ser Tyr Cys Arg Asn Pro
                            325                 330                 335

Gly Asn Gln Lys Glu Ala Pro Trp Cys Phe Thr Leu Asp Glu Asn Phe
                        340                 345                 350

Lys Ser Asp Leu Cys Asp Ile Pro Ala Cys Asp Ser Lys Asp Ser Lys
                    355                 360                 365

Glu Lys Asn Lys Met Glu Phe Cys
                370                 375

<210> SEQ ID NO 244
<211> LENGTH: 616
<212> TYPE: PRT
<213> ORGANISM: Artificial Sequence
<220> FEATURE:
<223> OTHER INFORMATION: Antibody Sequence

<400> SEQUENCE: 244

Gln Glu Thr Glu Leu Ser Val Ser Ala Glu Leu Val Pro Thr Ser Ser
        1               5                   10                  15

Trp Asn Ile Ser Ser Glu Leu Asn Lys Asp Ser Tyr Leu Thr Leu Asp
                            20                  25                  30

Glu Pro Met Asn Asn Ile Thr Thr Ser Leu Gly Gln Thr Ala Glu Leu
                        35                  40                  45

His Cys Lys Val Ser Gly Asn Pro Pro Thr Ile Arg Trp Phe Lys
            50                  55                  60

Asn Asp Ala Pro Val Val Gln Glu Pro Arg Arg Leu Ser Phe Arg Ser
        65                  70                  75                  80

Thr Ile Tyr Gly Ser Arg Leu Arg Ile Arg Asn Leu Asp Thr Thr Asp
                            85                  90                  95

Thr Gly Tyr Phe Gln Cys Val Ala Thr Asn Gly Lys Glu Val Val Ser
                        100                 105                 110

Ser Thr Gly Val Leu Phe Val Lys Phe Gly Pro Pro Thr Ala Ser
                    115                 120                 125

Pro Gly Tyr Ser Asp Glu Tyr Glu Glu Asp Gly Phe Cys Gln Pro Tyr
```

```
                130             135             140
Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
                180                 185                 190

Phe Ala Ile Pro Ser Leu Cys His Tyr Ala Phe Pro Tyr Cys Asp Glu
                195                 200                 205

Thr Ser Ser Val Pro Lys Pro Arg Asp Leu Cys Arg Asp Glu Cys Glu
                210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
                260                 265                 270

Pro Met Ala Asp Pro Ile Asn Lys Asn His Lys Cys Tyr Asn Ser Thr
                275                 280                 285

Gly Val Asp Tyr Arg Gly Thr Val Ser Val Thr Lys Ser Gly Arg Gln
                290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
                340                 345                 350

Lys Ser Asp Leu Cys Asp Ile Pro Ala Cys Asp Ser Lys Asp Ser Lys
                355                 360                 365

Glu Lys Asn Lys Met Glu Gly Gly Gly Ser Gly Gly Gly Gly Ser
                370                 375                 380

Gly Gly Gly Gly Ser Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
                420                 425                 430

Val Asp Val Ser His Glu Asp Pro Glu Val Lys Phe Asn Trp Tyr Val
                435                 440                 445

Asp Gly Val Glu Val His Asn Ala Lys Thr Lys Pro Arg Glu Glu Gln
                450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
                485                 490                 495

Leu Pro Ala Pro Ile Glu Lys Thr Ile Ser Lys Ala Lys Gly Gln Pro
                500                 505                 510

Arg Glu Pro Gln Val Tyr Thr Leu Pro Pro Ser Arg Glu Glu Met Thr
                515                 520                 525

Lys Asn Gln Val Ser Leu Thr Cys Leu Val Lys Gly Phe Tyr Pro Ser
                530                 535                 540

Asp Ile Ala Val Glu Trp Glu Ser Asn Gly Gln Pro Glu Asn Asn Tyr
545                 550                 555                 560
```

-continued

```
Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys
    610                 615

<210> SEQ ID NO 245
<211> LENGTH: 363
<212> TYPE: PRT
<213> ORGANISM: Artificial Sequence
<220> FEATURE:
<223> OTHER INFORMATION: Antibody Sequence

<400> SEQUENCE: 245

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
    50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Gly Gly Ser Gly Gly
        115                 120                 125

Gly Gly Ser Gly Gly Gly Gly Ser Asp Lys Thr His Thr Cys Pro Pro
    130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300
```

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
            325                 330                 335

Asn Val Phe Ser Cys Ser Val Met His Glu Ala Leu His Asn His Tyr
            340                 345                 350

Thr Gln Lys Ser Leu Ser Leu Ser Pro Gly Lys
        355                 360

<210> SEQ ID NO 246
<211> LENGTH: 377
<212> TYPE: PRT
<213> ORGANISM: Artificial Sequence
<220> FEATURE:
<223> OTHER INFORMATION: Antibody Sequence

<400> SEQUENCE: 246

Glu Glu Asp Gly Phe Cys Gln Pro Tyr Arg Gly Ile Ala Cys Ala Arg
1               5                   10                  15

Phe Ile Gly Asn Arg Thr Val Tyr Met Glu Ser Leu His Met Gln Gly
            20                  25                  30

Glu Ile Glu Asn Gln Ile Thr Ala Ala Phe Thr Met Ile Gly Thr Ser
        35                  40                  45

Ser His Leu Ser Asp Lys Cys Ser Gln Phe Ala Ile Pro Ser Leu Cys
    50                  55                  60

His Tyr Ala Phe Pro Tyr Cys Asp Glu Thr Ser Ser Val Pro Lys Pro
65                  70                  75                  80

Arg Asp Leu Cys Arg Asp Glu Cys Glu Ile Leu Glu Asn Val Leu Cys
                85                  90                  95

Gln Thr Glu Tyr Ile Phe Ala Arg Ser Asn Pro Met Ile Leu Met Arg
            100                 105                 110

Leu Lys Leu Pro Asn Cys Glu Asp Leu Pro Gln Pro Glu Ser Pro Glu
        115                 120                 125

Ala Ala Asn Cys Ile Arg Ile Gly Gly Gly Ser Gly Gly Gly Gly
    130                 135                 140

Ser Gly Gly Gly Gly Ser Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

```
Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
            325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
            355                 360                 365

Lys Ser Leu Ser Leu Ser Pro Gly Lys
            370                 375

<210> SEQ ID NO 247
<211> LENGTH: 322
<212> TYPE: PRT
<213> ORGANISM: Artificial Sequence
<220> FEATURE:
<223> OTHER INFORMATION: Antibody Sequence

<400> SEQUENCE: 247

Lys Cys Tyr Asn Ser Thr Gly Val Asp Tyr Arg Gly Thr Val Ser Val
1               5                   10                  15

Thr Lys Ser Gly Arg Gln Cys Gln Pro Trp Asn Ser Gln Tyr Pro His
                20                  25                  30

Thr His Thr Phe Thr Ala Leu Arg Phe Pro Glu Leu Asn Gly Gly His
            35                  40                  45

Ser Tyr Cys Arg Asn Pro Gly Asn Gln Lys Glu Ala Pro Trp Cys Phe
        50                  55                  60

Thr Leu Asp Glu Asn Phe Lys Ser Asp Leu Cys Asp Ile Pro Ala Cys
65                  70                  75                  80

Gly Gly Gly Gly Ser Gly Gly Gly Ser Gly Gly Gly Gly Ser Asp
                85                  90                  95

Lys Thr His Thr Cys Pro Pro Cys Pro Ala Pro Glu Leu Leu Gly Gly
                100                 105                 110

Pro Ser Val Phe Leu Phe Pro Pro Lys Pro Lys Asp Thr Leu Met Ile
            115                 120                 125

Ser Arg Thr Pro Glu Val Thr Cys Val Val Val Asp Val Ser His Glu
130                 135                 140

Asp Pro Glu Val Lys Phe Asn Trp Tyr Val Asp Gly Val Glu Val His
145                 150                 155                 160

Asn Ala Lys Thr Lys Pro Arg Glu Glu Gln Tyr Asn Ser Thr Tyr Arg
                165                 170                 175

Val Val Ser Val Leu Thr Val Leu His Gln Asp Trp Leu Asn Gly Lys
            180                 185                 190

Glu Tyr Lys Cys Lys Val Ser Asn Lys Ala Leu Pro Ala Pro Ile Glu
        195                 200                 205

Lys Thr Ile Ser Lys Ala Lys Gly Gln Pro Arg Glu Pro Gln Val Tyr
    210                 215                 220

Thr Leu Pro Pro Ser Arg Glu Glu Met Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Val
            260                 265                 270

Leu Asp Ser Asp Gly Ser Phe Phe Leu Tyr Ser Lys Leu Thr Val Asp
        275                 280                 285
```

```
Lys Ser Arg Trp Gln Gln Gly Asn Val Phe Ser Cys Ser Val Met His
        290                 295                 300

Glu Ala Leu His Asn His Tyr Thr Gln Lys Ser Leu Ser Leu Ser Pro
305                 310                 315                 320

Gly Lys

<210> SEQ ID NO 248
<211> LENGTH: 512
<212> TYPE: PRT
<213> ORGANISM: Artificial Sequence
<220> FEATURE:
<223> OTHER INFORMATION: Antibody Sequence

<400> SEQUENCE: 248

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Gly
            260                 265                 270

Gly Gly Ser Gly Gly Gly Gly Ser Gly Gly Gly Gly Ser Asp Lys Thr
        275                 280                 285

His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320
```

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
    370                 375                 380

Lys Cys Lys Val Ser Asn Lys Ala Leu Pro Ala Pro Ile Glu Lys Thr
385                 390                 395                 400

Ile Ser Lys Ala Lys Gly Gln Pro Arg Glu Pro Gln Val Tyr Thr Leu
                405                 410                 415

Pro Pro Ser Arg Glu Glu Met Thr Lys Asn Gln Val Ser Leu Thr Cys
            420                 425                 430

Leu Val Lys Gly Phe Tyr Pro Ser Asp Ile Ala Val Glu Trp Glu Ser
        435                 440                 445

Asn Gly Gln Pro Glu Asn Asn Tyr Lys Thr Thr Pro Pro Val Leu Asp
    450                 455                 460

Ser Asp Gly Ser Phe Phe Leu Tyr Ser Lys Leu Thr Val Asp Lys Ser
465                 470                 475                 480

Arg Trp Gln Gln Gly Asn Val Phe Ser Cys Ser Val Met His Glu Ala
                485                 490                 495

Leu His Asn His Tyr Thr Gln Lys Ser Leu Ser Leu Ser Pro Gly Lys
            500                 505                 510

<210> SEQ ID NO 249
<211> LENGTH: 469
<212> TYPE: PRT
<213> ORGANISM: Artificial Sequence
<220> FEATURE:
<223> OTHER INFORMATION: Antibody Sequence

<400> SEQUENCE: 249

Glu Glu Asp Gly Phe Cys Gln Pro Tyr Arg Gly Ile Ala Cys Ala Arg
1               5                   10                  15

Phe Ile Gly Asn Arg Thr Val Tyr Met Glu Ser Leu His Met Gln Gly
                20                  25                  30

Glu Ile Glu Asn Gln Ile Thr Ala Ala Phe Thr Met Ile Gly Thr Ser
            35                  40                  45

Ser His Leu Ser Asp Lys Cys Ser Gln Phe Ala Ile Pro Ser Leu Cys
    50                  55                  60

His Tyr Ala Phe Pro Tyr Cys Asp Glu Thr Ser Ser Val Pro Lys Pro
65                  70                  75                  80

Arg Asp Leu Cys Arg Asp Glu Cys Glu Ile Leu Glu Asn Val Leu Cys
                85                  90                  95

Gln Thr Glu Tyr Ile Phe Ala Arg Ser Asn Pro Met Ile Leu Met Arg
            100                 105                 110

Leu Lys Leu Pro Asn Cys Glu Asp Leu Pro Gln Pro Glu Ser Pro Glu
        115                 120                 125

Ala Ala Asn Cys Ile Arg Ile Gly Ile Pro Met Ala Asp Pro Ile Asn
    130                 135                 140

Lys Asn His Lys Cys Tyr Asn Ser Thr Gly Val Asp Tyr Arg Gly Thr
145                 150                 155                 160

Val Ser Val Thr Lys Ser Gly Arg Gln Cys Gln Pro Trp Asn Ser Gln
                165                 170                 175

```
Tyr Pro His Thr His Thr Phe Thr Ala Leu Arg Phe Pro Glu Leu Asn
            180                 185                 190

Gly Gly His Ser Tyr Cys Arg Asn Pro Gly Asn Gln Lys Glu Ala Pro
            195                 200                 205

Trp Cys Phe Thr Leu Asp Glu Asn Phe Lys Ser Asp Leu Cys Asp Ile
            210                 215                 220

Pro Ala Cys Gly Gly Gly Ser Gly Gly Gly Ser Gly Gly Gly
225                 230                 235                 240

Gly Ser Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 250
<211> LENGTH: 611
<212> TYPE: PRT
<213> ORGANISM: Artificial Sequence
<220> FEATURE:
<223> OTHER INFORMATION: Antibody Sequence

<400> SEQUENCE: 250

Glu Val Glu Val Leu Asp Pro Asn Asp Pro Leu Gly Pro Leu Asp Gly
1               5                   10                  15

Gln Asp Gly Pro Ile Pro Thr Leu Lys Gly Tyr Phe Leu Asn Phe Leu
            20                  25                  30

Glu Pro Val Asn Asn Ile Thr Ile Val Gln Gly Gln Thr Ala Ile Leu
            35                  40                  45

His Cys Lys Val Ala Gly Asn Pro Pro Pro Asn Val Arg Trp Leu Lys
            50                  55                  60
```

-continued

Asn Asp Ala Pro Val Val Gln Glu Pro Arg Arg Ile Ile Arg Lys
65                  70                  75                  80

Thr Glu Tyr Gly Ser Arg Leu Arg Ile Gln Asp Leu Asp Thr Thr Asp
                85                  90                  95

Thr Gly Tyr Tyr Gln Cys Val Ala Thr Asn Gly Met Lys Thr Ile Thr
            100                 105                 110

Ala Thr Gly Val Leu Phe Val Arg Leu Gly Pro Thr His Ser Pro Asn
            115                 120                 125

His Asn Phe Gln Asp Asp Tyr His Glu Asp Gly Phe Cys Gln Pro Tyr
        130                 135                 140

Arg Gly Ile Ala Cys Ala Arg Phe Ile Gly Asn Arg Thr Ile Tyr Val
145                 150                 155                 160

Asp Ser Leu Gln Met Gln Gly Glu Ile Glu Asn Arg Ile Thr Ala Ala
                165                 170                 175

Phe Thr Met Ile Gly Thr Ser Thr His Leu Ser Asp Gln Cys Ser Gln
            180                 185                 190

Phe Ala Ile Pro Ser Phe Cys His Phe Val Phe Pro Leu Cys Asp Ala
            195                 200                 205

Arg Ser Arg Thr Pro Lys Pro Arg Glu Leu Cys Arg Asp Glu Cys Glu
210                 215                 220

Val Leu Glu Ser Asp Leu Cys Arg Gln Glu Tyr Thr Ile Ala Arg Ser
225                 230                 235                 240

Asn Pro Leu Ile Leu Met Arg Leu Gln Leu Pro Lys Cys Glu Ala Leu
                245                 250                 255

Pro Met Pro Glu Ser Pro Asp Ala Ala Asn Cys Met Arg Ile Gly Ile
            260                 265                 270

Pro Ala Glu Arg Leu Gly Arg Tyr His Gln Cys Tyr Asn Gly Ser Gly
            275                 280                 285

Met Asp Tyr Arg Gly Thr Ala Ser Thr Thr Lys Ser Gly His Gln Cys
        290                 295                 300

Gln Pro Trp Ala Leu Gln His Pro His Ser His His Leu Ser Ser Thr
305                 310                 315                 320

Asp Phe Pro Glu Leu Gly Gly Gly His Ala Tyr Cys Arg Asn Pro Gly
                325                 330                 335

Gly Gln Met Glu Gly Pro Trp Cys Phe Thr Gln Asn Lys Asn Val Arg
            340                 345                 350

Met Glu Leu Cys Asp Val Pro Ser Cys Ser Pro Arg Asp Ser Ser Lys
            355                 360                 365

Met Gly Gly Gly Ser Gly Gly Gly Ser Gly Gly Gly Gly Ser
            370                 375                 380

Asp Lys Thr His Thr Cys Pro Pro Cys Pro Ala Pro Glu Leu Leu Gly
385                 390                 395                 400

Gly Pro Ser Val Phe Leu Phe Pro Pro Lys Pro Lys Asp Thr Leu Met
            405                 410                 415

Ile Ser Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
            435                 440                 445

His Asn Ala Lys Thr Lys Pro Arg Glu Glu Gln Tyr Asn Ser Thr Tyr
        450                 455                 460

Arg Val Val Ser Val Leu Thr Val Leu His Gln Asp Trp Leu Asn Gly
465                 470                 475                 480

Lys Glu Tyr Lys Cys Lys Val Ser Asn Lys Ala Leu Pro Ala Pro Ile

```
                    485                 490                 495
Glu Lys Thr Ile Ser Lys Ala Lys Gly Gln Pro Arg Glu Pro Gln Val
                500                 505                 510

Tyr Thr Leu Pro Pro Ser Arg Glu Glu Met Thr Lys Asn Gln Val Ser
            515                 520                 525

Leu Thr Cys Leu Val Lys Gly Phe Tyr Pro Ser Asp Ile Ala Val Glu
        530                 535                 540

Trp Glu Ser Asn Gly Gln Pro Glu Asn Asn Tyr Lys Thr Thr Pro Pro
545                 550                 555                 560

Val Leu Asp Ser Asp Gly Ser Phe Phe Leu Tyr Ser Lys Leu Thr Val
                565                 570                 575

Asp Lys Ser Arg Trp Gln Gln Gly Asn Val Phe Ser Cys Ser Val Met
            580                 585                 590

His Glu Ala Leu His Asn His Tyr Thr Gln Lys Ser Leu Ser Leu Ser
        595                 600                 605

Pro Gly Lys
    610

<210> SEQ ID NO 251
<211> LENGTH: 616
<212> TYPE: PRT
<213> ORGANISM: Artificial Sequence
<220> FEATURE:
<223> OTHER INFORMATION: Antibody Sequence

<400> SEQUENCE: 251

Gln Glu Thr Glu Leu Ser Val Ser Ala Glu Leu Val Pro Thr Ser Ser
1               5                   10                  15

Trp Asn Thr Ser Ser Glu Ile Asp Lys Gly Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Ser Ile Arg Trp Phe Lys
        50                  55                  60

Asn Asp Ala Pro Val Val Gln Glu Pro Arg Arg Ile Ser Phe Arg Ala
65                  70                  75                  80

Thr Asn Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Lys Val Val Ser
            100                 105                 110

Thr Thr Gly Val Leu Phe Val Lys Phe Gly Pro Pro Thr Ala Ser
        115                 120                 125

Pro Gly Ser Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Val Leu Glu Asn Val Leu Cys Gln Thr Glu Tyr Ile Phe Ala Arg Ser
```

```
                225                 230                 235                 240
Asn Pro Met Ile Leu Met Arg Leu Lys Leu Pro Asn Cys Glu Asp Leu
                    245                 250                 255
Pro Gln Pro Glu Ser Pro Glu Ala Ala Asn Cys Ile Arg Ile Gly Ile
                260                 265                 270
Pro Met Ala Asp Pro Ile Asn Lys Asn His Lys Cys Tyr Asn Ser Thr
            275                 280                 285
Gly Val Asp Tyr Arg Gly Thr Val Ser Val Thr Lys Ser Gly Arg Gln
        290                 295                 300
Cys Gln Pro Trp Asn Ser Gln Tyr Pro His Thr His Ser Phe Thr Ala
305                 310                 315                 320
Leu Arg Phe Pro Glu Leu Asn Gly Gly His Ser Tyr Cys Arg Asn Pro
                325                 330                 335
Gly Asn Gln Lys Glu Ala Pro Trp Cys Phe Thr Leu Asp Glu Asn Phe
            340                 345                 350
Lys Ser Asp Leu Cys Asp Ile Pro Ala Cys Asp Ser Lys Asp Ser Lys
        355                 360                 365
Glu Lys Asn Lys Met Glu Gly Gly Gly Ser Gly Gly Gly Gly Ser
    370                 375                 380
Gly Gly Gly Gly Ser Asp Lys Thr His Thr Cys Pro Pro Cys Pro Ala
385                 390                 395                 400
Pro Glu Leu Leu Gly Gly Pro Ser Val Phe Leu Phe Pro Pro Lys Pro
                405                 410                 415
Lys Asp Thr Leu Met Ile Ser Arg Thr Pro Glu Val Thr Cys Val Val
            420                 425                 430
Val Asp Val Ser His Glu Asp Pro Glu Val Lys Phe Asn Trp Tyr Val
        435                 440                 445
Asp Gly Val Glu Val His Asn Ala Lys Thr Lys Pro Arg Glu Glu Gln
    450                 455                 460
Tyr Asn Ser Thr Tyr Arg Val Val Ser Val Leu Thr Val Leu His Gln
465                 470                 475                 480
Asp Trp Leu Asn Gly Lys Glu Tyr Lys Cys Lys Val Ser Asn Lys Ala
                485                 490                 495
Leu Pro Ala Pro Ile Glu Lys Thr Ile Ser Lys Ala Lys Gly Gln Pro
            500                 505                 510
Arg Glu Pro Gln Val Tyr Thr Leu Pro Pro Ser Arg Glu Glu Met Thr
        515                 520                 525
Lys Asn Gln Val Ser Leu Thr Cys Leu Val Lys Gly Phe Tyr Pro Ser
    530                 535                 540
Asp Ile Ala Val Glu Trp Glu Ser Asn Gly Gln Pro Glu Asn Asn Tyr
545                 550                 555                 560
Lys Thr Thr Pro Pro Val Leu Asp Ser Asp Gly Ser Phe Phe Leu Tyr
                565                 570                 575
Ser Lys Leu Thr Val Asp Lys Ser Arg Trp Gln Gln Gly Asn Val Phe
            580                 585                 590
Ser Cys Ser Val Met His Glu Ala Leu His Asn His Tyr Thr Gln Lys
        595                 600                 605
Ser Leu Ser Leu Ser Pro Gly Lys
    610                 615

<210> SEQ ID NO 252
<211> LENGTH: 615
<212> TYPE: PRT
<213> ORGANISM: Artificial Sequence
```

-continued

<220> FEATURE:
<223> OTHER INFORMATION: Antibody Sequence

<400> SEQUENCE: 252

```
Gln Glu Thr Glu Leu Ser Val Ser Ala Glu Leu Val Pro Thr Ser Ser
1               5                   10                  15

Trp Asn Thr Ser Ser Glu Ile Asp Lys Asp Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Asn Ile Arg Trp Phe Lys
    50                  55                  60

Asn Asp Ala Pro Val Val Gln Glu Pro Arg Arg Ile Ser Phe Arg Ala
65                  70                  75                  80

Thr Asn Tyr Gly Ser Arg Leu Arg Ile Arg Asn Leu Asp Thr Thr Asp
                85                  90                  95

Thr Gly Tyr Phe Gln Cys Val Ala Thr Ser Gly Lys Lys Val Val Ser
            100                 105                 110

Thr Thr Gly Val Leu Phe Val Lys Phe Gly Pro Pro Thr Ala Ser
        115                 120                 125

Pro Gly Ser Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Val Leu Glu Asn Val Leu Cys His Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Ser Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
        355                 360                 365

Glu Lys Asn Lys Met Glu Gly Gly Gly Ser Gly Gly Gly Gly Ser
    370                 375                 380

Gly Gly Gly Gly Ser Asp Lys Thr His Thr Cys Pro Pro Cys Pro Ala
385                 390                 395                 400
```

```
Pro Glu Leu Leu Gly Gly Pro Ser Val Phe Leu Phe Pro Pro Lys Pro
            405                 410                 415

Lys Asp Thr Leu Met Ile Ser Arg Thr Pro Glu Val Thr Cys Val Val
            420                 425                 430

Val Asp Val Ser His Glu Asp Pro Glu Val Lys Phe Asn Trp Tyr Val
            435                 440                 445

Asp Gly Val Glu Val His Asn Ala Lys Thr Lys Pro Arg Glu Glu Gln
450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
            485                 490                 495

Leu Pro Ala Pro Ile Glu Lys Thr Ile Ser Lys Ala Lys Gly Gln Pro
            500                 505                 510

Arg Glu Pro Gln Val Tyr Thr Leu Pro Pro Ser Arg Glu Glu Met Thr
            515                 520                 525

Lys Asn Gln Val Ser Leu Thr Cys Leu Val Lys Gly Phe Tyr Pro Ser
            530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
            565                 570                 575

Ser Lys Leu Val Asp Lys Ser Arg Trp Gln Gln Gly Asn Val Phe Ser
            580                 585                 590

Cys Ser Val Met His Glu Ala Leu His Asn His Tyr Thr Gln Lys Ser
            595                 600                 605

Leu Ser Leu Ser Pro Gly Lys
            610             615

<210> SEQ ID NO 253
<211> LENGTH: 382
<212> TYPE: PRT
<213> ORGANISM: Artificial Sequence
<220> FEATURE:
<223> OTHER INFORMATION: Antibody Sequence

<400> SEQUENCE: 253

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
            20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
            85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Pro Thr Ala Ser
            115                 120                 125

Pro Gly Tyr Ser Asp Glu Tyr Glu Glu Asp Gly Phe Cys Gln Pro Tyr
            130                 135                 140
```

```
Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
        355                 360                 365

Glu Lys Asn Lys Met Glu His His His His His His His
    370                 375                 380

<210> SEQ ID NO 254
<211> LENGTH: 380
<212> TYPE: PRT
<213> ORGANISM: Artificial Sequence
<220> FEATURE:
<223> OTHER INFORMATION: Antibody Sequence

<400> SEQUENCE: 254

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Thr Ala Ser
        115                 120                 125
```

```
Pro Gly Tyr Ser Asp Glu Tyr Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
            195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
        355                 360                 365

Glu Lys Asn Lys Met Glu His His His His His
    370                 375                 380

<210> SEQ ID NO 255
<211> LENGTH: 126
<212> TYPE: PRT
<213> ORGANISM: Artificial Sequence
<220> FEATURE:
<223> OTHER INFORMATION: Antibody Sequence

<400> SEQUENCE: 255

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Thr Ile Arg Trp Phe Lys
50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
                100                 105                 110
```

```
Ser Thr Gly Val Leu Phe Val Lys Phe His His His His
        115                 120             125

<210> SEQ ID NO 256
<211> LENGTH: 382
<212> TYPE: PRT
<213> ORGANISM: Artificial Sequence
<220> FEATURE:
<223> OTHER INFORMATION: Antibody Sequence

<400> SEQUENCE: 256

Gln Glu Thr Glu Leu Ser Val Ser Ala Glu Leu Val Pro Thr Ser Ser
1               5                   10                  15

Trp Asn Thr Ser Ser Glu Ile Asp Lys Gly Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Pro Ser Ile Arg Trp Phe Lys
    50                  55                  60

Asn Asp Ala Pro Val Val Gln Glu Pro Arg Arg Ile Ser Phe Arg Ala
65                  70                  75                  80

Thr Asn Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Lys Val Val Ser
            100                 105                 110

Thr Thr Gly Val Leu Phe Val Lys Phe Gly Pro Pro Thr Ala Ser
        115                 120                 125

Pro Gly Ser Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Val Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Ser Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350
```

```
Lys Ser Asp Leu Cys Asp Ile Pro Ala Cys Asp Ser Lys Asp Ser Lys
        355                 360                 365

Glu Lys Asn Lys Met Glu His His His His His His
        370                 375                 380

<210> SEQ ID NO 257
<211> LENGTH: 361
<212> TYPE: PRT
<213> ORGANISM: Artificial Sequence
<220> FEATURE:
<223> OTHER INFORMATION: Antibody Sequence

<400> SEQUENCE: 257

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
            100                 105                 110

Gly Ser Asp Ile Lys Leu Gln Gln Ser Gly Ala Glu Leu Ala Arg Pro
        115                 120                 125

Gly Ala Ser Val Lys Met Ser Cys Lys Thr Ser Gly Tyr Thr Phe Thr
    130                 135                 140

Arg Tyr Thr Met His Trp Val Lys Gln Arg Pro Gly Gln Gly Leu Glu
145                 150                 155                 160

Trp Ile Gly Tyr Ile Asn Pro Ser Arg Gly Tyr Thr Asn Tyr Asn Gln
                165                 170                 175

Lys Phe Lys Asp Lys Ala Thr Leu Thr Thr Asp Lys Ser Ser Ser Thr
            180                 185                 190

Ala Tyr Met Gln Leu Ser Ser Leu Thr Ser Glu Asp Ser Ala Val Tyr
        195                 200                 205

Tyr Cys Ala Arg Tyr Tyr Asp Asp His Tyr Cys Leu Asp Tyr Trp Gly
    210                 215                 220

Gln Gly Thr Thr Leu Thr Val Ser Ser Gly Gly Gly Gly Ser Gly Gly
225                 230                 235                 240

Gly Gly Ser Gly Gly Gly Gly Ser Asp Ile Gln Leu Thr Gln Ser Pro
                245                 250                 255

Ala Ile Met Ser Ala Ser Pro Gly Glu Lys Val Thr Met Thr Cys Arg
            260                 265                 270

Ala Ser Ser Ser Val Ser Tyr Met Asn Trp Tyr Gln Gln Lys Ser Gly
        275                 280                 285

Thr Ser Pro Lys Arg Trp Ile Tyr Asp Thr Ser Lys Val Ala Ser Gly
    290                 295                 300

Val Pro Tyr Arg Phe Ser Gly Ser Gly Ser Gly Thr Ser Tyr Ser Leu
305                 310                 315                 320

Thr Ile Ser Ser Met Glu Ala Glu Asp Ala Ala Thr Tyr Tyr Cys Gln
                325                 330                 335
```

Gln Trp Ser Ser Asn Pro Leu Thr Phe Gly Ala Gly Thr Lys Leu Glu
                340                 345                 350

Leu Lys Ser His His His His His His
        355                 360

<210> SEQ ID NO 258
<211> LENGTH: 371
<212> TYPE: PRT
<213> ORGANISM: Artificial Sequence
<220> FEATURE:
<223> OTHER INFORMATION: Antibody Sequence

<400> SEQUENCE: 258

Ala Ser Val Asn Gln Thr Pro Arg Thr Ala Thr Lys Glu Thr Gly Glu
1               5                   10                  15

Ser Leu Thr Ile Asn Cys Val Val Thr Gly Ala Asn Tyr Gly Leu Ala
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
50                  55                  60

Ser Phe Ser Leu Arg Ile Lys Asp Leu Thr Val Ala Asp Ser Ala Thr
65                  70                  75                  80

Tyr Tyr Cys Lys Ala Tyr Pro Trp Gly Ala Gly Ala Pro Trp Leu Val
                85                  90                  95

Gln Trp Tyr Asp Gly Ala Gly Thr Val Leu Thr Val Asn Gly Gly Gly
                100                 105                 110

Gly Ser Gly Gly Gly Gly Ser Gly Gly Gly Gly Ser Asp Ile Lys Leu
            115                 120                 125

Gln Gln Ser Gly Ala Glu Leu Ala Arg Pro Gly Ala Ser Val Lys Met
130                 135                 140

Ser Cys Lys Thr Ser Gly Tyr Thr Phe Thr Arg Tyr Thr Met His Trp
145                 150                 155                 160

Val Lys Gln Arg Pro Gly Gln Gly Leu Glu Trp Ile Gly Tyr Ile Asn
                165                 170                 175

Pro Ser Arg Gly Tyr Thr Asn Tyr Asn Gln Lys Phe Lys Asp Lys Ala
                180                 185                 190

Thr Leu Thr Thr Asp Lys Ser Ser Thr Ala Tyr Met Gln Leu Ser
            195                 200                 205

Ser Leu Thr Ser Glu Asp Ser Ala Val Tyr Tyr Cys Ala Arg Tyr Tyr
        210                 215                 220

Asp Asp His Tyr Cys Leu Asp Tyr Trp Gly Gln Gly Thr Thr Leu Thr
225                 230                 235                 240

Val Ser Ser Gly Gly Gly Gly Ser Gly Gly Gly Gly Ser Gly Gly Gly
                245                 250                 255

Gly Ser Asp Ile Gln Leu Thr Gln Ser Pro Ala Ile Met Ser Ala Ser
            260                 265                 270

Pro Gly Glu Lys Val Thr Met Thr Cys Arg Ala Ser Ser Ser Val Ser
        275                 280                 285

Tyr Met Asn Trp Tyr Gln Gln Lys Ser Gly Thr Ser Pro Lys Arg Trp
290                 295                 300

Ile Tyr Asp Thr Ser Lys Val Ala Ser Gly Val Pro Tyr Arg Phe Ser
305                 310                 315                 320

Gly Ser Gly Ser Gly Thr Ser Tyr Ser Leu Thr Ile Ser Ser Met Glu
                325                 330                 335

```
Ala Glu Asp Ala Ala Thr Tyr Tyr Cys Gln Gln Trp Ser Ser Asn Pro
            340                 345                 350

Leu Thr Phe Gly Ala Gly Thr Lys Leu Glu Leu Lys Ser His His His
            355                 360                 365

His His His
    370

<210> SEQ ID NO 259
<211> LENGTH: 359
<212> TYPE: PRT
<213> ORGANISM: Artificial Sequence
<220> FEATURE:
<223> OTHER INFORMATION: Antibody Sequence

<400> SEQUENCE: 259

Thr Arg Val Asp Gln Thr Pro Arg Thr Ala Thr Lys Glu Thr Gly Glu
  1               5                  10                  15

Ser Leu Thr Ile Asn Cys Val Leu Thr Asp Thr Ser Tyr Gly Leu Tyr
             20                  25                  30

Ser Thr Ser Trp Phe Arg Lys Asn Pro Gly Thr Thr Asp Trp Glu Arg
         35                  40                  45

Met Ser Ile Gly Gly Arg Tyr Val Glu Ser Val Asn Lys Gly Ala Lys
     50                  55                  60

Ser Phe Ser Leu Arg Ile Lys Asp Leu Thr Val Ala Asp Ser Ala Thr
 65                  70                  75                  80

Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Gly Gly Gly Gly Ser
            100                 105                 110

Asp Ile Lys Leu Gln Gln Ser Gly Ala Glu Leu Ala Arg Pro Gly Ala
        115                 120                 125

Ser Val Lys Met Ser Cys Lys Thr Ser Gly Tyr Thr Phe Thr Arg Tyr
    130                 135                 140

Thr Met His Trp Val Lys Gln Arg Pro Gly Gln Gly Leu Glu Trp Ile
145                 150                 155                 160

Gly Tyr Ile Asn Pro Ser Arg Gly Tyr Thr Asn Tyr Asn Gln Lys Phe
                165                 170                 175

Lys Asp Lys Ala Thr Leu Thr Thr Asp Lys Ser Ser Ser Thr Ala Tyr
            180                 185                 190

Met Gln Leu Ser Ser Leu Thr Ser Glu Asp Ser Ala Val Tyr Tyr Cys
        195                 200                 205

Ala Arg Tyr Tyr Asp Asp His Tyr Cys Leu Asp Tyr Trp Gly Gln Gly
    210                 215                 220

Thr Thr Leu Thr Val Ser Ser Gly Gly Gly Ser Gly Gly Gly Gly
225                 230                 235                 240

Ser Gly Gly Gly Gly Ser Asp Ile Gln Leu Thr Gln Ser Pro Ala Ile
                245                 250                 255

Met Ser Ala Ser Pro Gly Glu Lys Val Thr Met Thr Cys Arg Ala Ser
            260                 265                 270

Ser Ser Val Ser Tyr Met Asn Trp Tyr Gln Gln Lys Ser Gly Thr Ser
        275                 280                 285

Pro Lys Arg Trp Ile Tyr Asp Thr Ser Lys Val Ala Ser Gly Val Pro
    290                 295                 300

Tyr Arg Phe Ser Gly Ser Gly Ser Gly Thr Ser Tyr Ser Leu Thr Ile
305                 310                 315                 320
```

Ser Ser Met Glu Ala Glu Asp Ala Ala Thr Tyr Tyr Cys Gln Gln Trp
            325                 330                 335

Ser Ser Asn Pro Leu Thr Phe Gly Ala Gly Thr Lys Leu Glu Leu Lys
            340                 345                 350

Ser His His His His His His
            355

<210> SEQ ID NO 260
<211> LENGTH: 369
<212> TYPE: PRT
<213> ORGANISM: Artificial Sequence
<220> FEATURE:
<223> OTHER INFORMATION: Antibody Sequence

<400> SEQUENCE: 260

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Asp Ile Lys Leu Gln Gln
            115                 120                 125

Ser Gly Ala Glu Leu Ala Arg Pro Gly Ala Ser Val Lys Met Ser Cys
        130                 135                 140

Lys Thr Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser Gly Gly Gly Gly Ser Gly Gly Gly Gly Ser Gly Gly Gly Gly Ser
                245                 250                 255

Asp Ile Gln Leu Thr Gln Ser Pro Ala Ile Met Ser Ala Ser Pro Gly
            260                 265                 270

Glu Lys Val Thr Met Thr Cys Arg Ala Ser Ser Ser Val Ser Tyr Met
        275                 280                 285

Asn Trp Tyr Gln Gln Lys Ser Gly Thr Ser Pro Lys Arg Trp Ile Tyr
    290                 295                 300

Asp Thr Ser Lys Val Ala Ser Gly Val Pro Tyr Arg Phe Ser Gly Ser
305                 310                 315                 320

```
Gly Ser Gly Thr Ser Tyr Ser Leu Thr Ile Ser Ser Met Glu Ala Glu
                325                 330                 335

Asp Ala Ala Thr Tyr Tyr Cys Gln Gln Trp Ser Ser Asn Pro Leu Thr
            340                 345                 350

Phe Gly Ala Gly Thr Lys Leu Glu Leu Lys Ser His His His His His
        355                 360                 365

His

<210> SEQ ID NO 261
<211> LENGTH: 491
<212> TYPE: PRT
<213> ORGANISM: Artificial Sequence
<220> FEATURE:
<223> OTHER INFORMATION: Antibody Sequence

<400> SEQUENCE: 261

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Ser Gly Gly Gly Gly Gly Ser Gly
        115                 120                 125

Gly Gly Ser Thr Arg Val Asp Gln Thr Pro Arg Thr Ala Thr Lys
    130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Gly Ala Lys Ser Phe Ser Leu Arg Ile Lys Asp Leu Thr Val Ala
        195                 200                 205

Asp Ser Ala Thr Tyr Tyr Cys Lys Ala Arg Glu Ala Arg His Pro Trp
    210                 215                 220

Leu Arg Gln Trp Tyr Asp Gly Ala Gly Thr Val Leu Thr Val Asn Gly
225                 230                 235                 240

Gly Gly Gly Ser Asp Ile Lys Leu Gln Gln Ser Gly Ala Glu Leu Ala
                245                 250                 255

Arg Pro Gly Ala Ser Val Lys Met Ser Cys Lys Thr Ser Gly Tyr Thr
            260                 265                 270

Phe Thr Arg Tyr Thr Met His Trp Val Lys Gln Arg Pro Gly Gln Gly
        275                 280                 285

Leu Glu Trp Ile Gly Tyr Ile Asn Pro Ser Arg Gly Tyr Thr Asn Tyr
    290                 295                 300
```

-continued

```
Asn Gln Lys Phe Lys Asp Lys Ala Thr Leu Thr Thr Asp Lys Ser Ser
305                 310                 315                 320

Ser Thr Ala Tyr Met Gln Leu Ser Ser Leu Thr Ser Glu Asp Ser Ala
            325                 330                 335

Val Tyr Tyr Cys Ala Arg Tyr Tyr Asp Asp His Tyr Cys Leu Asp Tyr
            340                 345                 350

Trp Gly Gln Gly Thr Thr Leu Thr Val Ser Ser Gly Gly Gly Gly Ser
            355                 360                 365

Gly Gly Gly Gly Ser Gly Gly Gly Ser Asp Ile Gln Leu Thr Gln
            370                 375                 380

Ser Pro Ala Ile Met Ser Ala Ser Pro Gly Glu Lys Val Thr Met Thr
385                 390                 395                 400

Cys Arg Ala Ser Ser Ser Val Ser Tyr Met Asn Trp Tyr Gln Gln Lys
                405                 410                 415

Ser Gly Thr Ser Pro Lys Arg Trp Ile Tyr Asp Thr Ser Lys Val Ala
                420                 425                 430

Ser Gly Val Pro Tyr Arg Phe Ser Gly Ser Gly Ser Gly Thr Ser Tyr
                435                 440                 445

Ser Leu Thr Ile Ser Ser Met Glu Ala Glu Asp Ala Ala Thr Tyr Tyr
450                 455                 460

Cys Gln Gln Trp Ser Ser Asn Pro Leu Thr Phe Gly Ala Gly Thr Lys
465                 470                 475                 480

Leu Glu Leu Lys Ser His His His His His
                485                 490

<210> SEQ ID NO 262
<211> LENGTH: 501
<212> TYPE: PRT
<213> ORGANISM: Artificial Sequence
<220> FEATURE:
<223> OTHER INFORMATION: Antibody Sequence

<400> SEQUENCE: 262

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
            100                 105                 110

Gly Gly Gly Gly Ser Gly Gly Gly Gly Ser Gly Gly Gly Gly Ser Gly
            115                 120                 125

Gly Gly Ser Thr Arg Val Asp Gln Thr Pro Arg Thr Ala Thr Lys
            130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175
```

Asp Trp Glu Arg Met Ser Ile Gly Gly Arg Tyr Val Glu Ser Val Asn
              180                 185                 190

Lys Gly Ala Lys Ser Phe Ser Leu Arg Ile Lys Asp Leu Thr Val Ala
         195                 200                 205

Asp Ser Ala Thr Tyr Tyr Cys Lys Ala Arg Glu Ala Arg His Pro Trp
     210                 215                 220

Leu Arg Gln Trp Tyr Asp Gly Ala Gly Thr Val Leu Thr Val Asn Gly
225                 230                 235                 240

Gly Gly Gly Ser Gly Gly Gly Ser Gly Gly Gly Ser Asp Ile
                245                 250                 255

Lys Leu Gln Gln Ser Gly Ala Glu Leu Ala Arg Pro Gly Ala Ser Val
             260                 265                 270

Lys Met Ser Cys Lys Thr Ser Gly Tyr Thr Phe Thr Arg Tyr Thr Met
         275                 280                 285

His Trp Val Lys Gln Arg Pro Gly Gln Gly Leu Glu Trp Ile Gly Tyr
     290                 295                 300

Ile Asn Pro Ser Arg Gly Tyr Thr Asn Tyr Asn Gln Lys Phe Lys Asp
305                 310                 315                 320

Lys Ala Thr Leu Thr Thr Asp Lys Ser Ser Thr Ala Tyr Met Gln
             325                 330                 335

Leu Ser Ser Leu Thr Ser Glu Asp Ser Ala Val Tyr Tyr Cys Ala Arg
         340                 345                 350

Tyr Tyr Asp Asp His Tyr Cys Leu Asp Tyr Trp Gly Gln Gly Thr Thr
     355                 360                 365

Leu Thr Val Ser Ser Gly Gly Gly Ser Gly Gly Gly Gly Ser Gly
         370                 375                 380

Gly Gly Ser Asp Ile Gln Leu Thr Gln Ser Pro Ala Ile Met Ser
385                 390                 395                 400

Ala Ser Pro Gly Glu Lys Val Thr Met Thr Cys Arg Ala Ser Ser Ser
             405                 410                 415

Val Ser Tyr Met Asn Trp Tyr Gln Gln Lys Ser Gly Thr Ser Pro Lys
         420                 425                 430

Arg Trp Ile Tyr Asp Thr Ser Lys Val Ala Ser Gly Val Pro Tyr Arg
     435                 440                 445

Phe Ser Gly Ser Gly Ser Gly Thr Ser Tyr Ser Leu Thr Ile Ser Ser
450                 455                 460

Met Glu Ala Glu Asp Ala Ala Thr Tyr Tyr Cys Gln Gln Trp Ser Ser
465                 470                 475                 480

Asn Pro Leu Thr Phe Gly Ala Gly Thr Lys Leu Glu Leu Lys Ser His
         485                 490                 495

His His His His
        500

<210> SEQ ID NO 263
<211> LENGTH: 359
<212> TYPE: PRT
<213> ORGANISM: Artificial Sequence
<220> FEATURE:
<223> OTHER INFORMATION: Antibody Sequence

<400> SEQUENCE: 263

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

```
Ser Thr Ser Trp Phe Arg Lys Asn Pro Gly Thr Thr Asp Trp Glu Arg
        35                  40                  45
Met Ser Ile Gly Gly Arg Tyr Val Glu Ser Val Asn Lys Gly Ala Lys
 50                  55                  60
Ser Phe Ser Leu Arg Ile Lys Asp Leu Thr Val Ala Asp Ser Ala Thr
 65                  70                  75                  80
Tyr Tyr Cys Lys Ala Gln Ser Leu Ala Ile Ser Thr Arg Ser Tyr Trp
                 85                  90                  95
Tyr Asp Gly Ala Gly Thr Val Leu Thr Val Asn Gly Gly Gly Ser
                100                 105                 110
Asp Ile Lys Leu Gln Gln Ser Gly Ala Glu Leu Ala Arg Pro Gly Ala
                115                 120                 125
Ser Val Lys Met Ser Cys Lys Thr Ser Gly Tyr Thr Phe Thr Arg Tyr
130                 135                 140
Thr Met His Trp Val Lys Gln Arg Pro Gly Gln Gly Leu Glu Trp Ile
145                 150                 155                 160
Gly Tyr Ile Asn Pro Ser Arg Gly Tyr Thr Asn Tyr Asn Gln Lys Phe
                165                 170                 175
Lys Asp Lys Ala Thr Leu Thr Thr Asp Lys Ser Ser Ser Thr Ala Tyr
                180                 185                 190
Met Gln Leu Ser Ser Leu Thr Ser Glu Asp Ser Ala Val Tyr Tyr Cys
                195                 200                 205
Ala Arg Tyr Tyr Asp Asp His Tyr Cys Leu Asp Tyr Trp Gly Gln Gly
                210                 215                 220
Thr Thr Leu Thr Val Ser Ser Gly Gly Gly Ser Gly Gly Gly Gly
225                 230                 235                 240
Ser Gly Gly Gly Gly Ser Asp Ile Gln Leu Thr Gln Ser Pro Ala Ile
                245                 250                 255
Met Ser Ala Ser Pro Gly Glu Lys Val Thr Met Thr Cys Arg Ala Ser
                260                 265                 270
Ser Ser Val Ser Tyr Met Asn Trp Tyr Gln Gln Lys Ser Gly Thr Ser
                275                 280                 285
Pro Lys Arg Trp Ile Tyr Asp Thr Ser Lys Val Ala Ser Gly Val Pro
290                 295                 300
Tyr Arg Phe Ser Gly Ser Gly Ser Gly Thr Ser Tyr Ser Leu Thr Ile
305                 310                 315                 320
Ser Ser Met Glu Ala Glu Asp Ala Ala Thr Tyr Tyr Cys Gln Gln Trp
                325                 330                 335
Ser Ser Asn Pro Leu Thr Phe Gly Ala Gly Thr Lys Leu Glu Leu Lys
                340                 345                 350
Ser His His His His His
        355

<210> SEQ ID NO 264
<211> LENGTH: 369
<212> TYPE: PRT
<213> ORGANISM: Artificial Sequence
<220> FEATURE:
<223> OTHER INFORMATION: Antibody Sequence

<400> SEQUENCE: 264

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Gly Leu Tyr
                20                  25                  30
```

```
Ser Thr Ser Trp Phe Arg Lys Asn Pro Gly Thr Thr Asp Trp Glu Arg
         35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Gln Ser Leu Ala Ile Ser Thr Arg Ser Tyr Trp
                 85                  90                  95

Tyr Asp Gly Ala Gly Thr Val Leu Thr Val Asn Gly Gly Gly Ser
                 100                 105                 110

Gly Gly Gly Gly Ser Gly Gly Gly Ser Asp Ile Lys Leu Gln Gln
             115                 120                 125

Ser Gly Ala Glu Leu Ala Arg Pro Gly Ala Ser Val Lys Met Ser Cys
130                 135                 140

Lys Thr Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                 165                 170                 175

Arg Gly Tyr Thr Asn Tyr Asn Gln Lys Phe Lys Asp Lys Ala Thr Leu
                 180                 185                 190

Thr Thr Asp Lys Ser Ser Thr Ala Tyr Met Gln Leu Ser Ser Leu
                 195                 200                 205

Thr Ser Glu Asp Ser Ala Val Tyr Tyr Cys Ala Arg Tyr Tyr Asp Asp
        210                 215                 220

His Tyr Cys Leu Asp Tyr Trp Gly Gln Gly Thr Thr Leu Thr Val Ser
225                 230                 235                 240

Ser Gly Gly Gly Ser Gly Gly Gly Ser Gly Gly Gly Ser
                 245                 250                 255

Asp Ile Gln Leu Thr Gln Ser Pro Ala Ile Met Ser Ala Ser Pro Gly
                 260                 265                 270

Glu Lys Val Thr Met Thr Cys Arg Ala Ser Ser Ser Val Ser Tyr Met
        275                 280                 285

Asn Trp Tyr Gln Gln Lys Ser Gly Thr Ser Pro Lys Arg Trp Ile Tyr
290                 295                 300

Asp Thr Ser Lys Val Ala Ser Gly Val Pro Tyr Arg Phe Ser Gly Ser
305                 310                 315                 320

Gly Ser Gly Thr Ser Tyr Ser Leu Thr Ile Ser Ser Met Glu Ala Glu
                 325                 330                 335

Asp Ala Ala Thr Tyr Tyr Cys Gln Gln Trp Ser Ser Asn Pro Leu Thr
                 340                 345                 350

Phe Gly Ala Gly Thr Lys Leu Glu Leu Lys Ser His His His His
             355                 360                 365

His

<210> SEQ ID NO 265
<211> LENGTH: 480
<212> TYPE: PRT
<213> ORGANISM: Artificial Sequence
<220> FEATURE:
<223> OTHER INFORMATION: Antibody Sequence

<400> SEQUENCE: 265

Thr Arg Val Asp Gln Thr Pro Arg Thr Ala Lys Glu Thr Gly Glu
1               5                  10                  15

Ser Leu Thr Ile Asn Cys Val Leu Thr Asp Thr Ser Tyr Gly Leu Tyr
```

```
            20                  25                  30
Ser Thr Ser Trp Phe Arg Lys Asn Pro Gly Thr Thr Asp Trp Glu Arg
        35                  40                  45
Met Ser Ile Gly Gly Arg Tyr Val Glu Ser Val Asn Lys Gly Ala Lys
        50                  55                  60
Ser Phe Ser Leu Arg Ile Lys Asp Leu Thr Val Ala Asp Ser Ala Thr
65                  70                  75                  80
Tyr Tyr Cys Lys Ala Arg Glu Ala Arg His Pro Trp Leu Arg Gln Trp
                85                  90                  95
Tyr Asp Gly Ala Gly Thr Val Leu Thr Val Asn Pro Gly Val Gln Pro
            100                 105                 110
Ser Pro Gly Gly Gly Ser Ala Ser Val Asn Gln Thr Pro Arg Thr
            115                 120                 125
Ala Thr Lys Glu Thr Gly Glu Ser Leu Thr Ile Asn Cys Val Val Thr
            130                 135                 140
Gly Ala Asn Tyr Gly Leu Ala Ala Thr Tyr Trp Tyr Arg Lys Asn Pro
145                 150                 155                 160
Gly Ser Ser Asn Gln Glu Arg Ile Ser Ile Ser Gly Arg Tyr Val Glu
                165                 170                 175
Ser Val Asn Lys Arg Thr Met Ser Phe Ser Leu Arg Ile Lys Asp Leu
            180                 185                 190
Thr Val Ala Asp Ser Ala Thr Tyr Tyr Cys Lys Ala Tyr Pro Trp Gly
            195                 200                 205
Ala Gly Ala Pro Trp Leu Val Gln Trp Tyr Asp Gly Ala Gly Thr Val
        210                 215                 220
Leu Thr Val Asn Gly Gly Gly Ser Asp Ile Lys Leu Gln Gln Ser
225                 230                 235                 240
Gly Ala Glu Leu Ala Arg Pro Gly Ala Ser Val Lys Met Ser Cys Lys
                245                 250                 255
Thr Ser Gly Tyr Thr Phe Thr Arg Tyr Thr Met His Trp Val Lys Gln
            260                 265                 270
Arg Pro Gly Gln Gly Leu Glu Trp Ile Gly Tyr Ile Asn Pro Ser Arg
        275                 280                 285
Gly Tyr Thr Asn Tyr Asn Gln Lys Phe Lys Asp Lys Ala Thr Leu Thr
        290                 295                 300
Thr Asp Lys Ser Ser Ser Thr Ala Tyr Met Gln Leu Ser Ser Leu Thr
305                 310                 315                 320
Ser Glu Asp Ser Ala Val Tyr Tyr Cys Ala Arg Tyr Tyr Asp Asp His
                325                 330                 335
Tyr Cys Leu Asp Tyr Trp Gly Gln Gly Thr Thr Leu Thr Val Ser Ser
            340                 345                 350
Gly Gly Gly Gly Ser Gly Gly Gly Ser Gly Gly Gly Gly Ser Asp
            355                 360                 365
Ile Gln Leu Thr Gln Ser Pro Ala Ile Met Ser Ala Ser Pro Gly Glu
        370                 375                 380
Lys Val Thr Met Thr Cys Arg Ala Ser Ser Ser Val Ser Tyr Met Asn
385                 390                 395                 400
Trp Tyr Gln Gln Lys Ser Gly Thr Ser Pro Lys Arg Trp Ile Tyr Asp
                405                 410                 415
Thr Ser Lys Val Ala Ser Gly Val Pro Tyr Arg Phe Ser Gly Ser Gly
            420                 425                 430
Ser Gly Thr Ser Tyr Ser Leu Thr Ile Ser Ser Met Glu Ala Glu Asp
            435                 440                 445
```

Ala Ala Thr Tyr Tyr Cys Gln Gln Trp Ser Ser Asn Pro Leu Thr Phe
    450                 455                 460

Gly Ala Gly Thr Lys Leu Glu Leu Lys Ser His His His His His
465                 470                 475                 480

<210> SEQ ID NO 266
<211> LENGTH: 490
<212> TYPE: PRT
<213> ORGANISM: Artificial Sequence
<220> FEATURE:
<223> OTHER INFORMATION: Antibody Sequence

<400> SEQUENCE: 266

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ser Pro Gly Gly Gly Ser Ala Ser Val Asn Gln Thr Pro Arg Thr
        115                 120                 125

Ala Thr Lys Glu Thr Gly Glu Ser Leu Thr Ile Asn Cys Val Val Thr
    130                 135                 140

Gly Ala Asn Tyr Gly Leu Ala Ala Thr Tyr Trp Tyr Arg Lys Asn Pro
145                 150                 155                 160

Gly Ser Ser Asn Gln Glu Arg Ile Ser Ile Ser Gly Arg Tyr Val Glu
                165                 170                 175

Ser Val Asn Lys Arg Thr Met Ser Phe Ser Leu Arg Ile Lys Asp Leu
            180                 185                 190

Thr Val Ala Asp Ser Ala Thr Tyr Tyr Cys Lys Ala Tyr Pro Trp Gly
        195                 200                 205

Ala Gly Ala Pro Trp Leu Val Gln Trp Tyr Asp Gly Ala Gly Thr Val
    210                 215                 220

Leu Thr Val Asn Gly Gly Gly Ser Gly Gly Gly Ser Gly Gly
225                 230                 235                 240

Gly Gly Ser Asp Ile Lys Leu Gln Gln Ser Gly Ala Glu Leu Ala Arg
                245                 250                 255

Pro Gly Ala Ser Val Lys Met Ser Cys Lys Thr Ser Gly Tyr Thr Phe
            260                 265                 270

Thr Arg Tyr Thr Met His Trp Val Lys Gln Arg Pro Gly Gln Gly Leu
        275                 280                 285

Glu Trp Ile Gly Tyr Ile Asn Pro Ser Arg Gly Tyr Thr Asn Tyr Asn
    290                 295                 300

Gln Lys Phe Lys Asp Lys Ala Thr Leu Thr Thr Asp Lys Ser Ser Ser
305                 310                 315                 320

Thr Ala Tyr Met Gln Leu Ser Ser Leu Thr Ser Glu Asp Ser Ala Val
                325                 330                 335

```
Tyr Tyr Cys Ala Arg Tyr Tyr Asp Asp His Tyr Cys Leu Asp Tyr Trp
            340                 345                 350

Gly Gln Gly Thr Thr Leu Thr Val Ser Ser Gly Gly Gly Ser Gly
        355                 360                 365

Gly Gly Gly Ser Gly Gly Gly Ser Asp Ile Gln Leu Thr Gln Ser
    370                 375                 380

Pro Ala Ile Met Ser Ala Ser Pro Gly Glu Lys Val Thr Met Thr Cys
385                 390                 395                 400

Arg Ala Ser Ser Ser Val Ser Tyr Met Asn Trp Tyr Gln Gln Lys Ser
                405                 410                 415

Gly Thr Ser Pro Lys Arg Trp Ile Tyr Asp Thr Ser Lys Val Ala Ser
                420                 425                 430

Gly Val Pro Tyr Arg Phe Ser Gly Ser Gly Ser Gly Thr Ser Tyr Ser
            435                 440                 445

Leu Thr Ile Ser Ser Met Glu Ala Glu Asp Ala Ala Thr Tyr Tyr Cys
            450                 455                 460

Gln Gln Trp Ser Ser Asn Pro Leu Thr Phe Gly Ala Gly Thr Lys Leu
465                 470                 475                 480

Glu Leu Lys Ser His His His His His His
            485                 490

<210> SEQ ID NO 267
<211> LENGTH: 483
<212> TYPE: PRT
<213> ORGANISM: Artificial Sequence
<220> FEATURE:
<223> OTHER INFORMATION: Antibody Sequence

<400> SEQUENCE: 267

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Pro Gly Val Gln Pro
            100                 105                 110

Ala Pro Gly Gly Gly Ser Ala Ser Val Asn Gln Thr Pro Arg Thr
        115                 120                 125

Ala Thr Lys Glu Thr Gly Glu Ser Leu Thr Ile Asn Cys Val Leu Thr
    130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

Ser Val Asn Lys Arg Ala Lys Ser Phe Ser Leu Arg Ile Lys Asp Leu
            180                 185                 190

Thr Val Ala Asp Ser Ala Thr Tyr Tyr Cys Lys Ala Gln Ser Gly Met
        195                 200                 205
```

```
Ala Ile Ser Thr Gly Ser Gly His Gly Tyr Asn Trp Tyr Asp Gly Ala
        210                 215                 220

Gly Thr Val Leu Thr Val Asn Gly Gly Gly Ser Asp Ile Lys Leu
225                 230                 235                 240

Gln Gln Ser Gly Ala Glu Leu Ala Arg Pro Gly Ala Ser Val Lys Met
                245                 250                 255

Ser Cys Lys Thr Ser Gly Tyr Thr Phe Thr Arg Tyr Thr Met His Trp
                260                 265                 270

Val Lys Gln Arg Pro Gly Gln Gly Leu Glu Trp Ile Gly Tyr Ile Asn
                275                 280                 285

Pro Ser Arg Gly Tyr Thr Asn Tyr Asn Gln Lys Phe Lys Asp Lys Ala
                290                 295                 300

Thr Leu Thr Thr Asp Lys Ser Ser Thr Ala Tyr Met Gln Leu Ser
305                 310                 315                 320

Ser Leu Thr Ser Glu Asp Ser Ala Val Tyr Tyr Cys Ala Arg Tyr Tyr
                325                 330                 335

Asp Asp His Tyr Cys Leu Asp Tyr Trp Gly Gln Gly Thr Thr Leu Thr
                340                 345                 350

Val Ser Ser Gly Gly Gly Gly Ser Gly Gly Gly Gly Ser Gly Gly Gly
                355                 360                 365

Gly Ser Asp Ile Gln Leu Thr Gln Ser Pro Ala Ile Met Ser Ala Ser
370                 375                 380

Pro Gly Glu Lys Val Thr Met Thr Cys Arg Ala Ser Ser Ser Val Ser
385                 390                 395                 400

Tyr Met Asn Trp Tyr Gln Gln Lys Ser Gly Thr Ser Pro Lys Arg Trp
                405                 410                 415

Ile Tyr Asp Thr Ser Lys Val Ala Ser Gly Val Pro Tyr Arg Phe Ser
                420                 425                 430

Gly Ser Gly Ser Gly Thr Ser Tyr Ser Leu Thr Ile Ser Ser Met Glu
                435                 440                 445

Ala Glu Asp Ala Ala Thr Tyr Tyr Cys Gln Gln Trp Ser Ser Asn Pro
                450                 455                 460

Leu Thr Phe Gly Ala Gly Thr Lys Leu Glu Leu Lys Ser His His His
465                 470                 475                 480

His His His

<210> SEQ ID NO 268
<211> LENGTH: 493
<212> TYPE: PRT
<213> ORGANISM: Artificial Sequence
<220> FEATURE:
<223> OTHER INFORMATION: Antibody Sequence

<400> SEQUENCE: 268

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
                35                  40                  45

Met Ser Ile Gly Gly Arg Tyr Val Glu Ser Val Asn Lys Gly Ala Lys
                50                  55                  60

Ser Phe Ser Leu Arg Ile Lys Asp Leu Thr Val Ala Asp Ser Ala Thr
65                  70                  75                  80
```

-continued

```
Tyr Tyr Cys Lys Ala Arg Glu Ala Arg His Pro Trp Leu Arg Gln Trp
                 85                  90                  95

Tyr Asp Gly Ala Gly Thr Val Leu Thr Val Asn Pro Gly Val Gln Pro
            100                 105                 110

Ala Pro Gly Gly Gly Gly Ser Ala Ser Val Asn Gln Thr Pro Arg Thr
        115                 120                 125

Ala Thr Lys Glu Thr Gly Glu Ser Leu Thr Ile Asn Cys Val Leu Thr
    130                 135                 140

Asp Thr Ser Tyr Gly Leu Tyr Ser Thr Ser Trp Phe Arg Lys Asn Pro
145                 150                 155                 160

Gly Thr Thr Asp Trp Glu Arg Met Ser Ile Gly Gly Arg Tyr Val Glu
                165                 170                 175

Ser Val Asn Lys Arg Ala Lys Ser Phe Ser Leu Arg Ile Lys Asp Leu
            180                 185                 190

Thr Val Ala Asp Ser Ala Thr Tyr Tyr Cys Lys Ala Gln Ser Gly Met
        195                 200                 205

Ala Ile Ser Thr Gly Ser Gly His Gly Tyr Asn Trp Tyr Asp Gly Ala
    210                 215                 220

Gly Thr Val Leu Thr Val Asn Gly Gly Gly Ser Gly Gly Gly Gly
225                 230                 235                 240

Ser Gly Gly Gly Gly Ser Asp Ile Lys Leu Gln Gln Ser Gly Ala Glu
                245                 250                 255

Leu Ala Arg Pro Gly Ala Ser Val Lys Met Ser Cys Lys Thr Ser Gly
            260                 265                 270

Tyr Thr Phe Thr Arg Tyr Thr Met His Trp Val Lys Gln Arg Pro Gly
        275                 280                 285

Gln Gly Leu Glu Trp Ile Gly Tyr Ile Asn Pro Ser Arg Gly Tyr Thr
    290                 295                 300

Asn Tyr Asn Gln Lys Phe Lys Asp Lys Ala Thr Leu Thr Thr Asp Lys
305                 310                 315                 320

Ser Ser Ser Thr Ala Tyr Met Gln Leu Ser Ser Leu Thr Ser Glu Asp
                325                 330                 335

Ser Ala Val Tyr Tyr Cys Ala Arg Tyr Tyr Asp Asp His Tyr Cys Leu
            340                 345                 350

Asp Tyr Trp Gly Gln Gly Thr Thr Leu Thr Val Ser Ser Gly Gly Gly
        355                 360                 365

Gly Ser Gly Gly Gly Gly Ser Gly Gly Gly Gly Ser Asp Ile Gln Leu
    370                 375                 380

Thr Gln Ser Pro Ala Ile Met Ser Ala Ser Pro Gly Glu Lys Val Thr
385                 390                 395                 400

Met Thr Cys Arg Ala Ser Ser Val Ser Tyr Met Asn Trp Tyr Gln
                405                 410                 415

Gln Lys Ser Gly Thr Ser Pro Lys Arg Trp Ile Tyr Asp Thr Ser Lys
            420                 425                 430

Val Ala Ser Gly Val Pro Tyr Arg Phe Ser Gly Ser Gly Ser Gly Thr
        435                 440                 445

Ser Tyr Ser Leu Thr Ile Ser Ser Met Glu Ala Glu Asp Ala Ala Thr
    450                 455                 460

Tyr Tyr Cys Gln Gln Trp Ser Ser Asn Pro Leu Thr Phe Gly Ala Gly
465                 470                 475                 480

Thr Lys Leu Glu Leu Lys Ser His His His His His
                485                 490
```

```
<210> SEQ ID NO 269
<211> LENGTH: 496
<212> TYPE: PRT
<213> ORGANISM: Artificial Sequence
<220> FEATURE:
<223> OTHER INFORMATION: Antibody Sequence

<400> SEQUENCE: 269

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Ser
            100                 105                 110

Gly Gly Gly Gly Ser Gly Gly Gly Ser Gly Gly Gly Ser Gly
            115                 120                 125

Gly Gly Gly Ser Ala Ser Val Asn Gln Thr Pro Arg Thr Ala Thr Lys
            130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
            180                 185                 190

Lys Arg Ala Lys Ser Phe Ser Leu Arg Ile Lys Asp Leu Thr Val Ala
        195                 200                 205

Asp Ser Ala Thr Tyr Tyr Cys Lys Ala Gln Ser Gly Met Ala Ile Ser
    210                 215                 220

Thr Gly Ser Gly His Gly Tyr Asn Trp Tyr Asp Gly Ala Gly Thr Val
225                 230                 235                 240

Leu Thr Val Asn Gly Gly Gly Ser Asp Ile Lys Leu Gln Gln Ser
                245                 250                 255

Gly Ala Glu Leu Ala Arg Pro Gly Ala Ser Val Lys Met Ser Cys Lys
            260                 265                 270

Thr Ser Gly Tyr Thr Phe Thr Arg Tyr Thr Met His Trp Val Lys Gln
        275                 280                 285

Arg Pro Gly Gln Gly Leu Glu Trp Ile Gly Tyr Ile Asn Pro Ser Arg
    290                 295                 300

Gly Tyr Thr Asn Tyr Asn Gln Lys Phe Lys Asp Lys Ala Thr Leu Thr
305                 310                 315                 320

Thr Asp Lys Ser Ser Ser Thr Ala Tyr Met Gln Leu Ser Ser Leu Thr
                325                 330                 335

Ser Glu Asp Ser Ala Val Tyr Tyr Cys Ala Arg Tyr Tyr Asp Asp His
            340                 345                 350

Tyr Cys Leu Asp Tyr Trp Gly Gln Gly Thr Thr Leu Thr Val Ser Ser
        355                 360                 365

Gly Gly Gly Gly Ser Gly Gly Gly Gly Ser Gly Gly Gly Gly Ser Asp
```

```
                    370                 375                 380
Ile Gln Leu Thr Gln Ser Pro Ala Ile Met Ser Ala Ser Pro Gly Glu
385                 390                 395                 400

Lys Val Thr Met Thr Cys Arg Ala Ser Ser Val Ser Tyr Met Asn
                    405                 410                 415

Trp Tyr Gln Gln Lys Ser Gly Thr Ser Pro Lys Arg Trp Ile Tyr Asp
                    420                 425                 430

Thr Ser Lys Val Ala Ser Gly Val Pro Tyr Arg Phe Ser Gly Ser Gly
                    435                 440                 445

Ser Gly Thr Ser Tyr Ser Leu Thr Ile Ser Ser Met Glu Ala Glu Asp
                    450                 455                 460

Ala Ala Thr Tyr Tyr Cys Gln Gln Trp Ser Ser Asn Pro Leu Thr Phe
465                 470                 475                 480

Gly Ala Gly Thr Lys Leu Glu Leu Lys Ser His His His His His His
                    485                 490                 495
```

<210> SEQ ID NO 270
<211> LENGTH: 506
<212> TYPE: PRT
<213> ORGANISM: Artificial Sequence
<220> FEATURE:
<223> OTHER INFORMATION: Antibody Sequence

<400> SEQUENCE: 270

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Ser Tyr Gly Leu Tyr
                20                  25                  30

Ser Thr Ser Trp Phe Arg Lys Asn Pro Gly Thr Thr Asp Trp Glu Arg
                35                  40                  45

Met Ser Ile Gly Gly Arg Tyr Val Glu Ser Val Asn Lys Gly Ala Lys
                50                  55                  60

Ser Phe Ser Leu Arg Ile Lys Asp Leu Thr Val Ala Asp Ser Ala Thr
65                  70                  75                  80

Tyr Tyr Cys Lys Ala Arg Glu Ala Arg His Pro Trp Leu Arg Gln Trp
                85                  90                  95

Tyr Asp Gly Ala Gly Thr Val Leu Thr Val Asn Gly Gly Gly Gly Ser
                100                 105                 110

Gly Gly Gly Gly Ser Gly Gly Gly Ser Gly Gly Gly Gly Ser Gly
                115                 120                 125

Gly Gly Ser Ala Ser Val Asn Gln Thr Pro Arg Thr Ala Thr Lys
                130                 135                 140

Glu Thr Gly Glu Ser Leu Thr Ile Asn Cys Val Leu Thr Asp Thr Ser
145                 150                 155                 160

Tyr Gly Leu Tyr Ser Thr Ser Trp Phe Arg Lys Asn Pro Gly Thr Thr
                165                 170                 175

Asp Trp Glu Arg Met Ser Ile Gly Gly Arg Tyr Val Glu Ser Val Asn
                180                 185                 190

Lys Arg Ala Lys Ser Phe Ser Leu Arg Ile Lys Asp Leu Thr Val Ala
                195                 200                 205

Asp Ser Ala Thr Tyr Tyr Cys Lys Ala Gln Ser Gly Met Ala Ile Ser
                210                 215                 220

Thr Gly Ser Gly His Gly Tyr Asn Trp Tyr Asp Gly Ala Gly Thr Val
225                 230                 235                 240

Leu Thr Val Asn Gly Gly Gly Gly Ser Gly Gly Gly Gly Ser Gly Gly
```

```
                245                 250                 255
Gly Gly Ser Asp Ile Lys Leu Gln Gln Ser Gly Ala Glu Leu Ala Arg
            260                 265                 270

Pro Gly Ala Ser Val Lys Met Ser Cys Lys Thr Ser Gly Tyr Thr Phe
            275                 280                 285

Thr Arg Tyr Thr Met His Trp Val Lys Gln Arg Pro Gly Gln Gly Leu
            290                 295                 300

Glu Trp Ile Gly Tyr Ile Asn Pro Ser Arg Gly Tyr Thr Asn Tyr Asn
305                 310                 315                 320

Gln Lys Phe Lys Asp Lys Ala Thr Leu Thr Thr Asp Lys Ser Ser Ser
            325                 330                 335

Thr Ala Tyr Met Gln Leu Ser Ser Leu Thr Ser Glu Asp Ser Ala Val
            340                 345                 350

Tyr Tyr Cys Ala Arg Tyr Asp Asp His Tyr Cys Leu Asp Tyr Trp
            355                 360                 365

Gly Gln Gly Thr Thr Leu Thr Val Ser Ser Gly Gly Gly Ser Gly
370                 375                 380

Gly Gly Gly Ser Gly Gly Gly Ser Asp Ile Gln Leu Thr Gln Ser
385                 390                 395                 400

Pro Ala Ile Met Ser Ala Ser Pro Gly Glu Lys Val Thr Met Thr Cys
            405                 410                 415

Arg Ala Ser Ser Ser Val Ser Tyr Met Asn Trp Tyr Gln Gln Lys Ser
            420                 425                 430

Gly Thr Ser Pro Lys Arg Trp Ile Tyr Asp Thr Ser Lys Val Ala Ser
            435                 440                 445

Gly Val Pro Tyr Arg Phe Ser Gly Ser Gly Ser Gly Thr Ser Tyr Ser
            450                 455                 460

Leu Thr Ile Ser Ser Met Glu Ala Glu Asp Ala Ala Thr Tyr Tyr Cys
465                 470                 475                 480

Gln Gln Trp Ser Ser Asn Pro Leu Thr Phe Gly Ala Gly Thr Lys Leu
            485                 490                 495

Glu Leu Lys Ser His His His His His His
            500                 505
```

ROR1-SPECIFIC ANTIGEN BINDING MOLECULES

RELATED APPLICATIONS

The present application is a U.S. National Stage application under 35 USC 371 of PCT Application Serial No. PCT/EP2018/086823, filed on 21 Dec. 2018; which claims priority from GB Patent Application No. 1721802.5, filed 22 Dec. 2017, the entirety of both of which are incorporated herein by reference.

SEQUENCE LISTING

The instant application contains a Sequence Listing, which has been submitted electronically in ASCII format and is hereby incorporated by reference in its entirety. Said ASCII copy, created on Feb. 24, 2021, is named K&S-029659-US-PCT SL.txt and is 549,545 bytes in size.

FIELD OF INVENTION

The present invention relates to receptor tyrosine kinase-like orphan receptor 1 (ROR1) specific antigen binding molecules and associated fusion proteins and conjugates. In a further aspect, the present invention relates to conjugated immunoglobulin-like shark variable novel antigen receptors (VNARs).

BACKGROUND

Receptor tyrosine kinase-like orphan receptor 1 (ROR1) is a 937 amino acid glycosylated type I single pass transmembrane protein. The extracellular region consists of three distinct domains composing an N-terminal immunoglobulin domain (Ig), followed by a cysteine rich fizzled domain (fz) which in turn is linked to the membrane proximal kringle domain (kr). The intracellular region of the protein contains a pseudo kinase domain followed by two Ser/Thr rich domains which are interspersed by a proline-rich region, and this same overall domain architecture is conserved in the closely related family member ROR2, with which it shares high sequence identity. (Rebagay G et al, Frontiers Oncology, 2012, 2, Borcherding N et al Protein Cell, 2014, 5, 496-502).

ROR1 is expressed during embryonic development, where it is prominently expressed in neural crest cells and in the necrotic and interdigital zones in the later stages of development. However, its expression is quickly silenced after birth, and is largely absent in normal adult tissue (Fukada PNAS, 2012, Baskar et al Clin. Cancer Res., 2008, 14, 396, Broome H E et al, Leuk. Res., 2011, 35, 1390; Balakrishnan A et al, Clin. Cancer. Res. 2017, 23, 3061-3071).

ROR1 expression has been observed at both the mRNA and protein level across a broad range of solid tumours and haematological malignancies including lung, breast, pancreatic, ovarian, colon, head and neck and prostate cancers, melanoma and renal cell carcinoma (Zhang S et al Am J. Pathol., 2012, 181, 1903-1910), breast cancer (Zhang S et al PLoS One 2012, 7, e31127; Oxford Biotherapeutics patent application WO2011054007) and Chronic lymphocytic leukemia (CLL) and acute lymphoblastic leukemia AML (Fukuda T et al, Proc Natl Acad Sci USA. 2008, 105, 3047-3052; Baskar S et al, Clin Cancer Res., 2008, 14, 396-404; Daneshmanesh A H et al, Int J Cancer. 2008, 123, 1190-1195; Dave H et al, PLOS ONE, 2012, 7, e52655).

Additionally, increased ROR1 expression is reported to correlate with poor clinical outcomes for a number of cancer indications including breast cancer (Chien H P et al, Virchows Arch., 2016, 468, 589-595; Zhang), ovarian cancer (Zhang H et al, Sci Rep., 2014, 4:5811. doi: 10.1038/srep05811), colorectal cancer (Zhou J K et al, Oncotarget, 2017, 8, 32864-32872), lung adenocarcinoma (Zheng Y Z et al, Sci Rep., 2016, 6, 36447) and CLL (Cui B et al, Blood, 2016, 128, 2931-2940).

Consistent with ROR1's expression pattern and the link to poor clinical prognosis, a functional role for ROR1 in tumourigenesis and disease progression has been demonstrated for a number of different cancer indications. ROR1 promotes epithelial-mesenchymal transition and metastasis in models of breast cancer (Cui B et al Cancer Res, 2013, 73, 3649-3660) and spheroid formation and tumour engraftment in models of ovarian cancer (Zhang S et al, Proc Natl Acad Sci., 2014, 11, 17266-17271). ROR1 is a transcript target of the NKX2-1/TTF-1 lineage survival factor oncogene in lung adenocarcinoma, where it sustains EGFR signalling and represses pro-apoptotic signalling (Yamaguchi T et al, Cancer Cell, 2012, 21, 348-361; Ida L et al, Cancer Science, 2016, 107, 155-161). ROR1 has also been shown to act as a scaffold to sustain caveolae structures and by-pass signalling mechanism that confer resistance to EGFR tyrosine kinase inhibitors (Yamaguchi T et al, Nat Commun., 2016, 7, 10060). Signalling through an ROR1-HER3 complex modulates the Hippo-YAP pathway and promotes breast cancer bone metastasis (Li C et al, Nature Cell Biol., 19, 1206-119) and the protein can promote Met-driven tumourigenesis (Gentile A et al, Cancer Res., 2011, 71, 3132-3140). Whilst in CLL, ROR1 has been reported to hetero-oligomerise with ROR2 in response to Wnt5a to transduce signalling and enhance proliferation and migration (Yu J et al, J. Clin. Invest., 2016, 2, 585-598)

Given the functional role of ROR1 in cancer pathology and the general lack of expression on normal adult tissue, this oncofetal protein is an attractive target for cancer therapy. Antibodies to ROR1 have been described in the literature WO2021097313 (4A5 kipps), WO2014031174 (UC961), WO2016187220 (Five Prime) WO2010124188 (2A2), WO2012075158 (R11, R12), WO2011054007 (Oxford Bio), WO2011079902 (Bioinvent) WO2017127664, WO2017127664 (NBE Therapeutics, SCRIPPS), WO2016094847 (Emergent), WO2017127499), and a humanised murine anti-ROR1 antibody, UC961, has entered clinical trials for relapsed or refractory chronic lymphocytic leukemia. Chimeric antigen receptor T-cells targeting ROR1 have also been reported (Hudecek M et al, Clin. Cancer Res., 2013, 19, 3153-64) and preclinical primate studies with UC961 and with CAR-T cells targeting ROR1 showed no overt toxicity, which is consistent with the general lack of expression of the protein on adult tissue (Choi M et al, Clinical Lymphoma, myeloma & leukemia, 2015, S167; Berger C et al, Cancer Immunol. Res., 2015, 3, 206).

Single domain binding molecules can be derived from an array of proteins from distinct species. The immunoglobulin isotope novel antigen receptor (IgNAR) is a homodimeric heavy-chain complex originally found in the serum of the nurse shark (*Ginglymostoma cirratum*) and other sharks and ray species. IgNARs do not contain light chains and are distinct from the typical immunoglobulin structure. Each molecule consists of a single-variable domain (VNAR) and five constant domains (CNAR). The nomenclature in the literature refers to IgNARs as immunoglobulin isotope novel antigen receptors or immunoglobulin isotope new antigen receptors and the terms are synonymous.

There are three main defined types of shark IgNAR known as I, II and III (Kovalena et al, Exp Opin Biol Ther 2014 14(10) 1527-1539). These have been categorized based on the position of non-canonical cysteine residues which are under strong selective pressure and are therefore rarely replaced.

All three types have the classical immunoglobulin canonical cysteines at positions 35 and 107 that stabilize the standard immunoglobulin fold, together with an invariant tryptophan at position 36. There is no defined CDR2 as such, but regions of sequence variation that compare more closely to TCR HV2 and HV4 have been defined in framework 2 and 3 respectively. Type I has germline encoded cysteine residues in framework 2 and framework 4 and an even number of additional cysteines within CDR3. Crystal structure studies of a Type I IgNAR isolated against and in complex with lysozyme enabled the contribution of these cysteine residues to be determined. Both the framework 2 and 4 cysteines form disulphide bridges with those in CDR3 forming a tightly packed structure within which the CDR3 loop is held tightly down towards the HV2 region. To date Type I IgNARs have only been identified in nurse sharks—all other elasmobranchs, including members of the same order have only Type II or variations of this type.

Type II IgNAR are defined as having a cysteine residue in CDR1 and CDR3 which form intramolecular disulphide bonds that hold these two regions in close proximity, resulting in a protruding CDR3 that is conducive to binding pockets or grooves. Type I sequences typically have longer CDR3s than type II with an average of 21 and 15 residues respectively. This is believed to be due to a strong selective pressure for two or more cysteine residues in Type I CDR3 to associate with their framework 2 and 4 counterparts. Studies into the accumulation of somatic mutations show that there are a greater number of mutations in CDR1 of type II than type I, whereas HV2 regions of Type I show greater sequence variation than Type II. This evidence correlates well with the determined positioning of these regions within the antigen binding sites. A third IgNAR type known as Type III has been identified in neonates. This member of the IgNAR family lacks diversity within CDR3 due to the germline fusion of the D1 and D2 regions (which form CDR3) with the V-gene. Almost all known clones have a CDR3 length of 15 residues with little or no sequence diversity.

Another structural type of VNAR, termed type (IIb or IV), has only two canonical cysteine residues (in framework 1 and framework 3b regions). So far, this type has been found primarily in dogfish sharks (Liu, J. L., et al. Mol. Immunol. 2007. 44(7): p. 1775-1783; Kovalenko O. V., et al. J Biol Chem. 2013. 288(24): p. 17408-19) and was also isolated from semisynthetic V-NAR libraries derived from wobbegong sharks (Streltsov, V. A. et al. (2004) Proc. Natl. Acad. Sci. U.S.A. 101(34): p. 12444-12449).

SUMMARY OF INVENTION

The present invention generally relates to specific antigen binding molecules. In a first aspect, there is provided a receptor tyrosine kinase-like orphan receptor 1 (ROR1) specific antigen binding molecule comprising an amino acid sequence represented by the formula (I):

FW1-CDR1-FW2-HV2-FW3a-HV4-FW3b-CDR3-FW4 (I)

wherein
FW1 is a framework region
CDR1 is a CDR sequence
FW2 is a framework region
HV2 is a hypervariable sequence
FW3a is a framework region
HV4 is a hypervariable sequence
FW3b is a framework region
CDR3 is a CDR sequence
FW4 is a framework region.

Framework region FW1 is preferably from 20 to 28 amino acids in length, more preferably from 22 to 26 amino acids in length, still more preferably from 23 to 25 amino acids in length. In certain preferred embodiments, FW1 is 26 amino acids in length. In other preferred embodiments, FW1 is 25 amino acids in length. In still other preferred embodiments, FW1 is 24 amino acids in length.

CDR region CDR1 is preferably from 7 to 11 amino acids in length, more preferably from 8 to 10 amino acids in length. In certain preferred embodiments, CDR1 is 9 amino acids in length. In other preferred embodiments, CDR1 is 8 amino acids in length.

Framework region FW2 is preferably from 6 to 14 amino acids in length, more preferably from 8 to 12 amino acids in length. In certain preferred embodiments, FW2 is 12 amino acids in length. In other preferred embodiments, FW2 is 10 amino acids in length. In other preferred embodiments, FW2 is 9 amino acids in length. In other preferred embodiments, FW2 is 8 amino acids in length.

Hypervariable sequence HV2 is preferably from 4 to 11 amino acids in length, more preferably from 5 to 10 amino acids in length. In certain preferred embodiments, HV2 is 10 amino acids in length. In certain preferred embodiments, HV2 is 9 amino acids in length. In other preferred embodiments, HV2 is 6 amino acids in length.

Framework region FW3a is preferably from 6 to 10 amino acids in length, more preferably from 7 to 9 amino acids in length. In certain preferred embodiments, FW3a is 8 amino acids in length. In certain preferred embodiments, FW3a is 7 amino acids in length.

Hypervariable sequence HV4 is preferably from 3 to 7 amino acids in length, more preferably from 4 to 6 amino acids in length. In certain preferred embodiments, HV4 is 5 amino acids in length. In other preferred embodiments, HV4 is 4 amino acids in length.

Framework region FW3b is preferably from 17 to 24 amino acids in length, more preferably from 18 to 23 amino acids in length, still more preferably from 19 to 22 amino acids in length. In certain preferred embodiments, FW3b is 21 amino acids in length. In other preferred embodiments, FW3b is 20 amino acids in length.

CDR region CDR3 is preferably from 8 to 21 amino acids in length, more preferably from 9 to 20 amino acids in length, still more preferably from 10 to 19 amino acids in length. In certain preferred embodiments, CDR3 is 17 amino acids in length. In other preferred embodiments, CDR3 is 14 amino acids in length. In still other preferred embodiments, CDR3 is 12 amino acids in length. In yet other preferred embodiments, CDR3 is 10 amino acids in length.

Framework region FW4 is preferably from 7 to 14 amino acids in length, more preferably from 8 to 13 amino acids in length, still more preferably from 9 to 12 amino acids in length. In certain preferred embodiments, FW4 is 12 amino acids in length. In other preferred embodiments, FW4 is 11 amino acids in length. In still other preferred embodiments, FW4 is 10 amino acids in length. In yet other preferred embodiments, FW4 is 9 amino acids in length.

Preferably, the ROR1-specific antigen binding molecule does not bind to receptor tyrosine kinase-like orphan receptor 2 (ROR2). More preferably, the ROR1-specific antigen binding molecule binds to both human ROR1 and murine ROR1 (mROR1). Yet more preferably, the ROR1-specific antigen binding molecule binds to deglycosylated ROR1.

Certain ROR1-specific antigen binding molecules of the invention do not bind to a linear peptide sequence selected from:

YMESLHMQGEIENQI (SEQ ID NO: 34)

CQPWNSQYPHTHTFTALRFP (SEQ ID NO: 35)

RSTIYGSRLRIRNLDTTDTGYFQ (SEQ ID NO: 36)

QCVATNGKEVVSSTGVLFVKFGPPPTASPGYSDEYE (SEQ ID NO: 37)

In preferred embodiments of the ROR1-specific antigen binding molecule:
  FW1 is a framework region of from 20 to 28 amino acids
  CDR1 is a CDR sequence selected from DTSYGLYS (SEQ ID NO: 1), GAKYGLAA (SEQ ID NO: 2), GAKYGLFA (SEQ ID NO: 3), GANYGLAA (SEQ ID NO: 4), or GANYGLAS (SEQ ID NO: 5)
  FW2 is a framework region of from 6 to 14 amino acids
  HV2 is a hypervariable sequence selected TTDWERMSIG (SEQ ID NO: 6), SSNQERISIS (SEQ ID NO: 7), or SSNKEQISIS (SEQ ID NO: 8)
  FW3a is a framework region of from 6 to 10 amino acids
  HV4 is a hypervariable sequence selected from NKRAK (SEQ ID NO: 9), NKRTM (SEQ ID NO: 10), NKGAK (SEQ ID NO: 11), or NKGTK (SEQ ID NO: 12)
  FW3b is a framework region of from 17 to 24 amino acids
  CDR3 is a CDR sequence selected from QSGMAISTGSGHGYNWY (SEQ ID NO: 13), QSGMAIDIGSGHGYNWY (SEQ ID NO: 14), YPWAMWGQWY (SEQ ID NO: 15), VFMPQHWHPAAHWY (SEQ ID NO: 16), REARHPWLRQWY (SEQ ID NO: 17), or YPWGAGAPWLVQWY (SEQ ID NO: 18)
  FW4 is a framework region of from 7 to 14 amino acids or a functional variant with at least 45% sequence identity thereto.

In other preferred embodiments of the ROR1-specific antigen binding molecule, FW1 is selected from: ASVNQTPRTATKETGESLTINCVLT (SEQ ID NO: 19), AKVDQTPRTATKETGESLTINCVLT (SEQ ID NO: 20), TRVDQTPRTATKETGESLTINCWT (SEQ ID NO: 21), TRVDQTPRTATKETGESLTINCVLT (SEQ ID NO: 22), ASVNQTPRTATKETGESLTINCWT (SEQ ID NO: 23), or TRVDQSPSSLSASVGDRVTITCVLT (SEQ ID NO: 24), FW2 is selected from: TSWFRKNPG (SEQ ID NO: 25), or TYWYRKNPG (SEQ ID NO: 26), FW3a is selected from: GRYVESV (SEQ ID NO: 27), or GRYSESV (SEQ ID NO: 28), FW3b is selected from: SFSLRIKDLTVADSATYYCKA (SEQ ID NO: 29), SFTLTISSLQPEDSATYYCRA (SEQ ID NO: 30), or SFTLTISSLQPEDFATYYCKA (SEQ ID NO: 31), and FW4 is selected from DGAGTVLTVN (SEQ ID NO: 32), or DGAGTKVEIK (SEQ ID NO: 33), or functional variants thereof with a sequence identity of at least 45%.

All possible combinations and permutations of the framework regions, complementarity determining regions and hypervariable regions listed above are explicitly contemplated herein.

Sequence identity referenced in relation to the molecules of the invention may be judged at the level of individual CDRs, HVs or FWs, or it may be judged over the length of the entire molecule. The CDR, HV and FW sequences described may also be longer or shorter, whether that be by addition or deletion of amino acids at the N- or C-terminal ends of the sequence or by insertion or deletion of amino acids with a sequence.

In a preferred embodiment of the ROR1-specific antigen binding molecule, FW1 is ASVNQTPRTATKETGESLTINCVLT (SEQ ID NO: 19); CDR1 is DTSYGLYS (SEQ ID NO: 1); FW2 is TSWFRKNPG (SEQ ID NO: 25); HV2 is TTDWERMSIG (SEQ ID NO: 6); FW3a is GRYVESV (SEQ ID NO: 27); HV4 is NKRAK (SEQ ID NO: 9); FW3b is SFSLRIKDLTVADSATYYCKA (SEQ ID NO: 29); CDR3 is QSGMAISTGSGHGYNWY (SEQ ID NO: 13); and FW4 is DGAGTVLTVN (SEQ ID NO: 32); or functional variants thereof with a sequence identity of at least 45%.

In another preferred embodiment of the ROR1-specific antigen binding molecule, FW1 is AKVDQTPRTATKETGESLTINCVLT (SEQ ID NO: 20); CDR1 is DTSYGLYS (SEQ ID NO: 1); FW2 is TSWFRKNPG (SEQ ID NO: 25); HV2 is TTDWERMSIG (SEQ ID NO: 6); FW3a is GRYVESV (SEQ ID NO: 27); HV4 is NKRAK (SEQ ID NO: 9); FW3b is SFSLRIKDLTVADSATYYCKA (SEQ ID NO: 29); CDR3 is QSGMAIDIGSGHGYNWY (SEQ ID NO: 14); and FW4 is DGAGTVLTVN (SEQ ID NO: 32); or functional variants thereof with a sequence identity of at least 45%.

In another preferred embodiment of the ROR1-specific antigen binding molecule, FW1 is TRVDQTPRTATKETGESLTINCWT (SEQ ID NO: 21); CDR1 is GAKYGLAA (SEQ ID NO: 2); FW2 is TYWYRKNPG (SEQ ID NO: 26); HV2 is SSNQERISIS (SEQ ID NO: 7); FW3a is GRYVESV (SEQ ID NO: 27); HV4 is NKRTM (SEQ ID NO: 10); FW3b is SFSLRIKDLTVADSATYYCKA (SEQ ID NO: 29); CDR3 is YPWAMWGQWY (SEQ ID NO: 15); and FW4 is DGAGTVLTVN (SEQ ID NO: 32); or functional variants thereof with a sequence identity of at least 45%.

In another preferred embodiment of the ROR1-specific antigen binding molecule, FW1 is TRVDQTPRTATKETGESLTINCWT (SEQ ID NO: 21); CDR1 is GAKYGLFA (SEQ ID NO: 3); FW2 is TYWYRKNPG (SEQ ID NO: 26); HV2 is SSNQERISIS (SEQ ID NO: 7); FW3a is GRYVESV (SEQ ID NO: 27); HV4 is NKRTM (SEQ ID NO: 10); FW3b is SFSLRIKDLTVADSATYYCKA (SEQ ID NO: 29); CDR3 is VFMPQHWHPAAHWY (SEQ ID NO: 16); and FW4 is DGAGTVLTVN (SEQ ID NO: 32); or functional variants thereof with a sequence identity of at least 45%.

In another preferred embodiment of the ROR1-specific antigen binding molecule, FW1 is TRVDQTPRTATKETGESLTINCVLT (SEQ ID NO: 22); CDR1 is DTSYGLYS (SEQ ID NO: 1); FW2 is TSWFRKNPG (SEQ ID NO: 25); HV2 is TTDWERMSIG (SEQ ID NO: 6); FW3a is GRYVESV (SEQ ID NO: 27); HV4 is NKGAK (SEQ ID NO: 11); FW3b is SFSLRIKDLTVADSATYYCKA (SEQ ID NO: 29); CDR3 is REARHPWLRQWY (SEQ ID NO: 17); and FW4 is DGAGTVLTVN (SEQ ID NO: 32); or functional variants thereof with a sequence identity of at least 45%.

In another preferred embodiment of the ROR1-specific antigen binding molecule, FW1 is ASVNQTPRTATKETGESLTINCVVT (SEQ ID NO: 23); CDR1 is GANYGLAA (SEQ ID NO: 4); FW2 is TYWYRKNPG (SEQ ID NO: 26); HV2 is SSNQERISIS (SEQ ID NO: 7); FW3a is GRYVESV (SEQ ID NO: 27); HV4 is NKRTM (SEQ ID NO: 10); FW3b is SFSLRIKDLTVADSATYYCKA (SEQ ID NO: 29); CDR3 is YPWGAGAPWLVQWY (SEQ ID NO: 18); and FW4 is DGAGTVLTVN (SEQ ID NO: 32); or functional variants thereof with a sequence identity of at least 45%.

In another preferred embodiment of the ROR1-specific antigen binding molecule, FW1 is TRVDQSPSSL-SASVGDRVTITCVLT (SEQ ID NO: 24); CDR1 is GANY-GLAS (SEQ ID NO: 5); FW2 is TYWYRKNPG (SEQ ID NO: 26); HV2 is SSNKEQISIS (SEQ ID NO: 8); FW3a is GRYSESV (SEQ ID NO: 28); HV4 is NKGTK (SEQ ID NO: 12); FW3b is SFTLTISSLQPEDSATYYCRA (SEQ ID NO: 30); CDR3 is YPWGAGAPWLVQWY (SEQ ID NO: 18); and FW4 is DGAGTKVEIK (SEQ ID NO: 33); or functional variants thereof with a sequence identity of at least 45%.

In another preferred embodiment of the ROR1-specific antigen binding molecule, FW1 is TRVDQSPSSL-SASVGDRVTITCVLT (SEQ ID NO: 24); CDR1 is GANY-GLAS (SEQ ID NO: 5); FW2 is TYWYRKNPG (SEQ ID NO: 26); HV2 is SSNQERISIS (SEQ ID NO: 7); FW3a is GRYSESV (SEQ ID NO: 28); HV4 is NKRTM (SEQ ID NO: 10); FW3b is SFTLTISSLQPEDSATYYCRA (SEQ ID NO: 30); CDR3 is YPWGAGAPWLVQWY (SEQ ID NO: 18); and FW4 is DGAGTKVEIK (SEQ ID NO: 33); or functional variants thereof with a sequence identity of at least 45%.

In another preferred embodiment of the ROR1-specific antigen binding molecule, FW1 is TRVDQSPSSL-SASVGDRVTITCVLT (SEQ ID NO: 24); CDR1 is DTSYGLYS (SEQ ID NO: 1); FW2 is TSWFRKNPG (SEQ ID NO: 25); HV2 is TTDWERMSIG (SEQ ID NO: 6); FW3a is GRYVESV (SEQ ID NO: 27); HV4 is NKGAK (SEQ ID NO: 11); FW3b is SFTLTISSLQPEDFATYYCKA (SEQ ID NO: 31); CDR3 is REARHPWLRQWY (SEQ ID NO: 17); and FW4 is DGAGTKVEIK (SEQ ID NO: 33); or functional variants thereof with a sequence identity of at least 45%.

In another preferred embodiment of the ROR1-specific antigen binding molecule, FW1 is TRVDQSPSSL-SASVGDRVTITCVLT (SEQ ID NO: 24); CDR1 is DTSYGLYS (SEQ ID NO: 1); FW2 is TYWYRKNPG (SEQ ID NO: 26); HV2 is SSNKEQISIS (SEQ ID NO: 8); FW3a is GRYSESV (SEQ ID NO: 28); HV4 is NKGTK (SEQ ID NO: 12); FW3b is SFTLTISSLQPEDSATYYCRA (SEQ ID NO: 30);

CDR3 is REARHPWLRQWY (SEQ ID NO: 17); and FW4 is DGAGTKVEIK (SEQ ID NO: 33); or functional variants thereof with a sequence identity of at least 45%.

In another preferred embodiment of the ROR1-specific antigen binding molecule, FW1 is TRVDQSPSSL-SASVGDRVTITCVLT (SEQ ID NO: 24); CDR1 is DTSYGLYS (SEQ ID NO: 1); FW2 is TYWYRKNPG (SEQ ID NO: 26); HV2 is TTDWERMSIG (SEQ ID NO: 6); FW3a is GRYSESV (SEQ ID NO: 28); HV4 is NKGAK (SEQ ID NO: 11); FW3b is SFTLTISSLQPEDSATYYCRA (SEQ ID NO: 30); CDR3 is REARHPWLRQWY (SEQ ID NO: 17); and FW4 is DGAGTKVEIK (SEQ ID NO: 33); or functional variants thereof with a sequence identity of at least 45%.

In yet further preferred embodiments, the ROR1-specific antigen binding molecule comprises an amino acid sequence selected from:
ASVNQTPRTATKETGESLTINCVLTDTSYGLYST-SWFRKNPGTTDWERMSIGGRYVESVNKRAKSFS LRIKDLTVADSATYYCKAQSGMAISTGSGHGY-NWYDGAGTVLTVN (SEQ ID NO: 39);

AKVDQTPRTATKETGESLTINCVLTDTSYGLYST-SWFRKNPGTTDWERMSIGGRYVESVNKRAKSFS LRIKDLTVADSATYYCKAQSGMAIDIGSGHGY-NWYDGAGTVLTVN (SEQ ID NO: 40);

TRVDQTPRTATKETGESLTINCVVTGAKYG-LAATYWYRKNPGSSNQERISISGRYVESVNK-RTMSFSL RIKDLTVADSATYYCKAYP-WAMWGQWYDGAGTVLTVN (SEQ ID NO: 41);

TRVDQTPRTATKETGESLTINCVVTGAKYGL-FATYWYRKNPGSSNQERISISGRYVESVNK-RTMSFSL RIKDLTVADSATYYCKAVFMPQHWH-PAAHWYDGAGTVLTVN (SEQ ID NO: 42);

TRVDQTPRTATKETGESLTINCVLTDTSYGLYST-SWFRKNPGTTDWERMSIGGRYVESVNK-GAKSFS LRIKDLTVADSATYYCKAREAR-HPWLRQWYDGAGTVLTVN (SEQ ID NO: 43);

ASVNQTPRTATKETGESLTINCVVTGANYG-LAATYWYRKNPGSSNQERISISGRYVESVNK-RTMSFSL RIKDLTVADSATYYCKAYPW-GAGAPWLVQWYDGAGTVLTVN (SEQ ID NO: 44);

TRVDQSPSSLSASVGDRVTITCVLTGANY-GLASTYWYRKNPGSSNKEQISISGRY-SESVNKGTKSFTL TISSLQPEDSATYYCRAYPW-GAGAPWLVQWYDGAGTKVEIK (SEQ ID NO: 45);

TRVDQSPSSLSASVGDRVTITCVLTGANY-GLASTYWYRKNPGSSNQERISISGRYSESVNK-RTMSFTL TISSLQPEDSATYYCRAYPW-GAGAPWLVQWYDGAGTKVEIK (SEQ ID NO: 46);

TRVDQSPSSLSASVGDRVTITCVLTDTSYGLYST-SWFRKNPGTTDWERMSIGGRYVESVNK-GAKSFT LTISSLQPEDFATYYCKAREAR-HPWLRQWYDGAGTKVEIK (SEQ ID NO: 47);

TRVDQSPSSLSASVGDRVTITCVLTDTSYG-LYSTYWYRKNPGSSNKEQISISGRY-SESVNKGTKSFTL TISSLQPEDSATYYCRAREAR-HPWLRQWYDGAGTKVEIK (SEQ ID NO: 48);

TRVDQSPSSLSASVGDRVTITCVLTDTSYG-LYSTYWYRKNPGTTDWERMSIGGRYSESVNK-GAKSFT LTISSLQPEDSATYYCRAREAR-HPWLRQWYDGAGTKVEIK (SEQ ID NO: 49), or a functional variant thereof with a sequence identity of at least 45%.

The ROR1-specific antigen binding molecule of the present invention may be humanized. The ROR1-specific antigen binding molecule of the present invention may be de-immunized. Examples of humanised sequences of the invention include, but are not limited to:

B1 G1
(SEQ ID NO: 45)
TRVDQSPSSLSASVGDRVTITCVLTGANYGLASTYWYRKNPGSSNKEQI
SISGRYSESVNKGTKSFTLTISSLQPEDSATYYCRAYPWGAGAPWLVQW
YDGAGTKVEIK;

B1 G2
(SEQ ID NO: 46)
TRVDQSPSSLSASVGDRVTITCVLTGANYGLASTYWYRKNPGSSNQERI
SISGRYSESVNKRTMSFTLTISSLQPEDSATYYCRAYPWGAGAPWLVQW
YDGAGTKVEIK;

```
P3A1 V1
                                          (SEQ ID NO: 47)
TRVDQSPSSLSASVGDRVTITCVLTDTSYGLYSTSWFRKNPGTTDWERM
SIGGRYSESVNKGAKSFTLTISSLQPEDFATYYCKAREARHPWLRQWYD
GAGTKVEIK;

P3A1 G1
                                          (SEQ ID NO: 48)
TRVDQSPSSLSASVGDRVTITCVLTDTSYGLYSTYWYRKNPGSSNKEQI
SISGRYSESVNKGTKSFTLTISSLQPEDSATYYCRAREARHPWLRQWYD
GAGTKVEIK;

P3A1 G2
                                          (SEQ ID NO: 49)
TRVDQSPSSLSASVGDRVTITCVLTDTSYGLYSTYWYRKNPGTTDWERM
SIGGRYSESVNKGAKSFTLTISSLQPEDSATYYCRAREARHPWLRQWYD
GAGTKVEIK;

D3 humanised ADV1
                                          (SEQ ID NO: 50)
ASVNQSPSSLSASVGDRVTITCVLTDTSYGLYSTSWFRKNPGTTDWERM
SIGGRYSESVNKGAKSFTLTISSLQPEDSATYYCKAQSGMAISTGSGHG
YNWYDGAGTKVEIK;

D3 humanised ADV2
                                          (SEQ ID NO: 51)
TRVDQSPSSLSASVGDRVTITCVLTDTSYGLYSTSWFRKNPGTTDWERM
SIGGRYSESVNKGAKSFTLTISSLQPEDSATYYCKAQSGMAISTGSGHG
YNWYDGAGTKVEIK;

D3 humanised ADV3
                                          (SEQ ID NO: 52)
ASVNQSPSSASASVGDRLTITCVLTDTSYGLYSTSWFRKNPGTTDWERM
SIGGRYSESVNKGAKSFTLTISSLQPEDSATYYCKAQSGMAISTGSGHG
YNWYDGAGTKLEVK;

B1 humanised V5
                                          (SEQ ID NO: 53)
ASVDQSPSSLSASVGDRVTITCVVTGANYGLAATYWYRKNPGSSNQERI
SISGRYSESVNKRTMSFTLTISSLQPEDSATYYCKAYPWGAGAPWLVQW
YDGAGTKVEIK;

B1 humanised V7
                                          (SEQ ID NO: 54)
ASVDQSPSSASASVGDRLTITCVVTGANYGLAATYWYRKNPGSSNQERI
SISGRYSESVNKRTMSFTLTISSLQPEDSATYYCKAYPWGAGAPWLVQW
YDGAGTKLEVK;

D3 humanised EL V1
                                          (SEQ ID NO: 55)
ASVNQSPSSLSASVGDRVTITCVLTDTSYGLYSTSWFRKNPGTTDWERM
SIGGRYVESVNKRAKSFSLRIKDLTVADSATYYCKAQSGMAISTGSGHG
YNWYDGAGTKVEIK;

D3 humanised EL V2
                                          (SEQ ID NO: 56)
ASVNQSPSSLSASVGDRVTITCVLTDTSYGLYSTSWFRKNPGTTDWERM
SIGGRYVESVNKRAKSFTLTISSLQPEDFATYYCKAQSGMAISTGSGHG
YNWYDGAGTKVEIK;

D3 humanised EL V3
                                          (SEQ ID NO: 57)
ASVNQSPSSLSASVGDRVTITCVLTDTSYGLYSTSWFRKNPGTTDWERM
SIGGRFSGSGSKRAKSFTLTISSLQPEDFATYYCKAQSGMAISTGSGHG
YNWYDGAGTKVEIK;

D3 humanised EL V4
                                          (SEQ ID NO: 58)
ASVNQSPSSLSASVGDRVTITCVLTDTSYGLYSTSWYQQKPGTTDWERM
SIGGRYVESVNKRAKSFTLTISSLQPEDFATYYCKAQSGMAISTGSGHG
YNWYDGAGTKVEIK;
and D3 humanised EL V5
                                          (SEQ ID NO: 59)
ASVNQSPSSLSASVGDRVTITCVLTDTSYGLYSTSWYQQKPGTTDWERM
SIGGRFSGSGSKRAKSFTLTISSLQPEDFATYYCKAQSGMAISTGSGHG
YNWYDGAGTKVEIK.
```

The ROR1-specific antigen binding molecule of the present invention may also be conjugated to a detectable label, dye, toxin, drug, pro-drug, radionuclide or biologically active molecule.

Preferably, the ROR1-specific antigen binding molecule selectively interacts with ROR1 protein with an affinity constant of approximately 0.01 to 50 nM, preferably 0.1 to 30 nM, even more preferably 0.1 to 10 nM.

Furthermore, the ROR1-specific antigen binding molecule is preferably capable of mediating killing of ROR1-expressing tumour cells or is capable of inhibiting cancer cell proliferation.

The ROR1-specific antigen binding molecule may also be capable of being endocytosed upon binding to ROR1. In other embodiments, the ROR1-specific antigen binding molecule may not be endocytosed upon binding to ROR1.

In a second aspect of the present invention, there it is provided a recombinant fusion protein comprising a specific antigen binding molecule of the first aspect. Preferably, in the recombinant fusion protein of the second aspect, the specific antigen binding molecule is fused to one or more biologically active proteins. The specific antigen binding molecule may be fused to one or more biologically active proteins via one or more linker domains. Preferred linkers include but are not limited to $[G_4S]_x$, where x is 1, 2, 3, 4, 5, or 6. Particular preferred linkers are $[G_4S]_3$ (SEQ ID NO: 60) and $[G_4S]_5$ (SEQ ID NO: 61). Other preferred linkers include the sequences PGVQPSP (SEQ ID NO: 62), PGVQPSPGGGS (SEQ ID NO: 63) and PGVQPAPGGGS (SEQ ID NO: 64). These linkers may be particularly useful when recombinant fusion proteins are expressed in different expression systems that differ in glycosylation patterns, such as CHO and insect, and those that do not glycosylate expressed proteins (e.g. *E. coli*).

It will also be appreciated that the fusion proteins of the invention can be constructed in any order, i.e., with the ROR1-specific antigen binding molecule at the N-terminus, C-terminus, or at neither terminus (e.g. in the middle of a longer amino acid sequence).

Preferred biologically active proteins include, but are not limited to an immunoglobulin, an immunoglobulin Fc region, an immunoglobulin Fab region, a single chain Fv (scFv), a diabody, a triabody, a tetrabody, a bispecific t-cell engager (BiTE), an intein, a VNAR domain, a single domain antibody (sdAb), a VH domain, or a scaffold protein (affibodies, centyrins, darpins etc.). A particularly preferred biologically active protein is an immunoglobulin Fc region. Other preferred fusion proteins include VNAR-VNAR and VNAR-VNAR-VNAR.

Any part of the fusion protein of the invention may be engineered to enable conjugation. In a preferred example, where an immunoglobulin Fc region is used, it may be engineered to include a cysteine residue as a conjugation site. Preferred introduced cysteine residues include, but are not limited to S252C and S473C (Kabat numbering), which correspond to S239C and S442C in EU numbering, respectively.

In accordance with the second aspect, recombinant fusions comprising multiple VNAR domains are provided. Accordingly, the recombinant fusions of the invention may be dimers, trimers or higher order multimers of VNARs. In such recombinant fusions, the specificity of each VNAR may be the same or different. Recombinant fusions of the invention include, but are not limited to, bi-specific or tri-specific molecules in which each VNAR domain binds to a different antigen, or to different epitopes on a single antigen (bi-paratopic binders). The term "bi-paratopic" as used herein is intended to encompass molecules that bind to multiple epitopes on a given antigen. Molecules that bind three or more eptiopes on a given antigen are also contemplated herein and where the term "bi-paratopic" is used, it should be understood that the potential for tri-paratopic or multi-paratopic molecules is also encompassed.

Also in accordance with the second aspect, recombinant fusions are provided which include a ROR1-specific antigen binding molecule of the first aspect and a humanised VNAR domain. Humanised VNAR domains may be referred to as soloMERs and include but are not limited to the VNAR BA11, which is a humanised VNAR that binds with high affinity to human serum albumin (Kovalenko et al, J. Biol. Chem., 2013 JBC).

Examples of bi-paratopic and multivalent fusion proteins include, but are not limited to:

| | | |
|---|---|---|
| B1-BA11 | P3A1-D3 | P3A1-BA11-D3 |
| B1-BA11 | D3-B1 Cys | B1G1-B1G1 |
| BA11-B1 | B1-D3 Cys | B1G2-B1G2 |
| 2V-BA11 | D3-P3A1 Cys | P3A1-(L$_2$)-B1 |
| BA11-2V | P3A1-D3 Cys | P3A1-(L$_3$)-B1 |
| D3-D3-BA11 | B1-BA11-B1 | B1-(L$_4$)-P3A1 |
| 2V-2V-BA11 | D3-BA11-D3 | P3A1-(L$_4$)-B1 |
| B1-BA11 Cys | P3A1-BA11-P3A1 | D3-(L$_4$)-P3A1 |
| B1-BA11 Cys | E9-BA11-E9 | P3A1-(L$_4$)-D3 |
| D3-D3-BA11 Cys | B1-BA11-P3A1 | B1-(L$_4$)-D3 |
| 2V-BA11 Cys | BA11-BA11-B1 | B1-(L$_4$)-BA11- |
| D3-B1 | B1-BA11-D3 | (L$_4$)-P3A1 |
| B1-D3 | D3-BA11-B1 | BA11-(L$_4$)-B1- |
| D3-P3A1 | D3-BA11-P3A1 | (L$_4$)-P3A1 |
| P3A1-(L$_4$)-BA11- | BA11-(L$_4$)-B1- | D3-(L$_5$)-BA11- |
| (L$_4$)-B1 | (L$_4$)-D3 | (L$_5$)-P3A1 |
| D3-(L$_4$)-P3A1-(L$_4$)- | D3-(L$_4$)-BA11- | P3A1-(L$_5$)-D3 |
| BA11 | (L$_4$)-B1 | P3A1-(L$_5$)-BA11- |
| D3-(L$_4$)-BA11-(L$_4$)- | P3A1-(L$_4$)-BA11- | (L$_5$)-D3 |
| P3A1 | (L$_4$)-P3A1 | P3A1-(L$_5$)-D3- |
| P3A1-(L$_4$)-BA11- | BA11-(L$_4$)-P3A1- | (L$_5$)-BA11 |
| (L$_4$)-D3 | (L$_4$)-P3A1 | 2V-(L$_4$)-2V |
| P3A1-(L$_4$)-D3-(L$_4$)- | D3-(L$_5$)-P3A1 | 2V-(L$_4$)-BA11- |
| BA11 | D3-(L$_5$)-P3A1- | (L$_4$)-2V |
| B1-(L$_4$)-BA11-(L$_4$)- | (L$_5$)-BA11 | |
| D3 | | |

Wherein:

(SEQ ID NO: 44)
B1 is
ASVNQTPRTATKETGESLTINCVVTGANYGLAATYWYRKNPGSSNQERIS
ISGRYVESVNKRTMSFSLRIKDLTVADSATYYCKAYPWGAGAPWLVQWYD
GAGTVLTVN (SEQ ID NO: 65)
2V is
TRVDQTPRTATKETGESLTINCVLTDTSYGLYSTSWFRKNPGTTDWERMS
IGGRYVESVNKGAKSFSLRIKDLTVADSATYYCKAQSLAISTRSYWYDGA
GTVLTVN (SEQ ID NO: 43)
P3A1 is
TRVDQTPRTATKETGESLTINCVLTDTSYGLYSTSWFRKNPGTTDWERMS
IGGRYVESVNKGAKSFSLRIKDLTVADSATYYCKAREARHPWLRQWYDGA
GTVLTVN (SEQ ID NO: 39)
D3 is
ASVNQTPRTATKETGESLTINCVLTDTSYGLYSTSWFRKNPGTTDWERMS
IGGRYVESVNKRAKSFSLRIKDLTVADSATYYCKAQSGMAISTGSGHGYN
WYDGAGTVLTVN (SEQ ID NO: 66)
BA11; is
TRVDQSPSSLSASVGDRVTITCVLTDTSYPLYSTYWYRKNPGSSNKEQIS
ISGRYSESVNKGTKSFTLTISSLQPEDSATYYCRAMSTNIWTGDGAGTKV
EIK (SEQ ID NO: 40)
E9 is
AKVDQTPRTATKETGESLTINCVLTDTSYGLYSTSWFRKNPGTTDWERMS
IGGRYVESVNKRAKSFSLRIKDLTVADSATYYCKAQSGMAIDIGSGHGYN
WYDGAGTVLTVN (SEQ ID NO: 46)
B1G2 is
TRVDQSPSSLSASVGDRVTITCVLTGANYGLASTYWYRKNPGSSNQERIS
ISGRYSESVNKRTMSFTLTISSLQPEDSATYYCRAYPWGAGAPWLVQWYD
GAGTKVEIK (SEQ ID NO: 45)
B1G1;
TRVDQSPSSLSASVGDRVTITCVLTGANYGLASTYWYRKNPGSSNKEQIS
ISGRYSESVNKGTKSFTLTISSLQPEDSATYYCRAYPWGAGAPWLVQWYD
GAGTKVEIK and
Where no linker is defined (-) corresponds to a linker of -(G$_4$S)$_5$-
(L$_2$)- corresponds to a linker of -(G$_4$S)$_3$-
(L$_3$)- corresponds to a linker of -(G$_4$S)$_7$-
(L$_4$)- corresponds to the linker Wobbe-G$_4$S, which in turn is PGVQPSPGGGGS (SEQ ID NO: 63)
(L$_5$)- corresponds to the linker Wobbe-G$_4$S-GM, which in turn is PGVQPAPGGGGS (SEQ ID NO: 64) Cys—corresponds to a Cys containing C-terminal tag—for example QACGAHHHHHHGAEFEQKLISEEDL (SEQ ID NO: 67)

In certain embodiments, the specific binding molecules or recombinant fusions of the invention may be expressed with N- or C-terminal tags to assist with purification. Examples include but are not limited to Hiss and/or Myc. In addition, the N- or C-terminal tag may be further engineered to include additional cysteine residues to serve as conjugation points. It will therefore be appreciated that reference to specific binding molecules or recombinant fusions in all aspects of the invention is also intended to encompass such molecules with a variety of N- or C-terminal tags, which tags may also include additional cysteines for conjugation.

Additional recombinant fusions are listed below. It will be appreciated that not every combination of linker and VNAR or fusion partner is listed below. However, all such combinations are expressly encompassed by the present invention.

| Monovalent-BA11 fusions | Dimeric biparatopic BA11 fusions | Trimeric-Biparatopics |
|---|---|---|
| BA11-B1 | B1-D3-BA11 | B1-B1-D3 |
| B1-BA11 | D3-B1-BA11 | B1-D3-B1 |
| P3A1-BA11 | B1-BA11-D3 | D3-B1-B1 |
| BA11-P3A1 | D3-BA11-B1 | B1-B1-P3A1 |
| D3-BA11 | BA11-B1-D3 | B1-P3A1-B1 |
| BA11-D3 | BA11-D3-B1 | P3A1-B1-B1 |
| E9-BA11 | B1-P3A1-BA11 | B1-B1-E9 |
| BA11-E9 | P3A1-B1-BA11 | B1-E9-B1 |
| Divalent- | B1-BA11-P3A1 | E9-B1-B1 |
| BA11 fusions | P3A1-BA11-B1 | D3-D3-P3A1 |
| P3A1-P3A1-BA11 | BA11-B1-P3A1 | D3-P3A1-D3 |
| BA11-P3A1-P3A1 | BA11-P3A1-B1 | P3A1-D3-D3 |
| P3A1-BA11-P3A1 | D3-P3A1-BA11 | D3-D3-E9 |
| D3-D3-BA11 | P3A1-D3-BA11 | D3-E9-D3 |
| D3-BA11-D3 | D3-BA11-P3A1 | E9-D3-D3 |
| BA11-D3-D3 | P3A1-BA11-D3 | D3-D3-B1 |

-continued

| | | |
|---|---|---|
| B1-B1-BA11 | BA11-D3-P3A1 | D3-B1-D3 |
| B1-BA11-B1 | BA11-P3A1-D3 | B1-D3-D3 |
| BA11-B1-B1 | D3-E9-BA11 | P3A1-P3A1-B1 |
| E9-E9-BA11 | E9-D3-BA11 | P3A1-B1-P3A1 |
| E9-BA11-E9 | E9-BA11-D3 | B1-P3A1-P3A1 |
| BA11-E9-E9 | D3-BA11-E9 | P3A1-P3A1-D3 |
| Biparatopic | BA11-D3-E9 | P3A1-D3-P3A1 |
| Dimers | BA11-E9-D3 | D3-P3A1-P3A1 |
| | | |
| B1-P3A1 | E9-P3A1-BA11 | P3A1-P3A1-E9 |
| P3A1-B1 | P3A1-E9-BA11 | P3A1-E9-P3A1 |
| B1-D3 | E9-BA11-P3A1 | E9-P3A1-P3A1 |
| D3-B1 | P3A1-BA11-E9 | E9-E9-B1 |
| D3-P3A1 | BA11-E9-P3A1 | E9-B1-E9 |
| P3A1-D3 | BA11-P3A1-E9 | B1-E9-E9 |
| E9-B1 | B1-E9-BA11 | E9-E9-P3A1 |
| B1-E9 | E9-B1-BA11 | E9-P3A1-E9 |
| E9-P3A1 | B1-BA11-E9 | P3A1-E9-E9 |
| P3A1-E9 | E9-BA11-B1 | E9-E9-D3 |
| E9-D3 | BA11-B1-E9 | E9-D3-E9 |
| D3-E9 | BA11-E9-B1 | D3-E9-E9 |

Where the linkers between the VNAR domains are preferentially, but not limited to $(G_4S)_5$, $(G_4S)_3$, $(G_4S)_7$, PGVQPSPGGGGS (SEQ ID NO: 63) (Wobbe-$G_4$S), PGVQPAPGGGGS (SEQ ID NO: 64) (Wobbe-$G_4$S GM) and wherein different combinations of different linkers can be combined within the same construct.

Whereby, additional C-terminal (or N-terminal) tag sequences may or may not be present. C-terminal tags include, but are not limited to, tags that contain poly-Histidine sequences to facilitate purification (such as Hiss), contain c-Myc sequences (such as EQKLISEEDL (SEQ ID NO: 68)) to enable detection and/or contain Cysteine residues to enable labelling and bioconjugation using thiol reactive payloads and probes and combinations thereof. Preferential C-terminal tags include but are not limited to:

(SEQ ID NO: 69)
QASGAHHHHHHGAEFEQKLISEEDL (SEQ ID NO: 67)
QACGAHHHHHHGAEFEQKLISEEDL (SEQ ID NO: 70)
QACKAHHHHHHGAEFEQKLISEEDL (SEQ ID NO: 71)
AAAHHHHHHGAEFEQKLISEEDL (SEQ ID NO: 72)
ACAHHHHHHGAEFEQKLISEEDL (SEQ ID NO: 73)
QASGAHHHHHH (SEQ ID NO: 74)
QACGAHHHHHH (SEQ ID NO: 75)
QACKAHHHHHH (SEQ ID NO: 76)
AAAHHHHHH (SEQ ID NO: 77)
ACAHHHHHH (SEQ ID NO: 78)
QASGA (SEQ ID NO: 79)
QACGA (SEQ ID NO: 80)
QACKA (SEQ ID NO: 81)
ACA (SEQ ID NO: 82)
SAPSA

Wherein:

(SEQ ID NO: 44)
B1 is
ASVNQTPRTATKETGESLTINCVVTGANYGLAATYWYRKNPGSSNQERIS
ISGRYVESVNKRTMSFSLRIKDLTVADSATYYCKAYPWGAGAPWLVQWYD
GAGTVLTVN (SEQ ID NO: 65)
2V is
TRVDQTPRTATKETGESLTINCVLTDTSYGLYSTSWFRKNPGTTDWERMS
IGGRYVESVNKGAKSFSLRIKDLTVADSATYYCKAQSLAISTRSYWYDGA
GTVLTVN (SEQ ID NO: 43)
P3A1 is
TRVDQTPRTATKETGESLTINCVLTDTSYGLYSTSWFRKNPGTTDWERMS
IGGRYVESVNKGAKSFSLRIKDLTVADSATYYCKAREARHPWLRQWYDGA
GTVLTVN (SEQ ID NO: 39)
D3 is
ASVNQTPRTATKETGESLTINCVLTDTSYGLYSTSWFRKNPGTTDWERMS
IGGRYVESVNKRAKSFSLRIKDLTVADSATYYCKAQSGMAISTGSGHGYN
WYDGAGTVLTVN (SEQ ID NO: 66)
BA11; is
TRVDQSPSSLSASVGDRVTITCVLTDTSYPLYSTYWYRKNPGSSNKEQIS
ISGRYSESVNKGTKSFTLTISSLQPEDSATYYCRAMSTNIWTGDGAGTKV
EIK (SEQ ID NO: 40)
E9 is
AKVDQTPRTATKETGESLTINCVLTDTSYGLYSTSWFRKNPGTTDWERMS
IGGRYVESVNKRAKSFSLRIKDLTVADSATYYCKAQSGMAIDIGSGHGYN
WYDGAGTVLTVN

As stated above, all combinations of VNAR and linker are expressly encompassed herein. Humanised derivatives of the VNARs are also encompassed herein.

Also in accordance with the second aspect, recombinant fusions are provided which include a ROR1-specific antigen binding molecule of the first aspect and a recombinant toxin. Examples of recombinant toxins include but are not limited to *Pseudomonas* exotoxin PE38 and diphtheria toxin.

Also in accordance with the second aspect, recombinant fusions are provided which include a ROR1-specific antigen binding molecule of the first aspect and a recombinant CD3 binding protein. Examples of recombinant ROR1 and CD3 binding agents include but are not limited to:

B1 CD3

(SEQ ID NO: 83)
ASVNQTPRTATKETGESLTINCVVTGANYGLAATYWYRKNPGSSNQERISISGRYVESVNKRTMSFSL
RIKDLTVADSATYYCKAYPWGAGAPWLVQWYDGAGTVLTVNGGGGSDIKLQQSGAELARPGASVKM
SCKTSGYTFTRYTMHWVKQRPGQGLEWIGYINPSRGYTNYNQKFKDKATLTTDKSSSTAYMQLSSLT

-continued

SEDSAVYYCARYYDDHYCLDYWGQGTTLTVSSGGGGSGGGGSGGGGSDIQLTQSPAIMSASPGEK
VTMTCRASSSVSYMNWYQQKSGTSPKRWIYDTSKVASGVPYRFSGSGSGTSYSLTISSMEAEDAAT
YYCQQWSSNPLTFGAGTKLELKSHHHHHH

B1 CD3 [G4S]3
(SEQ ID NO: 84)
ASVNQTPRTATKETGESLTINCVVTGANYGLAATYWYRKNPGSSNQERISISGRYVESVNKRTMSFSL
RIKDLTVADSATYYCKAYPWGAGAPWLVQWYDGAGTVLTVNGGGGSGGGGSGGGGSDIKLQQSGA
ELARPGASVKMSCKTSGYTFTRYTMHWVKQRPGQGLEWIGYINPSRGYTNYNQKFKDKATLTTDKS
SSTAYMQLSSLTSEDSAVYYCARYYDDHYCLDYWGQGTTLTVSSGGGGSGGGGSGGGGSDIQLTQ
SPAIMSASPGEKVTMTCRASSSVSYMNWYQQKSGTSPKRWIYDTSKVASGVPYRFSGSGSGTSYSL
TISSMEAEDAATYYCQQWSSNPLTFGAGTKLELKSHHHHHH

P3A1 CD3
(SEQ ID NO: 85)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNGGGGSDIKLQQSGAELARPGASVKMS
CKTSGYTFTRYTMHWVKQRPGQGLEWIGYINPSRGYTNYNQKFKDKATLTTDKSSSTAYMQLSSLTS
EDSAVYYCARYYDDHYCLDYWGQGTTLTVSSGGGGSGGGGSGGGGSDIQLTQSPAIMSASPGEKV
TMTCRASSSVSYMNWYQQKSGTSPKRWIYDTSKVASGVPYRFSGSGSGTSYSLTISSMEAEDAATY
YCQQWSSNPLTFGAGTKLELKSHHHHHH

P3A1 CD3 [G4S]3
(SEQ ID NO: 86)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNGGGGSGGGGSGGGGSDIKLQQSGAE
LARPGASVKMSCKTSGYTFTRYTMHWVKQRPGQGLEWIGYINPSRGYTNYNQKFKDKATLTTDKSS
STAYMQLSSLTSEDSAVYYCARYYDDHYCLDYWGQGTTLTVSSGGGGSGGGGSGGGGSDIQLTQS
PAIMSASPGEKVTMTCRASSSVSYMNWYQQKSGTSPKRWIYDTSKVASGVPYRFSGSGSGTSYSLTI
SSMEAEDAATYYCQQWSSNPLTFGAGTKLELKSHHHHHH

P3A1 P3A1 CD3
(SEQ ID NO: 87)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNGGGGSGGGGSGGGGSGGGGSGGGG
STRVDQTPRTATKETGESLTINCVLTDTSYGLYSTSWFRKNPGTTDWERMSIGGRYVESVNKGAKSF
SLRIKDLTVADSATYYCKAREARHPWLRQWYDGAGTVLTVNGGGGSDIKLQQSGAELARPGASVKM
SCKTSGYTFTRYTMHWVKQRPGQGLEWIGYINPSRGYTNYNQKFKDKATLTTDKSSSTAYMQLSSLT
SEDSAVYYCARYYDDHYCLDYWGQGTTLTVSSGGGGSGGGGSGGGGSDIQLTQSPAIMSASPGEK
VTMTCRASSSVSYMNWYQQKSGTSPKRWIYDTSKVASGVPYRFSGSGSGTSYSLTISSMEAEDAAT
YYCQQWSSNPLTFGAGTKLELKSHHHHHH

P3A1 P3A1 CD3 [G4S]3
(SEQ ID NO: 88)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNGGGGSGGGGSGGGGSGGGGSGGGG
STRVDQTPRTATKETGESLTINCVLTDTSYGLYSTSWFRKNPGTTDWERMSIGGRYVESVNKGAKSF
SLRIKDLTVADSATYYCKAREARHPWLRQWYDGAGTVLTVNGGGGSGGGGSGGGGSDIKLQQSGA
ELARPGASVKMSCKTSGYTFTRYTMHWVKQRPGQGLEWIGYINPSRGYTNYNQKFKDKATLTTDKS
SSTAYMQLSSLTSEDSAVYYCARYYDDHYCLDYWGQGTTLTVSSGGGGSGGGGSGGGGSDIQLTQ
SPAIMSASPGEKVTMTCRASSSVSYMNWYQQKSGTSPKRWIYDTSKVASGVPYRFSGSGSGTSYSL
TISSMEAEDAATYYCQQWSSNPLTFGAGTKLELKSHHHHHH

P3A1-[PGVQPSPGGGGS]-B1-[G4S]-CD3
(SEQ ID NO: 89)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNPGVQPSPGGGGSASVNQTPRTATKET
GESLTINCVVTGANYGLAATYWYRKNPGSSNQERISISGRYVESVNKRTMSFSLRIKDLTVADSATYY
CKAYPWGAGAPWLVQWYDGAGTVLTVNGGGGSDIKLQQSGAELARPGASVKMSCKTSGYTFTRYT
MHWVKQRPGQGLEWIGYINPSRGYTNYNQKFKDKATLTTDKSSSTAYMQLSSLTSEDSAVYYCARY
YDDHYCLDYWGQGTTLTVSSGGGGSGGGGSGGGGSDIQLTQSPAIMSASPGEKVTMTCRASSSVS
YMNWYQQKSGTSPKRWIYDTSKVASGVPYRFSGSGSGTSYSLTISSMEAEDAATYYCQQWSSNPLT
FGAGTKLELKSHHHHHH

P3A1-[PGVQPSPGGGGS]-B1-[G4S]3-CD3
(SEQ ID NO: 90)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNPGVQPSPGGGGSASVNQTPRTATKET
GESLTINCVVTGANYGLAATYWYRKNPGSSNQERISISGRYVESVNKRTMSFSLRIKDLTVADSATYY
CKAYPWGAGAPWLVQWYDGAGTVLTVNGGGGSGGGGSGGGGSDIKLQQSGAELARPGASVKMS
CKTSGYTFTRYTMHWVKQRPGQGLEWIGYINPSRGYTNYNQKFKDKATLTTDKSSSTAYMQLSSLTS
EDSAVYYCARYYDDHYCLDYWGQGTTLTVSSGGGGSGGGGSGGGGSDIQLTQSPAIMSASPGEKV
TMTCRASSSVSYMNWYQQKSGTSPKRWIYDTSKVASGVPYRFSGSGSGTSYSLTISSMEAEDAATY
YCQQWSSNPLTFGAGTKLELKSHHHHHH

P3A1-[PGVQPAPGGGGS]-D3-[G4S]-CD3
(SEQ ID NO: 91)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNPGVQPAPGGGGSASVNQTPRTATKET
GESLTINCVLTDTSYGLYSTSWFRKNPGTTDWERMSIGGRYVESVNKRAKSFSLRIKDLTVADSATYY
CKAQSGMAISTGSGHGYNWYDGAGTVLTVNGGGGSDIKLQQSGAELARPGASVKMSCKTSGYTFT

-continued

RYTMHWVKQRPGQGLEWIGYINPSRGYTNYNQKFKDKATLTTDKSSSTAYMQLSSLTSEDSAVYYC
ARYYDDHYCLDYWGQGTTLTVSSGGGGSGGGGSGGGGSDIQLTQSPAIMSASPGEKVTMTCRASS
SVSYMNWYQQKSGTSPKRWIYDTSKVASGVPYRFSGSGSGTSYSLTISSMEAEDAATYYCQQWSSN
PLTFGAGTKLELKSHHHHHH

P3A1-[PGVQPAPGGGGS]-D3-[G₄S]3-CD3

(SEQ ID NO: 92)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNPGVQPAPGGGGSASVNQTPRTATKET
GESLTINCVLTDTSYGLYSTSWFRKNPGTTDWERMSIGGRYVESVNKRAKSFSLRIKDLTVADSATYY
CKAQSGMAISTGSGHGYNWYDGAGTVLTVNGGGGSGGGGSGGGGSDIKLQQSGAELARPGASVK
MSCKTSGYTFTRYTMHWVKQRPGQGLEWIGYINPSRGYTNYNQKFKDKATLTTDKSSSTAYMQLSS
LTSEDSAVYYCARYYDDHYCLDYWGQGTTLTVSSGGGGSGGGGSGGGGSDIQLTQSPAIMSASPG
EKVTMTCRASSSVSYMNWYQQKSGTSPKRWIYDTSKVASGVPYRFSGSGSGTSYSLTISSMEAEDA
ATYYCQQWSSNPLTFGAGTKLELKSHHHHHH

P3A1-[G₄S]₅-D3-[G₄S]-CD3

(SEQ ID NO: 93)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNGGGGSGGGGSGGGGSGGGGSGGGG
SASVNQTPRTATKETGESLTINCVLTDTSYGLYSTSWFRKNPGTTDWERMSIGGRYVESVNKRAKSF
SLRIKDLTVADSATYYCKAQSGMAISTGSGHGYNWYDGAGTVLTVNGGGGSDIKLQQSGAELARPGA
SVKMSCKTSGYTFTRYTMHWVKQRPGQGLEWIGYINPSRGYTNYNQKFKDKATLTTDKSSSTAYMQ
LSSLTSEDSAVYYCARYYDDHYCLDYWGQGTTLTVSSGGGGSGGGGSGGGGSDIQLTQSPAIMSAS
PGEKVTMTCRASSSVSYMNWYQQKSGTSPKRWIYDTSKVASGVPYRFSGSGSGTSYSLTISSMEAE
DAATYYCQQWSSNPLTFGAGTKLELKSHHHHHH

P3A1-[G₄S]₅-D3-[G₄S]₃-CD3

(SEQ ID NO: 94)
TRVDQTPRTATKETGESLTINCVLTDTSYGLYSTSWFRKNPGTTDWERMSIGGRYVESVNKGAKSFS
LRIKDLTVADSATYYCKAREARHPWLRQWYDGAGTVLTVNGGGGSGGGGSGGGGSGGGGSGGGG
SASVNQTPRTATKETGESLTINCVLTDTSYGLYSTSWFRKNPGTTDWERMSIGGRYVESVNKRAKSF
SLRIKDLTVADSATYYCKAQSGMAISTGSGHGYNWYDGAGTVLTVNGGGGSGGGGSGGGGSDIKLQ
QSGAELARPGASVKMSCKTSGYTFTRYTMHWVKQRPGQGLEWIGYINPSRGYTNYNQKFKDKATLT
TDKSSSTAYMQLSSLTSEDSAVYYCARYYDDHYCLDYWGQGTTLTVSSGGGGSGGGGSGGGGSDI
QLTQSPAIMSASPGEKVTMTCRASSSVSYMNWYQQKSGTSPKRWIYDTSKVASGVPYRFSGSGSGT
SYSLTISSMEAEDAATYYCQQWSSNPLTFGAGTKLELKSHHHHHH

In a third aspect of the present invention, there is provided a ROR1-specific chimeric antigen receptor (CAR), comprising at least one ROR1-specific antigen binding molecule as defined by the first aspect of the invention, fused or conjugated to at least one transmembrane region and at least one intracellular domain.

The present invention also provides a cell comprising a chimeric antigen receptor according to the third aspect, which cell is preferably an engineered T-cell.

In a fourth aspect of the invention, there is provided a nucleic acid sequence comprising a polynucleotide sequence that encodes a specific antigen binding molecule, recombinant fusion protein or chimeric antigen receptor according to the first, second or third aspects of the invention.

There is also provided a vector comprising a nucleic acid sequence in accordance with the fourth aspect and a host cell comprising such a nucleic acid.

A method for preparing a specific antigen binding molecule, recombinant fusion protein or chimeric antigen receptor, of the first, second or third aspect is provided, the method comprising cultivating or maintaining a host cell comprising the polynucleotide or vector described above under conditions such that said host cell produces the specific antigen binding molecule, recombinant fusion protein or chimeric antigen receptor, optionally further comprising isolating the specific antigen binding molecule, recombinant fusion protein or chimeric antigen receptor.

In a fifth aspect of the invention, there is provided a pharmaceutical composition comprising the specific antigen binding molecule, fusion protein or chimeric antigen receptor of the first, second or third aspects. The pharmaceutical composition may contain a variety of pharmaceutically acceptable carriers. Pharmaceutical compositions of the invention may be for administration by any suitable method known in the art, including but not limited to intravenous, intramuscular, oral, intraperitoneal, or topical administration. In preferred embodiments, the pharmaceutical composition may be prepared in the form of a liquid, gel, powder, tablet, capsule, or foam.

The specific antigen binding molecule, recombinant fusion protein or chimeric antigen receptor of the first, second or third aspects may be for use in therapy. More specifically, the specific antigen binding molecule, recombinant fusion protein or chimeric antigen receptor of the first, second or third aspects may be for use in the treatment of cancer. Preferably, the cancer is a ROR1-positive cancer type. More preferably, the cancer is selected from the group comprising blood cancers such as lymphomas and leukemias, chronic lymphocytic leukaemia (CLL), mantle cell lymphoma (MCL), B-cell acute lymphoblastic leukaemia (B-ALL), marginal zone lymphoma (MZL), non-Hodgkin lymphomas (NHL), acute myeloid leukemia (AML) and solid tumours including neuroblastoma, renal cancer, lung cancer, colon cancer, ovarian cancer, pancreatic cancer, breast cancer, skin cancer, uterine cancer, prostate cancer, thyroid cancer, Head and Neck cancer, bladder cancer, stomach cancer or liver cancer.

Also provided herein is the use of a specific antigen binding molecule, recombinant fusion protein or chimeric antigen receptor of the first, second or third aspects in the manufacture of a medicament for the treatment of a disease in a patient in need thereof.

Furthermore, in accordance with the present invention there is provided a method of treatment of a disease in a patient in need of treatment comprising administration to said patient of a therapeutically effective dosage of a specific antigen binding molecule, recombinant fusion protein or chimeric antigen receptor of the first, second or third aspects or a pharmaceutical composition of the fifth aspect.

Preferably, the cancer is a ROR1-positive cancer type. More preferably, the cancer is selected from the group comprising blood cancers such as lymphomas and leukemias, chronic lymphocytic leukaemia (CLL), mantle cell lymphoma (MCL), B-cell acute lymphoblastic leukaemia (B-ALL), marginal zone lymphoma (MZL), non-Hodgkin lymphomas (NHL), acute myeloid leukemia (AML) and solid tumours including neuroblastoma, renal cancer, lung cancer, colon cancer, ovarian cancer, pancreatic cancer, breast cancer, skin cancer, uterine cancer, prostate cancer, thyroid cancer, Head and Neck cancer, bladder cancer, stomach cancer or liver cancer.

Also provided herein is a method of assaying for the presence of a target analyte in a sample, comprising the addition of a detectably labelled specific antigen binding molecule of the first aspect, or a recombinant fusion protein of the second aspect, to the sample and detecting the binding of the molecule to the target analyte.

In addition, there is provided herein a method of imaging a site of disease in a subject, comprising administration of a detectably labelled specific antigen binding molecule of the first aspect or a detectably labelled recombinant fusion protein of the second aspect to a subject.

There is also provided herein a method of diagnosis of a disease or medical condition in a subject comprising administration of a specific antigen binding molecule of the first aspect or a recombinant fusion protein of the second aspect.

Also contemplated herein is an antibody, antibody fragment or antigen-binding molecule that competes for binding to ROR1 with the ROR1-specific antigen binding molecule of the first aspect. The term "compete" when used in the context of antigen binding proteins (e.g., neutralizing antigen binding proteins or neutralizing antibodies) means competition between antigen binding proteins as determined by an assay in which the antigen binding protein (e.g., antibody or functional fragment thereof) under test prevents or inhibits specific binding of a the antigen binding molecule defined herein (e.g., specific antigen binding molecule of the first aspect) to a common antigen (e.g., ROR1 in the case of the specific antigen binding molecule of the first aspect).

Also described herein is a kit for diagnosing a subject suffering from cancer, or a pre-disposition thereto, or for providing a prognosis of the subject's condition, the kit comprising detection means for detecting the concentration of antigen present in a sample from a test subject, wherein the detection means comprises a ROR1-specific antigen binding molecule of the first aspect, a recombinant fusion protein of the second aspect, a chimeric antigen receptor of the third aspect or a nucleic acid sequence of the fourth aspect, each being optionally derivatized, wherein presence of antigen in the sample suggests that the subject suffers from cancer. Preferably the antigen comprises ROR1 protein, more preferably an extracellular domain thereof. More preferably, the kit is used to identify the presence or absence of ROR1-positive cells in the sample, or determine the concentration thereof in the sample. The kit may also comprise a positive control and/or a negative control against which the assay is compared and/or a label which may be detected.

The present invention also provides a method for diagnosing a subject suffering from cancer, or a pre-disposition thereto, or for providing a prognosis of the subject's condition, the method comprising detecting the concentration of antigen present in a sample obtained from a subject, wherein the detection is achieved using a ROR1-specific antigen binding molecule of the first aspect, a recombinant fusion protein of the second aspect, a chimeric antigen receptor of the third aspect or a nucleic acid sequence of the fourth aspect, each being optionally derivatized, and wherein presence of antigen in the sample suggests that the subject suffers from cancer.

Also contemplated herein is a method of killing or inhibiting the growth of a cell expressing ROR1 in vitro or in a patient, which method comprises administering to the cell a pharmaceutically effective amount or dose of (i) ROR1-specific antigen binding molecule of the first aspect, a recombinant fusion protein of the second aspect, a nucleic acid sequence of the third aspect, or the CAR or cell according the fourth aspect, or (ii) of a pharmaceutical composition of the fifth aspect. Preferably, the cell expressing ROR1 is a cancer cell. More preferably, the ROR1 is human ROR1.

In a sixth aspect of the present invention, there is provided a specific antigen binding molecule comprising an amino acid sequence represented by the formula (II):

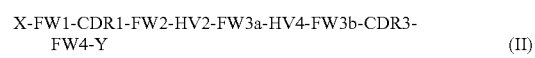

wherein
FW1 is a framework region
CDR1 is a CDR sequence
FW2 is a framework region
HV2 is a hypervariable sequence
FW3a is a framework region
HV4 is a hypervariable sequence
FW3b is a framework region
CDR3 is a CDR sequence
FW4 is a framework region
X and Y are optional amino acid sequences
wherein the specific antigen binding molecule is conjugated to a second moiety.

In certain preferred embodiments, the specific antigen binding molecule according to this aspect of the invention may additionally be conjugated to a third, fourth or fifth moiety. Conjugation of further moieties is also contemplated. In some cases, a third, fourth or fifth moiety may be conjugated to the second moiety. Accordingly, it will be understood that any of the moieties according to this aspect of the invention may have additional moieties conjugated thereto. Description of preferred features of the second moiety as set out below apply to the third, fourth, fifth or higher order moiety mutatis mutandis.

Preferably X or Y are individually either absent or selected from the group comprising an immunoglobulin, an immunoglobulin Fc region, an immunoglobulin Fab region, a single chain Fv (scFv), a diabody, a triabody, a tetrabody, a bispecific t-cell engager (BiTE), an intein, a VNAR domain, a single domain antibody (sdAb), a VH domain, a scaffold protein (affibodies, centyrins, darpins etc.), or a toxin including but not limited to *Pseudomonas* exotoxin PE38, diphtheria toxin.

Preferably, the conjugation is via a cysteine residue in the amino acid sequence of the specific antigen binding molecule. The cysteine residue may be anywhere in the sequence, including in optional sequences X or Y (if present).

The conjugation may be via a thiol, aminoxy or hydrazinyl moiety incorporated at the N-terminus or C-terminus of the amino acid sequence of the specific antigen binding molecule.

Preferably, the second moiety is selected from the group comprising detectable label, dye, toxin, drug, pro-drug, radionuclide or biologically active molecule.

More preferably, the second moiety is at least one toxin selected from the group comprising:
- maytansinoids,
- auristatins,
- anthracyclins, preferably PNU-derived anthracyclins
- calicheamicins,
- amanitin derivatives, preferably α-amanitin derivatives
- tubulysins
- duocarmycins
- radioisotopes for example alpha-emitting radionuclide, such as 227 Th or 225 Ac
- liposomes comprising a toxic payload,
- protein toxins
- taxanes,
- pyrrolbenzodiazepines
- indolinobenzodiazepine pseudodimers and/or
- spliceosome inhibitors
- CDK11 inhibitors
- Pyridinobenzodiazepines In other preferred embodiments in accordance with this aspect, the second moiety may be from the group comprising an immunoglobulin, an immunoglobulin Fc region, an immunoglobulin Fab region, a single chain Fv (scFv), a diabody, a triabody, a tetrabody, a bispecific t-cell engager (BiTE), an intein, a VNAR domain, a single domain antibody (sdAb), a VH domain, a scaffold protein (affibodies, centyrins, darpins etc.), or a toxin including but not limited to *Pseudomonas* exotoxin PE38, diphtheria toxin.

In particularly preferred embodiments, the second moiety is a VNAR domain, which may be the same or different to the specific antigen binding molecule according to this aspect. Accordingly, dimers, trimers or higher order multimers of VNAR domains linked by chemical conjugation are explicitly contemplated herein. In such embodiments, each individual VNAR domain may have the same antigen specificity as the other VNAR domains, or they may be different.

In accordance with this aspect, the specific antigen binding molecule may comprise, for example, bi-paratopic specific antigen binding molecules as described in relation to the first to fifth aspects fused to further biologically active molecules (including but not limited to molecules for half-life extension, for example BA11) and then further conjugated to a second moiety, including but not limited to cytotoxic payloads In accordance with this aspect, the specific antigen binding molecule may be a receptor tyrosine kinase-like orphan receptor 1 (ROR1) specific antigen binding molecule. This may be a ROR1-specific antigen binding molecule of the first aspect of the invention. Accordingly, any of the preferred features described above in relation to the first, second and third aspects apply mutatis mutandis to the sixth aspect.

The specific antigen binding molecule of the sixth aspect may be for use in therapy. More specifically, the specific antigen binding molecule of the sixth aspect may be for use in the treatment of cancer. Preferably, the cancer is a ROR1-positive cancer type. More preferably, the cancer is selected from the group comprising blood cancers such as lymphomas and leukemias, chronic lymphocytic leukaemia (CLL), mantle cell lymphoma (MCL), B-cell acute lymphoblastic leukaemia (B-ALL), marginal zone lymphoma (MZL), non-Hodgkin lymphomas (NHL), acute myeloid leukemia (AML) and solid tumours including neuroblastoma, renal cancer, lung cancer, colon cancer, ovarian cancer, pancreatic cancer, breast cancer, skin cancer, uterine cancer, prostate cancer, thyroid cancer, Head and Neck cancer, bladder cancer, stomach cancer or liver cancer.

Also provided herein is the use of a specific antigen binding molecule of the sixth aspect in the manufacture of a medicament for the treatment of a disease in a patient in need thereof.

Pharmaceutical compositions comprising the specific antigen binding molecule of the sixth aspect are also provided. The pharmaceutical composition may contain a variety of pharmaceutically acceptable carriers Furthermore, in accordance with the present invention there is provided a method of treatment of a disease in a patient in need of treatment comprising administration to said patient of a therapeutically effective dosage of a specific antigen binding molecule of the sixth aspect or a pharmaceutical composition comprising a specific antigen binding molecule of the sixth aspect.

Preferably, the cancer is a ROR1-positive cancer type. More preferably, the cancer is selected from the group comprising blood cancers such as lymphomas and leukemias, chronic lymphocytic leukaemia (CLL), mantle cell lymphoma (MCL), B-cell acute lymphoblastic leukaemia (B-ALL), marginal zone lymphoma (MZL), non-Hodgkin lymphomas (NHL), acute myeloid leukemia (AML) and solid tumours including neuroblastoma, renal cancer, lung cancer, colon cancer, ovarian cancer, pancreatic cancer, breast cancer, skin cancer, uterine cancer, prostate cancer, thyroid cancer, Head and Neck cancer, bladder cancer, stomach cancer or liver cancer.

Also provided herein is a method of assaying for the presence of a target analyte in a sample, comprising the addition of a detectably labelled specific antigen binding molecule of the sixth aspect to the sample and detecting the binding of the molecule to the target analyte.

In addition, there is provided herein a method of imaging a site of disease in a subject, comprising administration of a detectably labelled specific antigen binding molecule of the sixth aspect to a subject.

There is also provided herein a method of diagnosis of a disease or medical condition in a subject comprising administration of a specific antigen binding molecule of the sixth aspect.

Furthermore, any of the features described in respect of any of the above-mentioned aspects of the invention may be combined mutatis mutandis with the other aspects of the invention.

DESCRIPTION OF FIGURES

FIG. 1: anti-ROR1 phage monoclonals displaying VNAR domains: binding to human or mouse recombinant ROR1-Fc in ELISA. B1, P3A1 and E7-specific ROR1 binders, H2—non-specific phage.

FIG. 2: ROR1 binding sequences obtained from screening the synthetic VNAR library using human ROR1 (B1 and E7) and mouse ROR1 (P3A1 and CPF7). Sequences shown without and with the C-terminal His$_6$Myc tag (His$_6$ Myc sequence in italics).

FIG. 3: Generation of the immunised VNAR library using human ROR1: analysis of three spiny dogfish pre- and post-immunisation plasma binding to murine or human ROR1.

FIG. 4: anti-ROR1 phage monoclonals from immunised VNAR library: binding to human or mouse recombinant ROR1-Fc in ELISA. E9 and D3-specific ROR1 binders, H1—non-specific VNAR binder displayed on phage.

FIG. 5: ROR1 binding sequences E9 and D3 obtained from screening the immunised VNAR library using mouse ROR1. Sequences shown without and with the C-terminal His$_6$Myc tag (His$_6$ Myc sequence in italics).

FIG. 6: Far UV CD spectra of VNAR no tag, VNAR 6×His and VNAR-His$_6$-Myc in 50 mM NaCl 20 mM NaP buffer pH 6.0 at room temperature.

FIG. 10: Linker mouse IgG and linker human IgG sequences used in VNAR IgG Fc fusion proteins. Engineered hIgG1 Fc fusion proteins incorporate an engineered cysteine substitution in the hIgG1 Fc sequence, for example at position S252C or S473C (Kabat numbering) to enable site specific labelling.

FIG. 11: Intein cleavage reagents and the corresponding VNAR C-terminal derivatives.

FIG. 15: Bar chart depicting VNAR-hFc molecule cell surface binding to A549 (ROR1$^{hi}$) vs A427 (ROR1$^{low}$) lung cancer cell lines. VNAR hFc binding was detected using a PE-anti-human antibody (Jackson ImmunoResearch Labs/Stratech) and a ThermoFisher Attune NxT flow cytometer.

FIG. 16: Internalisation of VNAR-Fc fusions. Cell surface binding of VNAR-Fc to MDA-MB-231 breast cancer cells for 2 hrs at 4° C. or 37° C. Loss of cell surface signal at 37° C. is suggestive of ROR1 internalisation.

FIG. 18.1: B1 forms a complex with ROR1 Ig domain by SEC. A, Overlayed SEC analysis (Superdex 200 Increase 10/300, GE Healthcare) of human ROR1 Ig domain with and without B1 his (orange and blue traces, respectively). B, SDS PAGE analysis of peak fractions.

FIG. 18.2: SEC analysis of ROR1-specific VNAR B1 binding to non-glycosylated version of ROR1 Ig domain (IgHis). Running Conditions: 20 mM Hepes, 150 mM NaCl, pH7.5. Arrow indicates peak selected for mass spectrometry analysis.

FIG. 18.3: Mass spectrometry analysis of additional peak formed when non-glycosylated version of ROR1 Ig domain (IgHis) and ROR1-specific VNAR B1 were analysed by SEC (FIG. 18.2). IgHis expected MW: 12,218.6 Da; IgHis observed MW: 12,217.9 Da. B1 expected MW: 12,506.8 Da; B1 observed MW: 12,506.0 Da. These data demonstrate that a complex between B1 and non-glycosylated IgHis has formed.

FIG. 18.4. Binding of VNAR domains D3 and P3A1 to ROR1 domains as assessed by SEC/SDS-PAGE analysis

FIG. 30: Cell surface binding of B1-, P3A1- and 2V-hFc molecules vs the MMAE-conjugated versions in A549 (ROR1$^{hi}$) vs A427 (ROR1$^{low}$) lung cancer cell lines. VNAR hFc binding was detected using a PE-anti-human antibody (Jackson ImmunoResearch Labs/Stratech) and a ThermoFisher Attune NxT flow cytometer.

FIG. 31: Analysis of VNAR hFc conjugates. A&B, SDS PAGE analysis of VNAR hFc (S252C) proteins and conjugates (4-12% and 12% Bis Tris gel, respectively). Lanes 1, untreated protein, 2, refolded protein and 3, MMAE conjugate (+/− reduction with DTT). C&D, Example of mass spec analysis of deglycosylated, reduced VNAR hFc (S252C) fusion proteins before and after MMAE conjugation, respectively. Expected masses: unconjugated 38,997.8 Da and MMAE conjugate (DAR 2) 40,310.0 Da. E&F SDS PAGE analysis of VNAR hFc (S473C) protein conjugates. Lanes 3, MMAE conjugates and 4, AF488 conjugates (+/− reduction with DTT). G&H Mass spec analysis of deglycosylated, reduced B1- and P3A1 hFc (S473C) MMAE conjugates, respectively. Expected masses: B1 conjugate 40,170.5 Da and P3A1 conjugate 40,308.5 Da (DARs of 2) [* corresponds to MS artefact due to in source fragmentation]. I&J Mass spec analysis of deglycosylated, reduced B1- and P3A1 hFc (S473C) AF488 conjugates, respectively. Expected masses: B1 conjugate 39,552.4 Da and P3A1 conjugate 39,690.4 Da (DARs of 2).

FIG. 32: Schematic of VNAR hFc PBD dimer, amanitin and PNU conjugates.

FIG. 33: Cell viability following treatment with B1 mFc MMAE or 2V mFc-MMAE molecules (72 hr) in a panel of different human cancer cell lines. Cell Titre Glo reagent (Promega) was used to quantify ATP which correlates with the number of metabolically active cells in culture. IC50 values were determined using GraphPad Prism software.

FIG. 34: Cell viability following treatment with VNAR hFc PBD conjugates (96 hr) in 2 different human cancer cell lines (DU145 and Jeko-1). Cell Titre Glo reagent (Promega) was used to quantify ATP which correlates with the number of metabolically active cells in culture. IC50 values were determined using GraphPad Prism software. VNAR hFc conjugates were generated by reacting VNAR hIgG1 Fc(S252C) fusions with MA PEG4 va PBD (see FIG. 32).

FIG. 36 QC data of B1-[(G4S)5]-D3 Alexa Fluor 488 conjugate. Top. SDS-PAGE analysis of the Alexa Fluor 488 VNAR conjugate. Visualisation using Coomassie Brilliant Blue or UV. SDS-PAGE carried out under reductive (+0.1 M DTT) or non-reductive (−0.1 M DTT) conditions. Bottom. Deconvoluted mass spectrum of the Alexa Fluor 488 VNAR conjugate. Observed mass (26286.8 Da) is consistent with the theoretical mass (29285.1 Da) expected for the selectively-labelled conjugate.

FIG. 37 QC data of P3A1-[(G4S)5]-BA11-[(G4S)5]-D3 Alexa Fluor 488 conjugate. Top. SDS-PAGE analysis of the Alexa Fluor 488 VNAR conjugate. Visualisation using Coomassie Brilliant Blue or UV. SDS-PAGE carried out under reductive (+0.1 M DTT) or non-reductive (−0.1 M DTT) conditions. Bottom. Deconvoluted mass spectrum of the Alexa Fluor 488 VNAR conjugate. Observed mass (42273.81 Da) is consistent with the theoretical mass (42, 279.1) expected for the selectively-labelled conjugate.

FIG. 38 QC data of BA11-[PGVQPSPGGGGS]-131 Alexa Fluor 488 conjugate. Top. SDS-PAGE analysis of the Alexa Fluor 488 VNAR conjugate. Visualisation using Coomassie Brilliant Blue or UV. SDS-PAGE carried out under reductive (+0.1 M DTT) or non-reductive (−0.1 M DTT) conditions. Bottom. Deconvoluted mass spectrum of the Alexa Fluor 488 VNAR conjugate. Observed mass (27821.12 Da) is consistent with the theoretical mass (27, 819.99 Da) expected for the selectively-labelled conjugate.

Figure 7:
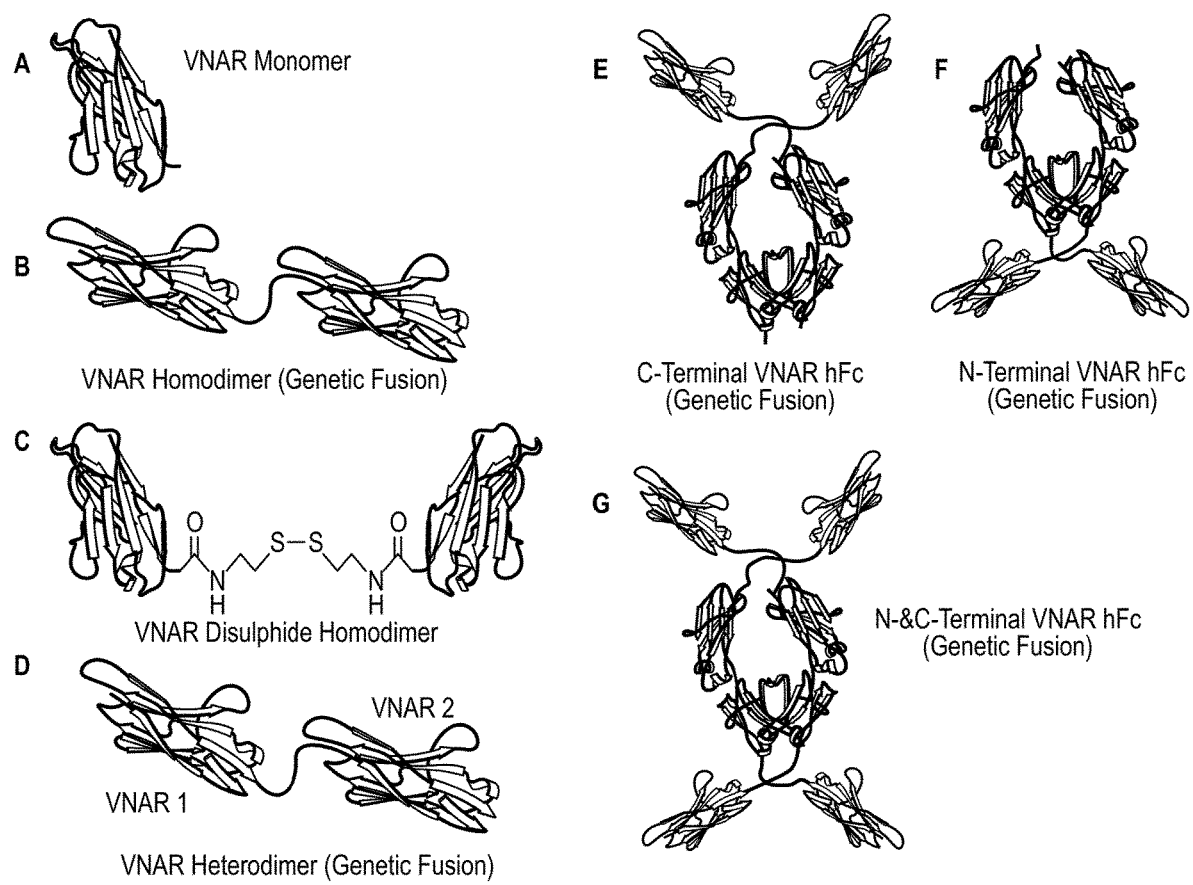
FIG. 7: VNAR reformatting A: monomeric VNAR, B: homodimers, C: conjugated homodimers via C-terminal intermolecular disulphide bond, D: heterodimers, E: VNAR IgG Fc fusions, F: IgG Fc—VNAR fusions, G: VNAR-(IgG Fc)—VNAR fusions.

In addition to the sequences mentioned the following sequences are expressly disclosed. Certain of these sequences relate to examples of molecules of the invention described herein:

| SEQ ID NO: | Sequence name |
|---|---|
| 115 | B1 Wobbe-G$_4$S-P3A1 CysHisMyc |
| 116 | P3A1 Wobbe-G$_4$S-B1 CysHisMyc |
| 117 | D3 Wobbe-G$_4$S-P3A1 CysHisMyc |
| 118 | P3A1 Wobbe-G$_4$S-D3 CysHisMyc |
| 119 | B1 Wobbe-G$_4$S-D3 CysHisMyc |
| 120 | B1 Wobbe-G$_4$S-BA11-Wobbe-G$_4$S-P3A1 CysHisMyc |
| 121 | BA11-Wobbe-G$_4$S-B1 -Wobbe-G$_4$S-P3A1 CysHisMyc |
| 122 | P3A1 Wobbe-G$_4$S-BA11-Wobbe-G$_4$S-B1 CysHisMyc |
| 123 | D3 Wobbe-G$_4$S-P3A1-Wobbe-G$_4$S-BA11 CysHisMyc |
| 124 | D3 Wobbe-G$_4$S-BA11 Wobbe-G$_4$S-P3A1 CysHisMyc |
| 125 | P3A1 Wobbe-G$_4$S-BA11-Wobbe-G$_4$S-D3 CysHisMyc |
| 126 | P3A1 Wobbe-G$_4$S-D3 Wobbe-G$_4$S-BA11 CysHisMyc |
| 127 | B1 Wobbe-G$_4$S-BA11-Wobbe-G$_4$S-D3 CysHisMyc |
| 128 | BA11-Wobbe-G$_4$S-B1-Wobbe-G$_4$S-D3 CysHisMyc |
| 129 | D3-Wobbe-G$_4$S-BA11-Wobbe-G$_4$S-B1 CysHisMyc |
| 130 | D3 Wobbe-G$_4$S-GM-P3A1 CysHisMyc |
| 131 | D3 Wobbe-G$_4$S-GM-P3A1-Wobbe-G$_4$S-GM-BA11 CysHisMyc |
| 132 | D3 Wobbe-G$_4$S-GM-BA11 Wobbe-G$_4$S-GM-P3A1 CysHisMyc |
| 133 | P3A1 Wobbe-G$_4$S-GM-D3 CysHisMyc |
| 134 | P3A1 Wobbe-G$_4$S-GM-BA11-Wobbe-G$_4$S-GM-D3 CysHisMyc |
| 135 | P3A1 Wobbe-G$_4$S-GM-D3 Wobbe-G$_4$S-GM-BA11 CysHisMyc |
| 136 | P3A1 Wobbe-G$_4$S-BA11-Wobbe-G$_4$S-P3A1 CysHisMyc |
| 137 | BA11 Wobbe-G$_4$S-P3A1-Wobbe-G$_4$S-P3A1-CysHisMyc |
| 138 | 2V-Wobbe-G$_4$S-2V CysHisMyc |
| 139 | 2V-Wobbe-G$_4$S-BA11-Wobbe-G$_4$S-2V CysHisMyc |
| 140 | BA11-Wobbe-G$_4$S-B1 CysHisMyc |
| 141 | BA11-Wobbe-G$_4$S-GM-B1 CysHisMyc |
| 142 | BA11-Wobbe-G$_4$S-B1 HisMyc |
| 143 | BA11-Wobbe-G$_4$S-GM-B1 HisMyc |
| 144 | B1-D3 HisMyc |
| 145 | D3-P3A1 HisMyc |
| 146 | P3A1-D3 HisMyc |
| 147 | D3-B1 CysHisMyc |
| 148 | B1-D3 CysHisMyc |
| 149 | D3-P3A1 CysHisMyc |
| 150 | P3A1-D3 CysHisMyc |
| 151 | B1-BA11-P3A1 HisMyc |
| 152 | B1-BA11-D3 HisMyc |
| 153 | D3-BA11-B1 CysHisMyc |
| 154 | D3-BA11-B1 HisMyc |
| 155 | D3-BA11-P3A1 HisMyc |
| 156 | P3A1-BA11-D3 CysHisMyc |
| 157 | P3A1-BA11-D3 HisMyc |

| SEQ ID NO: | Sequence name |
|---|---|
| 158 | P3A1-B1 HisMyc |
| 159 | P3A1-D3 His |
| 160 | P3A1-B1 SAPSA |
| 161 | 2V-BA11CysHisMyc |
| 162 | 2V-BA11HisMyc |
| 163 | BA11-2V HisMyc |
| 164 | D3-D3-BA11 HisMyc |
| 165 | D3-D3-BA11 CysHisMyc |
| 166 | E9-BA11-E9 HisMyc |
| 167 | D3-BA11-D3 HisMyc |
| 168 | P3A1-BA11-P3A1 HisMyc |
| 169 | BA11-B1 HisMyc |
| 170 | B1-Hinge-BA11 CysHisMyc |
| 171 | BA11-Hinge-B1 CysHisMyc |
| 172 | BA11 Helical B1 CysHisMyc |
| 173 | BA11-DoubleHinge-B1 CysHisMyc |
| 174 | B1-Hinge-BA11 CysHisMyc |
| 175 | BA11-Hinge-B1 CysHisMyc |
| 176 | BA11 Helical B1 CysHisMyc |
| 177 | BA11-DoubleHinge-B1 CysHisMyc |
| 178 | P3A1-(G4S)3-B1 HisMyc |
| 179 | P3A1-(G4S)7-B1 HisMyc |
| 180 | BA11-(G4S)3-B1 CysHisMyc |
| 181 | 2V |
| 182 | B1 his myc |
| 183 | B1 [QASGA] his |
| 184 | B1 [QASGA] |
| 185 | B1 [QACGA] his |
| 186 | B1 [QACKA] his |
| 187 | B1 SAPSA |
| 188 | B1 Hinge |
| 189 | B1 his myc(HEK293) |
| 190 | P3A1 his myc |
| 191 | P3A1 his |
| 192 | P3A1 |
| 193 | D3 his myc |
| 194 | E9 his myc |
| 195 | E7 his myc |
| 196 | CPF7 his myc |
| 197 | BA11 |
| 198 | B1G1 |
| 199 | B1G2 |
| 200 | B1V1 |
| 201 | B1V5 |
| 202 | B1V7 |
| 203 | D3V1 |
| 204 | D3V2 |
| 205 | D3V3 |
| 206 | D3 ELV1 |
| 207 | D3 ELV2 |
| 208 | D3 ELV3 |
| 209 | D3 ELV4 |
| 210 | D3 ELV5 |
| 211 | P3A1-P3A1 his myc |
| 212 | P3A1-P3A1 his |
| 213 | P3A1-P3A1 [SAPSA] |
| 214 | D3-D3 his myc |
| 215 | D3-D3 his |
| 216 | CPF7-CPF7 his myc |
| 217 | D3-D3 QACGA |
| 218 | D3-D3 QACGA His |
| 219 | P3A1V1 dimer |
| 220 | P3A1G1 dimer |
| 221 | P3A1G2 dimer |
| 222 | D3V1 dimer |
| 223 | D3V2 dimer |
| 224 | D3V3 dimer |
| 225 | B1G1-B1G1 HisMyc |
| 226 | B1G2-B1G2 HisMyc |
| 227 | B1 mFc |
| 228 | 2VmFc |
| 229 | B1 hFc (S252C) |
| 230 | B1G1 hFc (S252C) |
| 231 | B1G2 hFc (S252C) |
| 232 | B1 hFc (S473C) |
| 233 | P3A1 hFc (S252C) |
| 234 | hFc (S252C) P3A1 |
| 235 | P3A1 hFc(S473C) |
| 236 | D3 hFc (S252C) |
| 237 | hFc(S252C) D3 |
| 238 | D3D3 hFc (S252C) |
| 239 | hFc (S252C) D3D3 |
| 240 | E9 hFc (S252C) |
| 241 | 2V hFc (S252C) |
| 242 | 2V hFc (S473C) |
| 243 | human ROR1-Fc (HEH293) |
| 244 | human ROR1-Fc (CHO) |
| 245 | human ROR1 (Ig domain)-Fc (CHO) |
| 246 | human ROR1 (FZ domain)-Fc (CHO) |
| 247 | human ROR1 (KR domain)-Fc (CHO) |
| 248 | human ROR1 (IgFZ domains)-Fc (CHO) |
| 249 | human ROR1 (FZKR domains)-Fc (CHO) |
| 250 | human ROR2-Fc (CHO) |
| 251 | mouse ROR1-Fc (CHO) |
| 252 | rat ROR1-Fc (CHO) |
| 253 | human ROR1-His (HEK293 |
| 254 | human ROR1-His (CHO) |
| 255 | human ROR1 (Ig domain)-His |
| 256 | mouse ROR1-His (HEK293) |
| 257 | B1 x CD3 [G4S] his |
| 258 | B1 x CD3 [G4S]3 his |
| 259 | P3A1 x CD3 [G4S] his |
| 260 | P3A1 x CD3 [G4S]4 his |
| 261 | P3A1-P3A1 x CD3 [G4S] his |
| 262 | P3A1-P3A1 x CD3 [G4S]5 his |
| 263 | 2V x CD3 [G4S] his |
| 264 | 2V x CD3 [G4S]3 his |
| 265 | P3A1-[W]-B1-[G4S]-CD3 his |
| 266 | P3A1-[W]-B1-[G4S]3-CD3 his |
| 267 | P3A1-[WGM]-D3-[G4S]-CD3 his |
| 268 | P3A1-[WGM]-D3-[G4S]3-CD3 his |
| 269 | P3A1-[G4S]5-D3-[G4S]-CD3 his |
| 270 | P3A1-[G4S]5-D3-[G4S]3-CD3 his |

DETAILED DESCRIPTION

The present invention generally relates to specific antigen binding molecules. Specifically, the invention provides immunoglobulin-like shark variable novel antigen receptors (VNARs) specific for receptor tyrosine kinase-like orphan receptor 1 (ROR1) and associated fusion proteins, chimeric antigen receptors, conjugates, and nucleic acids, as well as accompanying methods. The ROR1-specific VNAR domains are described herein as ROR1-specific antigen binding molecules.

The Novel or New antigen receptor (IgNAR) is an approximately 160 kDa homodimeric protein found in the sera of cartilaginous fish (Greenberg A. S., et al., Nature, 1995. 374(6518): p. 168-173, Dooley, H., et al, Mol. Immunol, 2003. 40(1): p. 25-33; Müller, M. R., et al., mAbs, 2012. 4(6): p. 673-685)). Each molecule consists of a single N-terminal variable domain (VNAR) and five constant domains (CNAR). The IgNAR domains are members of the immunoglobulin-superfamily. The VNAR is a tightly folded domain with structural and some sequence similarities to the immunoglobulin and T-cell receptor Variable domains and to cell adhesion molecules and is termed the VNAR by analogy to the N Variable terminal domain of the classical immunoglobulins and T Cell receptors. The VNAR shares limited sequence homology to immunoglobulins, for example 25-30% similarity between VNAR and human light chain sequences (Dooley, H. and Flajnik, M. F., Eur. J. Immunol., 2005. 35(3): p. 936-945).

Kovaleva M. et al Expert Opin. Biol. Ther. 2014. 14(10): p. 1527-1539 and Zielonka S. et al mAbs 2015. 7(1): p.

15-25 provided summaries of the structural characterization and generation of the VNARs, which are hereby incorporated by reference.

The VNAR does not appear to have evolved from a classical immunoglobulin antibody ancestor. The distinct structural features of VNARs are the truncation of the sequences equivalent to the CDR2 loop present in conventional immunoglobulin variable domains and the lack of the hydrophobic VH/VL interface residues which would normally allow association with a light chain domain, which is not present in the IgNAR structure. Furthermore, unlike classical immunoglobulins some VNAR subtypes include extra cysteine residues in the CDR regions that are observed to form disulphide bridges in addition to the canonical Immunoglobulin superfamily bridge between the Cysteines in the Framework 1 and 3 regions N terminally adjacent to CDRs 1 and 3.

To date, there are three defined types of shark IgNAR known as I, II and III. These have been categorized based on the position of non-canonical cysteine residues which are under strong selective pressure and are therefore rarely replaced.

All three types have the classical immunoglobulin canonical cysteines at positions 35 and 107 (numbering as in Kabat, E. A. et al. Sequences of proteins of immunological interest. 5th ed. 1991, Bethesda: US Dept. of Health and Human Services, PHS, NIH) that stabilize the standard immunoglobulin fold, together with an invariant tryptophan at position 36. There is no defined CDR2 as such, but regions of sequence variation that compare more closely to TCR HV2 and HV4 have been defined in framework 2 and 3 respectively. Type I has germline encoded cysteine residues in framework 2 and framework 4 and an even number of additional cysteines within CDR3. Crystal structure studies of a Type I IgNAR isolated against and in complex with lysozyme enabled the contribution of these cysteine residues to be determined. Both the framework 2 and 4 cysteines form disulphide bridges with those in CDR3 forming a tightly packed structure within which the CDR3 loop is held tightly down towards the HV2 region. To date Type I IgNARs have only been identified in nurse sharks—all other elasmobranchs, including members of the same order have only Type II or variations of this type.

Type II IgNAR are defined as having a cysteine residue in CDR1 and CDR3 which form intramolecular disulphide bonds that hold these two regions in close proximity, resulting in a protruding CDR3 (FIG. 2) that is conducive to binding pockets or grooves. Type I sequences typically have longer CDR3s than type II with an average of 21 and 15 residues respectively. This is believed to be due to a strong selective pressure for two or more cysteine residues in Type I CDR3 to associate with their framework 2 and 4 counterparts. Studies into the accumulation of somatic mutations show that there are a greater number of mutations in CDR1 of type II than type I, whereas HV2 regions of Type I show greater sequence variation than Type II. This evidence correlates well with the determined positioning of these regions within the antigen binding sites.

A third IgNAR type known as Type III has been identified in neonates. This member of the IgNAR family lacks diversity within CDR3 due to the germline fusion of the D1 and D2 regions (which form CDR3) with the V-gene. Almost all known clones have a CDR3 length of 15 residues with little or no sequence diversity.

Another structural type of VNAR, termed type (IIb or IV), has only two canonical cysteine residues (in framework 1 and framework 3b regions). So far, this type has been found primarily in dogfish sharks (Liu, J. L., et al. Mol. Immunol. 2007. 44(7): p. 1775-1783; Kovalenko O. V., et al. J Biol Chem. 2013. 288(24): p. 17408-19) and was also isolated from semisynthetic V-NAR libraries derived from wobbegong sharks (Streltsov, V. A. et al. (2004) Proc. Natl. Acad. Sci. U.S.A. 101(34): p. 12444-12449).

It has been shown however specific VNARs isolated from synthetic libraries formed from the VNAR sequences can bind with high affinity to other proteins (Shao C. Y. et al. Mol Immunol. 2007. 44(4): p. 656-65; WO2014/173959) and that the IgNAR is part of the adaptive immune system as cartilaginous fish can be immunized with antigen and responsive IgNARs obtained that bind to the antigen (Dooley, H., et al, Mol. Immunol, 2003. 40(1): p. 25-33; WO2003/014161). It has been shown that the IgNAR has a mechanism for combinatorial joining of V like sequences with D and J sequences similar to that of immunoglobulins and the T cell receptor (summarized by Zielonka S. et al mAbs 2015. 7(1): p. 15-25).

The VNAR binding surface, unlike the variable domains in other natural immunoglobulins, derives from four regions of diversity: CDR1, HV2, HV4 and CDR3 (see also Stanfield, R. L., et al, Science, 2004. 305(5691): p. 1770-1773; Streltsov, V. A., et al, Protein Sci., 2005. 14(11): p. 2901-2909; Stanfield, R. L., et al., J Mol. Biol., 2007. 367(2): p. 358-372), joined by intervening framework sequences in the order: FW1-CDR1-FW2-HV2-FW3a-HV4-FW3b-CDR3-FW4. The combination of a lack of a natural light chain partner and lack of CDR2 make VNARs the smallest naturally occurring binding domains in the vertebrate kingdom.

The IgNAR shares some incidental features with the heavy chain only immunoglobulin (HCAb) found in camelidae (camels, dromedaries and llamas, Hamers-Casterman, C. et al. Nature, 1993. 363, 446-448; Wesolowski, J., et al., Med Microbiol Immunol, 2009. 198(3): p. 157-74) Unlike the IgNAR the HCAb is clearly derived from the immunoglobulin family and shares significant sequence homology to standard immunoglobulins. Importantly one key distinction of VNARs is that the molecule has not had at any point in its evolution a partner light chain, unlike classical immunoglobulins or the HCAbs. Flajnik M. F. et al PLoS Biol 2011. 9(8): e1001120 and Zielonka S. et al mAbs 2015. 7(1): p. 15-25 have commented on the similarities and differences between, and the possible and distinct evolutionary origins of, the VNAR and the immunoglobulin-derived VHH single binding domain from the camelids.

Although antibodies to ROR1 have been reported in the literature, the high sequence identity between the extracellular domain of human, mouse and rat ROR1 and between human ROR1 and ROR2 family members means generating high affinity hROR1-specific binding agents is not trivial. Additionally, the large size of antibodies compromises their ability to penetrate into solid tumours and render regions of target proteins inaccessible due to steric factors, which can be particularly acute for cell-surface proteins where oligomerisation or receptor clustering is observed.

As a result there is a need in the art for improved anti-ROR1 binding protein agents with different functional or physical characteristics or properties to antibodies and the development of therapeutics and diagnostic agents for malignancies associated with ROR1 expression. The present invention provides such agents in the form of the ROR1-specific antigen binding molecules described herein.

The presently-described ROR1-specific antigen binding molecules have been shown to bind to both human and murine ROR1. Furthermore, the ROR1-specific antigen binding molecules of the present invention bind to deglycosylated forms of ROR1 and do not bind to a number of linear peptides associated with anti-ROR1 antibodies described in the prior art. The presently-described ROR1-specific antigen binding molecules are therefore thought to bind to novel epitopes in the ROR1 sequence.

Binding of the ROR1-specific antigen binding molecules of the invention to cancer cell lines, as well as internalisation, have been demonstrated. This confirms the potential for the use of such molecules in the treatment of cancers, specifically cancers which express ROR1.

Various forms of the ROR1-specific antigen binding molecules are described, including fusion proteins of several types. Fusion proteins including an immunoglobulin Fc region are described, as well as both homo and heterodimers. Fusion of proteins to an Fc domain can improve protein solubility and stability, markedly increase plasma half-life and improve overall therapeutic effectiveness.

The present inventors have also, for the first time, created VNAR molecules conjugated to a variety of moieties and payloads. The present invention therefore also provides chemically conjugated VNARs. More specifically, ROR1-specific antigen molecules in several conjugated formats are provided.

Definitions

An antigen specific binding molecule of the invention comprises amino acid sequence derived from a synthetic library of VNAR molecules, or from libraries derived from the immunization of a cartilaginous fish. The terms VNAR, IgNAR and NAR may be used interchangeably also.

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "Complementarity Determining Regions" or CDRs (i.e., CDR1 and CDR3) refers to the amino acid residues of a VNAR domain the presence of which are typically involved in antigen binding. Each VNAR typically has two CDR regions identified as CDR1 and CDR3. Additionally, each VNAR domain comprises amino acids from a "hypervariable loop" (HV), which may also be involved in antigen binding. In some instances, a complementarity determining region can include amino acids from both a CDR region and a hypervariable loop. In other instances, antigen binding may only involve residues from a single CDR or HV. According to the generally accepted nomenclature for VNAR molecules, a CDR2 region is not present.

"Framework regions" (FW) are those VNAR residues other than the CDR residues. Each VNAR typically has five framework regions identified as FW1, FW2, FW3a, FW3b and FW4.

The boundaries between FW, CDR and HV regions in VNARs are not intended to be fixed and accordingly some variation in the lengths and compositions of these regions is to be expected. This will be understood by those skilled in the art, particularly with reference to work that have been carried out in analyzing these regions. (Anderson et al., PLoS ONE (2016) 11 (8); Lui et al., Mol Immun (2014) 59, 194-199; Zielonka et al., Mar Biotechnol (2015). 17, (4) 386-392; Fennell et al., J Mol Biol (2010) 400. 155-170; Kovalenko et al., J Biol Chem (2013) 288. 17408-17419; Dooley et al., (2006) PNAS 103 (6). 1846-1851). The molecules of the present invention, although defined by reference to FW, CDR and HV regions herein, are not limited to these strict definitions. Variation in line with the understanding in the art as the structure of the VNAR domain is therefore expressly contemplated herein.

A "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein.

A codon set is typically represented by 3 capital letters in italics, e.g. NNK, NNS, XYZ, DVK etc. A "nonrandom codon set" therefore refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al.; J. Mol. Biol. (1999), 296, 57-86); Garrard & Henner, Gene (1993), 128, 103). Such sets of oligonucleotides having certain codon sets can be synthesized using commercial nucleic acid synthesizers (available from, for example, Applied Biosystems, Foster City, CA), or can be obtained commercially (for example, from Life Technologies, Rockville, MD). A set of oligonucleotides synthesized having a particular codon set will typically include a plurality of oligonucleotides with different sequences, the differences established by the codon set within the overall sequence. Oligonucleotides used according to the present invention have sequences that allow for hybridization to a VNAR nucleic acid template and also may where convenient include restriction enzyme sites.

"Cell", "cell line", and "cell culture" are used interchangeably (unless the context indicates otherwise) and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, etc. Eukaryotic cells use control sequences such as promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "fusion protein" in this text means, in general terms, one or more proteins joined together by chemical means, including hydrogen bonds or salt bridges, or by peptide bonds through protein synthesis or both. Typically fusion proteins will be prepared by DNA recombination techniques and may be referred to herein as recombinant fusion proteins.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from an allogenic or xenogenic source. The DNA may, optionally, include marker or selection genes, for example, antibiotic resistance genes, temperature resistance genes, etc.

A "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR or HV regions.

"Identity" describes the relationship between two or more polypeptide sequences or two or more polynucleotide sequences, as determined by comparing the sequences. Identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. (1990) 215, 403).

Preferably, the amino acid sequence of the protein has at least 45% identity, using the default parameters of the BLAST computer program (Atschul et al., J. Mol. Biol. (1990) 215, 403-410) provided by HGMP (Human Genome Mapping Project), at the amino acid level, to the amino acid sequences disclosed herein.

More preferably, the protein sequence may have at least 45%, 46%, 47%, 48%, 49%, 50%, 55%, 60%, 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 45%, 46%, 47%, 48%, 49%, 50%, 50%, 55%, 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto A "library" refers to a plurality of VNARs or VNAR fragment sequences (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Natural" or "naturally occurring" VNARs, refers to VNARs identified from a non-synthetic source, for example, from a tissue source obtained ex vivo, or from the serum of an animal of the Elasmobranchii subclass. These VNARs can include VNARs generated in any type of immune response, either natural or otherwise induced. Natural VNARs include the amino acid sequences, and the nucleotide sequences that constitute or encode these antibodies. As used herein, natural VNARs are different than "synthetic VNARs", synthetic VNARs referring to VNAR sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promotor or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

The term "protein" means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein.

Examples of protein analogues and derivatives include peptide nucleic acids, and DARPins (Designed Ankyrin Repeat Proteins).

A fragment, analogue, variant or derivative of the protein may be at least 25 preferably 30 or 40, or up to 50 or 100, or 60 to 120 amino acids long, depending on the length of the original protein sequence from which it is derived. A length of 90 to 120, 100 to 110 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

"Oligonucleotides" are short-length, single- or double-stranded polydeoxynucleotides that are chemically synthesized by known methods (such as phosphotriester, phosphite, or phosphoramidite chemistry, using solid-phase techniques). Further methods include the polymerase chain reaction (PCR) used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation. DNA is "purified" when the DNA is separated from non-nucleic acid impurities (which may be polar, non-polar, ionic, etc.).

A "source" or "template" VNAR, as used herein, refers to a VNAR or VNAR antigen binding fragment whose antigen binding sequence serves as the template sequence upon which diversification according to the criteria described herein is performed. An antigen binding sequence generally includes within a VNAR preferably at least one CDR, preferably including framework regions.

A "transcription regulatory element" will contain one or more of the following components: an enhancer element, a promoter, an operator sequence, a repressor gene, and a transcription termination sequence.

"Transformation" means a process whereby a cell takes up DNA and becomes a "transformant". The DNA uptake may be permanent or transient. A "transformant" is a cell which has taken up and maintained DNA as evidenced by the expression of a phenotype associated with the DNA (e.g., antibiotic resistance conferred by a protein encoded by the DNA).

A "variant" or "mutant" of a starting or reference polypeptide (for example, a source VNAR or a CDR thereof), such as a fusion protein (polypeptide) or a heterologous polypeptide (heterologous to a phage), is a polypeptide that (1) has an amino acid sequence different from that of the starting or reference polypeptide and (2) was derived from the starting or reference polypeptide through either natural or artificial mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a non-random codon set that encodes a sequence with a variant amino acid (with respect to the amino acid found at the corresponding position in a source VNAR or antigen binding fragment) would be a variant polypeptide with respect to a source VNAR or antigen binding fragment. Thus, a variant CDR refers to a CDR comprising a variant sequence with respect to a starting or reference polypeptide sequence (such as that of a source VNAR or antigen binding fragment). A variant amino acid, in this context, refers to an amino acid different from the amino acid at the corresponding position in a starting or reference polypeptide sequence (such as that of a source VNAR or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type" or "reference" sequence or the sequence of a "wild-type" or "reference" protein/polypeptide, such as a coat protein, or a CDR of a source VNAR, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man induced means. The products of such processes are "variant" or "mutant" forms of the original "wild-type" protein or gene.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of an antigen-specific binding protein, such as a monoclonal antibody or VNAR, onto a T cell, thereby allowing a large number of specific T cells to be generated, for example, for use in adoptive cell therapy. CARs may direct the specificity of the cell to a tumour associated antigen, for example. CARs may comprise an intracellular activation domain, a transmembrane domain, and an extracellular domain comprising a tumour associated antigen binding region. In particular aspects, CARs comprise fusions of single-chain variable fragments (scFv) derived from monoclonal antibodies fused to CD3-zeta transmembrane and endodomains. In other particular aspects, CARs comprise fusions of the VNAR domains described herein with CD3-zeta transmembrane and endodomains. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD 19. In certain cases, the spacing of the antigen-recognition domain can be modified to reduce activation-induced cell death. In certain cases, CARs comprise domains for additional co-stimulatory signalling, such as CD3-zeta, FcR, CD27, CD28, CD 137, DAP 10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "conjugation" as used herein may refer to any method of chemically linking two or more chemical moieties. Typically, conjugation will be via covalent bond. In the context of the present invention, at least one of the chemical moieties will be a polypeptide and in some cases the conjugation will involve two or more polypeptides, one or more of which may be generated by recombinant DNA technology. A number of systems for conjugating polypeptides are known in the art. For example, conjugation can be achieved through a lysine residue present in the polypeptide molecule using N-hydroxy-succinimide or through a cysteine residue present in the polypeptide molecule using maleimidobenzoyl sulfosuccinimide ester. In some embodiments, conjugation occurs through a short-acting, degradable linkage including, but not limited to, physiologically cleavable linkages including ester, carbonate ester, carbamate, sulfate, phosphate, acyloxyalkyl ether, acetal, and ketal, hydrazone, oxime and disulphide linkages. In some embodiments linkers that are cleavable by intracellular or extracellular enzymes, such as cathepsin family members, cleavable under reducing conditions or acidic pH are incorporated to enable releases of conjugated moieties from the polypeptide or protein to which it is conjugated.

Figure 11:
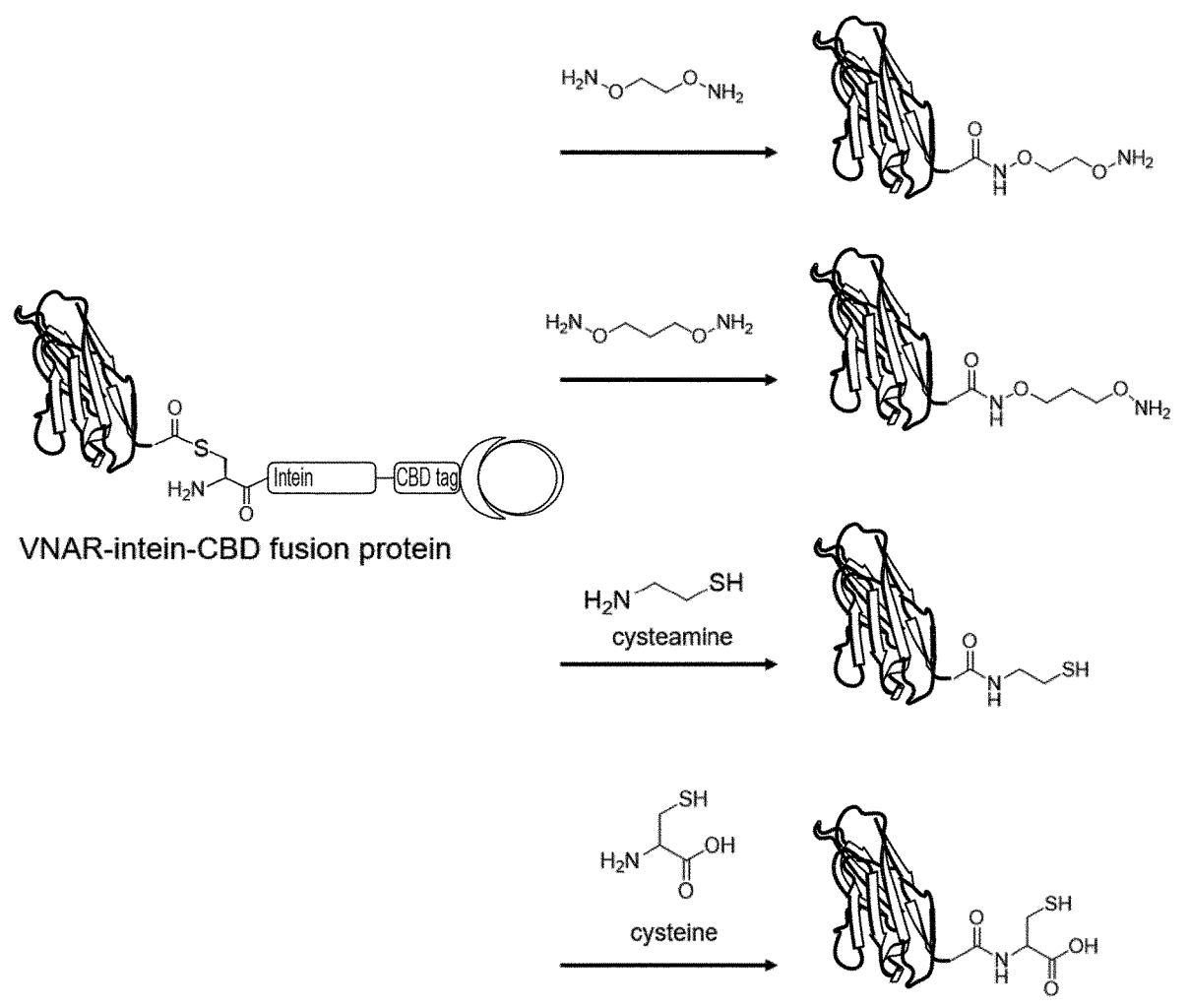
Figure 25:
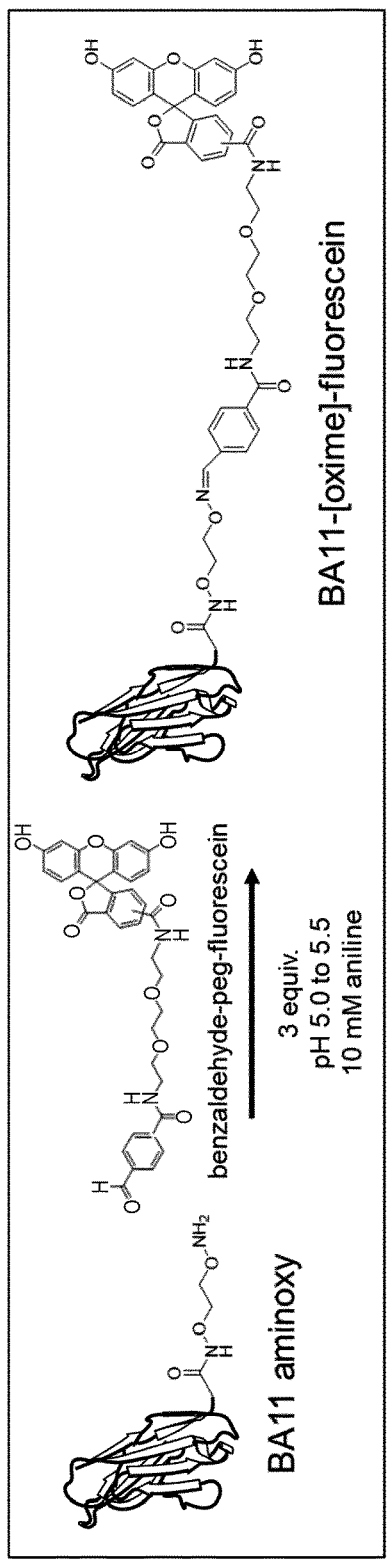
FIG. 25: Schematic of BA11 aminoxy conjugation to benzaldehyde fluorescein.
Figure 26:
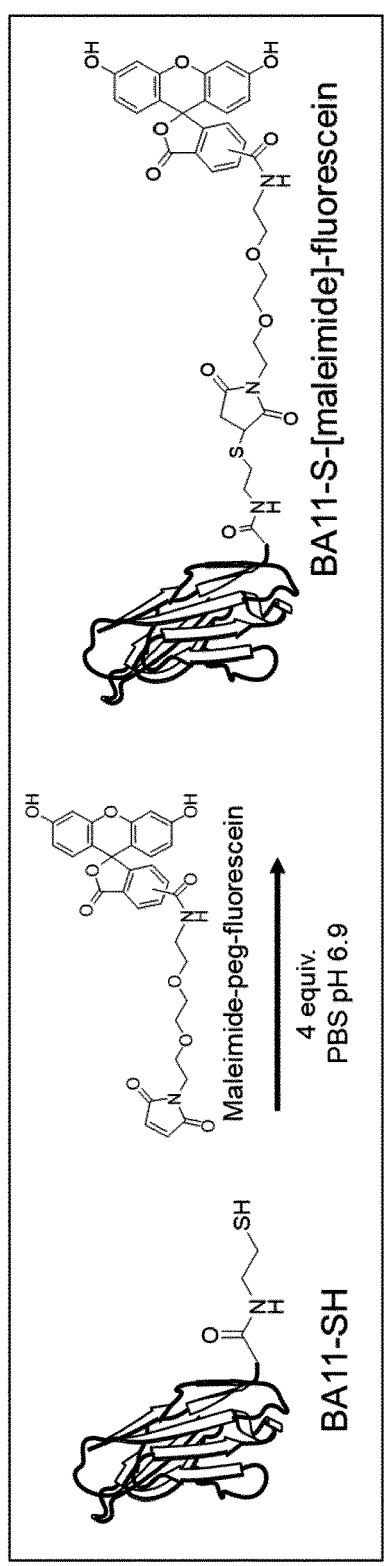
FIG. 26: Schematic of BA11 thiol conjugation to maleimide fluorescein.
Figure 27:
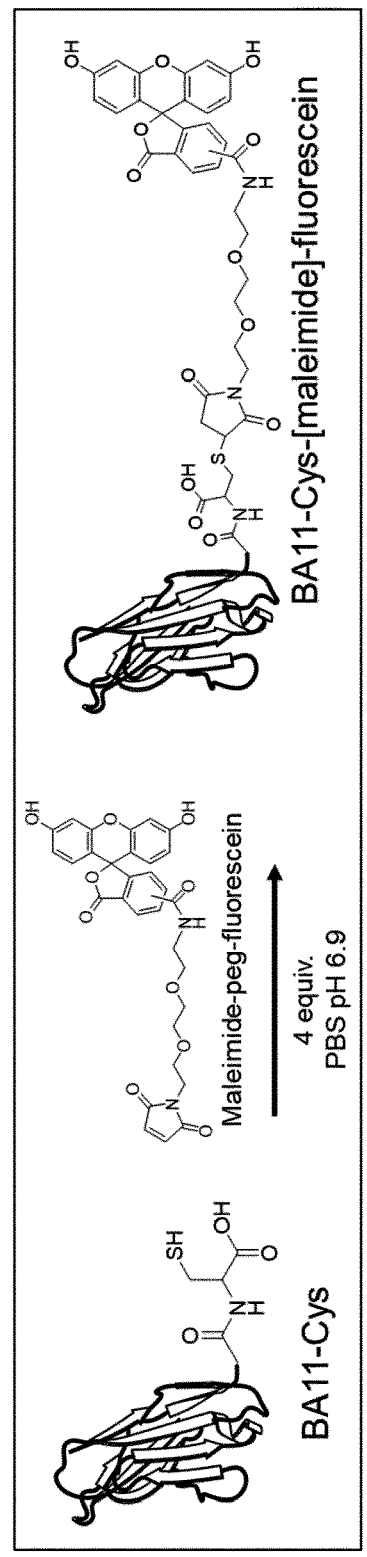
FIG. 27: Schematic of BA11 C-terminal cysteine derivative conjugation to maleimide fluorescein

A particularly preferred method of conjugation is the use of intein-based technology (US2006247417) Briefly, the protein of interest is expressed as an N terminal fusion of an engineered intein domain (Muir 2006 Nature 442, 517-518). Subsequent N to S acyl shift at the protein-intein union results in a thioester linked intermediate that can be chemically cleaved with bis-aminoxy agents or amino-thiols to give the desired protein C-terminal aminoxy or thiol derivative, respectively (FIG. 11). These C-terminal aminoxy and thiol derivatives can be reacted with aldehyde/ketone and maleimide functionalised moieties, respectively, in a chemoselective fashion to give the site-specific C-terminally modified protein (FIGS. 25-27).

In another preferred method of conjugation the VNARs are directly expressed with an additional cysteine at or near the C-terminal region of the VNAR or incorporated within a short C-terminal tag sequence enabling conjugation with thiol reactive payloads such as maleimide functionalised moieties.

Conjugation as referred to herein is also intended to encompass the use of a linker moiety, which may impart a number of useful properties. Linker moieties include, but are not limited to, peptide sequences such as poly-glycine, gly-ser, val-cit or val-ala. In certain cases, the linker moiety may be selected such that it is cleavable under certain conditions, for example via the use of enzymes, nucleophilic/basic reagents, reducing agents, photo-irradiation, electrophilic/acidic reagents, organometallic and metal reagents, or oxidizing reagents, or the linker may be specifically selected to resist cleavage under such conditions.

Polypeptides may be conjugated to a variety of functional moieties in order to achieve a number of goals. Examples of functional moieties include, but are not limited to, polymers such as polyethylene glycol in order to reduce immunogenicity and antigenicity or to improve solubility. Further non-limiting examples include the conjugation of a polypeptide to a therapeutic agent or a cytotoxic agent.

The term "detectable label" is used herein to specify that an entity can be visualized or otherwise detected by spectroscopic, photochemical, biochemical, immunochemical, electrical, optical, chemical or other means. The detectable label may be selected such that it generates a signal which can be measured and whose intensity is proportional to the amount of bound entity. A wide variety of systems for labelling and/or detecting proteins and peptides are known in the art. A label may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionuclides, fluorophores, chemiluminescent agents, microparticles, enzymes, colorimetric labels, magnetic labels, haptens, molecular beacons, and aptamer beacons.

Methods of killing or inhibiting the growth of a cells expressing ROR1 in vitro or in a patient are contemplated herein, In general, them "killing" as used herein in the context of cells means causing a cell death. This may be achieved by a number of mechanisms, such as necrosis or other cells injury, or the induction of apoptosis. The phrases "inhibiting the growth" or "inhibiting proliferation" when used herein are intended to encompass the prevention of cell development, more specifically the prevention of cell division.

The present invention will be further understood by reference to the following examples.

EXAMPLES

Example 1—Generation of Specific Anti-ROR1 VNAR Sequences

Specific VNAR Sequences from Synthetic Library

Two selection campaigns were adopted for screening a VNAR synthetic domain library (WO2014173959) for specific ROR1 binders. The first campaign made use of human ROR1 antigen and the second used mouse ROR1 antigen. Both recombinant ROR1 proteins were biotinylated as per manufacturer's instructions (Thermo Scientific Sulfo-NHS-LC-Biotin protocol, Cat N 21327) to aid the antigen presentation and selection process. VNAR domains were isolated after 3 rounds of selection using these biotinylated ROR1 antigens immobilised on streptavidin-coated beads. Post selection and following the screening of individual clones, 70% of monoclonal phage displaying VNAR domains (selected against human ROR1 protein) were found to be specific to human and mouse ROR1, but not a closely related ROR2 protein (the lead clones from this selection were called B1—40% and E7—30% (FIG. 1). Similarly, 45% of monoclonal phage selected with mouse ROR1 were specific to human and mouse ROR1, but not ROR2 (lead clone from this selection was called P3A1, FIG. 1). Another specific clone obtained from mouse ROR1 screening was CPF7 which was present as a single sequence out of 200 screened clones.

The sequences obtained from screening with human ROR1 are B1 and E7, and from screening with mouse ROR1 is P3A1 and CPF7. (FIG. 2)

Specific VNAR Sequences from Immunised Libraries

Libraries Construction.

Three spiny dogfish were immunised with extracellular domain of recombinant human ROR1 protein and a target-specific IgNAR immune response was monitored through the analysis of post-immunised sera as described in Müller M. R. et al. Generation and Isolation of Target-Specific Single-Domain Antibodies from Shark Immune Repertoires, Humana Press 2012. Sera samples pre- and post-immunisation were taken from animals and tested for antigen binding in ELISA. An IgNAR titre increase, specific for human ROR1, was observed after 16 weeks in all animals (FIG. 3). The specificity of post-immune sera to mouse ROR1 was also observed indicating the presence in immunised animals of species cross-reactive ROR1 specific IgNAR binders (FIG. 3).

The VNAR repertoire (binding sites of IgNAR) was amplified from dogfish blood using specific PCR primers and cloned into a phage display vector, which contained an in-frame coat protein pIII of the bacteriophage M13 gene as described in Müller M. R. et al. Generation and Isolation of Target-Specific Single-Domain Antibodies from Shark Immune Repertoires, Humana Press 2012. The library sizes were calculated and are shown in Table 1:

TABLE 1

| Fish # | Library | Size (unique transformants) |
|---|---|---|
| 154 | ELSI 5 | 6 × 10⁷ |
| 156 | ELSI 6 | 1.7 × 10⁷ |
| 161 | ELSI 7 | 2 × 10⁷ |

Screening of the Immunised Libraries for Antigen Specific VNAR Sequences.

Recombinant mouse ROR1 protein was used for screening the immunised libraries (ELSI 5-7). Following a protocol similar to that used to screen the synthetic library, VNAR domains were isolated after 3 rounds of selection using biotinylated ROR1 antigen immobilised on streptavidin-coated beads. Following the selection process, 45% of monoclonal phage displaying a VNAR domain (from the combined output from the 3 libraries) was specific to human and mouse ROR1. One third of the ROR1 specific VNAR were found to have the sequence D3 (FIGS. 4 and 5) and the remaining two thirds—to the sequence E9 (FIGS. 4 and 5).

The sequences obtained from screening with mouse ROR1 are E9 and D3. (FIG. 5)

All lead anti-ROR1 VNAR proteins were expressed in TG1 *E. coli* or HEK293 mammalian cells and IMAC purified from the periplasmic fraction or the cell supernatant, respectively.

Methods

IGNAR TITRE IN SERA ELISA

ELISA were carried out using the following protocol:

1. Coat an ELISA plate with 100 μl/well of 1 mg/ml of human ROR1-Fc or mouse ROR1-Fc in or PBS. Incubate at 4° C. overnight.

2. Wash plates 3× with PBST.

3. Block plates by adding 200 μl/well 2% (w/v) M-PBS and incubate at 37° C. for 1 h.

4. Wash plates 3× with PBST.

5. Serially dilute dogfish sera in PBS from no less than 1:10 up to 1:1000 and add 100 μl/well. Incubate at room temperature for 1 h.

6. Wash plates 3× with PBST.

7. Add 100 μl/well primary antibody (mouse monoclonal anti-IgNAR antibody, GA8) diluted as hybridoma tissue culture supernatant in PBST.

8. Wash plates 3× with PBST.

9. Add 100 μl/well of a suitable secondary anti-mouse IgG HRP conjugate diluted in PBS. Incubate for 1 h.

10. Wash plates 2× with PBST followed by 2× with PBS.

11. Add 100 μl/well of TMB substrate to the plate and incubate until the appearance of signal/onset of saturation. Stop the colour development by adding 100 μl/well of 0.18 M H2SO4.

12. Read at 450 nm with a microtiter plate reader.

Library Screening

1. To rescue library phage for selections, cultures from library glycerol stocks were grown at 37° C. and 250 rpm, in 2×TY, 2% glucose, 100 μg/ml ampicillin to an OD600 of 0.5.

2. Cells were super-infected with 109 M13K07 helper phage (NEB) and then incubated overnight in 2×TY, 100 μg/ml ampicillin, 50 μg/ml kanamycin at 25° C. and 250 rpm.

3. The phage was PEG-precipitated (20% PEG/2.5 M NaCl) twice from the bacterial culture and the resulting phage pellets were resuspended in 1 ml PBS.

4. 200 μl of Dynabeads M-280 Streptavidin (Invitrogen #11205D), pre-blocked with 2% (w/v) MPBS, were coated with 400 nM biotinylated mouse ROR1 rotating at 20 rpm, at room temperature for 1 h.

5. Library phage was de-selected by incubation with Dynabeads for 1 h rotating at room temperature and then added to the antigen-coated beads.

6. Beads were washed 5-10 times with PBST and 5-10 times with PBS, eluted by rotating for 8 min in 400 μl 100 mM TEA and neutralised by the addition of 200 μl 1 M Tris-HCl pH 7.5.

7. *E. coli* TG1 cells (10 ml) were infected with 300 μl of eluted phage for 30 min at 37° C. and grown overnight at 37° C. on TYE agar plates containing 2% (w/v) glucose and 100 μg/ml ampicillin.

8. Three further rounds of selection were conducted and outputs were screened for antigen-specific binding by monoclonal phage and periplasmic extract ELISAs against human or mouse ROR1. Phage binders were detected using HRP-conjugated anti-M13 antibody (GE Healthcare, 27942101) and periplasmic protein was detected using HRP-conjugated anti-c-Myc antibody (Roche, 118 141 50 001).

VNAR Expression in *E. coli*

1. Dilute the overnight culture 1:50 in TB media with phosphate salts, 1% glucose, 100 ug/ml Ampicillin and incubate at 37° C. with vigorous shaking (250 rpm) all day.

2. Pellet the cells by centrifugation at 3,000×g for 20 min at 20° C.

3. Re-suspend the cells in the same volume of TB media with phosphate salts, 100 ug/ml Ampicillin (no glucose).

4. Add IPTG to a final concentration of 1 mM IPTG and incubate at 16° C. overnight (16 h) with shaking at 250 rpm.

5. Collect the cells by centrifugation at 6,000×g for 30 min (the pellet could be frozen at this point at −20° C.).

6. Re-suspend the pellet in 10% culture volume ice-cold TES and shake gently on ice for 15 min.

7. Add an equal volume ice-cold 5 mM MgSO4 (for 2.5 mM final concentration of MgSO4) and continue shaking gently on ice for a further 15 min.

8. Pellet the suspension by centrifugation at 15,000×g for 30 min at 4° C. and carefully decant the supernatant containing released periplasmic proteins into a clean falcon.

9. Add 10×PBS pH 7.4 [final concentration of 1×PBS] to peri-prep extract prior to IMAC incubation.

VNAR Expression in HEK293

10 µg DNA in water (sterile filtrated) for 10 ml culture.

Use 10 ml of cells (~106/ml) in a 50 ml bioreactor tube (exponentially growing cells in fresh media)

Add OptiMEM media to DNA to a total volume of 500 µl.

Add 25 µl of PEI (1 mg/ml stock made up in water) to a separate 500 µl OptiMEM media.

Incubated DNA and PEI at room temperature for up to 15 min.

Mix 500 µl of PEI in media to each 500 µl of DNA in media.

Incubated at room temperature for 20-30 min facilitating complex formation.

Add 1 ml of mixture to the cells and incubate at 37° C., 5%002 sharking 140 rpm.

Next day feed cells by addition of 250 µl of 20% (w/v) tryptone to 10 ml of cells to obtain the final concentration of tryptone 0.5%

Leave cells to express for 3-5 days.

Spin the cells and assess supernatant for secreted protein to determine productivity.

Add 10×PBS pH 7.4 [final concentration of 1×PBS] to peri-prep extract prior to IMAC incubation.

This protocol can be scaled up or down as required for protein production.

Protein Expression (Scale Up)

ROR1 binding VNAR proteins expressed well in many different forms in several different expression systems. The addition of standard C terminal tags, including His and His$_6$Myc, to aid protein purification, handling and protein analysis, did not affect the binding of ROR1 VNARs to target ROR1 (Table 2).

TABLE 2

SPR data for binding of VNARs with different C-terminal tags to human ROR1 and ROR2

| VNAR | C-terminal tag | hROR1 | | | hROR2 |
|---|---|---|---|---|---|
| | | Ka (M$^{-1}$s$^{-1}$) | Kd (s$^{-1}$) | K$_D$ (nM) | |
| B1 | 6xHis | 2.33E+06 | 1.91E-04 | 0.11 | No binding |
| | 6xHis myc | 7.47E+05 | 6.09E-04 | 0.83 | No binding |
| P3A1 | 6xHis | 2.92E+06 | 2.06E-02 | 7.8 | No binding |
| | 6xHis myc | 9.8E+05 | 2.5E-02 | 25.6 | No binding |
| P3A1 | No tag | 1.67E+06 | 5.98E-04 | 0.36 | No binding |
| dimer | 6xHis myc | 2.08E+06 | 6.37E-04 | 0.35 | No binding |

In addition, VNAR C-terminal tags do not affect VNAR structure as measured by circular dichroism (FIG. 6—CD spectra of VNARs) (Glasgow University, UK).

VNARs were also expressed genetically fused to mouse and human IgG Fc sequences, and as N-terminal fusions to engineered inteins, enabling site specific conjugation to labels and drugs.

Expression systems used include *E. coli* (periplasmic and cytoplasmic expression), HEK 293 and CHO (Evitria Fc fusion proteins).

Example 2—VNAR Reformatting

Homodimers

Figure 9:
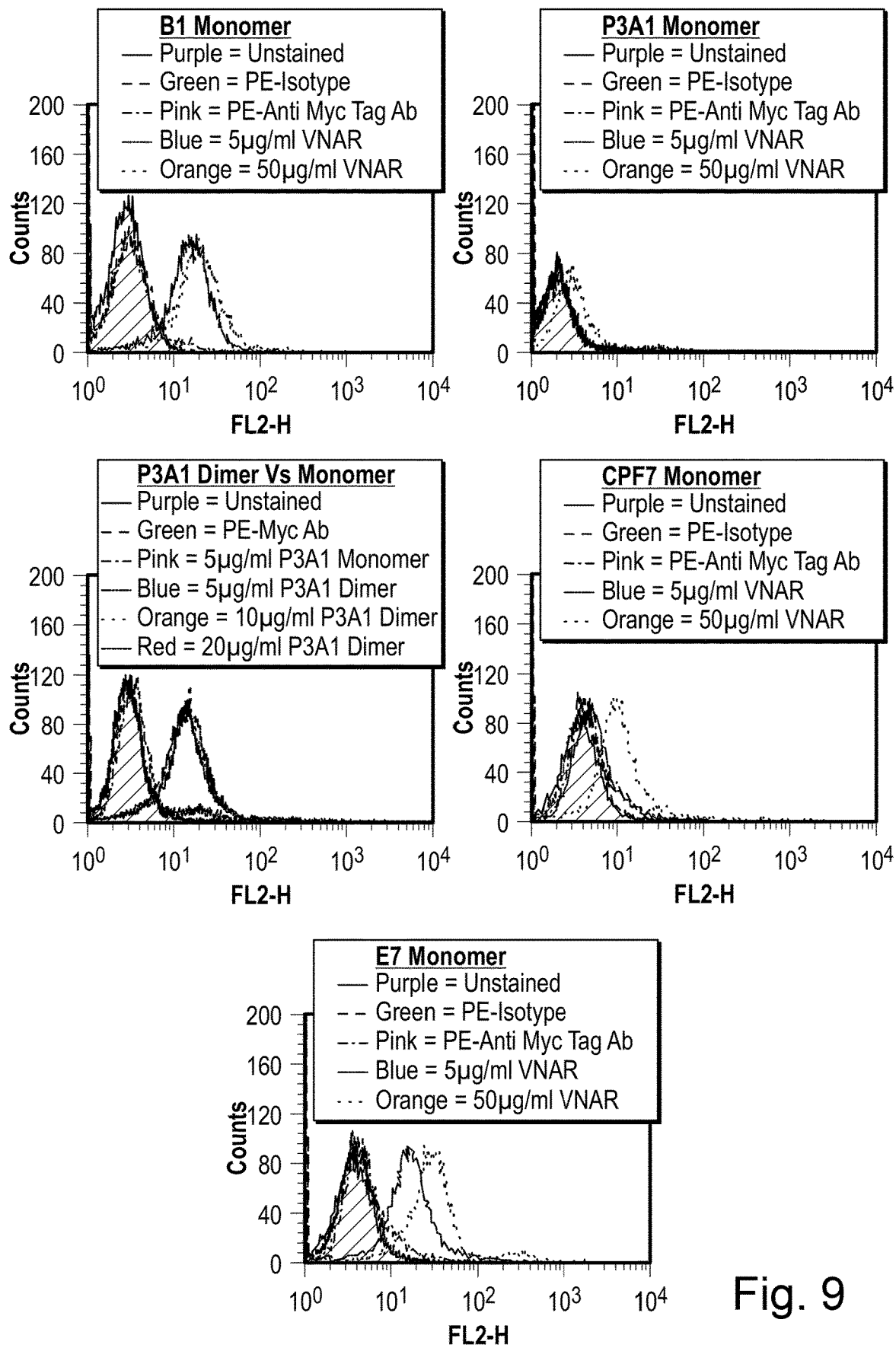
FIG. 9: Cell surface binding of VNAR (His$_6$Myc tag) molecules to A549 (ROR1$^{hi}$) lung cancer cells by flow cytometry. B1 and E7 monomers and P3A1-P3A1 dimer bind strongly to A549 cells at all concentrations tested. CPF7 and P3A1 monomers bind at 50 µg/ml to A549 cells. VNAR binding was detected using PE-anti Myc tag Ab (CST) and analysed using a BD Biosciences FACSCalibur flow cytometer.
Figure 12:
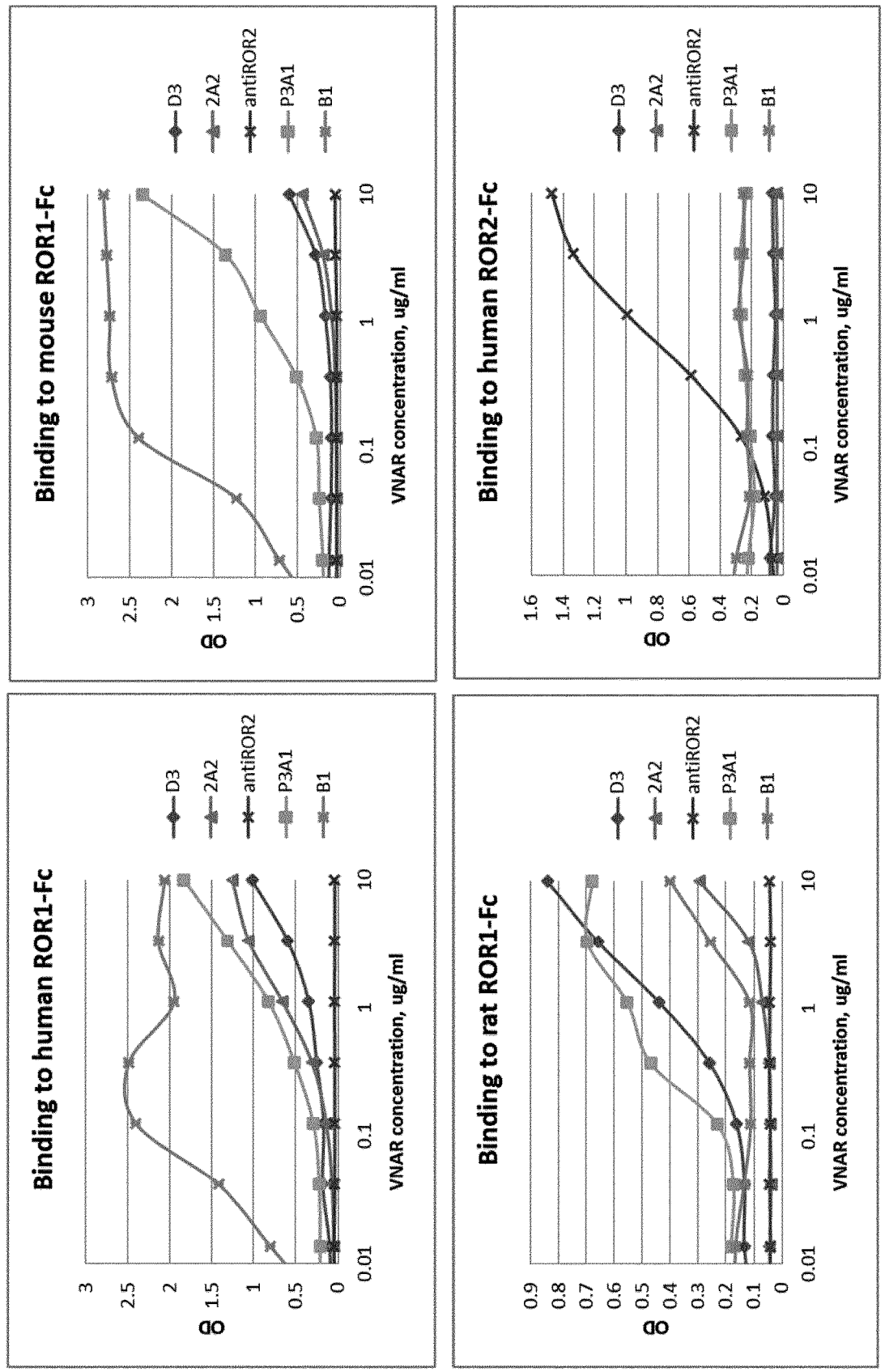
FIG. 12: VNAR binding to human, mouse and rat ROR1 and human ROR2 by ELISA. All VNARs were found to be species cross-reactive to ROR1. None of the VNAR clones cross-reacted with human ROR2.

ROR1 binding VNARs were successfully reformatted into homodimers by genetic fusion using standard GlySer based linkers (FIG. 7B). Homodimers were shown to have increased affinity for recombinant hROR1 by SPR and ELISA, and increased binding to cell surface ROR1 on ROR1 positive cancer cell lines by flow cytometry (FIG. 9). Flow cytometry experiments are described in more detail in Example 4.

Figure 8:
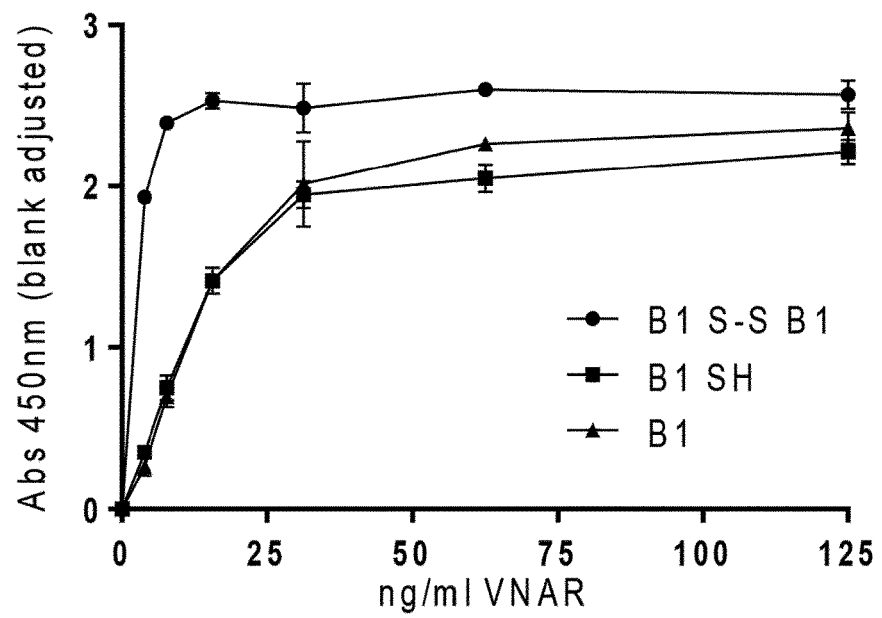
FIG. 8: Binding of B1 C-terminally linked homodimer to hROR1. B1, B1 C-terminal thiol (B1 SH) and B1 C-terminal disulphide dimer (B1 S—S B1) binding to human ROR1 by ELISA.

In addition, ROR1 binding VNAR homodimers were successfully generated through chemical conjugation. VNARs were expressed as intein fusion proteins and cleaved with cysteamine to generate C-terminal thiol derivatives, which then self-associated into homodimers via C terminal intermolecular disulphide formation (FIG. 7C). These disulphide linked homodimers showed increased binding affinity to recombinant hROR1 by ELISA (FIG. 8). Production of intein fusion proteins is discussed in more detail in Example 8.

Heterodimers

ROR1 binding VNAR heterodimers were generated by genetic fusion with standard GlySer linkers or alternatively with PGVQPSPGGGGS (SEQ ID NO: 63) or PGVQPAPGGGGS (SEQ ID NO: 64) linkers (FIG. 7D) and demonstrated high affinity specific binding to recombinant ROR1 and ROR1 positive cells. Heterodimeric VNAR proteins can also be generated by chemical conjugation.

Results for binding characterisation experiments are tabulated in Table 3 and 4 (see Example 3) and Tables 18, 19, 20 (see Example 10).

VNAR Fc Fusion Proteins

Fusion of proteins to an Fc domain can improve protein solubility and stability, markedly increase plasma half-life and improve overall therapeutic effectiveness. ROR1 binding VNARs were genetically fused to the N terminus of mouse IgG2a Fc (mFc) and both the N and C termini of human IgG1 (hFc) via standard GlySer linkers (FIG. 7 E, F, G). Examples of Fc sequences Mouse IgG2a Fc (mFc)
(SEQ ID NO: 95)
EPRGPTIKPCPPCKCPAPNLLGGPSVFIFPPKIKDVLMISLSPIVTCVVV
DVSEDDPDVQISWFVNNVEVHTAQTQTHREDYNSTLRVVSALPIQHQDWM
SGKEFKCKVNNKDLPAPIERTISKPKGSVRAPQVYVLPPPEEEMTKKQVT
LTCMVTDFMPEDIYVEWTNNGKTELNYKNTEPVLDSDGSYFMYSKLRVEK
KNWVERNSYSCSVVHEGLHNHHTTKSFSRTPGK Human IgG1 Fc (hFc)
(SEQ ID NO: 96)
EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK VNAR Fc fusion proteins were expressed as secreted protein in CHO K1 cells and purified from the media using MabSelect™ SuRe™ (Evitria, Switzerland). Purified proteins were analysed by SEC (AdvanceBio, Agilent), SDS PAGE and mass spectrometry to confirm sequence and protein integrity. The resulting VNAR Fc fusion proteins bind recombinant human ROR1 by SPR (Table 6) and ROR1 positive cells with high affinity (FIG. 15) and were shown to internalise into ROR1 positive cells. ROR1 binding VNARs were also genetically fused to engineered hIgG1 Fc fusion proteins that incorporated an engineered cysteine substitution in the hIgG1 Fc sequence, for example at position S252C or S473C (Kabat numbering) to enable site specific labelling (FIG. 10).

Typical Method for Expression of VNAR Intein Fusion Proteins

For expression as intein fusions, DNA encoding VNARs was optimised for *E. coli* expression (GeneArt, Thermo) and cloned into the NdeI/SapI sites of the pTXB1 vector (NEB) and derivatives thereof. This results in a gene encoding the VNAR protein of interest fused to an engineered intein domain which in turn is fused to a chitin binding domain (CBD) to enable purification on a chitin column. pTXB1 vector derivatives encode alternative inteins as the fusion proteins.

Transformed *E. coli* cells were grown in 1 L shaker flasks until OD600=~0.6, cold shocked 4° C. for 2 hours then protein expression induced with 0.5 mM IPTG at 18° C. overnight. Cells were lysed by sonication in lysis buffer (50 mM sodium phosphate pH7.4, 0.5M NaCl, 15% glycerol, 0.5 mM EDTA, 0.1% Sarkosyl, 1 mM AEBSF) and centrifuged to remove cell debris. VNAR intein fusion protein was purified from clarified cell lysate by immobilising on chitin beads (NEB, S6651). Beads were washed extensively with lysis buffer followed by cleavage buffer (50 mM sodium phosphate pH6.9, 200 mM NaCl) and VNARs released from the beads by overnight chemical cleavage in 400 mM dioxyamine, or O,O'-1,3-propanediylbishydroxylamine, or 100 mM cysteine or cysteamine to generate the corresponding C-terminal aminoxy, C-terminal cysteine or C-terminal thiol derivative of the VNARs (FIG. 11).

Cleaved VNAR supernatant was then further purified by SEC (Superdex75 26/60 GE healthcare) and/or IMAC (His-Trap HP, GE Healthcare). Concentrations were determined from absorbance at 280 nm using the theoretical extinction coefficient predicted from the amino acid sequence. All proteins were characterised by reducing and non-reducing SDS PAGE analysis and mass spectrometry. The formation of the desired disulphide bond was confirmed by mass spectrometry methods.

Example 3—Anti-ROR1 VNAR Characterisation

Binding to ROR1 and ROR2 by SPR and ELISA
Species Cross-Reactivity of ROR1 VNAR Binders Soluble VNAR protein clones (B1, P3A1 and D3) were analysed for species cross-reactivity with human, mouse and rat ROR1 along with a positive control antibody 2A2 and an anti ROR2 specific antibody control. 2A2 is an anti-human ROR1 specific mouse monoclonal antibody (BioLegend Cat #2357802) and the anti ROR2 antibody is a commercial monoclonal mouse antibody from R&D Systems (Cat #MAB2064).

VNAR B1 was observed to be a very strong binder to both mouse and human ROR1. All VNARs are species cross-reactive to ROR1 derived from a human, mouse and rat origin (Table 3 and Table 4). None of the VNAR clones cross-reacted with human ROR2 (Table 3).

Determination of Binding Kinetics to Human ROR1, Human ROR2, Mouse ROR1 or Rat ROR1

Binding kinetics were determined using a Pioneer Surface Plasmon Resonance (SPR) instrument (SensiQ/Pall ForteBio). ROR1-hFc or ROR2-hFc fusion proteins (extracelluar domains) were immobilised in sodium acetate pH5 buffer to COOH$_2$ chips using amine coupling. VNARs and VNAR-Fc molecules were tested at various concentrations and the Ka ($M^{-1}s^{-1}$), Kd ($s^{-1}$) and KD (nM) values were determined using QDat software (SensiQ/Pall ForteBio). ROR1 2A2 mAb (Biolegend) and ROR2 mAb (R&D Systems) were included as controls for positive/negative binding to ROR1 and ROR2. 2V is a control VNAR sequence, derived from a naïve VNAR library, so is representative of this protein class but has no known target.

TABLE 3

SPR data for binding of VNAR molecules to human ROR1 (hROR1) and human ROR2 (hROR2). C-terminal His$_6$ or His$_6$Myc tagged VNARs were expressed.

| VNAR | Expression System | hROR1 | | | hROR2 |
|---|---|---|---|---|---|
| | | Ka ($M^{-1}s^{-1}$) | Kd ($s^{-1}$) | KD (nM) | |
| B1 | *E. coli* | 6.29E+05 | 7.93E−04 | 1.6 | No binding |
| B1 | HEK293 | 5.36E+05 | 2.26E−03 | 0.63 | No binding |
| P3A1 | *E. coli* | 2.47E+06 | 4.42E−02 | 19.1 | No binding |
| CPF7 | *E. coli* | 2.33E+06 | 2.96E−02 | 13.6 | No binding |
| E7 | *E. coli* | 1.11E+06 | 1.18E−02 | 11.1 | No binding |
| D3 | *E. coli* | 2.09E−05 | 3.24E−02 | 159.1 | No binding |
| D3 | HEK293 | 1.39E+06 | 7.52E−02 | 54.5 | No binding |
| E9 | HEK293 | 4.23E+05 | 4.45E−02 | 136.6 | No binding |
| P3A1-[G$_4$S]$_5$-P3A1 | HEK293 | 4.9E+06 | 1.12E−03 | 0.30 | No binding |
| D3-[G$_4$S]$_5$-D3 | *E. coli* | 2.95E+06 | 3.38E−03 | 2.33 | No binding |
| P3A1-[G$_4$S]$_5$-B1 | *E. coli* | 3.13E+06 | 2.08E−03 | 1.0 | No binding |
| P3A1-[G$_4$S]$_3$-B1 | *E. coli* | 1.09E+06 | 2.84E−03 | 2.7 | No binding |
| P3A1-[G$_4$S]$_7$-B1 | *E. coli* | 1.49E+06 | 6.44E−03 | 4.3 | No binding |
| 2V | *E. coli* | No binding | No binding | No binding | No binding |
| 2V-[G$_4$S]$_5$-2V | *E. coli* | No binding | No binding | No binding | No binding |

TABLE 4

SPR data for binding to mouse ROR1 (mROR1) and rat ROR1 (rROR1)

| | | mROR1 | | | rROR1 | | |
|---|---|---|---|---|---|---|---|
| VNAR | Expression System | Ka ($M^{-1}s^{-1}$) | Kd ($s^{-1}$) | KD (nM) | Ka ($s^{-1}$) | Kd ($M^{-1}s^{-1}$) | KD (nM) |
| B1 | E. coli | 4.32E+05 | 2.09E−03 | 5.2 | 1.2E+05 | 1.11E−02 | 94.5 |
| B1 | HEK293 | 7.2E+05 | 1.51E−03 | 2.18 | 1.16E+05 | 6.51E−03 | 56.5 |
| P3A1 | E. coli | 2.95E+06 | 4.08E−02 | 14.3 | 2.86E+06 | 4.5E−02 | 17.7 |
| CPF7 | E. coli | 2.26E+06 | 3.2E−02 | 19.1 | 7.72E+05 | 3.66E−02 | 68.6 |
| E7 | E. coli | 1.41E+06 | 2.0E−03 | 1.4 | ND | ND | ND |
| P3A1-[$G_4S$]$_5$-P3A1 | HEK293 | 4.17E+06 | 1.45E−03 | 0.396 | 3.18E+06 | 1.73E−03 | 0.57 |
| 2V | E. coli | No binding | No binding | No binding | No binding | No binding | No binding |
| 2V-[$G_4S$]$_5$-2V | E. coli | No binding | No binding | No binding | No binding | No binding | No binding |

VNAR proteins have been developed, which bind with high affinity to human ROR1 ECD in monomeric and multimeric formats (both homo and hetero dimeric forms), show no binding to the closely related family member human ROR2 and cross react with high affinity to mouse and rat orthologues of ROR1. Reformatting the P3A1 and D3 proteins as dimers significantly increased the binding affinity to human ROR1 with a significant reduction in the dissociation rate constants being observed.

The binding of a chemically conjugated B1 homodimer to hROR1 was also assessed by ELISA. To generate this molecule a B1 derivative was generated with a unique C-terminal thiol functionality through chemical cleavage of the corresponding B1-intein fusion protein precursor with cysteamine. Intermolecular disulphide bond formation was used to covalently link the C-termini of the two proteins to generate a homodimer of unnatural but defined topology (B1-S—S-B1, FIG. 7C). Binding of the B1-S—S-B1 to hROR1 was compared to the B1 monomer by ELISA.

In brief, ELISA method as follows. Wells coated with 100 ng antigen and incubated, covered, at room temperature for 2 hr. Plates washed 3×400 ul per well with PBST (PBS+0.05% Tween 20 (v/v)), then blocked with 4% skimmed milk powder (w/v) in PBST for 1 hour at 37° C. Plates washed as before plus additional wash in PBS alone. Binding proteins were diluted in 4% milk PBST and incubated overnight at 4° C. Plates washed 3× with PBST, 3×PBS and binding detected using appropriate secondary detection antibody in 4% milk PBST, room temperature 1 hour. Secondary antibodies used include:

Anti-c-Myc, HRP (Invitrogen #R951-25)
Rabbit anti-Human IgG H&L, HRP (Abcam #ab6759)
Rabbit anti-Mouse IgG H&L, HRP (Abcam #ab97046)
Mouse anti-polyHis, HRP (Sigma #A7058)

Plates washed 3× with PBST. 100 μL TMB substrate (Thermo #34029) added and reaction allowed to proceed at r.t. for 10 mins. 100 μL of 2M H2504 added to quench the reaction. Plate centrifuged briefly before absorbance at 450 nm read on a CLARIOstar plate reader (BMG Labtech). Whilst B1 monomer and the C-terminal thiol derivative binds strongly to human ROR1, an increase in human ROR1 binding was observed for the chemically linked B1-S—S-B1 dimer (FIG. 8).

Example 4—Anti-ROR1 VNAR Characterisation—Cell Binding and Internalisation by Flow Cytometry Cell Surface Binding Adherent human cancer cells were detached from tissue culture flasks by incubating with 0.1% EDTA/PBS solution at 37° C. for ~10 minutes or until cells detached easily. Cells were re-suspended in 5 ml ice-cold PBS/2% FCS in 15 ml tubes and centrifuged at 1500 rpm for 5 mins at 4° C. Supernatant was removed and the cell pellet re-suspended in 1-2 ml of PBS/2% FCS. A cell count was performed using a Z1 Coulter Particle Counter (Beckman Coulter) and 5×10^5 cells were aliquoted per test sample. Cells were incubated with 100 μl of either VNAR ($His_6$Myc tagged), VNAR-Fc molecules or ROR1 mAb and IgG controls for 1 hour on ice. Excess VNAR, VNAR-Fc or mAb was removed by adding 5 ml of ice-cold PBS/2% FCS, followed by centrifugation at 1500 rpm for 5 mins at 4° C. The supernatant was removed and a second wash performed by re-suspending the cell pellet in 1 ml of ice-cold PBS/2% FCS and adding a further 4 ml of ice-cold PBS/2% FCS. Samples were again centrifuged at 1500 rpm for 5 min at 4° C. Supernatant was removed and excess liquid removed by blotting the tubes on tissue paper. Appropriate secondary antibodies were used to detect bound VNAR ($His_6$Myc), VNAR-hFc, VNAR-mFc or ROR1 mAb (PE-anti-Myc tag antibody (CST), PE-anti-human antibody (JIR labs/Stratech), and PE-anti-mouse antibody (JIR/Stratech) respectively). Cells were incubated with chosen secondary antibody for 30 min on ice. Cells were washed to remove excess antibody as described earlier. Cell pellets were re-suspended in 0.5 ml of ice-cold PBS/2% FCS and left on ice in the dark prior to analysis on either a FACS Calibur (BD Biosciences) or an Attune NxT (ThermoFisher) flow cytometer.

Binding of VNARs to a Panel of Cancer Cell-Lines

FIG. 9 shows representative flow cytometry histograms for binding of anti ROR1 VNARs binding to the ROR1$^{hi}$ A549 lung adenocarcinoma cells.

Figure 13:
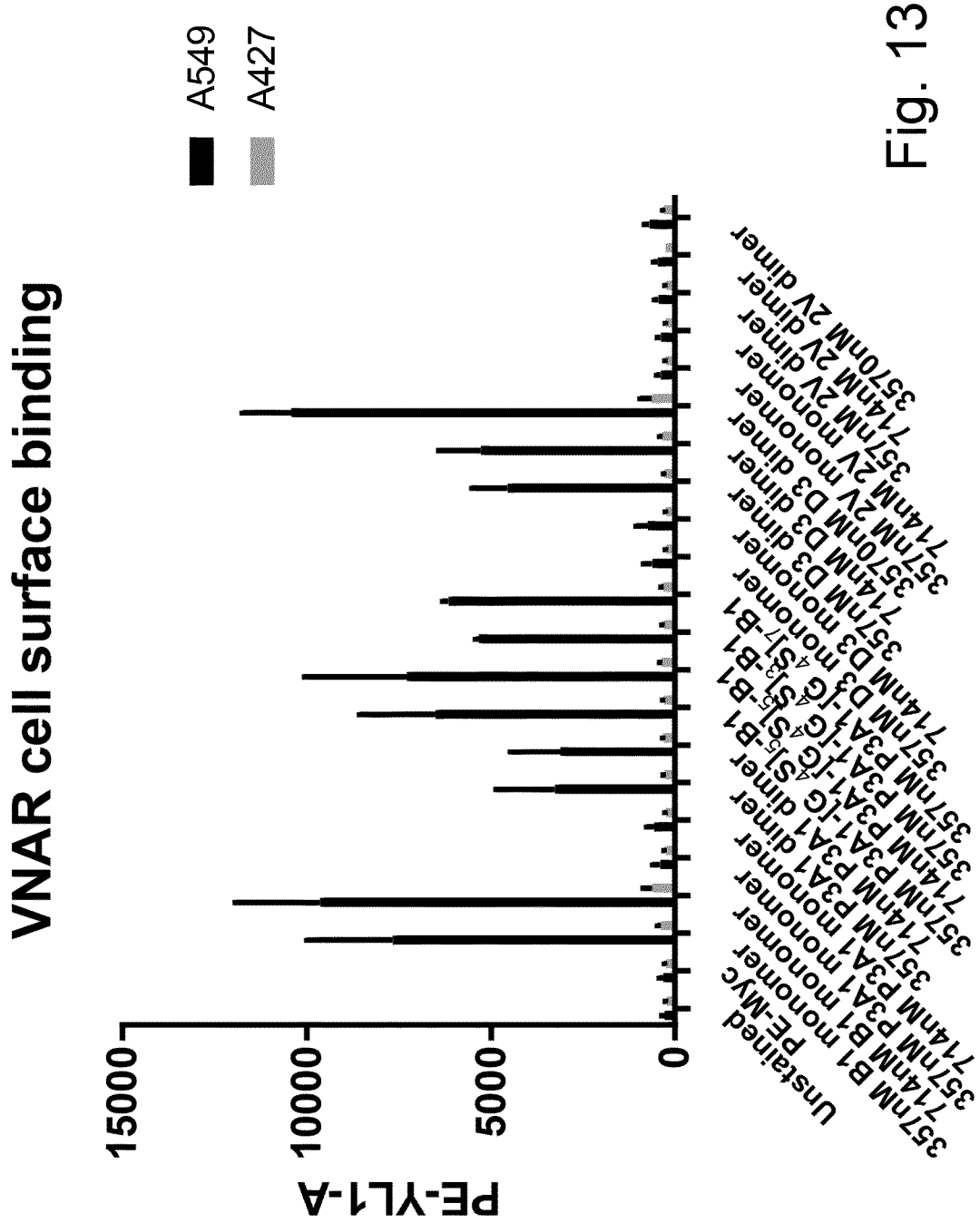
FIG. 13: VNAR cell surface binding to A549 (ROR1$^{hi}$) vs A427 (ROR1$^{low}$) lung cancer cell lines by flow cytometry.

FIG. 13 shows the binding of different VNARs to the ROR1$^{hi}$ A549 lung adenocarcinoma cells and the ROR1$^{low}$ lung cancer cell-line A427 by flow cytometry at a fixed concentration of protein. Table 5 shows a summary of flow cytometry data for binding of VNAR proteins to a variety of ROR1 and ROR1$^{low}$ cancer cell-lines.

TABLE 5

Relative ranking of VNAR cell surface binding in human cancer cell lines, ascertained by flow Cytometry.

Based on Median (YL1-PE) or Geo Mean (FL2-PE)

| Molecule | A549 (ROR1$^{hi}$) | A427 (ROR1$^{low}$) | MDA-MB-231 (ROR1$^{hi}$) | T47D (ROR1$^{low}$) | HT-29 (ROR1$^{hi}$) | Colo205 (ROR1$^{low}$) |
|---|---|---|---|---|---|---|
| B1 | +++++ | + | +++ | ++ | +++ | + |
| E7 | ++++ | + | +++ | ++ | +++ | + |
| P3A1 | + | − | + | +/− | + | − |
| CPF7 | ++ | − | + | +/− | + | − |
| P3A1-[G$_4$S]$_5$-P3A1 dimer | +++ | − | ++ | / | / | / |
| CPF7-[G$_4$S]$_5$-CPF7 dimer | +++ | ++ | / | / | / | / |
| P3A1-[G$_4$S]$_5$-B1 | ++++ | − | +++ | / | / | / |
| D3 | + | − | / | / | / | / |
| D3-[G$_4$S]$_5$-D3 dimer | ++++ | − | ++ | / | / | / |
| 2V | − | − | − | − | − | − |
| 2V-[G$_4$S]$_5$-2V dimer | − | − | − | − | − | − |

Number of
'+' corresponds to binding strength.
'−' indicates no binding.
'/' not determined in this cell line.

Robust binding of the VNARs to ROR1 expressing cancer cell-lines is observed as compared to the ROR1$^{low}$ cancer cell-lines where little to no staining was observed for the majority of the ROR1 binding VNARs tested.

The cell-surface staining for P3A1-P3A1 is not as strong as for B1 or D3-D3 proteins, which may reflect differences in the epitopes of these binders and that in the cellular context some regions of the extracellular domain of ROR1 are potentially more accessible for binding than others.

Cell-Surface Staining Following Incubation at 37° C. Vs 4° C.

Briefly, 5×10^5 MDA-MB-231 cells were incubated with VNAR, VNAR-Fc, ROR1 2A2 mAb or IgG1 control for 1 hr on ice. Cells were washed twice by addition of 5 ml of ice-cold PBS/2% FCS followed by centrifugation at 1500 rpm for 5 mins at 4° C. Following the final centrifugation step, excess supernatant was removed and the tubes blotted on tissue paper. Each cell pellet was re-suspended in 200 μl of PBS/2% FCS and either placed on ice or at 37° C. for 2 hours. Bound VNAR (His$_6$Myc tagged), VNAR-hFc, VNAR-mFc or ROR1 2A2 mAb was detected using either PE-conjugated anti-Myc tag antibody (CST), PE-conjugated anti-human antibody (JIR/Stratech) or PE-conjugated anti-mouse antibody (JIR/Stratech). Loss of signal at 37° C. with respect to samples incubated on ice is indicative of ROR1 internalisation.

Figure 14:
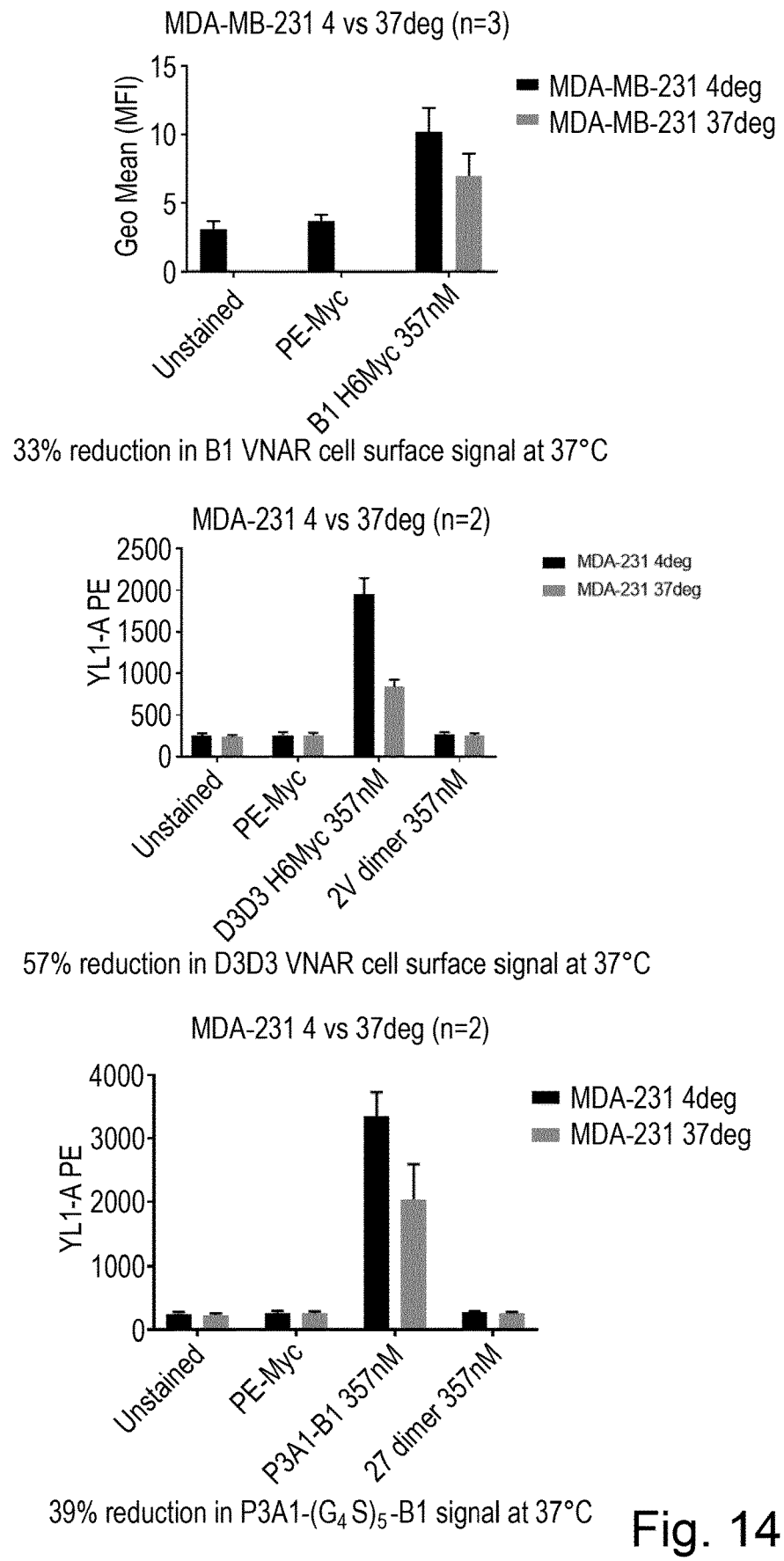
FIG. 14: Cell surface binding of VNARs to MDA-MB-231 breast cancer cells for 2 hrs at 4° C. or 37° C. Loss of cell surface signal at 37° C. is suggestive of ROR1 internalisation. VNAR binding was detected using PE-anti Myc tag Ab (CST) and analysed using a BD Biosciences FACS Calibur (B1) or a ThermoFisher Attune NxT flow cytometer.

A decrease in cell-surface binding after incubation at 37° C. versus 4° C. was observed for antiROR1 VNAR constructs both as monomer and as multimers, comprising the same or different VNAR binding modules, (FIG. 14), which is consistent with binding and internalisation of the proteins by ROR1.

Example 5—Characterisation of Anti-ROR1 VNAR-Fc Fusion Proteins

Binding to ROR1 and ROR2 by SPR and Cell Surface Binding and Internalisation

ROR1 binding VNARs were expressed fused to the N terminus of mouse IgG2a Fc (mFc) and the N terminus and C-terminus of human IgG1 (hFc) via standard GlySer linkers. Fusion of the human IgG1 Fc were also generated whereby Ser252 in the Fc region (Kabat numbering) was replaced with a Cys (FIG. 10).

Binding to ROR1 and ROR2 by SPR

Using the procedures outlined above the binding of VNAR-Fc fusions to human, mouse and rat ROR1 and human ROR2 were determined by SPR.

TABLE 6

SPR data for binding of VNAR-Fc fusions to human ROR1 and human ROR2

| Molecule | hROR1 | | | hROR2 |
|---|---|---|---|---|
| | Ka (M$^{-1}$s$^{-1}$) | Kd (s$^{-1}$) | KD (nM) | |
| B1 mFc | 4.19E+05 | 3.356E−04 | 0.8 | No binding |
| 2V mFc | No binding | No binding | No binding | No binding |
| B1 hFc | 3.08E+06 | 9.53E−05 | 0.032 | No binding |
| P3A1 hFc | 1.07E+07 | 5.64E−04 | 0.084 | No binding |
| D3 hFc | 1.21E+06 | 2.88E−03 | 2.6 | No binding |
| E9 hFc | 7.07E+05 | 3.64E−03 | 5.3 | No binding |
| D3-D3 hFc | 4.96E+06 | 9.88E−04 | 0.25 | No binding |
| hFc-P3A1 | 2.38E+06 | 7.76E−04 | 0.35 | No binding |
| hFc-D3 | 1.10E+06 | 2.35E−03 | 2.37 | No binding |
| hFc-D3-D3 | 2.35E+06 | 1.01E−03 | 0.49 | No binding |

TABLE 6-continued

SPR data for binding of VNAR-Fc
fusions to human ROR1 and human ROR2

| Molecule | hROR1 | | | hROR2 |
|---|---|---|---|---|
| | Ka (M$^{-1}$s$^{-1}$) | Kd (s$^{-1}$) | KD (nM) | |
| 2V hFc | No binding | No binding | No binding | No binding |
| 2V-2V hFc | No binding | No binding | No binding | No binding |

As shown in Table 6 anti ROR1 VNAR-Fc proteins bind with high affinity to human ROR1, with no binding to human ROR2 observed. Strong binding to mouse and rat ROR1 ECD was also observed. As VNAR-Fc fusions, a significant decrease in the KID apparent values for ROR1 binding is observed with respect to the corresponding VNAR monomers. This is consistent with these VNAR-Fc fusions binding in a bivalent fashion to the ROR1-chip surface in the SPR experiments. Both N- and C-terminal VNAR Fc fusions bind with high affinity to human ROR1 but do not bind to human ROR2.

Binding of VNARs to Cancer Cell-Lines

Binding of the VNAR-Fc fusions to the surface of a panel of cancer cell lines was measured by flow cytometry using the methods outlined previously. FIG. 15 shows the binding of different VNAR-Fc fusions to the ROR1$^{hi}$ A549 lung adenocarcinoma cells and the ROR1$^{low}$ lung cancer cell-line A427 by flow cytometry at a fixed concentration of protein.

Table 7 summarises the binding data for VNAR-Fc proteins with a variety of ROR1$^{hi}$ cancer cell-lines.

TABLE 7

Relative ranking of VNAR hFc molecule cell surface binding in ROR1$^{hi}$ human cancer cell lines. The number of '+' indicates the strength of binding. '−' indicates no binding. '/' indicates that it has not been determined. hFc molecules were detected using a PE-anti-human antibody (Jackson Immune Research/Stratech) and a ThermoFisher Attune NxT flow cytometer.

| | Based on Median (YL1-PE) | | | |
|---|---|---|---|---|
| Molecule | A549 | MDA-MB-231 | PC-9 | NCI-H1975 |
| B1 hFc | ++++ | +++++ | +++++ | +++++ |
| P3A1 hFc | ++ | +++ | ++ | ++ |
| D3 hFc | + | ++ | / | / |
| E9 hFc | + | / | / | / |
| D3-D3 hFc | ++ | ++++ | / | / |
| 2V hFc | − | − | − | − |
| 2V-2V hFc | + | / | / | / |

Robust binding of the VNARs to ROR1 expressing cancer cell-lines is observed as compared to the ROR1$^{low}$ cancer cell-lines, where little to no staining was detected for the majority of the ROR1 binding VNARs tested.

Differences in the mean cell-surface staining may indicate that different regions of ROR1 may be more accessible than others when the protein is expressed on the cell surface. For targeting less accessible regions of ROR1 on cancer cells, it would be advantageous to use small protein binders such as VNARs as opposed to large antibodies that will be sterically occluded.

Cell-Surface Staining Following Incubation at 37° C. Vs 4° C.

The binding of VNAR-Fc fusions to MDA-MB-231 cells after incubation at 37° C. or 4° C. was determined by flow cytometry using the methods described previously. For the B1-hFc, P3A1-hFc, D3-hFc and D3D3-hFc proteins tested there was a loss of cell-surface staining after incubation at 37° C. versus 4° C. (FIG. 16), consistent with binding and internalisation of these VNAR-hFc fusion proteins.

Internalisation by Immunofluorescence Following Incubation at 37° C. Vs 4° C.

The cellular localisation of human IgG1 Fc and mouse IgG2a Fc fusion proteins can be detected by immunofluorescence using fluorescently labelled secondary antibodies targeting these domains. Immunofluorescence methods were used to detect internalisation of VNAR-Fc by ROR1 on cancer cells.

Black, clear bottom 96-well plates (Greiner) were coated with 100 μg/ml Collagen I (Sigma) to aid cell attachment. Cells were seeded in complete growth media (Gibco) into the coated 96 well plates and incubated at 5% CO2, 37° C. for 24 hr. The media was removed and replaced with serum-free media (Gibco) on the following day and left overnight. On the following morning, media was removed and cells were treated with various concentrations of VNAR-Fc, ROR1 2A2 mAb or IgG1 negative control (both BioLegend). Plates were incubated on ice for 1 hour. Treatments were removed and replaced with 104l of PBS/2% FCS per well. One plate was kept on ice and the other was placed at 37° C., 5% CO2 for 2 hours. Following this 2 hour incubation, the PBS/2% FCS solution was removed and cells were fixed with 4% Paraformaldehyde in ice cold PBS for 20 min on ice. The PFA solution was removed and replaced with 0.05% Saponin (Sigma) made up in PBS/2% FCS for 15 min at room temperature. This step permeabilises the cell membranes. Secondary antibody staining was performed using; AF488-anti-human Ab (1:250; ThermoFisher) to detect VNAR-hFc fusion proteins and AF488-anti-mouse Ab (1:500; CST) to detect the VNAR-mFc fusion molecule and ROR1 2A2 mAb. All secondary antibody working stocks were made up in 0.05% Saponin/PBS/2% FCS. Plates were incubated at 4° C. overnight in the dark. On the following day, secondary AF488-conjugated antibodies were removed and the cells were washed ×3 using 0.05% Saponin/PBS/2% FCS. Lamp-1 antibody (1:200; CST) or EEA1 antibody (1:50; Santa Cruz) were added to detect lysosome and early endosome compartments respectively. Plates were incubated in the dark at room temperature for 2 hours. The Lamp-1 and EEA1 antibodies were then removed and the cells were washed ×3 with 0.05% Saponin/PBS/2% FCS. AF647-anti rabbit antibody (1:1000; CST) was then added to detect Lamp1 and EEA1 antibody binding. A further incubation in the dark at room temperature for 2 hours was performed before removing the AF647-secondary antibody and washing the cells ×3 with 0.05% Saponin/PBS/2% FCS. Cell nuclei were stained using 10 μM Hoechst reagent (Sigma) in 0.05% Saponin/PBS/2% FCS for 20 min at room temperature in the dark. Finally, this solution was removed and replaced with PBS. Plates were stored at 4° C. in the dark prior to imaging using a GE Healthcare InCell 2000 instrument.

Internalisation of B1 hFc and B1 mFc was observed in MDA-MB-231 breast cancer cells following incubation at 37° C. for 2 hours. The VNAR-Fc-ROR1 complex appears to overlay with Lamp-1 and EEA1 staining following internalisation which is suggestive of ROR1 cellular trafficking via early endosomal and lysosomal compartments. ROR1-VNAR-Fc staining remained predominantly at the cell surface when the samples were incubated on ice for 2 hours. No cell surface binding or internalisation was observed following incubation with 2V Fc protein (non-binding negative control VNAR). B1-hFc and B1-mFc were not internalised by the ROR1$^{low}$) lung cancer cell-line A427.

Example 6—Humanisation and Further Engineering

A number of humanised sequence derivatives of two lead ROR1 binding VNARs were generated using two different strategies.

Humanised sequences were designed based on the human germ line Vκ1 sequence, DPK-9. For example, in P3A1 V1 the framework regions 1, 3 and 4 of the VNAR were mutated to align with the framework regions of DPK-9.

The second strategy involved grafting the binding loops of the ROR1 binding VNARs onto a previously humanised VNAR framework (Kovalenko et al JBC 2013 288(24) 17408-17419; WO2013/167883). For the first construct (G1) only the CDR1 and CDR3 loops were grafted. The second construct (G2) had both the CDRs and HV loops grafted.

Humanised D3 sequences were designed using a combination of approaches.

Examples of humanised/grafted VNAR sequences:

B1 G1
(SEQ ID NO: 45)
TRVDQSPSSLSASVGDRVTITCVLTGANYGLASTYWYRKNPGSSNKEQIS
ISGRYSESVNKGTKSFTLTISSLQPEDSATYYCRAYPWGAGAPWLVQWYD
GAGTKVEIK

B1 G2
(SEQ ID NO: 46)
TRVDQSPSSLSASVGDRVTITCVLTGANYGLASTYWYRKNPGSSNQERIS
ISGRYSESVNKRTMSFTLTISSLQPEDSATYYCRAYPWGAGAPWLVQWYD
GAGTKVEIK

P3A1 V1
(SEQ ID NO: 47)
TRVDQSPSSLSASVGDRVTITCVLTDTSYGLYSTSWFRKNPGTTDWERMS
IGGRYVESVNKGAKSFTLTISSLQPEDFATYYCKAREARHPWLRQWYDGA
GTKVEIK

P3A1 G1
(SEQ ID NO: 48)
TRVDQSPSSLSASVGDRVTITCVLTDTSYGLYSTYWYRKNPGSSNKEQIS
ISGRYSESVNKGTKSFTLTISSLQPEDSATYYCRAREARHPWLRQWYDGA
GTKVEIK

P3A1 G2
(SEQ ID NO: 49)
TRVDQSPSSLSASVGDRVTITCVLTDTSYGLYSTYWYRKNPGTTDWERMS
IGGRYVESVNKGAKSFTLTISSLQPEDSATYYCRAREARHPWLRQWYDGA
GTKVEIK

D3 humanised ADV1
(SEQ ID NO: 50)
ASVNQSPSSLSASVGDRVTITCVLTDTSYGLYSTSWFRKNPGTTDWERMS
IGGRYSESVNKGAKSFTLTISSLQPEDSATYYCKAQSGMAISTGSGHGYN
WYDGAGTKVEIK D3 humanised ADV2
(SEQ ID NO: 51)
TRVDQSPSSLSASVGDRVTITCVLTDTSYGLYSTSWFRKNPGTTDWERMS
IGGRYSESVNKGAKSFTLTISSLQPEDSATYYCKAQSGMAISTGSGHGYN
WYDGAGTKVEIK D3 humanised ADV3
(SEQ ID NO: 52)
ASVNQSPSSASASVGDRLTITCVLTDTSYGLYSTSWFRKNPGTTDWERMS
IGGRYSESVNKGAKSFTLTISSLQPEDSATYYCKAQSGMAISTGSGHGYN
WYDGAGTKLEVK B1 humanised V5
(SEQ ID NO: 53)
ASVDQSPSSLSASVGDRVTITCVVTGANYGLAATYWYRKNPGSSNQERIS
ISGRYSESVNKRTMSFTLTISSLQPEDSATYYCKAYPWGAGAPWLVQWYD
GAGTKVEIK B1 humanised V7
(SEQ ID NO: 54)
ASVDQSPSSASASVGDRLTITCVVTGANYGLAATYWYRKNPGSSNQERIS
ISGRYSESVNKRTMSFTLTISSLQPEDSATYYCKAYPWGAGAPWLVQWYD
GAGTKLEVK DNA encoding the humanised constructs was codon optimised for expression in *E. coli* and synthesised by GeneArt (Thermo). P3A1 sequences were designed as dimers with a $[G_4S]_5$ linker connecting the VNAR domains. All humanised sequences were generated with the following C terminal $His_6$myc tag:

(SEQ ID NO: 97)
QASGAHHHHHHGAEFEQKLISEEDLG

DNA encoding these proteins was sub cloned into the intein expression vectors, expressed in *E. coli* and purified as described previously in "Typical method for expression of VNAR intein fusion proteins" section.

Further humanised versions of D3 were created as follows:

D3 humanised EL V1
(SEQ ID NO: 55)
ASVNQSPSSLSASVGDRVTITCVLTDTSYGLYSTSWFRKNPGTTDWERMS
IGGRYVESVNKRAKSFSLRIKDLTVADSATYYCKAQSGMAISTGSGHGYN
WYDGAGTKVEIK D3 humanised EL V2
(SEQ ID NO: 56)
ASVNQSPSSLSASVGDRVTITCVLTDTSYGLYSTSWFRKNPGTTDWERMS
IGGRYVESVNKRAKSFTLTISSLQPEDFATYYCKAQSGMAISTGSGHGYN
WYDGAGTKVEIK D3 humanised EL V3
(SEQ ID NO: 57)
ASVNQSPSSLSASVGDRVTITCVLTDTSYGLYSTSWFRKNPGTTDWERMS
IGGRFSGSGSKRAKSFTLTISSLQPEDFATYYCKAQSGMAISTGSGHGYN
WYDGAGTKVEIK D3 humanised EL V4
(SEQ ID NO: 58)
ASVNQSPSSLSASVGDRVTITCVLTDTSYGLYSTSWYQQKPGTTDWERMS
IGGRYVESVNKRAKSFTLTISSLQPEDFATYYCKAQSGMAISTGSGHGYN
WYDGAGTKVEIK D3 humanised EL V5
(SEQ ID NO: 59)
ASVNQSPSSLSASVGDRVTITCVLTDTSYGLYSTSWYQQKPGTTDWERMS
IGGRFSGSGSKRAKSFTLTISSLQPEDFATYYCKAQSGMAISTGSGHGYN
WYDGAGTKVEIK Humanised ROR1 binding VNAR variants demonstrated high affinity binding to human ROR1 by SPR and improved thermal stability. SPR was performed as described previously using human ROR1 ECD-Fc immobilised to the chip surface. Thermal stability assays used Applied Biosystems StepOne Real Time PCR system with the Protein Thermal Shift™ dye kit (Thermo). The assay mix was set up so that the protein was at a final concentration of 20 OA in 20 μL. 5 μL of Thermal Shift™ buffer was added alongside 2.5 uL 8× Thermal Shift™ Dye. Assays were run using the StepOne software and data analysed using Protein Thermal Shift™ software. All data are from first derivative analysis.

TABLE 8

Thermal stability and hROR1 binding data for humanised VNAR variants

| Construct | Tm (° C.) | hROR1 binding (SPR) | | |
|---|---|---|---|---|
| | | Ka (M$^{-1}$s$^{-1}$) | Kd (s$^{-1}$) | K$_D$ (nM) |
| B1 | 54.2 | 7.45E+05 | 6.09E-04 | 0.83 |
| B1G1 | 58.0 | 2.20E+05 | 1.62E-02 | 82.8 |
| B1G2 | 59.9 | 1.85E+05 | 7.90E-03 | 45.9 |
| B1V5 | 46.05 | 5.20E+04 | 3.85E-05 | 0.74 |
| B1V7 | 43.91 | 7.74E+04 | 5.54E-05 | 0.77 |
| P3A1 dimer | 60.7 | 3.78E+05 | 1.17E-03 | 0.30 |
| P3A1 V1 dimer | 48.5 | 4.78E+05 | 8.46E-04 | 0.18 |
| P3A1 G1 dimer | 57.1 | 4.30E+05 | 1.47E-03 | 0.43 |
| P3A1 G2 dimer | 54.0 | 1.88E+05 | 1.19E-03 | 0.77 |
| B1G1-hFc | ND | 2.4E+05 | 2.66E-03 | 11.8 |
| B1G2-hFc | ND | 6.26E+05 | 1.41E-03 | 2.55 |
| D3 ADV1 dimer | 54.66 | 6.36E+05 | 5.67E-03 | 8.92 |
| D3 ADV2 dimer | 56.18 | 6.09E+05 | 1.60E-02 | 26.2 |
| D3 WT | 64.4 | 1.21E+06 | 9.43E-05 | 15.5 |
| D3 AD V2 | 56.98 | 4.58E+04 | 2.36E-03 | 51.6 |
| D3 EL V1 | 53.25 | 1.50E+06 | 1.58E-04 | 16.1 |
| D3 EL V2 | 56.50 | 1.85E+06 | 1.63E-04 | 18.9 |
| D3 EL V4 | 54.1 | 1.38E+06 | 5.45E-04 | 58.5 |

Grafting the HV and/or CDR loops of B1 onto a humanised VNAR framework and substituting P3A1 sequences with regions from the human DPK-9 sequence, yielded substantially engineered proteins that are stable and maintain hROR1 binding with nanomolar and picomolar affinity respectively. Similar approaches yielded humanised variants of D3 that maintained similar binding characteristics as the wild type (WT) VNAR.

Example 7—Epitope Mapping

Binding of Proteins to Deglycosylated Human ROR1

ELISA was used to compare VNAR binding to glycosylated and deglycosylated human ROR1 protein. To generate deglycosylated human ROR1, 0.2 mg/ml protein was incubated overnight at room temperature with 1U PNGaseF (Roche) per 2 μg ROR1 protein. Control, glycosylated human ROR1 was prepared in parallel without adding PNGaseF. SDS PAGE analysis showed shift on PNGaseF treatment, consistent with ROR1 deglycosylation (FIG. 17A).

These ROR1 proteins were used to coat ELISA plates and ELISAs were performed as previously described in the "Anti ROR1 VNAR characterisation" section. VNARs (B1, P3A1-P3A1, D3-D3, B1 mFc) bound equally well to both glycosylated and deglycoylated ROR1 proteins by ELISA (FIGS. 17B & 17C) indicating ROR1 binding is independent of ROR1 glycosylation.

Figure 17:
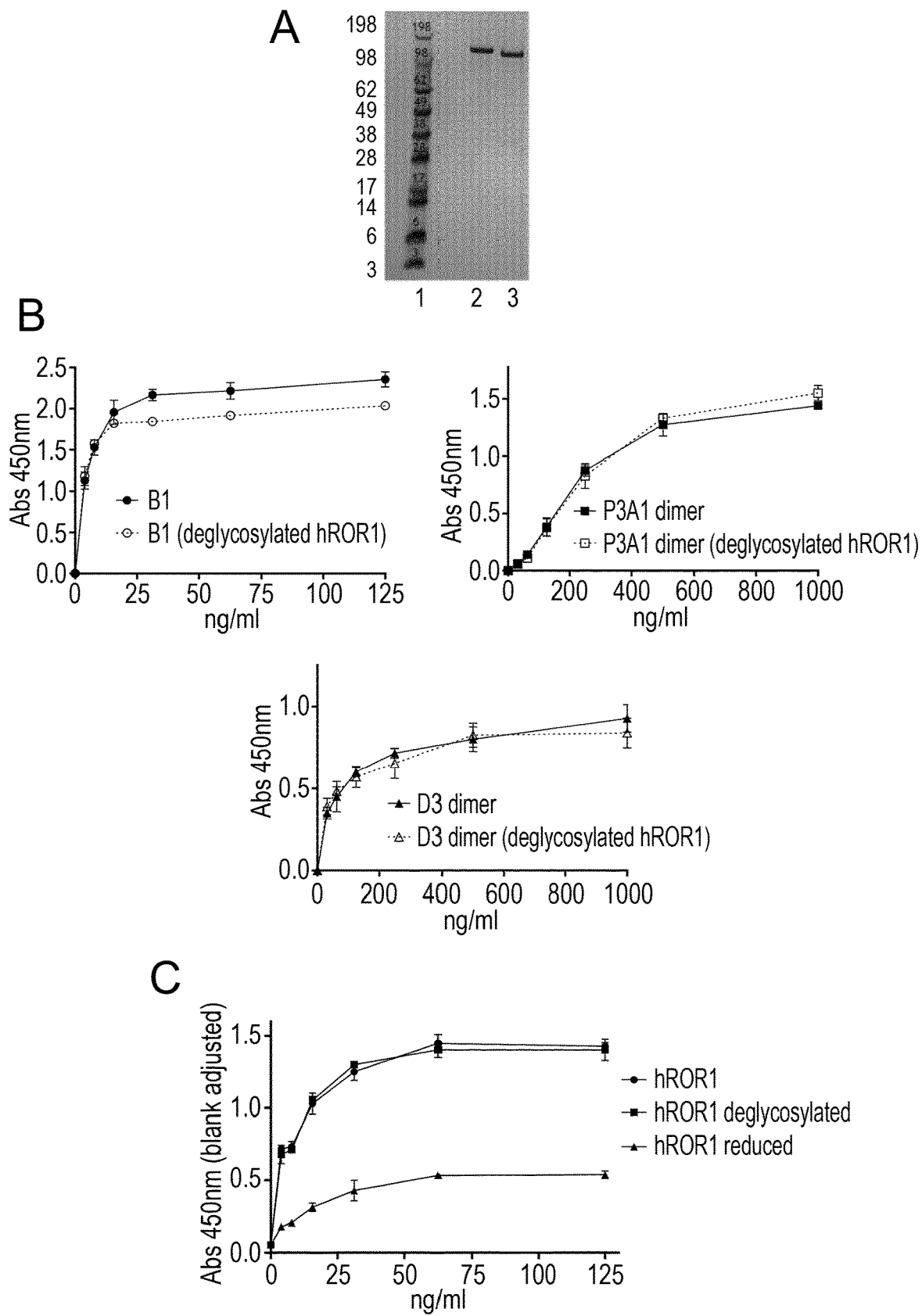
FIG. 17: VNARs bind to human ROR1 independent of glycosylation. A, SDS PAGE analysis of hROR1 (lane 2) and deglycosylated hROR1 (lane 3). Mwt markers (lane 1). B, ROR1 binding VNARs B1, P3A1-P3A1 and D3-D3 bind equally well to deglycosylated hROR1 by ELISA. C, B1 mFc binds equally well to glycosylated and deglycosylated hROR1 by ELISA. Binding to unfolded hROR1 (reduced with 28 mM DTT, 0.5% Sarkosyl) was significantly reduced, consistent with B1 VNAR binding to conformational epitope(s).

Binding of B1 to unfolded hROR1 (reduced with 28 mM DTT, 0.5% Sarkosyl) was significantly reduced, consistent with B1 VNAR binding to conformational epitope(s) (FIG. 17C)

Binding of B1 to ROR1 Ig Domain by SEC

B1 VNAR forms a complex with ROR1 Ig domain by SEC (FIG. 18.1). 1:1 VNAR:ROR1 domain or ROR1 domain pairs was incubated on ice for 30 mins then run on a the Superdex 200 increase 10/300 column (GE Healthcare) in PBS and fractions analysed by SDS-PAGE. Under these conditions, B1 formed a complex with the ROR1 Ig domain.

Binding of VNAR B1 to Non-Glycosylated ROR1 Ig Domain

In order to assess the involvement of glycosylation in the binding of VNAR B1 to ROR1, the ROR1 Ig domain was generated via expression in *E. coli* to produce a non-glycosylated form of the protein.

This non-glycosylated ROR1 Ig domain was then incubated on ice for 30 minutes with excess VNAR B1 (ratio 1:2) and assessed by size exclusion chromatography (SEC) using an analytical size exclusion column (S75 increase 10/300 GL analytical SEC column). Chromatography was carried out in 20 mM Hepes, 150 mM NaCl, pH7.5.

SEC analysis shows a new peak is formed eluting at a volume corresponding to a higher molecular weight species than ROR1 Ig or B1 alone (FIG. 18.2). MS analysis of this earlier elute peak shows that it corresponds to a complex between ROR1 Ig and B1 (FIG. 18.3).

Further Domain Mapping

In order to determine the particular ROR1 domain to which individual VNARs bind, sub-domains and domain pairs of human ROR1 extracellular domain (ECD) were expressed as Fc fusion proteins. Complex formation was then assessed using analytical SEC.

Specifically, the following ROR1 domain fusions were created:

Ig-Fc

Ig-Fz-Fc

Fz-Kr-Fc

Fz-Fc

Kr-Fc

Results of SEC analysis/SDS-PAGE are shown in FIG. 18.4 for (D3), and (P3A1). These data demonstrate that D3 binds to the ROR1 Ig domain, while P3A1 binds to either Fz alone or the Fz-Kr interface.

Epitope Binning Experiments

Competition of binding studies were completed using SPR. Human ROR1 (hROR1) was immobilised to flow channels 1 and 3 (FC1 and FC3) of a COOH$_2$ chip by amine coupling. FC2 was used as the reference channel. A chosen VNAR e.g. B1, P3A1 dimer; or ROR1 2A2 mAb (BioLegend) was then captured to hROR1 on FC1. Test analytes were then assessed for binding to i) hROR1 with either VNAR or ROR1 2A2 mAb previously captured, or ii) to hROR1 in the absence of bound VNAR or mAb. The hROR1 chip surface was regenerated following each test analyte using Glycine pH2. Prior to testing the next analyte, VNAR or ROR1 2A2 mAb was again captured to hROR1 in FC1 and so on. Binding kinetics were determined using QDat software. For non-competing molecules, binding kinetics and sensogram profiles were similar/unaffected to hROR1+/− captured binder. For competing molecules, the sensogram profile and binding kinetics were significantly altered.

Figure 19A:
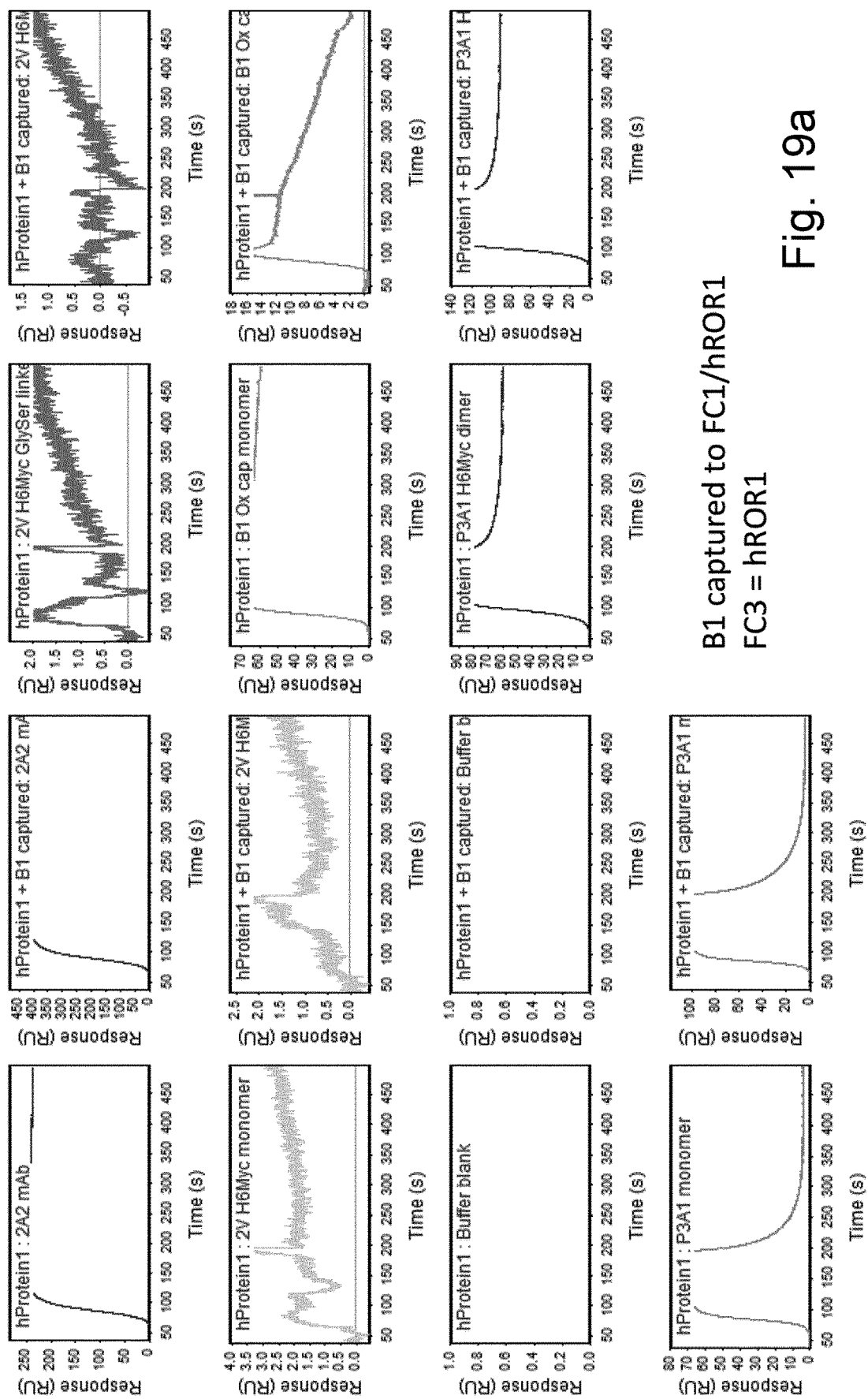
FIG. 19a: SPR sensograms depicting binding of VNARs to hROR1+/− previously captured B1 His$_6$Myc VNAR. 2V monomer or dimer did not bind under any of these conditions.
Figure 19B:
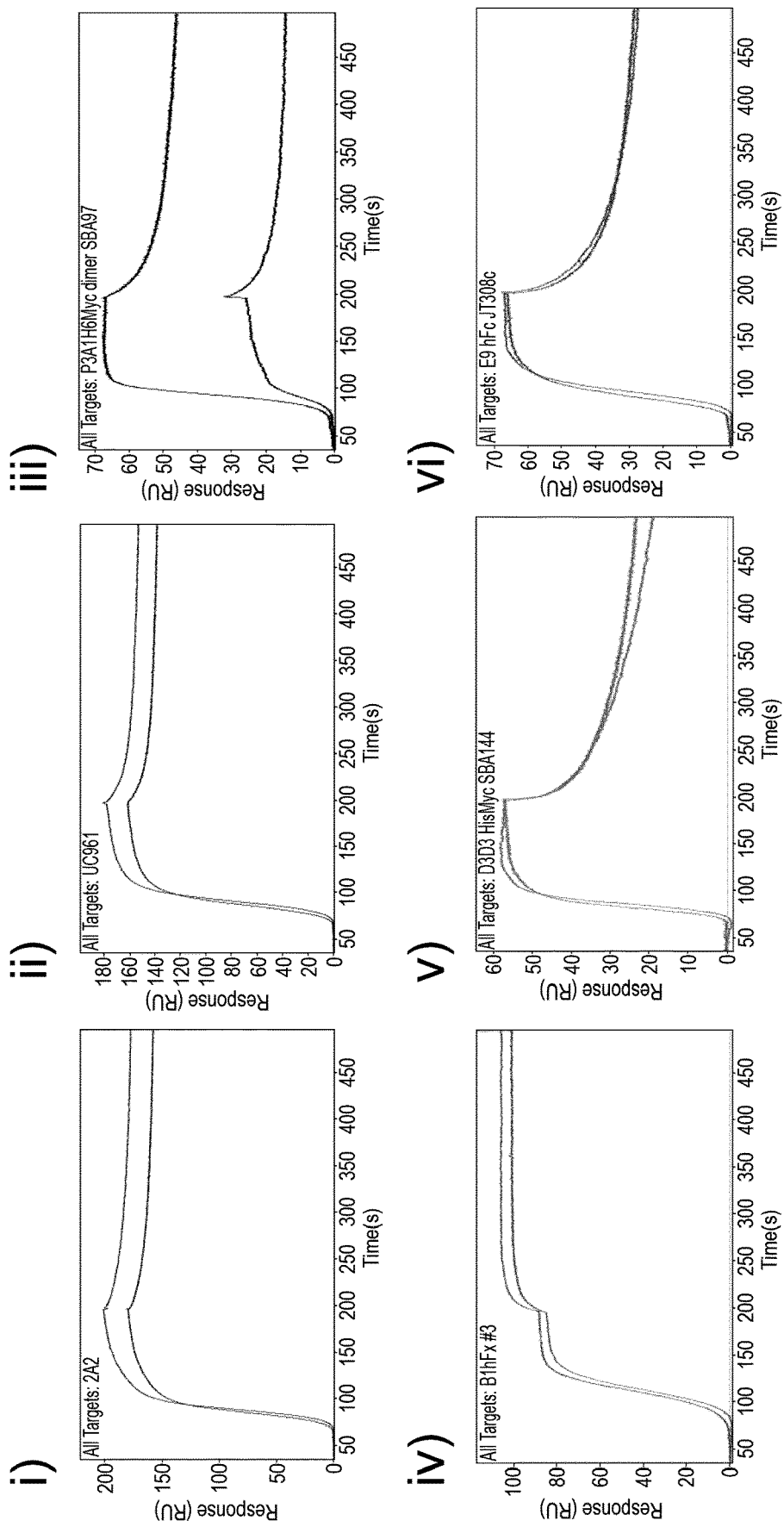
FIG. 19b: Representative SPR sensograms depicting binding of i) ROR1 2A2 mAb, ii) UC961 based mAb, iii) P3A1, iv) B1, v) D3 and vi) E9 to hROR1+/− previously captured P3A1 His$_6$Myc dimer VNAR. No competition of binding to hROR1 was observed other than P3A1 self-competition (iii).

FIG. 19 shows representative sensograms and binding kinetics for binding of the VNARs to human ROR1 without and with prior incubation with B1. The results demonstrated that B1 and P3A1 VNARs do not compete with each other, nor with the ROR1 mAb 2A2 for binding to hROR1. When B1 VNAR was captured to hROR1 on the chip surface, further binding of B1 was significantly hindered, however the binding profiles of P3A1 monomer, P3A1 dimer or ROR1 2A2 mAb to hROR1 were the same in the absence and presence of pre-captured B1 (FIG. 19). The kinetic parameters derived for binding of these molecules to hROR1 in the presence or absence of captured B1 VNAR confirm that they do not compete with B1 (with the exception of B1, which competes with itself as expected).

TABLE 9

Binding kinetic data derived by SPR analysis of VNARs or ROR1 2A2 mAb to hROR1 +/− previously captured B1 VNAR. Data demonstrates that B1 binding does not compete with P3A1 or 2A2. VNARs were expressed with C-terminal His$_6$Myc tags.

| Molecule | hROR1 binding | | | B1 pre-captured to hROR1 | | |
|---|---|---|---|---|---|---|
| | Ka (M$^{-1}$s$^{-1}$) | Kd (s$^{-1}$) | KD (nM) | Ka (M$^{-1}$s$^{-1}$) | Kd (s$^{-1}$) | KD (nM) |
| B1 | 1.04E+06 | 4.40E−04 | 0.424 nM | No/poor binding | | |
| P3A1-P3A1 | 1.63E+06 | 6.28E−04 | 0.385 nM | 1.52E+06 | 5.36E−04 | 0.352 nM |
| P3A1 | 2.58E+06 | 4.11E−02 | 15.9 nM | 1.94E+06 | 3.20E−02 | 16.45 nM |
| ROR1 2A2 mAb (Biolegend) | 9.79E+05 | 2.11E−04 | 0.21 nM | 8.35E+05 | 8.47E−05 | 0.101 nM |

Binding of VNARs, 2A2 mAb or UC-961 based mAb to hROR1 with and without pre-capture of P3A1 derivatives were similarly assessed. The results are summarised in (FIG. 19b and Table 9b), which showed that P3A1 does compete with B1, D3 or E9 or the mAb 2A2 or mAb based on UC-961 (by Kipps/Oncternal, Heavy Chain: SEQ ID NO:98; Light Chain: SEQ ID NO: 99). Table 9c further summarises the findings by SPR for competition of binding studies between the VNARs.

TABLE 9b

Binding kinetic data derived by SPR analysis of VNAR sequences, UC961 based mAb or ROR1 2A2 mAb to hROR1 +/− previously captured P3A1 His$_6$Myc dimer VNAR. Data demonstrates that no competition of binding to hROR1 was observed between P3A1 and the other ROR1 binders, other than P3A1 self-competition

| Molecule | hROR1 binding | | | P3A1 dimer pre-captured to hROR1 | | |
|---|---|---|---|---|---|---|
| | Ka (M$^{-1}$s$^{-1}$) | Kd (s$^{-1}$) | KD (nM) | Ka (M$^{-1}$s$^{-1}$) | Kd (s$^{-1}$) | KD (nM) |
| B1hFc | Strong binder, unable to determine Kd (off-rate) | | | Strong binder, unable to determine Kd (off-rate) | | |
| P3A1 dimer | 2.62E+06 | 1.41E−03 | 0.538 | 7.34E+05 | 2.26E−03 | 3.08 |
| D3 dimer | 1.34E+06 | 3.62E−03 | 2.7 | 1.29E+06 | 4.47E−03 | 3.46 |
| E9hFc | 4.23E+05 | 3.45E−03 | 8.15 | 3.72E+05 | 3.74E−03 | 10.1 |
| UC961-like | 5.77E+06 | 4.51E−04 | 0.078 | 5.48E+06 | 4.44E−04 | 0.081 |
| 2A2 | 1.47E+06 | 3.42E−04 | 0.233 | 1.39E+06 | 3.22E−04 | 0.231 |

TABLE 9c

Summary or results obtained using SPR to determine competition of binding between molecules to hROR1. P3A1 did not compete with any other sequences. B1, D3 and E9 exhibit competition of binding, suggesting these sequences bind to overlapping epitopes of hROR1. Competition of binding to hROR1 by SPR (Yes/No)

| Sequence | B1 | P3A1 | D3 | E9 |
|---|---|---|---|---|
| B1 | YES | NO | YES | YES |
| P3A1 | NO | YES | NO | NO |
| D3 | YES | NO | YES | YES |
| E9 | YES | NO | YES | YES |

Epitope Mapping of Anti-ROR1 VNARs Using Anti-ROR1 Peptides

Figure 20:
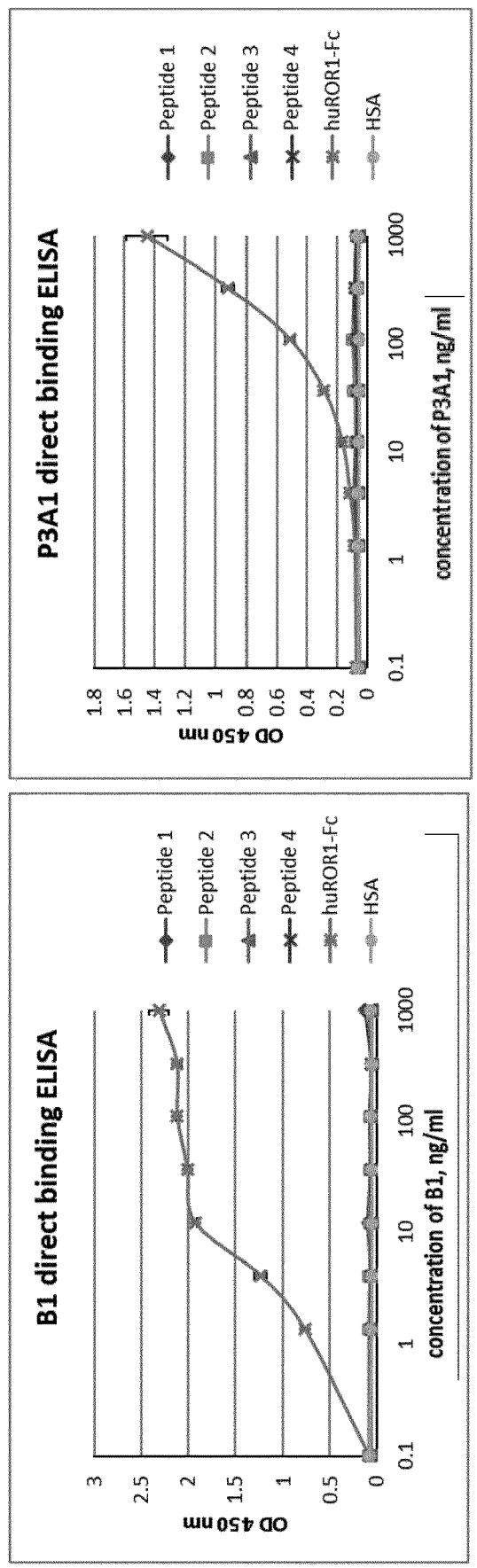
FIG. 20: B1 and P3A1 do not bind to selected linear ROR1 peptides by ELISA. Binding to human ROR1 is included as a positive control.
Figure 21:
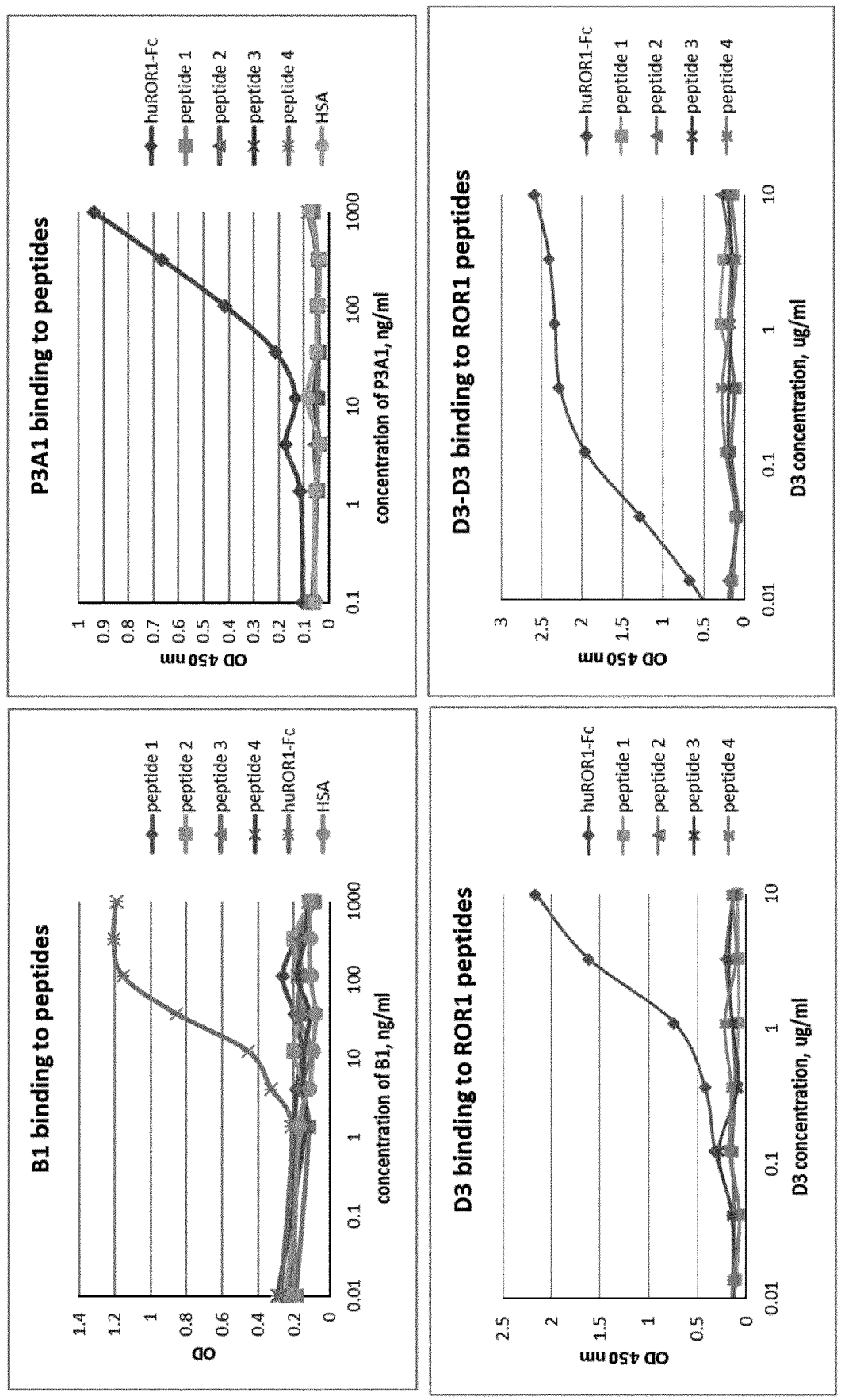
FIG. 21: B1, P3A1, D3 and D3-D3 do not bind to selected linear ROR1 peptides by ELISA. Binding to human ROR1 is included as a positive control.
Figure 21:
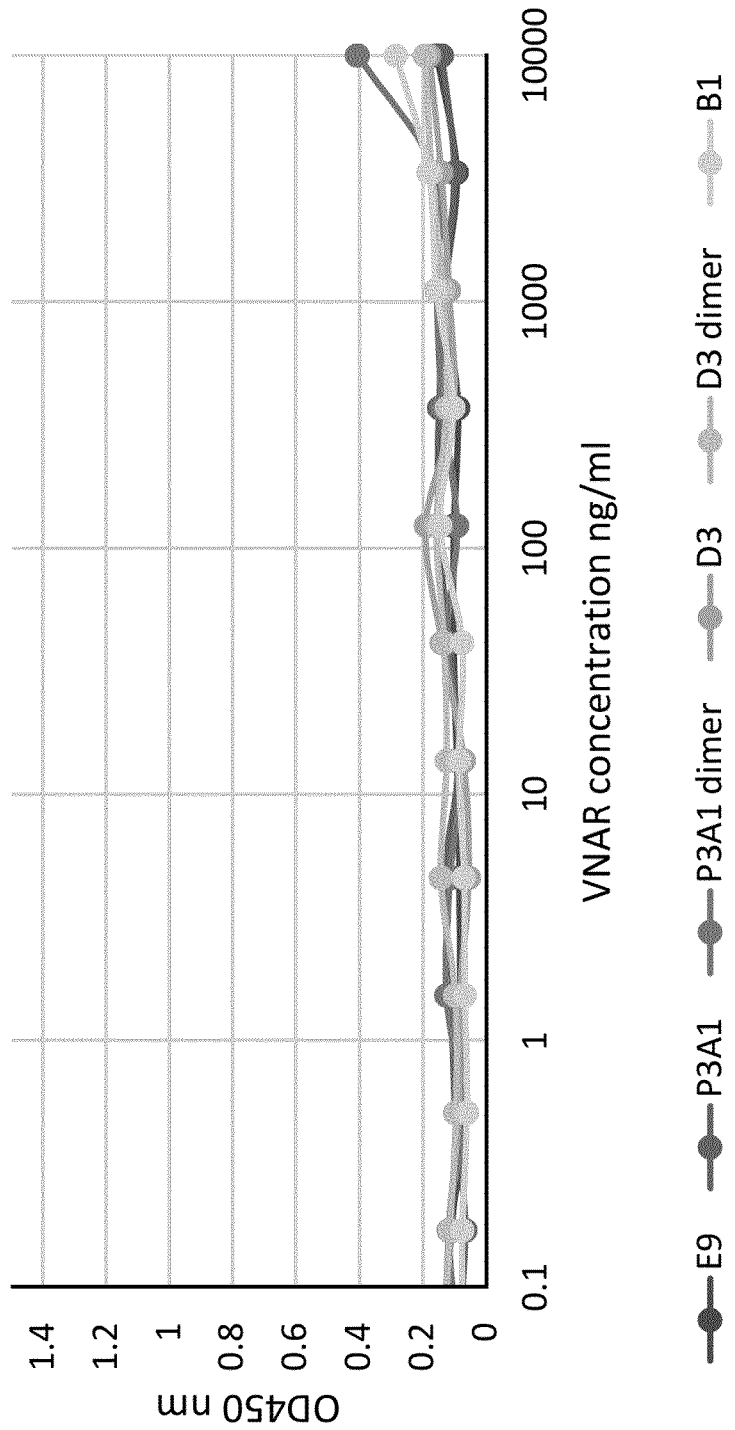
Figure 22:
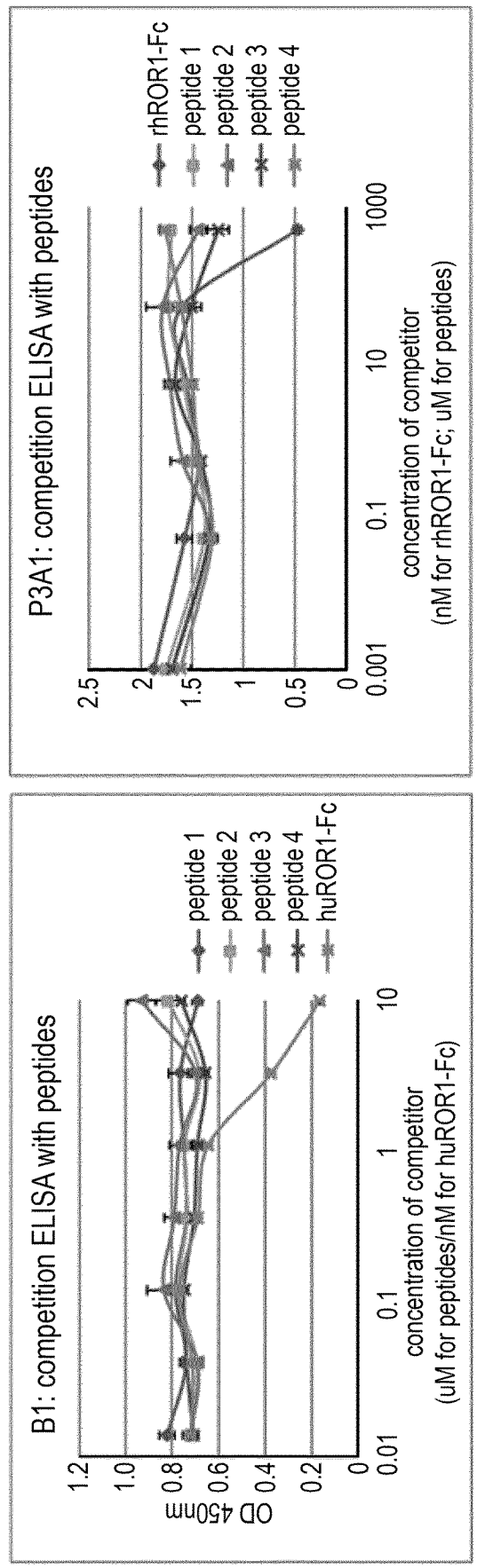
FIG. 22: Competition ELISA experiments.
Figure 22:
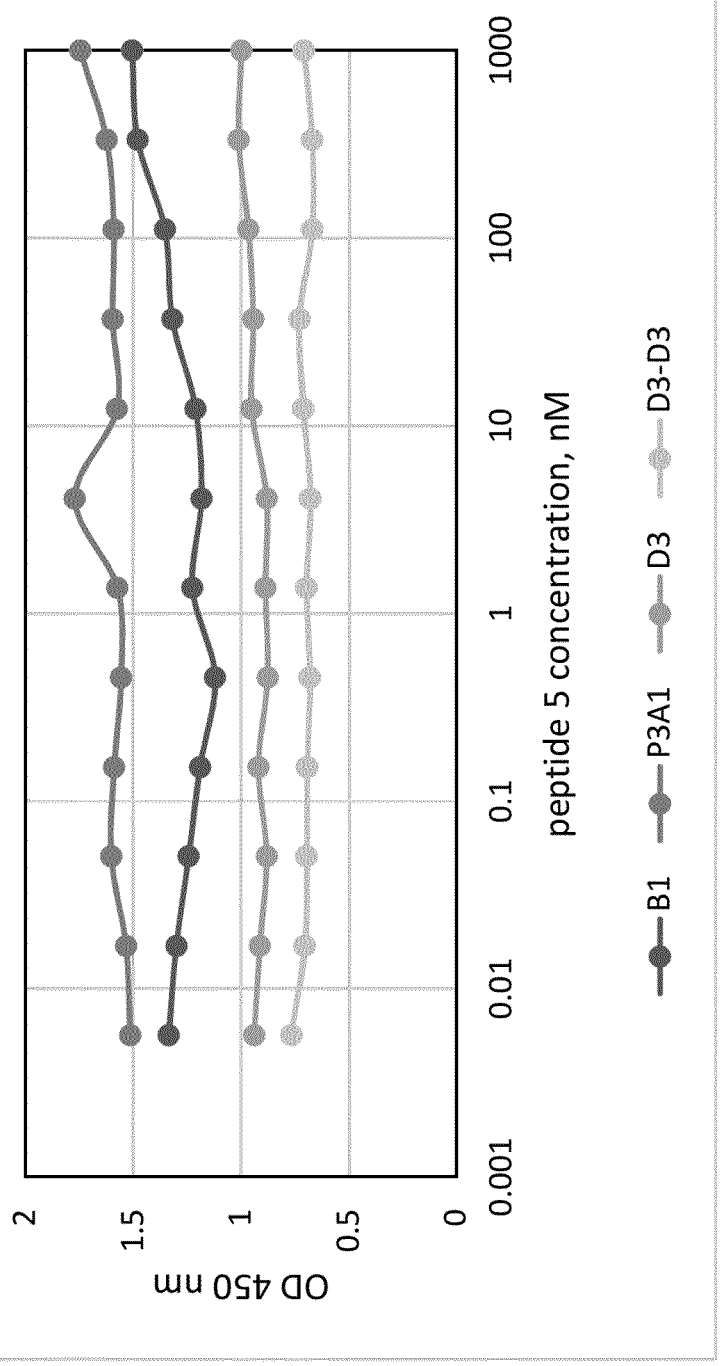
Figure 23:
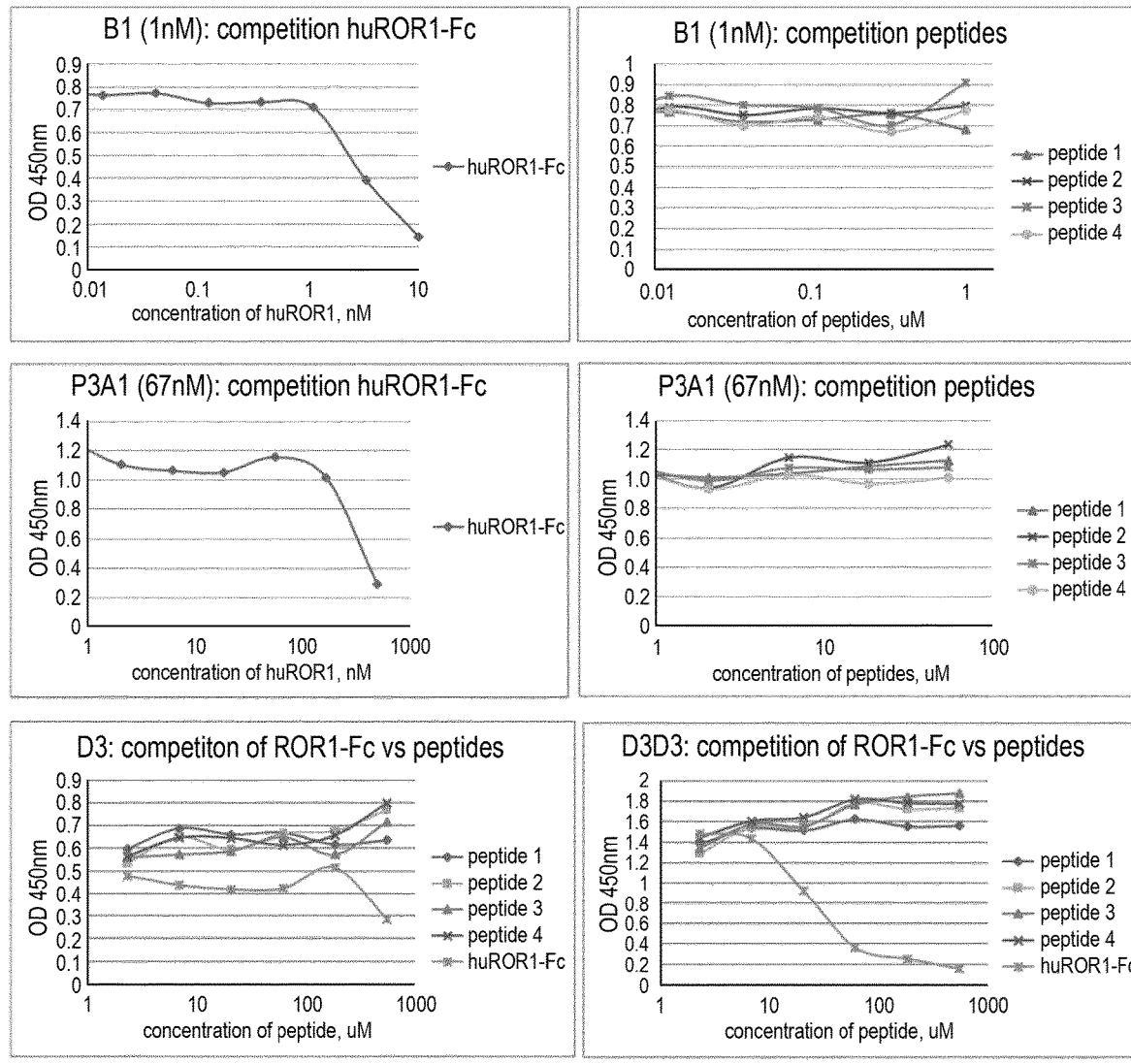
FIG. 23: Competition ELISA experiments.

ELISA analysis was used to determine whether the lead anti-ROR1 VNAR domains, B1, P3A1 and D3 bound to the same or overlapping epitopes on ROR1 (defined here as four ECD peptides). Initial analysis of direct binding with peptides (in PBS and DMSO) immobilised onto ELISA plates indicated that none of the VNARs bound any of the peptides but did bind to the immobilised ECD hROR1-Fc protein control included as part of the same ELISA (FIG. 20 and FIG. 21). To interrogate this further, a competition assay was designed where VNARs were incubated with increasing concentrations of the four test peptides (or human ROR1 ECD-Fc) in solution and an assessment of residual binding to ROR1-Fc immobilised on an ELISA plate was then observed. Competition was evident between the VNARs and human ROR1 ECD-Fc, which was used as a positive control. However, no decrease signal was evident in the presence of the peptides, clearly indicating that no binding of VNAR to these specific ECD peptides had occurred (FIG. 22 and FIG. 23).

Further, B1, P3A1 and D3 VNARs do not bind any overlapping linear 15mer peptides spanning the entire ECD of hROR1. Nor do they bind to hROR1 previously sonicated in SDS containing buffer under reducing conditions, conditions that typically denature protein (Pepscan data not shown). Together this indicates B1, P3A1 and D3 VNARs bind to distinct conformational epitope(s) on human ROR1-ECD protein.

Direct Binding of VNARs to ECD Peptides

The following peptides were synthesised and dissolved in PBS pH 7.4:

```
                                         (SEQ ID NO: 34)
Peptide 1 - YMESLHMQGEIENQI (SEQ ID NO: 38)
Peptide 2 - RSTIYGSRLRINLDTTDTGYFQ (SEQ ID NO: 35)
Peptide 3 - CQPWNSQYPHTHTFTALRFP (SEQ ID NO: 37)
Peptide 4 - QCVATNGKEVVSSTGVLFVKFGPPPTASPGYSDEYE (SEQ ID NO: 36)
Peptide 5 - RSTIYGSRLRIRNLDTTDTGYFQ
```

Clones B1 and P3A1 isolated from ELSS1 were assessed as monomers and D3 from an immunized library as both a monomer and a homodimer.

Both B1 and P3A1 demonstrated binding to ROR1 with no binding evident to any of the five peptides. HSA was included as a non-specific control (FIG. 20).

However as peptide 2 was insoluble in PBS, the direct binding ELISAs were repeated with the peptides dissolved in 25% DMSO. D3 and D3-D3 as a protein dimer fusion were included in these datasets and again no binding to the peptides was observed (FIG. 21).

Methods

Direct Peptide Binding ELISA
1. Coated 96 well plates with 10 or 50 nM huROR1-Fc in PBS or 10 µM of peptides in PBS or 25% DMSO. Incubated o/n at 4° C.
2. Washed 2×PBS
3. Blocked with 200 µl/well of 4% MPBS for 1 h at RT.
4. Washed 2×PBS
5. Added B1 or P3A1 at 1 µg/ml (67 nM); D3 and D3-D3 at 10 µg/ml (670 nM) and 1:3 serial dilutions across the plate. Incubated for 1 h at RT.
6. Washed 3×PBST
7. Incubated plates with 100 ul of anti-his-HRP SIGMA (1:1000 in PBST) for 1 h at RT
8. Washed 2×PBST and 2×PBS
9. Added 100 µl/well of TMB substrate. Stopped reaction with 1 M H2SO4

Competition Assays of VNARs and ROR1 Peptides

Competition assays were conducted as described in the methods with all four peptides reconstituted in PBS. In these assays no binding was observed by VNARs B1 or P3A1 to any of the four peptides immobilised in typical binding ELISA format (FIG. 22). Therefore there was no evidence that these peptides represented epitopes on ROR1 that are recognised by B1 or P3A1.

Following the conditions used in FIG. 21 (due to peptide 2 being insoluble in PBS), all the competition assays were repeated with peptides dissolved in 25% DMSO. For the assay D3 and D3-D3 dimer were also included in these datasets. These results confirmed that the VNAR domains B1, P3A1 and D3 recognise a different epitope (or epitopes) from those represented by the 4 peptides tested.

Methods

Competition ELISA
1. Coated 96 well plates with 50 nM of huROR1-Fc for P3A1; 10 nM of huROR1-Fc for B1, D3 and D3-D3 dimer in PBS. Incubated o/n at 4° C.
2. Washed 2×PBS
3. Blocked with 200 µl/well 4% MPBS for 1 h at RT
4. Washed 2×PBS
5. Pre-incubated for 30 min at RT
   B1=15 nM
   Plus peptides (in PBS or 25% DMSO) at start concentration of 1 µM (then 1:3 serial dilutions across the plate) or huROR1-Fc at start concentration of 100 nM (then 1:3 serial dilutions across the plate)
   P3A1=670 nM
   Plus peptides (in PBS or 25% DMSO) at starting concentration of 50 µM (then 1:3 serial dilutions across the plate) or of huROR1-Fc at a starting concentration 1 µM (then 1:3 serial dilutions across the plate)
   D3 67 nM
   Plus peptides or huROR1-Fc (in PBS or 25% DMSO) at starting concentration of 500 nM (then 1:3 serial dilutions across the plate)
   D3-D3=0.67 nM
   Plus peptides or huROR1-Fc (in PBS or 25% DMSO) at starting concentration of 500 nM (then 1:3 serial dilutions across the plate)
6. Add 100 µl/well of pre-incubated samples. Incubated 1 h at RT
7. Washed 3×PBST
8. Incubated plates with 100 µl/well of anti-His-HRP (1:1000 in PBST). Incubated 1 h at RT
9. Washed 2×PBST and 2×PBS
10. Added 100 µl/well of TMB substrate. Stopped reaction with 50 µl/well 1 M H2SO4

Epitope Mapping of Anti-ROR1 VNARs Using Recombinant ROR1 Domains

The ROR1 ECD is made up of three distinct protein domains: Ig-like, Frizzle and Kringle. To determine if the epitope recognised by each of these VNARs was within a specific sub-domain of the whole ROR1 protein the following ELISA analysis was performed.

Direct Binding of VNARs to ROR1 Domains

Anti-ROR1 VNARs B1, P3A1 and D3 were assessed for binding to the three extracellular domains of human ROR1 (Ig-like, Frizzle and Kringle) by direct binding ELISA. B1 and P3A1 were assessed as monomers and D3 as both a monomer and a homodimer (D3-D3). 2A2 anti-ROR1 antibody was also incorporated into the assay as a positive control.

Figure 24:
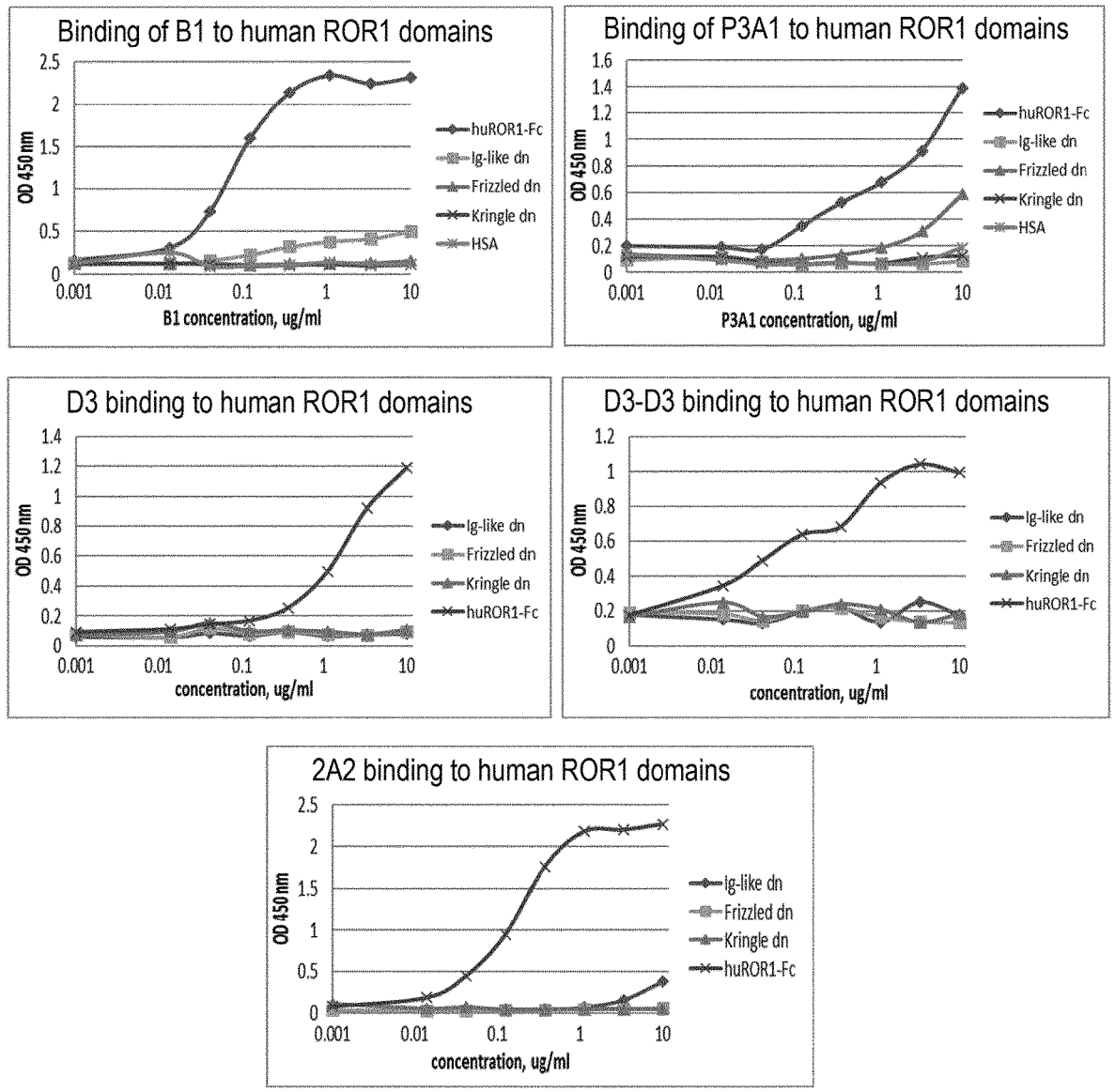
FIG. 24: Binding of B1, P3A1, D3 monomer and D3-D3 dimer to different ROR1 domains.

B1 and 2A2 recognised the Ig-like domain, however this binding to Ig-like domain was much weaker compared to their binding of the whole extracellular huROR1. P3A1 recognised the Frizzled domain but again weaker binding than to the intact ROR1 protein (FIG. 24 and Table 10). D3 and D3-D3 homodimer bound full length ROR1 ECD but no binding to individual ROR1 ECD sub domains was observed (FIG. 24 and Table 10).

All results are summarised in a Table 10.

TABLE 10

| | B1 | P3A1 | D3 | 2A2 |
|---|---|---|---|---|
| rhROR1-Fc | +++ | +++ | +++ | +++ |
| Ig-like domain | + | − | − | + |
| Frizzle domain | − | + | − | − |
| Kringle domain | − | − | − | − |

Methods

Direct Binding ELISA to ROR1 Domains
1. Coated 96 well plates with 1 µg/ml of huROR1-Fc or huROR1 domains in PBS. Incubated o/n at 4° C.
2. Washed 2×PBS
3. Blocked with 200 µl/well of 4% MPBS for 1 h at RT.
4. Washed 2×PBS
5. Added D3, D3-D3 dimer or 2A2 mAb at start concentration 10 µg/ml for VNAR and 1:150 dilution for mAb. Made 3-fold serial dilutions across the plate. Incubated for 1 h at RT.
6. Washed 3×PBST
7. Incubated plates with 100 µl of anti-c-myc-HRP (1:1000 in PBST) for 1 h at RT.
8. Washed 2×PBST and 2×PBS 9. Added 100 μl/well of TMB substrate. Stopped reaction with 1 M H2SO4.

Example 8—VNAR Conjugation Chemistries

Labelling of BA11 as Proof of Concept for Site-Specific VNAR Conjugation

Currently there are no methods for the site-specific conjugation of labels and drugs to VNARs, therefore there is a need to establish such conjugation methods. The VNAR BA11 is a humanised variant of E06 that binds with high affinity to human serum albumin (Kovalenko et al, J. Biol. Chem., 2013 JBC) and has applications as a half-life extension technology. BA11 was used as a model VNAR to determine whether site-specifically conjugated VNARs can be generated in good yield without compromising the binding activity of the VNAR domain. The C-terminus of VNARs is distal to the CDR1 & 3 and HV2 & 4 regions, which are the regions of the VNAR generally used to bind its target.

Therefore intein based technology (US2006247417) was used to assess the site-specific conjugation of payloads to the C-terminus of VNARs via different chemistries. Briefly, the protein of interest is expressed as an N terminal fusion of an engineered intein domain (Muir T W 2006 Nature 442, 517-518). Subsequent N to S acyl shift at the protein-intein union results in a thioester linked intermediate that can be chemically cleaved with bis-aminoxy agents or amino-thiols to give the desired protein C-terminal aminoxy or thiol derivative, respectively (FIG. 11). These C-terminal aminoxy and thiol derivatives can be reacted with aldehyde/ketone and maleimide functionalised moieties, respectively, in a chemoselective fashion to give the site-specific C-terminally modified protein (FIGS. 25-27). Using this approach BA11 fluorescein conjugates were generated via oxime and thioether forming chemistry in good yields and these conjugates maintained binding to human serum albumin protein.

Initially, the BA11 intein-CBD fusion protein, immobilised on chitin beads, was generated as described previously with typical yields 10 mg/L from cytosolic expression in *E. coli*. This precursor fusion protein was then cleaved under aqueous buffered conditions with different small molecule agents to generate BA11 with unique chemically reactive functionalities at its C-terminus.

Generation of BA11-Aminoxy (FIG. 11)

Immobilised BA11 intein-CBD fusion protein was cleaved overnight in 400 mM dioxyamine ($NH_2$—O—$(CH_2)_2$—O—$NH_2$) in cleavage buffer pH6.9 resulting in ~75% cleavage.

Cleavage supernatant containing BA11 aminoxy was drained and purified on a Superdex75 26/60 (GE Healthcare) in 20 mM sodium phosphate pH6.9, 200 mM NaCl. This yielded soluble, derivatised, folded protein with yields of >2 mg/L *E. coli*. All protein was characterised by reducing and non-reducing SDS PAGE analysis and mass spectrometry. The formation of the desired disulphide bond was confirmed by mass spec methods.

Generation of BA11-Oxime-Fluorescein (FIG. 25)

Purified BA11 aminoxy was mixed with 3 molar equivalents benzaldehyde-peg-fluorescein in pH5.5 buffer with 10% acetonitrile and 10 mM aniline catalyst, room temperature overnight. SDS PAGE and mass spectrometry showed 98% reaction and conjugate was purified by SEC as above, and confirmed by reducing and non-reducing SDS PAGE analysis and mass spectrometry.

Generation of BA11 C-Terminal Thiol Derivatives (FIG. 11)

BA11 intein-CBD fusion protein immobilised on chitin beads was cleaved overnight in 100 mM cysteamine (Sigma) in cleavage buffer with 2 mM TCEP to generate the corresponding C-terminal thiol derivative of the VNAR. The cleavage supernatant containing BA11 thiol was drained, treated with 2 mM TCEP to reduce any cysteamine adducts on the introduced C-term thiol group, and protein purified on a Superdex75 26/60 (GE Healthcare) in 20 mM sodium phosphate pH6.9, 200 mM NaCl. Yields~1.6 mg/L *E. coli* for BA11 SH were obtained. All proteins were characterised by reducing and non-reducing SDS PAGE analysis and mass spectrometry. The formation of the desired disulphide bond and free C-terminal thiol were confirmed by mass spec methods.

Generation of BA11-C Term Thiol-Maleimide-Peg-Fluorescein (FIG. 26)

BA11 generated with a C-terminal thiol (BA11 SH) was mixed with 4 molar equivalents maleimide-peg-fluorescein in pH6.9 buffer with 0.3% DMF final, room temperature 0.5-1 hour. SDS PAGE and mass spectrometry showed 98% reaction. Conjugate was purified by SEC as above, and confirmed by reducing and non-reducing SDS PAGE analysis and mass spectrometry.

Generation of BA11 C-Terminal Cysteine Derivatives (FIG. 11)

BA11 Intein-CBD fusion protein immobilised on chitin beads was cleaved overnight in 100 mM cysteine in cleavage buffer with 2 mM TCEP to generate the corresponding C-terminal cysteine derivative of the VNAR. The cleavage supernatant containing BA11 Cys was drained, treated with 2 mM TCEP to reduce any cysteine adducts on the introduced C-term thiol group, and protein purified on a Superdex75 26/60 (GE Healthcare) in 20 mM sodium phosphate pH6.9, 200 mM NaCl. Yields~>3 mg/L *E. coli* for BA11-cys were obtained. All proteins were characterised by reducing and non-reducing SDS PAGE analysis and mass spectrometry. The formation of the desired disulphide bond and free C-terminal cysteine thiol were confirmed by mass spec methods.

Generation of BA11-C Terminal Cysteine-Maleimide-Peg-Fluorescein (FIG. 27)

BA11 generated with a C-terminal cysteine (BA11 cys) was mixed with 4 molar equivalents maleimide-peg-fluorescein in pH6.9 buffer with 0.3% DMF final, room temperature 0.5-1 hour. SDS PAGE and mass spectrometry showed 60-80% reaction for BA11 cys, lower reaction was due to significant BA11 cys dimer formation. Conjugate was purified by SEC as above, and confirmed by reducing and non-reducing SDS PAGE analysis and mass spectrometry.

The binding of BA11 and the corresponding C-terminal derivatives and conjugates to serum albumins was determined by SPR Determination of the binding kinetics of the half-life extension VNAR (BA11) or Fluorescein-conjugated-BA11 to human, mouse, rat and cynomolgous serum albumin Binding kinetics were determined using SPR. The serum albumins or negative control protein were immobilised to $COOH_2$ chips by amine coupling using optimised buffer conditions as follows: —Human serum albumin (HSA) and mouse serum albumin (MSA) were immobilised in sodium acetate pH5 buffer. Rat serum albumin (RSA) and cynomolgous serum albumin (CSA) in sodium acetate pH 4.5 buffer and the negative control hen egg lysozyme (HEL) protein was immobilised in sodium acetate pH 5.5 buffer.

Analytes (BA11, BA11-Fluorescein or 2V negative control binder) were tested at various concentrations and the $K_a$ ($M^{-1}s^{-1}$), $K_d(s^{-1})$ and KID (nM) values were determined using QDat software (SensiQ/Pall ForteBio). For each analyte test experiment, binding to the chosen serum albumin protein was assayed alongside the negative control protein (HEL).

TABLE 11

Summary of SPR data ($K_D$ nM) for BA11 C terminal derivatives and subsequent fluorescein conjugates with different conjugation chemistries binding to serum albumin proteins.

| | Serum Albumin | | | | | | | |
|---|---|---|---|---|---|---|---|---|
| | Human | | Rat | | Mouse | | Cyano | |
| | | | | pH | | | | |
| | 7.4 | 5.5 | 7.4 | 5.5 | 7.4 | 5.5 | 7.4 | 5.5 |
| BA11 | 0.636 | 0.910 | 2.969 | 4.389 | 1.902 | 4.804 | 3.360 | 1.109 |
| BA11-aminoxy | 1.118 | ND | 10.85 | ND | 8.767 | 21.20 | 7.970 | ND |
| BA11-oxime-Fl | 0.677 | 1.296 | 5.725 | 5.928 | 4.238 | 7.442 | 1.748 | 5.540 |
| BA11-cys | 0.756 | 1.956 | 3.370 | 3.215 | ND | 3.775 | 2.103 | ND |
| BA11-cys-mal-Fl | 1.097 | 3.160 | 4.775 | 7.240 | 5.064 | 13.645 | 3.681 | 8.205 |
| BA11-SH | 0.774 | 2.229 | 7.671 | 12.10 | 4.764 | 11.08 | 3.414 | 6.738 |
| BA11-S-mal-Fl | 1.417 | 1.912 | 5.297 | 7.925 | 5.004 | 10.60 | 2.300 | 7.010 |
| 2V | | | | Did not bind | | | | |

Fl, fluorescein;
cys, cysteine;
mal, maleimide;
SH, thiol;
2V, non-binding VNAR negative control.

All BA11 derivatives and conjugates showed high affinity binding to the different serum albumin proteins at both pH7.4 and pH5.5. Therefore the methodologies described provide robust high yielding approaches for the site-specific modification and conjugation of VNARs that maintain the binding activity of the protein.

ROR1 Binding VNARs—AF488 and MMAE Conjugates

Figure 28:
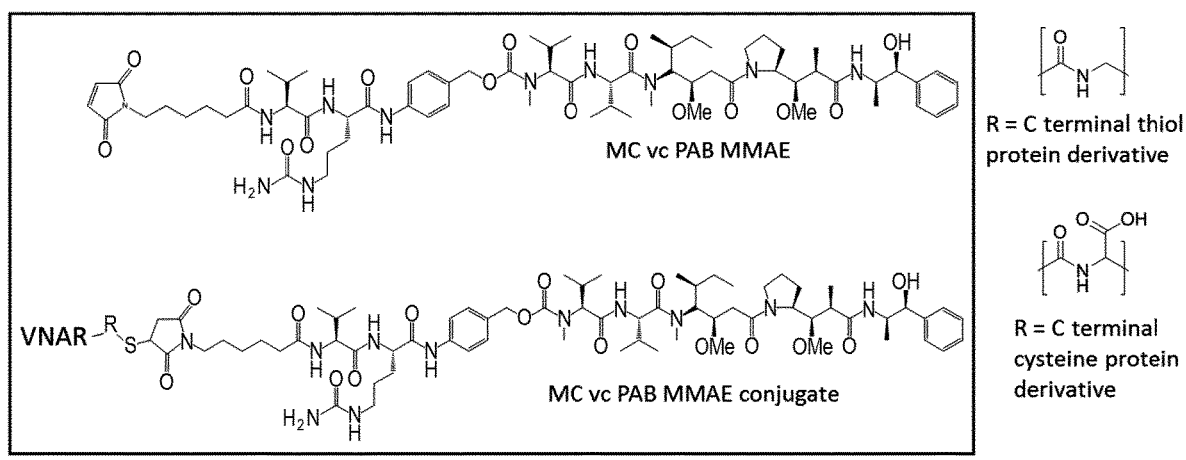
FIG. 28: Examples of labels and payloads used for conjugation.

Expression of ROR1 binding VNARs as C-terminal intein fusion proteins enabled generation of ROR1 binding VNARs with unique C-terminal aminoxy and C-terminal thiol groups. This in turn enabling site specific, C-terminal conjugation to fluorescent labels and cytotoxic payloads via oxime forming conjugation chemistry and maleimide chemistry, respectively. Examples of labels and payloads used are shown in FIG. 28.

Figure 29:
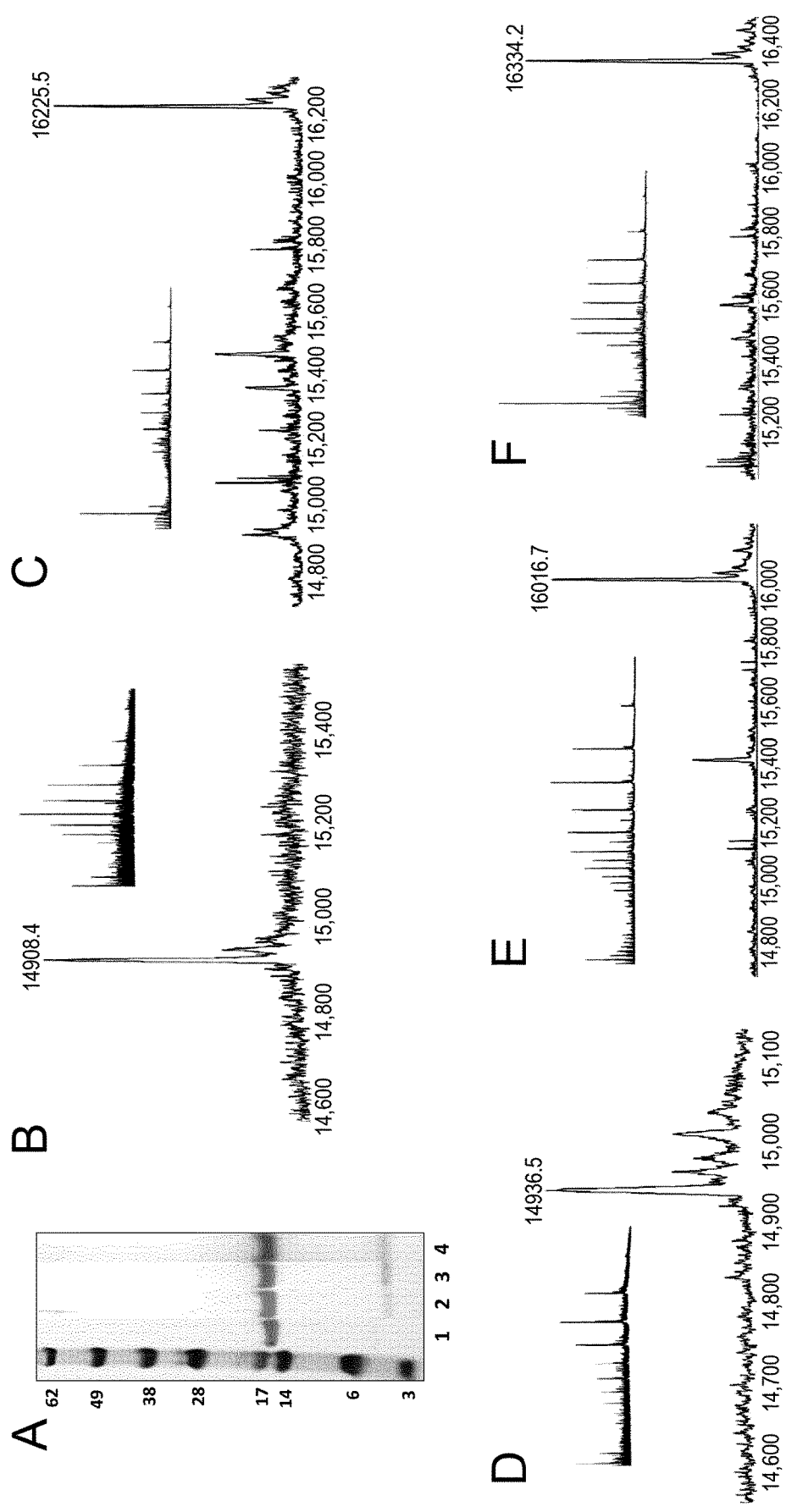
FIG. 29: Analysis of B1 MMAE conjugates. A, SDS PAGE analysis of B1 his myc derivatives and conjugates—lanes 1, B1 aminoxy; 2, B1 oxime MMAE; 3, B1 oxime vc MMAE; 4, B1 SH vc MMAE. B-F, electrospray mass spectra of B1 his myc derivatives and conjugates—B, B1 SH (expected mass; 14908.9 Da, observed mass 14908.4 Da); C, B1 SH vc MMAE (expected mass 16225.5 Da, observed mass 16225.5 Da); D, B1 aminoxy (expected mass 14937.4 Da, observed mass 14936.5 Da); E, B1 oxime MMAE (expected mass 16015.4 Da, observed mass 16016.7 Da); F, B1 oxime vc MMAE (expected mass 16334.4 Da, observed mass 16334.2 Da).

ROR1 Binding VNAR Intein CBD Fusion Protein Immobilised on Chitin Beads was Generated as Described Above Generation of VNAR-Ox-vcMMAE and VNAR-Ox-MMAE The immobilised VNAR intein fusion protein was cleaved with 400 mM O,O'-1,3-propanediylbishydroxylamine ($NH_2$—O—$(CH_2)_3$—O—$NH_2$) in cleavage buffer pH 6.9, room temperature overnight. The resulting VNAR containing a C-terminal aminoxy group (VNAR aminoxy) was purified by IMAC or SEC and reacted with 3 molar equivalents of benzaldehyde PEG2 vc PAB MMAE or benzaldehyde PEG4 MMAE in 10% acetonitrile with 10 mM aniline catalyst final, room temperature overnight. Conjugates were purified by IMAC or SEC, sterile filtered and formation of the desired material and final purity confirmed by reducing and non-reducing SDS PAGE analysis and mass spectrometry (FIG. 29)

Generation of VNAR-S-Mal-vcMMAE

The immobilised VNAR intein fusion protein was cleaved with 100 mM cysteamine in cleavage buffer pH 6.9 with 2 mM TCEP, room temperature overnight. The resulting VNAR containing a C-terminal thiol group (VNAR SH) was purified by IMAC or SEC and reacted with 4 molar equivalents of MC vc PAB MMAE or malAF488. Conjugates were purified by IMAC or SEC, and sterile filtered and formation of the desired material and final purity confirmed by reducing and non-reducing SDS PAGE analysis and mass spectrometry (FIG. 29)

Characterisation of Anti ROR1 VNAR-MMAE Conjugates—Binding to ROR1 and ROR2 by SPR and Cell Surface Binding by Flow Cytometry Binding of VNAR Conjugates to ROR1 and ROR2 by SPR The ability of the VNAR-MMAE conjugates and VNAR-fluorescein conjugates to bind to human ROR1 ECD was determined by SPR using the procedures described above.

As shown in Table 12 VNAR conjugates that were prepared through oxime ligation of benzaldehyde payloads to C-terminal aminoxy VNARs; through thioether ligation of malemide functionalised payloads to C-terminal thiol VNARs and through thioether ligation of malemide functionalised payloads to C-terminal Cysteine VNARs all maintain high affinity for human ROR1 but do not bind to human ROR2. Conjugates were prepared using enzyme cleavable linkers (Val-Cit) or non-cleavable linkers and showed similar binding to human ROR1.

TABLE 12

SPR data for binding of VNARs and corresponding Fluorescein and MMAE conjugates to human ROR1 and ROR2.
VNARs were expressed with C-terminal $His_6Myc$ tags.

| | hROR1 | | | |
|---|---|---|---|---|
| VNAR | Ka ($M^{-1}s^{-1}$) | Kd ($s^{-1}$) | KD (nM) | hROR2 |
| B1 | 4.75E+05 | 7.56E−04 | 1.65 | No binding |
| B1-S-mal-Fluorescein | 4.7E+05 | 3.67E−04 | 0.81 | No binding |
| 2V | No binding | No binding | No binding | No binding |
| 2V-S-mal-vcMMAE | No binding | No binding | No binding | No binding |
| 2V-Ox-vcMMAE | No binding | No binding | No binding | No binding |
| 2V-Ox-MMAE | No binding | No binding | No binding | No binding |
| P3A1-P3A1 | 1.86E+06 | 2.96E−03 | 1.61 | No binding |
| P3A1-P3A1-S-mal-vcMMAE | 4.96E+06 | 2.6E−03 | 0.59 | No binding |
| P3A1-P3A1-Ox-vcMMAE | 2.07E+06 | 2.77E−03 | 1.43 | No binding |
| P3A1-P3A1-Ox-MMAE | 4.20E+06 | 3.20E−03 | 0.78 | No binding |
| 2V-2V | No binding | No binding | No binding | No binding |
| 2V-2V-S-mal-vcMMAE | No binding | No binding | No binding | No binding |
| 2V-2V-Ox-vcMMAE | No specific binding | No specific binding | No specific binding | No binding |
| 2V-2V-Ox-MMAE | No binding | No binding | No binding | No binding |

Binding of VNAR Conjugates to Cancer Cell-Lines

Binding of B1 and P3A1 MMAE conjugates to cancer cell-lines was determined by flow cytometry using methods described above. B1 and P3A1 conjugates maintain binding to the ROR1$^{hi}$ A549 lung adenocarcinoma cells and do not bind the ROR1$^{low}$ lung cancer cell-line A427 by flow cytometry at a fixed concentration of protein.

VNAR mFc Fusion Protein Conjugates

B1 mIgG2a Fc and nonbinding 2V mIgG2a Fc fusion proteins were labelled with mal AF488 and mc vc PAB MMAE via protocols adapted from the partial reduction and labelling of antibody interchain disulfides (Methods in Molecular Biology vol 1045 chapter 9; Sun et al, Bioconj Chem 2005). Briefly VNAR mIgG2a Fc proteins at 1 mg/ml in PBS+100 mM L-Arg with 1 mM EDTA added were partially reduced with 2.75 molar equivalents fresh TCEP; 37° C. 2 hours. 1.1 molar equivalents maleimide label to free protein thiol was added, incubated on ice 45 mins and L-cysteine added to stop the reaction. Reactions were dialysed to remove unreacted label/drug, sterile filtered and analysed by SDS PAGE. Typical DAR of 4.4 for B1-mFc-AF488, and 3.9 for 2V-mFc-AF488.

VNAR hFc Fusion Protein Drug Conjugates

Another approach for generating ADCs is to engineer cysteine substitutions or additions at positions on the light and heavy chains of antibodies and these cysteines provide reactive thiol groups for site specific labelling (Junutula 2008 Nature Biotechnology 26, 925-932, Jeffrey 2013, Sutherland 2016).

Anti ROR1 VNARs were genetically fused to engineered hIgG1 Fc domains that contained a cysteine substitution in the hIgG1 Fc sequence, S252C or S473C (Kabat numbering). This enabled site specific labelling with maleimide derivatives of fluorescent labels (AF488) and cytotoxic drugs (MC vc PAB MMAE, MC vc PAB NHC$_6$ α-amanitin, MA PEG4 va PBD, MA PEG8 va PAB SG3199, MA PEG4 vc PAB DMAE PNU 159682) (FIG. 32).

Generation of VNAR-hFc—Drug Conjugates

A partial reduction, refolding and labelling method to label the VNAR Fc S252C or VNAR Fc S473 was adapted from the literature (Junutula et al, 2008 Nat Biotech, Jeffrey et al, 2013 Bioconj Chem). Briefly, 1 mg/ml VNAR hFc solutions were prepared in PBS+100 mM L-Arginine pH7.4 with 1 mM EDTA. 20 molar equivalents TCEP added and incubated at 4° C. for a minimum of 48 hours. 30 molar equivalents DHAA added, pH adjusted to 6.5 and incubated at room temperature for 1 hour. Refolded VNAR Fc S252C or S473C was extensively dialysed or buffer exchanged into PBS+50 mM L-Arginine and quantified by UV before reacting with 4 molar equivalents maleimide label/drug solution, room temperature 1 hour to overnight depending on label/drug. Conjugates were dialysed/buffer exchanged directly or purified further by SEC or IEX before dialysis/buffer exchange.

This approach was used to generate MMAE conjugates of B1, P3A1 and 2V Fc fusion proteins whereby the corresponding hIgG1 Fc (S252C or S473C) derivative was labelled with a maleimide functionalised MMAE payload incorporating an enzyme cleavable (Cathepsin B) linker.

SDS-PAGE and mass spectrometry analysis of the final conjugates determined that the labelling had proceeded in a quantitative fashion to give highly pure homogenous VNAR-hFc—MMAE conjugates with drug to antibody ratio (DAR) of 2 (FIG. 31 shows conjugation to VNAR-hFc (S252C). Similar procedures were used to generate PBD dimer, α-amanitin and PNU conjugates of cysteine engineered VNAR-hFc fusion proteins (Levena Biopharma, San Diego). Whereby VNAR (B1, P3A1, 2V) hIgG1 Fc(S252C) fusions were reacted with MC vc PAB NHC$_6$ α-amanitin, MA PEG4 va PBD, MA PEG8 va PAB SG3199, MA PEG4 vc PAB DMAE PNU 159682 (FIG. 32).

Binding of VNAR-hFc—MMAE Conjugates to hROR1 and Cancer Cell-Lines

The ability of the VNAR-hFc conjugates to bind to human ROR1 ECD was determined by SPR using the procedures described above.

TABLE 13

SPR data for binding of VNAR human Fc (hFc) and MMAE conjugated versions to human ROR1 and human ROR2

| Molecule set | hROR1 | | | hROR2 |
|---|---|---|---|---|
| | Ka (M$^{-1}$s$^{-1}$) | Kd (s$^{-1}$) | KD (nM) | |
| B1 hFc | 3.08E+06 | 9.53E-05 | 0.032 | No binding |
| B1 hFc-MMAE | 1.22E+06 | 1.29E-04 | 0.105 | No binding |
| P3A1 hFc | 1.07E+07 | 5.64E-04 | 0.084 | No binding |
| P3A1 hFc-MMAE | 2.68E+06 | 1.00E-03 | 0.38 | No binding |
| 2V hFc | No binding | No binding | No binding | No binding |
| 2V hFc-MMAE | No binding | No binding | No binding | No binding |
| 2V-2V hFc | No binding | No binding | No binding | No binding |

B1 and P3A1 VNAR-hIgG Fc (S252C)—vcMMAE conjugates demonstrated high affinity binding to ROR1 but do not bind to human ROR2. 2V is a non-binding VNAR and the corresponding 2V-hFc drug conjugates were generated as non-binding controls.

Binding of B1 and P3A1 hFc—vcMMAE conjugates to ROR1$^{hi}$ A549 lung adenocarcinoma cell-line and the ROR1$^{low}$ A427 lung cancer cell-line was determined by flow cytometry using methods described above.

FIG. 30 shows that B1 and P3A1 hFc-vcMMAE conjugates bind strongly to the ROR1$^{hi}$ cancer cells but not the ROR1$^{low}$ cancer cells. Whilst the 2V-hFc-vcMMAE conjugate does not bind to either cell-line.

In vitro cell viability assays for cancer cells treated with anti ROR1 VNAR drug conjugates Cells were seeded into white, clear bottom 96 well plates (Costar) and incubated at 37° C., 5% CO$_2$ for 24 hours. On the following day, dilution series were set up for each test agent at ×10 working stocks. The dose response ×10 stock was: 10000, 5000, 1000, 500, 100, 50, 10, 5, 1, 0.5 nM. 10 µL of the ×10 stock solutions were added to the cell plates (90 µl per well) using a multichannel pipette. This resulted in a 1:10 dilution into the well and dose responses ranging from 1000 nM (column 1) to 0.05 nM (column 10). 10 µl of vehicle control (PBS) was added to the control wells (columns 11 and 12). Plates were incubated at 37° C., 5% CO2 for 72-96 hours. Promega Cell Titre Glo reagent was used as per the manufacturer's instructions to assess cell viability. Briefly, assay plates were removed from incubator and allowed to equilibrate to room temperature before adding 100 µl of room temperature Cell Titre Glo reagent to each 100 µl assay well. Plates were placed on a plate shaker for 2 minutes at 600 rpm. Plates were allowed to sit for a further 10 minutes at room temperature prior to measuring luminescence read-out using a Clariostar plate-reader (BMG). Data was analysed by calculating the average for untreated (vehicle only) control wells and determining the % of control for each treated well. % of control data was then plotted against Log [Treatment] concentration and the IC50 value derived using non-linear regression fitting in GraphPad Prism software.

Cell Lines
  DU145 prostate cancer cells: EMEM, 10% hiFCS
  JeKo-1 Mantle cell lymphoma cells: RPMI 1640, 20% hiFCS
  Kasumi-2 B cell precursor leukemia cells: RPMI 1640, 10% hiFCS
  PA-1 ovarian cancer cells: EMEM, 10% hiFCS
  PA-1 ROR1 knockout cells: EMEM, 10% hiFCS
  A549 cells: DMEM, 10% hiFCS
  MDA-MB-231 cells: DMEM, 10% hiFCS
FIG. 33 shows dose response curves, with corresponding 1050 values, for cell-killing of the ROR1 positive cancer cell-lines A549 (lung adenocarcinoma), MDA-MB-231 (breast cancer), DU145 (prostate cancer), Kasumi-2 (ALL cells) and Jeko1 (MCL cells) by B1-mFc-vcMMAE and 2V-mFc-vcMMAE conjugates. B1-mFc-vcMMAE conjugates show potent cell-killing of the ROR1 positive cancer cells and show superior potency to the corresponding 2V-mFc-vcMMAE conjugate across each of the cell-lines.

TABLE 14

IC50 values for cell-killing by B1-mFc-MMAE and 2V-mFc-MMAE per cell line.

| Cell line | IC50 (nM) | |
|---|---|---|
| | B1 mFc MMAE | 2V mFc MMAE |
| A549 | 24.2 | 228 |
| MDA-231 | 36.6 | 212 |
| DU145 | 15 | 75 |
| Kasumi-2 | 26 | 240 |
| JeKo-1 | 8.1 | 66 |

FIG. 34 shows dose response curves, with corresponding 1050 values, for cell-killing of A) the ROR1 positive DU145 prostate cancer cells by B1-hFc-PBD, D3-hFc-PBD and 2V-hFc-PBD conjugates and B) ROR1 positive Jeko1 MCL cells by B1-hFc-PBD, P3A1-hFc-PBD, D3-hFc-PBD and 2V-hFc-PBD conjugates.

TABLE 15

IC50 values (nM) determined for VNAR hFc-PBD molecules in DU145 and Jeko-1 cancer cell lines at 96 hr.

| Cell Line | IC50 (nM) | | | |
|---|---|---|---|---|
| | B1 hFc-PBD | P3A1 hFc-PBD | D3 hFc-PBD | 2V hFc-PBD |
| DU145 | 4.6 | / | 29.2 | 226.2 |
| JeKo-1 | 0.36 | 1.9 | 12.6 | 25.4 |

The ROR1 targeting VNAR-PBD conjugates show potent killing of both cancer cell-lines and show increased potency with respect to the 2V-hFc-PBD conjugate, with the 1050 values for the B1-hFc conjugate at least 49 fold lower than 2V-hFc conjugate.

Figure 35:
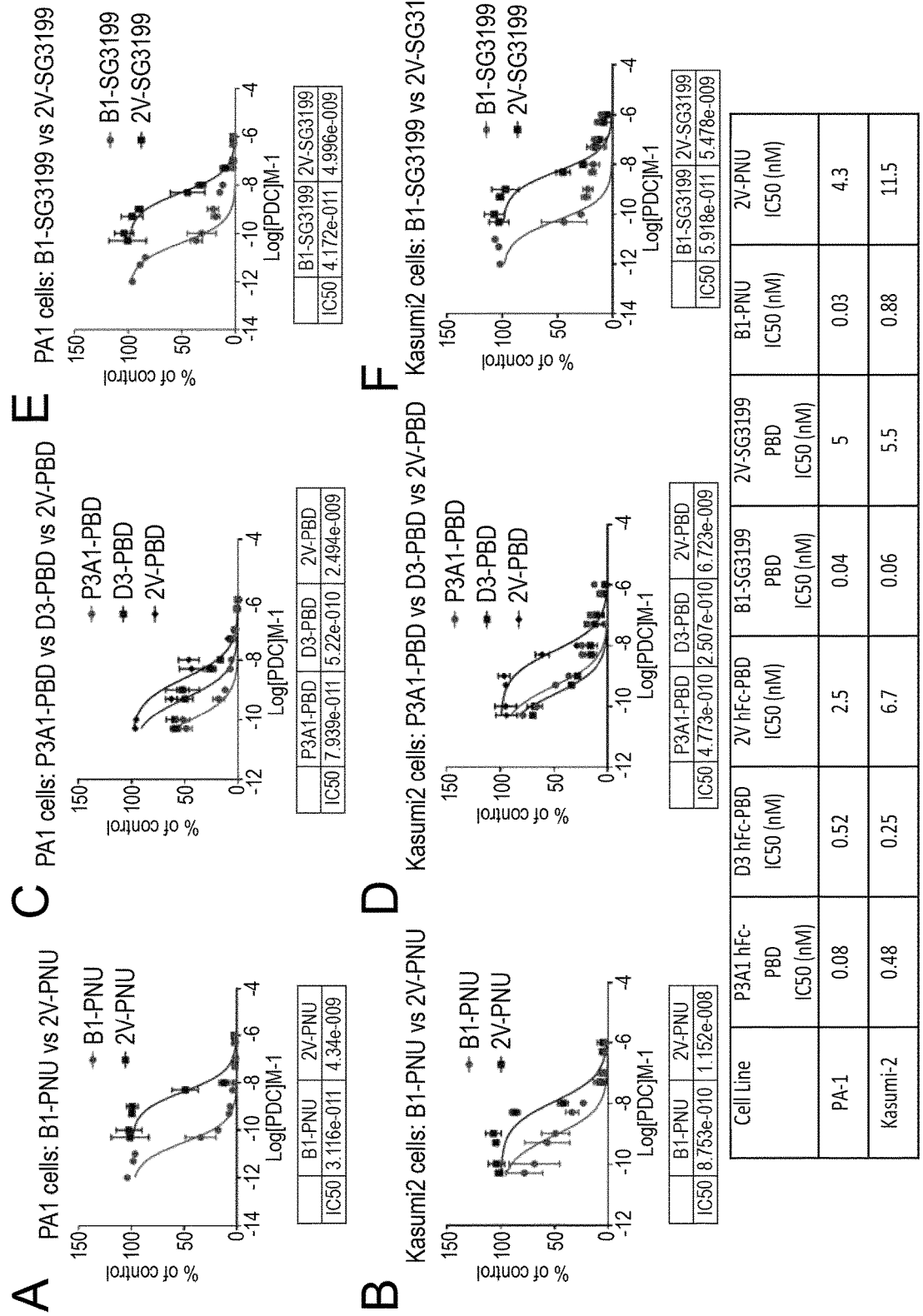
FIG. 35: Cell viability following treatment with VNAR hFc PBD, SG3199 PBD and PNU (PEG4 vc PAB DMAE PNU159682) conjugates (96 hr) in 2 different human cancer cell lines (PA-1 and Kasumi-2). Cell Titre Glo reagent (Promega) was used to quantify ATP which correlates with the number of metabolically active cells in culture. IC50 values were determined using GraphPad Prism software. Whereby VNAR hFc conjugates were generated by reacting VNAR hIgG1 Fc(S252C) fusions with MA PEG4 va PBD, MA PEG8 va PAB SG3199, MA PEG4 vc PAB DMAE PNU 159682 (see FIG. 32).

FIG. 35 shows dose response curves, with corresponding 1050 values, for cell-killing of the ROR1 positive PA-1 ovarian cancer cells (A, C, E) and Kasumi-2 B-cell precursor leukaemia cells (B, D, F) by B1-hFc-PNU, 2V-hFc-PNU conjugates (PEG4-vc PAB DMAE PNU 159682), P3A1-hFc-PBD, D3-hFc-PBD and 2V-hFc-PBD conjugates and B1-hFc SG3199 PBD and 2V-hFc SG3199 PBD conjugates.

TABLE 16

Calculated IC50 values (nM) for the cell-killing of PA-1 and Kasumi-2 cancer cells by VNAR-hFc conjugates. PA-1 ROR1 ko is PA-1 cancer cell-line where ROR1 expression has been knocked out.

| Cell Line | P3A1 hFc-va-PBD-SGD1882 IC50 (nM) | D3 hFc-va-PBD-SGD1882 IC50 (nM) | 2V hFc-va-PBD-SGD1882 IC50 (nM) | B1 hFc-va-PAB-SG3199 IC50 (nM) | 2V hFc-va-PAB-SG3199 IC50 (nM) | B1 hFc-vc-PAB-DMAE-PNU159682 IC50 (nM) | P3A1 hFc-vc-PAB-DMAE-PNU159682 IC50 (nM) | 2V-hFc-vc-PAB-DMAE-PNU159682 IC50 (nM) |
|---|---|---|---|---|---|---|---|---|
| PA-1 | 0.065 | 0.34 | 2.5 | 0.03 | 5.9 | 0.028 | 0.0027 | 3.13 |
| PA-1 ROR1 ko | ND | ND | ND | 0.79 | 10.5 | 1.5 | 3.4 | 4.5 |
| Kasumi-2 | 0.52 | 0.25 | 6.6 | 0.06 | 4.4 | 0.8 | 5.1 | 11 |

Figure 35B:
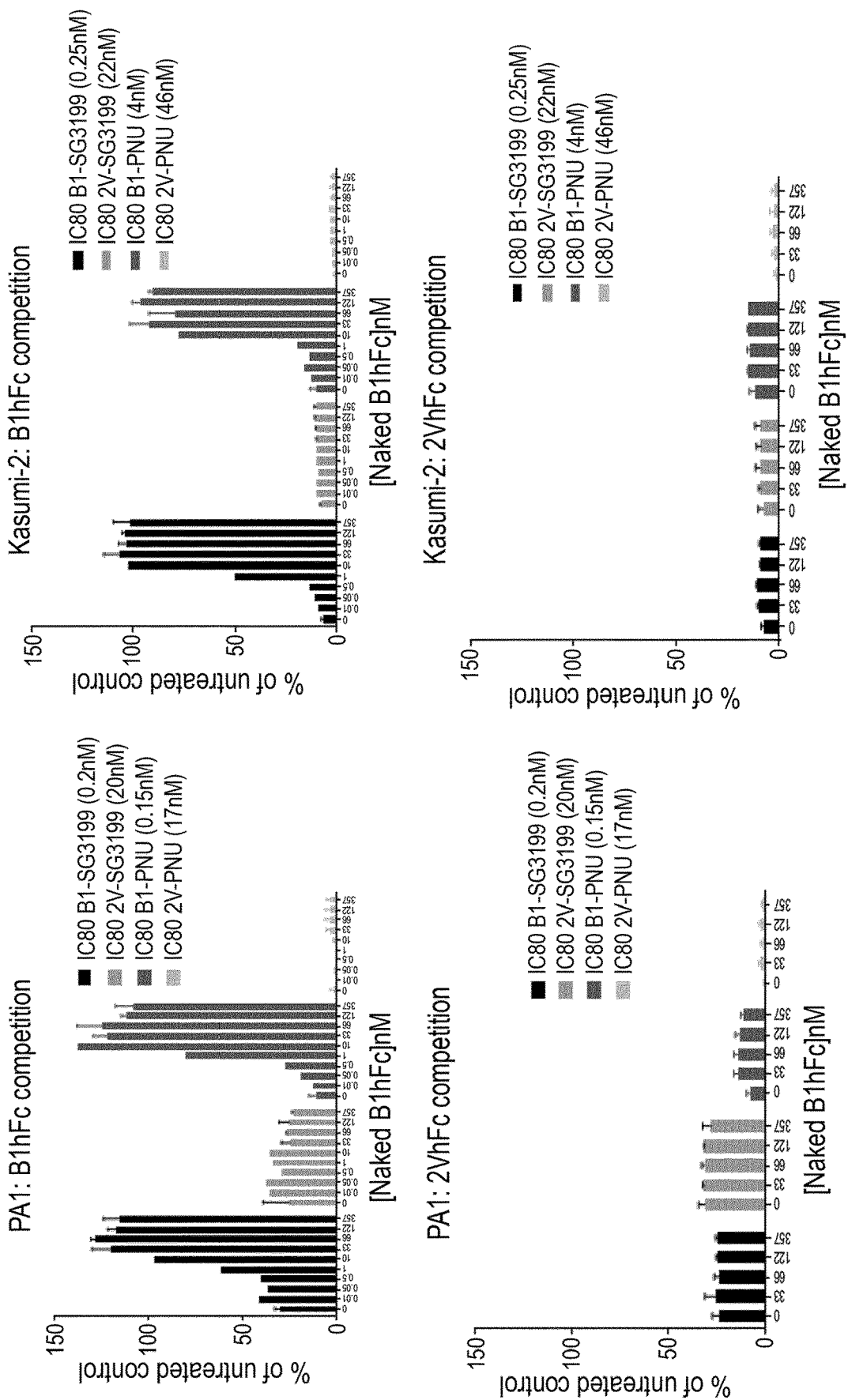
FIG. 35*b*: PA-1 cells and Kasumi-2 cells were treated with IC80 concentrations of B1hFc-SG3199, B1 hFc-PNU or 2VhFc non-binding controls in the presence or absence of increasing amounts of unconjugated B1 hFc or 2VhFc. Cell viability was assessed using Cell Titer Glo assay (Promega). Effects on cell viability following treatment with the protein-drug conjugate molecules were abrogated with increasing amounts of competing unconjugated B1hFc but not with 2VhFc protein.

The ROR1 targeting VNAR-conjugates show potent killing of both PA-1 and Kasumi-2 cancer cell-lines and show increased potency with respect to the corresponding 2V-hFc conjugates, with the 1050 values for a number of ROR1 targeting conjugates >100 fold lower than the corresponding 2V-hFc conjugate controls. Furthermore, the cell-killing effects of B1hFc-SG3199 and B1hFc-PNU are ROR-1 dependent—competition experiments in PA-1 and Kasumi-2 cell lines (FIG. 35b). B1hFc inhibits cell killing by B1hFc-SG3199 and B1hFc-PNU in a dose-dependent manner 2VhFc did not inhibit the cell killing by these drug-conjugate molecules (FIG. 35b).

Example 10

ROR1 VNAR Bi-Specifics

Bispecific target combinations for ROR1 binding VNARs include, for example, HSA for half-life extension; bispecific engagement of ROR1 and serum albumin RTKs e.g. EGFR, Her3; bispecific targeting both EGFR and ROR1 or HER3 and ROR1 on the surface of cells.

The VNAR BA11, already discussed and exemplified herein, is an example of a HSA-binding VNAR. Bi-specific molecules comprising a HSA-binding VNAR (such as BA11) and another specific binding molecule are discussed.

ROR1×CD3 bispecific sequences combining N-terminal ROR1 VNARs with a C-terminal anti-CD3 scFv (clone OKT3) via 2 different length G4S linkers were expressed in CHO cells (Evitria) and purified by IMAC (HisTrap Excel, GE Healthcare) followed by SEC (Superdex 200 26/60, GE Healthcare). Similarly, biparatopic ROR1×CD3 bispecific sequences combining N-terminal biparatopic ROR1 VNARs with the C-terminal anti-CD3 scFv were also expressed in CHO (Evitria).

CD3 BiTE-like approach; examples of CD3 binding sequences for use as an ROR1 VNAR bispecific Anti CD3 scFv clone OKT3 (WO 2014028776 Zyngenia) and orientation and humanised derivatives thereof VH-[G$_4$S]$_3$-VL
(SEQ ID NO: 100)
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSGGGGSGGGGSGGGGSDIQLTQSPAIMSASPG

EKVTMTCRASSSVSYMNWYQQKSGTSPKRWIYDTSKVASGVPYRFSGSGS

GTSYSLTISSMEAEDAATYYCQQWSSNPLTFGAGTKLELKS

Humanised anti CD3 scFv UCHT1 (Arnett et al PNAS 2004 101(46) 16268-16273) and derivatives thereof VL-[G$_4$S]$_3$-VH
(SEQ ID NO: 101)
MDIQMTQTTSSLSASLGDRVTISCRASQDIRNYLNWYQQKPDGTVKLLIY

YTSRLHSGVPSKFSGSGSGTDYSLTISNLEQEDIATYFCQQGNTLPWTFA

GGTKLEIKGGGGSGGGGSGGGGSEVQLQQSGPELVKPGASMKISCKASGY

SFTGYTMNWVKQSHGKNLEWMGLINPYKGVSTYNQKFKDKATLTVDKSSS

TAYMELLSLTSEDSAVYYCARSGYYGDSDWYFDVWGQGTTLTVFS

TABLE 17

Characterisation of ROR1 × CD3 constructs

| Name | Linker | MW, Da Expected | MW, Da Observed | ROR1 binding |
|---|---|---|---|---|
| B1 × CD3 | G4S | 39,137.3 | 39,136.6 | Yes |
|  | [G4S]3 | 39,767.9 | 39,768.2 | Yes |
| P3A1 × CD3 | G4S | 39,275.4 | 39,275.5 | Yes |
|  | [G4S]3 | 39,905.9 | 39,906.8 | Yes |
| 2V × CD3 | G4S | 39,053.1 | 39,051.7 | n/d |
|  | [G4S]3 | 39,683.7 | 39,682.6 | n/d |

Biparatopic VNAR Molecules

Several biparatopic VNAR constructs were designed and cloned using a (G$_4$S)$_5$ linker.

Binding kinetics were determined using a SPR (as previously described) or using Biolayer interferometry (K2 Octet instrument/Pall ForteBio). For BLI experiments ROR1-hFc, ROR2-hFc fusion proteins (extracelluar domain) and HSA were immobilised in sodium acetate pH5 buffer to AR2G sensors using amine coupling. VNARs and VNAR-Fc molecules were tested at various concentrations and the Ka (M−1s−1), Kd (s−1) and KD (nM) values were determined using the Octet data analysis HT software (Pall ForteBio). 2V is a control VNAR sequence, derived from a naïve VNAR library, so is representative of this protein class but has no known target.

Binding kinetics for hROR1 binding were also performed with saturating levels of HSA (200 nM) in the baseline, association and dissociation conditions.

TABLE 18

Characterisation of biparatopic VNAR constructs

| VNAR | Linker | Expression System | ELISA(binding at fixed known conc.) ROR1 | ELISA ROR2 | ELISA HSA | Octet or SPR hROR1 binding KD (nM) | Cell Surface Binding based on Median YL1-PE at 4° C. A549 (ROR1$^{hi}$) | Cell Surface Binding based on Median YL1-PE at 4° C. A427 (ROR1$^{low}$) | Cell Surface Binding based on Median YL1-PE MDA-MB-231 (ROR1$^{hi}$) 4° C. | % internalisation at 37° C. |
|---|---|---|---|---|---|---|---|---|---|---|
| B1-BA11-D3 | -[G$_4$S]$_5$- | Tni(Insect) | ++++ | − | +++++ | ND | 11277 | 949 | 8079 | 38.5 |
| D3-BA11-B1 | -[G$_4$S]$_5$- | Tni(Insect) | +++ | − | ++++ | <0.05 | 10607 | 692 | 7142 | 48.5 |
| BA11-B1 | -[G$_4$S]$_5$- | CHO | +++ | − | +++++ | ND | 8853 | 959 | 5026 | 29.5 |

TABLE 18-continued

Characterisation of biparatopic VNAR constructs

| VNAR | Linker | Expression System | ELISA(binding at fixed known conc.) ROR1 | ROR2 | HSA | Octet or SPR hROR1 binding KD (nM) | Cell Surface Binding based on Median YL1-PE at 4° C. A549 (ROR1$^{hi}$) | A427 (ROR1$^{low}$) | Cell Surface Binding based on Median YL1-PE MDA-MB-231 (ROR1$^{hi}$) 4° C. | % internalisation at 37° C. |
|---|---|---|---|---|---|---|---|---|---|---|
| B1HisMyc monomer | NA | E. coli | ++++ | – | – | 0.5 | 8440 | 557 | 5159 | 44 |
| B1-D3 | -[G$_4$S]$_5$- | CHO | ND | | | <0.05 | 7541 | 539 | 5763 | 33.5 |
| P3A1-[G$_4$S]$_5$-B1 | -[G$_4$S]$_5$- | E. coli | ++++ | – | – | 1.0 | 6511 | 304 | 3351 | 39 |
| B1-BA11-P3A1 | -[G$_4$S]$_5$- | CHO | ND | | | ND | 6500 | 703 | 2928 | 61.5 |
| P3A1-[G$_4$S]$_7$-B1 | -[G$_4$S]$_7$- | E. coli | ND | | | 4.3 | 6153 | 313 | 4174 | 39 |
| BA11-B1 | PGVQPSPGGGGS- | CHO | ND | | | 0.78 | 6063 | 368 | 3576 | 40 |
| P3A1-BA11-D3 | -[G$_4$S]$_5$- | Tni(Insect) | +++++ | – | +++++ | 4.46 | 5843 | 608 | 4952 | 56 |
| P3A1-[G$_4$S]$_3$-B1 | -[G$_4$S]$_3$- | E. coli | ND | | | 2.72 | 5345 | 297 | 3908 | 30 |
| P3A1-D3 Cys | -[G$_4$S]$_5$- | CHO | ND | | | 1.03 | 4628 | 326 | 2687 | 0 |
| D3-BA11-P3A1 | -[G$_4$S]- | Tni(Insect) | ++ | – | ++ | 1.81 | 3666 | 480 | 2534 | 57 |
| D3-D3HisMyc | -[G$_4$S]$_5$- | E. coli | ++++ | – | – | 1.7 | 3168 | 302 | 1947 | 57 |
| D3-P3A1 Cys | -[G$_4$S]$_5$- | CHO | ND | | | 1.63 | 2588 | 242 | / | / |
| P3A1-P3A1HisMyc | -[G$_4$S]$_5$- | HEK293 | ++++ | – | – | 0.3 | 2335 | 257 | / | / |
| D3-BA11-D3 | -[G$_4$S]$_5$- | CHO | +++ | – | +++++ | 4.21 | 2126 | 259 | 1140 | 65.5 |
| D3-D3-BA11 Cys | -[G$_4$S]$_5$- | CHO | ND | | | 0.76 | 2018 | 298 | 1654 | 64.5 |
| B1G1-B1G1 | -[G$_4$S]$_5$- | Tni(Insect) | ND | | | ND | 1474 | 372 | / | / |
| E9-BA11-E9 | -[G$_4$S]$_5$- | CHO | ND | | | 1.75 | 978 | 367 | / | / |
| BA11-2V | -[G$_4$S]$_5$- | CHO | – | – | +++++ | ND | 446 | 246 | / | / |
| 2VHisMyc monomer | NA | E. coli | – | – | – | No binding | 226 | 213 | / | / |

TABLE 19

Characterisation of additional biparatopic VNAR constructs

| VNAR | Linker | Expression System | Octet or SPR hROR1 binding KD (nM) |
|---|---|---|---|
| D3-D3-BA11 | —[G4S]5— | CHO | 0.764 |
| D3-P3A1 | —[G4S]5— | CHO | 1.63 |
| P3A1-D3 | —[G4S]5— | CHO | 1.03 |
| D3-B1 Cys | —[G4S]5— | CHO | <0.05 |

In addition, a number of bi-paratopic VNAR constructs were created using the -PGVQPSPGGGGS- linker (also termed Wobbe-G4S) and —PGVQPAPGGGGS- linker (also termed Wobbe-G4S—GM-) sequences. All were expressed using a QACKA HisMyc tag (SEQ ID NO: 80) and characterised and assessed as described previously.

TABLE 20

Additional data

| Construct | Linker | hROR1 binding (BLI) | | | HSA binding (BLI) | | | hROR1 binding (+HSA) |
|---|---|---|---|---|---|---|---|---|
| | | Ka (M⁻¹s⁻¹) | Kd (s⁻¹) | Kd (nM) | Ka (M⁻¹s⁻¹) | Kd (s⁻¹) | Kd (nM) | Kd (nM) |
| D3-P3A1 | -PGVQPSPGGGGS- | 5.64E+05 | 5.33E-04 | 0.945 | — | — | No binding | 2.27 |
| P3A1-D3 | -PGVQPSPGGGGS- | 9.50E+04 | 2.52E-04 | 2.66 | — | — | No binding | 2.55 |
| B1-D3 | -PGVQPSPGGGGS- | — | — | <0.05 | — | — | No binding | 0.252 |
| BA11-B1-P3A1 | -PGVQPSPGGGGS- | 4.05E+04 | 2.90E-05 | 0.718 | 2.08E+05 | 3.86E-04 | 1.86 | <0.05 |
| D3-P3A1-BA11 | -PGVQPSPGGGGS- | 2.74E+05 | 3.63E-04 | 1.33 | 2.05E+05 | 1.31E-03 | 6.37 | 1.97 |
| D3-BA11-P3A1 | -PGVQPSPGGGGS- | 2.29E+05 | 2.48E-04 | 1.08 | 1.37E+05 | 1.22E-03 | 8.88 | 2.01 |
| P3A1-BA11-D3 | -PGVQPSPGGGGS- | 1.11E+05 | 1.94E-04 | 1.74 | 1.03E+05 | 8.65E-04 | 8.37 | 3.21 |
| P3A1-D3-BA11 | -PGVQPSPGGGGS- | 1.69E+05 | 3.34E-04 | 1.98 | 2.13E+05 | 1.01E-03 | 4.73 | 2.00 |
| BA11-B1-DS | -PGVQPSPGGGGS- | 1.44E+05 | <1.0E-07 | <0.05 | 5.58E+04 | 4.72E-04 | 8.47 | <0.05 |
| D3-BA11-B1 | -PGVQPSPGGGGS- | 1.46E+05 | 1.32E-07 | <0.05 | 2.40E+05 | 9.26E-04 | 3.86 | <0.05 |
| D3-P3A1 | -PGVQPAPGGGGS- | 1.42E+05 | 3.02E-04 | 2.12 | No binding | No binding | No binding | 1.84 |
| D3-P3A1-BA11 | -PGVQPAPGGGGS- | 2.68E+05 | 4.14E-04 | 1.54 | 2.43E+05 | 9.24E-04 | 3.81 | 1.81 |
| D3-BA11-P3A1 | -PGVQPAPGGGGS- | 2.40E+05 | 3.35E-04 | 1.39 | 1.75E+05 | 1.04E-03 | 5.94 | 1.36 |
| P3A1-D3 | -PGVQPAPGGGGS- | 1.50E+05 | 3.61E-04 | 2.41 | — | — | No binding | 1.25 |
| P3A1-BA11-D3 | -PGVQPAPGGGGS- | 1.28E+05 | 3.23E-04 | 2.53 | 1.87E+05 | 6.92E-04 | 3.7 | 2.38 |
| P3A1-D3-BA11 | -PGVQPAPGGGGS- | 8.30E+04 | 2.37E-04 | 2.86 | 1.23E+05 | 8.37E-04 | 6.78 | 6.46 |

TABLE 20-continued

Additional data

| | | | | | | | | |
|---|---|---|---|---|---|---|---|---|
| P3A1-BA11-P3A1 | -PGVQPSPGGGGS- | 1.73E+05 | 4.40E-04 | 2.54 | 1.24E+05 | 6.90E-04 | 5.58 | 1.60 |
| BA11-P3A1-P3A1 | -PGVQPSPGGGGS- | 1.29E+05 | 4.47E-04 | 3.47 | 1.11E+05 | 5.66E-04 | 5.08 | 2.53 |
| BA11-B1 | -PGVQPAPGGGGS- | 5.03E+04 | 2.89E-05 | 0.58 | / | / | / | / |

| | ELISA | | | | Cell surface signal at 4° C. (Median YL1-PE) | |
|---|---|---|---|---|---|---|
| Construct | hROR1 | mROR1 | hROR2 | HSA | A549 | A427 |
| D3-P3A1 | ++++ | +++ | − | − | 1166 | 236 |
| P3A1-D3 | +++ | ++ | − | − | 1470 | 232 |
| B1-D3 | +++++ | ++++++ | − | − | 5573 | 1024 |
| BA11-B1-P3A1 | ++++ | ++++++ | − | ++++++ | 3230 | 584 |
| D3-P3A1-BA11 | +++++ | +++ | − | ++++ | 1204 | 264 |
| D3-BA11-P3A1 | ++++ | ++ | − | ++++ | 1807 | 312 |
| P3A1-BA11-D3 | +++++ | ++++ | − | +++ | 2465 | 282 |
| P3A1-D3-BA11 | +++++ | ++++ | − | ++ | 1816 | 243 |
| BA11-B1-D3 | +++ | ++++ | − | + | 4069 | 387 |
| D3-BA11-B1 | +++ | ++++ | − | +++ | 3239 | 279 |
| D3-P3A1 | ++++ | +++ | − | − | 1197 | 229 |
| D3-P3A1-BA11 | +++ | ++++ | − | +++ | 1496 | 242 |
| D3-BA11-P3A1 | ++++ | +++ | − | ++ | 1487 | 257 |
| P3A1-D3 | +++++ | +++++ | − | − | 1805 | 231 |
| P3A1-BA11-D3 | +++++ | ++++ | − | +++ | 2531 | 261 |
| P3A1-D3-BA11 | ++++ | ++++ | − | ++ | 2043 | 247 |
| P3A1-BA11-P3A1 | +++++ | ++ | − | +++ | 1294 | 258 |
| BA11-P3A1-P3A1 | +++ | ++++ | − | +++++ | 1005 | 269 |
| BA11-B1 | / | / | / | / | / | / |

The bi-paratopic VNAR constructs mentioned herein have also been successfully coupled with maleimide Alexa488 fluorophore, demonstrating that the constructs are suitable for conjugation to other moieties. This proof of concept work shows that conjugation of bi-paratopic molecules to other payloads will be possible.

Selective labelling of VNARs with Alexa Fluor 488 C5 maleimide (Thermo Fisher Scientific, U.K.) was carried out after Ni2+ IMAC purification of the VNAR in IMAC elution buffer (typically 50 mM NaPi pH 6.9, 150 mM NaCl, 50 mM L-Arginine, 250 mM imidazole, with addition of 2 mM TCEP to remove any capping from the Cys. incorporated for conjugation). Approximately 4 molar equivalents of the Alexa Fluor 488 dye were added to the VNAR solution (typical protein concentration was 2-30 μM), and the reaction mixture was incubated in darkness for 1 hour at r.t., with gentle agitation. Reaction was monitored by LC-MS (ESI) to ensure that no unreacted VNAR remained in solution. To remove the unreacted dye, the reaction mixture was diluted with 50 mM NaPi pH 6.9, 150 mM NaCl, 50 mM L-Arginine to 50 mM imidazole concentration, and Ni2+ IMAC was carried out on AKTA Pure system using HisTrap Excel column (both GE Healthcare, U.K.). Protein eluted in 50 mM *NaPi* pH 6.9, 150 mM NaCl, 50 mM L-Arginine, 250 mM imidazole. Elution fractions containing the Alexa488 VNAR conjugate were pooled and stored at 4° C. until required. Proteins were buffer exchanged into PBS pH 7.4 or PBS pH 7.4, 50 mM L-Arg by SEC or dialysis. See FIGS. 36 to 38.

Example 11—ROR1 CAR-T Approaches

Chimeric antigen receptors (CARs) based on the ROR1-specific antigen binding molecules described in the present application may be generated. Furthermore, engineered T cells expressing such a CAR may also be generated, which may then be used in, for example, adoptive cell therapy.

In brief, a nucleic acid construct encoding a ROR1-specific CAR may be produced. The ROR1-specific CAR may include an intracellular activation domain, a transmembrane domain, and an extracellular domain comprising the ROR1-specific antigen binding molecule described herein. The nucleic acid construct may then be incorporated into a viral vector, such as a retroviral vector (e.g., a lentiviral vector).

T cells may be isolated from a patient in need of treatment, which may then be modified to express the nucleic acid construct encoding the CAR, for example by retroviral transfection or gene-editing using approaches such as CRISPR-CAS-9.

The engineered T cells may then be re-infused into the patient in order to treat the condition, such as treatment of cancer.

The invention claimed is:

1. A receptor tyrosine kinase-like orphan receptor 1 (ROR1) specific antigen binding molecule comprising an amino acid sequence represented by the formula (I):

FW1-CDR1-FW2-HV2-FW3a-HV4-FW3b-CDR3-FW4     (I)

wherein
FW1 is a framework region;
CDR1 is a CDR sequence of DTSYGLYS (SEQ ID NO: 1);
FW2 is a framework region;
HV2 is a hypervariable sequence of TTDWERMSIG (SEQ ID NO: 6);
FW3a is a framework region;
HV4 is a hypervariable sequence of NKGAK (SEQ ID NO: 11);
FW3b is a framework region;
CDR3 is a CDR sequence of REARHPWLRQWY (SEQ ID NO: 17); and
FW4 is a framework region.

2. The ROR1-specific antigen binding molecule of claim 1, wherein the ROR1-specific antigen binding molecule does not bind to receptor tyrosine kinase-like orphan receptor 2 (ROR2).

3. The ROR1-specific antigen binding molecule of claim 1, wherein the ROR1-specific antigen binding molecule binds to both human ROR1 and murine ROR1 (mROR1).

4. The ROR1-specific antigen binding molecule of claim 1, wherein the ROR1-specific antigen binding molecule binds to deglycosylated ROR1.

5. The ROR1-specific antigen binding molecule of claim 1, wherein the ROR1-specific antigen binding molecule does not bind to a linear peptide sequence selected from:

(SEQ ID NO: 34)
YMESLHMQGEIENQI;

(SEQ ID NO: 35)
CQPWNSQYPHTHTFTALRFP;

(SEQ ID NO: 36)
RSTIYGSRLRIRNLDTTDTGYFQ; and (SEQ ID NO: 37)
QCVATNGKEVVSSTGVLFVKFGPPPTASPGYSDEYE.

6. The ROR1-specific antigen binding molecule of claim 1, wherein
   FW1 is a framework region of from 20 to 28 amino acids;
   FW2 is a framework region of from 6 to 14 amino acids;
   FW3a is a framework region of from 6 to 10 amino acids;
   FW3b is a framework region of from 17 to 24 amino acids; and
   FW4 is a framework region of from 7 to 14 amino acids.

7. The ROR1-specific antigen binding molecule of claim 6, wherein FW1 is selected from: ASVNQTPRTATKETGESLTINCVLT (SEQ ID NO: 19), AKVDQTPRTATKETGESLTINCVLT (SEQ ID NO: 20), TRVDQTPRTATKETGESLTINCVVT (SEQ ID NO: 21), TRVDQTPRTATKETGESLTINCVLT (SEQ ID NO: 22), ASVNQTPRTATKETGESLTINCVVT (SEQ ID NO: 23), TRVDQSPSSLSASVGDRVTITCVLT (SEQ ID NO: 24);
   FW2 is selected from: TSWFRKNPG (SEQ ID NO: 25), and TYWYRKNPG (SEQ ID NO: 26);
   FW3a is selected from: GRYVESV (SEQ ID NO: 27), GRYSESV (SEQ ID NO: 28;
   FW3b is selected from: SFSLRIKDLTVADSATYYCKA (SEQ ID NO: 29), SFTLTISSLQPEDSATYYCRA (SEQ ID NO: 30), SFTLTISSLOPEDFATYYCKA (SEQ ID NO: 31); and
   FW4 is selected from: DGAGTVLTVN (SEQ ID NO: 32), DGAGTKVEIK (SEQ ID NO: 33).

8. The ROR1-specific antigen binding molecule of claim 1, wherein the ROR1-specific antigen binding molecule comprises an amino acid sequence of TRVDQTPRTATKETGESLTINCVLTDTSYGLYSTSWFRKNPGTTDWERMSIGGRYVESVNKGAKSFS LRIKDLTVADSATYYCKAREARHPWLRQWYDGAGTVLTVN (SEQ ID NO: 43).

9. The ROR1-specific antigen binding molecule of claim 1, wherein the ROR1-specific antigen binding molecule is humanized.

10. The ROR1-specific antigen binding molecule of claim 1, wherein the ROR1-specific antigen binding molecule is de-immunized.

11. The ROR1-specific antigen binding molecule of claim 1, wherein the ROR1-specific antigen binding molecule is conjugated to a detectable label, dye, toxin, drug, pro-drug, radionuclide or biologically active molecule.

12. The ROR1-specific antigen binding molecule of claim 1, wherein the specific antigen binding molecule selectively interacts with ROR1 protein with an affinity constant of approximately 0.01 to 50 nM.

13. The ROR1-specific antigen binding molecule of claim 1, wherein the specific antigen binding molecule is capable of mediating killing of ROR1-expressing tumour cells.

14. The ROR1-specific antigen binding molecule of claim 1, wherein the specific antigen binding molecule is capable of inhibiting cancer cell proliferation.

15. The ROR1-specific antigen binding molecule of claim 1, wherein the specific antigen binding molecule is capable of being endocytosed upon binding to ROR1.

16. A recombinant fusion protein comprising a specific antigen binding molecule as claimed in claim 1.

17. A recombinant fusion protein as claimed in claim 16, in which the specific antigen binding molecule is fused to one or more biologically active proteins.

18. A recombinant fusion protein as claimed in claim 17, wherein the specific antigen binding molecule is fused to one or more biologically active proteins via one or more linker domains.

19. The recombinant fusion protein as claimed in claim 17, wherein at least one biologically active protein is an immunoglobin, an immunoglobulin Fc region, an immuno-globin Fab region, a single chain Fv (scFv), a diabody, a triabody, a tetrabody, a bispecific t-cell engager (BITE), an intein, a VNAR domain, a single domain antibody (sdAb), a VH domain, or a scaffold protein.

20. The recombinant fusion protein as claimed in claim 19, wherein at least one biologically active protein is an immunoglobulin Fc region.

21. A ROR1-specific chimeric antigen receptor (CAR), comprising at least one ROR1-specific antigen binding molecule as defined in claim 1, fused or conjugated to at least one transmembrane region and at least one intracellular domain.

22. A cell comprising a chimeric antigen receptor according to claim 21.

23. A nucleic acid sequence comprising a polynucleotide sequence that encodes a specific antigen binding molecule of claim 1.

24. A vector comprising a nucleic acid sequence as claimed in claim 23, optionally further comprising one or more regulatory sequences.

25. A host cell comprising a vector as claimed in claim 24.

26. A method for preparing a specific antigen binding molecule, recombinant fusion protein or chimeric antigen receptor, comprising cultivating or maintaining a host cell comprising the polynucleotide of claim 23 under conditions such that said host cell produces the binding molecule, optionally further comprising isolating the binding molecule.

27. A pharmaceutical composition comprising the specific antigen binding molecule of claim 1.

28. A method of treatment of a disease that expresses ROR1 in a patient in need of treatment comprising administration to said patient of a therapeutically effective dosage of a specific antigen binding molecule of claim 1.

29. The method of claim 28, wherein the disease is a ROR1-positive cancer.

30. The method of claim 29, wherein the cancer is selected from the group comprising blood cancers such as lymphomas and leukaemias, chronic lymphocytic leukaemia (CLL), mantle cell lymphoma (MCL), B-cell acute lymphoblastic leukaemia (B-ALL), marginal zone lymphoma (MZL), non-Hodgkin lymphomas (NHL), acute myeloid leukemia (AML) and solid tumours including neuroblastoma, renal cancer, lung cancer, colon cancer, ovarian cancer, pancreatic cancer, breast cancer, skin cancer, uterine cancer, prostate cancer, thyroid cancer, Head and Neck cancer, bladder cancer, stomach cancer or liver cancer.

31. A method of assaying for the presence of a target analyte in a sample, comprising the addition of a detectably labelled specific antigen binding molecule of claim 1 to the sample and detecting the binding of the molecule to the target analyte, wherein the target analyte is ROR1.

32. A method of imaging a site of a disease that expresses ROR1 in a subject, comprising administration of a detectably labelled specific antigen binding molecule as claimed in claim 1 to a subject.

33. A method of diagnosis of a disease or medical condition in a subject comprising administration of a specific antigen binding molecule as claimed in claim 1 wherein the disease or medical condition expresses ROR1.

34. A kit for diagnosing a subject suffering from a ROR1-positive cancer or for providing a prognosis of the subject's condition, the kit comprising detection means for detecting the concentration of ROR1 antigen present in a sample from a test subject, wherein the detection means comprises a ROR1-specific antigen binding molecule as defined in claim 1, wherein presence of ROR1 antigen in the sample suggests that the subject suffers from cancer.

35. The kit according to claim 34, wherein the kit is used to identify the presence or absence of ROR1-positive cells in the sample, or determine the concentration thereof in the sample.

36. The kit according to claim 34, wherein the kit comprises a positive control and/or a negative control against which the assay is compared.

37. The kit according to claim 34, wherein the kit further comprises a label which may be detected.

38. A method for diagnosing a subject suffering from a ROR1-positive cancer or for providing a prognosis of the subject's condition, the method comprising detecting the concentration of ROR1 antigen present in a sample obtained from the subject, wherein the detection is achieved using a ROR1-specific antigen binding molecule as defined in claim 1, and wherein presence of ROR1 antigen in the sample suggests that the subject suffers from cancer.

39. A method of killing or inhibiting the growth of a cell expressing ROR1 in vitro or in a patient, wherein the method comprises administering to the cell a pharmaceutically effective amount or dose of the ROR1-specific antigen binding molecule as defined in claim 1.

40. The method of claim 39, wherein the cell expressing ROR1 is a cancer cell.

41. The method according to claim 39, wherein the ROR1 is human ROR1.

42. A ROR1 specific antigen binding molecule comprising an amino acid sequence represented by the formula (II):

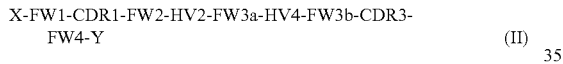

$$X\text{-}FW1\text{-}CDR1\text{-}FW2\text{-}HV2\text{-}FW3a\text{-}HV4\text{-}FW3b\text{-}CDR3\text{-}FW4\text{-}Y \quad \text{(II)}$$

wherein
  FW1 is a framework region;
  CDR1 is a CDR sequence of DTSYGLYS (SEQ ID NO: 1);
  FW2 is a framework region;
  HV2 is a hypervariable sequence of TTDWERMSIG (SEQ ID NO: 6);
  FW3a is a framework region;
  HV4 is a hypervariable sequence of NKGAK (SEQ ID NO: 11);
  FW3b is a framework region;
  CDR3 is a CDR sequence of REARHPWLRQWY (SEQ ID NO: 17); and
  FW4 is a framework region;
  wherein the terminal X and Y are optional amino acid sequences; and
  wherein the specific antigen binding molecule is conjugated to a second moiety.

43. The specific antigen binding molecule of claim 42, wherein X or Y are individually either absent or selected from the group comprising an immunoglobulin, an immunoglobulin Fc region, an immunoglobulin Fab region, a single chain Fv (scFv), a diabody, a triabody, a tetrabody, a bispecific t-cell engager (BiTE), an intein, a VNAR domain, a single domain antibody (sdAb), a VH domain, or a scaffold protein.

44. The specific antigen binding molecule of claim 42, wherein the conjugation is via a cysteine residue in the amino acid sequence of the specific antigen binding molecule.

45. The specific antigen binding molecule of claim 42, wherein the conjugation is via a thiol, aminoxy or hydrazinyl moiety incorporated at the N-terminus or C-terminus of the amino acid sequence of the specific antigen binding molecule.

46. The specific antigen binding molecule of claim 42, wherein the second moiety is selected from the group comprising an immunoglobulin, an immunoglobulin Fc region, an immunoglobulin Fab region, a single chain Fv (scFv), a diabody, a triabody, a tetrabody, a bispecific t-cell engager (BiTE), an intein, a VNAR domain, a single domain antibody (sdAb), a VH domain, or a scaffold protein.

47. The specific antigen binding molecule of claim 42, wherein the second moiety is selected from the group comprising detectable label, dye, toxin, drug, pro-drug, radionuclide or biologically active molecule.

48. The specific antigen binding molecule according to claim 42, wherein the second moiety is at least one toxin selected from the group consisting of:
  maytansinoids,
  auristatins,
  anthracyclins
  PNU-derived anthracyclins,
  amanitin derivatives
  α-amanitin derivatives,
  calicheamicins,
  tubulysins,
  duocarmycins,
  radioisotopes,
  an alpha-emitting radionuclide,
  a 227 Th or 225 Ac label,
  liposomes comprising a toxic payload,
  protein toxins,
  taxanes,
  pyrrolbenzodiazepines,
  indolinobenzodiazepine pseudodimers,
  spliceosome inhibitors,
  CDK11 inhibitors, and
  Pyridinobenzodiazepines.

49. The specific antigen binding molecule according to claim 42, wherein the ROR1-specific antigen binding molecule does not bind to receptor tyrosine kinase-like orphan receptor 2 (ROR2).

50. The specific antigen binding molecule according to claim 42, wherein the ROR1-specific antigen binding molecule binds to both human ROR1 and murine ROR1 (mROR1).

51. The specific antigen binding molecule according to claim 42, wherein the ROR1-specific antigen binding molecule binds to deglycosylated ROR1.

52. The specific antigen binding molecule according to claim 42, wherein the ROR1-specific antigen binding molecule does not bind to a linear peptide sequence selected from:

```
                                      (SEQ ID NO: 34)
YMESLHMQGEIENQI;

(SEQ ID NO: 35)
CQPWNSQYPHTHTFTALRFP;

(SEQ ID NO: 36)
RSTIYGSRLRIRNLDTTDTGYFQ; and (SEQ ID NO: 37)
QCVATNGKEVVSSTGVLFVKFGPPPTASPGYSDEYE.
```

53. The specific antigen binding molecule according to claim 42, wherein:

FW1 is a framework region of from 20 to 28 amino acids,
FW2 is a framework region of from 6 to 14 amino acids,
FW3a is a framework region of from 6 to 10 amino acids,
FW3b is a framework region of from 17 to 24 amino acids, and
FW4 is a framework region of from 7 to 14 amino acids.

54. The specific antigen binding molecule according to claim 42, wherein FW1 is selected from ASVNQTPRTATKETGESLTINCVLT (SEQ ID NO: 19), AKVDQTPRTATKETGESLTINCVLT (SEQ ID NO: 20), TRVDQTPRTATKETGESLTINCVVT (SEQ ID NO: 21), TRVDQTPRTATKETGESLTINCVLT (SEQ ID NO: 22), ASVNQTPRTATKETGESLTINCVVT (SEQ ID NO: 23), TRVDQSPSSLSASVGDRVTITCVLT (SEQ ID NO: 24);

FW2 is selected from TSWFRKNPG (SEQ ID NO: 25), and TYWYRKNPG (SEQ ID NO: 26);

FW3a is selected from GRYVESV (SEQ ID NO: 27), and GRYSESV (SEQ ID NO: 28), and;

FW3b is selected from SFSLRIKDLTVADSATYYCKA (SEQ ID NO: 29), SFTLTISSLOPEDSATYYCRA (SEQ ID NO: 30), SFTLTISSLQPEDFATYYCKA (SEQ ID NO: 31); and FW4 is selected from DGAGTVLTVN (SEQ ID NO: 32), and DGAGTKVEIK (SEQ ID NO: 33).

55. The specific antigen binding molecule according to claim 42, wherein the ROR1-specific antigen binding molecule comprises an amino acid sequence of TRVDQTPRTATKETGESLTINCVLTDTSYGLYSTSWFRKNPGTTDWERMSIGGRYVESVNKGAKSFSLRIKDLTVADSATYYCKAREARHPWLRQWYDGAGTVLTVN (SEQ ID NO: 43).

56. The specific antigen binding molecule according to claim 42, wherein the ROR1-specific antigen binding molecule is humanized.

57. The specific antigen binding molecule according to claim 42, wherein the ROR1-specific antigen binding molecule is de-immunized.

* * * * *